(12) United States Patent
Staudt et al.

(10) Patent No.: US 7,711,492 B2
(45) Date of Patent: May 4, 2010

(54) METHODS FOR DIAGNOSING LYMPHOMA TYPES

(75) Inventors: Louis M. Staudt, Silver Spring, MD (US); George Wright, Takoma Park, MD (US); Sandeep Dave, Washington, DC (US); Bruce Tan, Chicago, IL (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 273 days.

(21) Appl. No.: 10/934,930

(22) Filed: Sep. 3, 2004

(65) Prior Publication Data

US 2005/0164231 A1 Jul. 28, 2005

Related U.S. Application Data

(60) Provisional application No. 60/500,377, filed on Sep. 3, 2003.

(51) Int. Cl.
*G01N 33/48* (2006.01)
*C12Q 1/68* (2006.01)
*C12N 15/00* (2006.01)
*C12N 15/11* (2006.01)

(52) U.S. Cl. ............... 702/19; 702/20; 435/6; 435/320.1; 536/23.1; 536/24.1

(58) Field of Classification Search ............ None
See application file for complete search history.

(56) References Cited

FOREIGN PATENT DOCUMENTS

| WO | WO 02/24956 | 3/2002 |
|---|---|---|
| WO | WO 03/021229 | 3/2003 |

OTHER PUBLICATIONS

Alizadeh, A.A., et al. 1999. The Lymphochip: a specialized cDNA microarray for the genomic-scale analysis of gene expression in normal and malignant lymphocytes. Cold Spring Harbor Symp Quant Biol 64:71-78.
Alon, U., et al. 1999. Broad patterns of gene expression revealed by clustering analysis of tumor and normal colon tissues probed by oligonucleotide arrays. Proc Natl Acad Sci USA 96:6745-6750.
Copie-Bergman, C., et al. 2002. MAL expression in lymphoid cells: further evidence for MAL as a distinct molecular marker of primary mediastinal large B-cell lymphomas. Mod Pathol 15:1172-1180.
Copie-Bergman, C., et al. 2003. Interleukin 4-induced gene 1 is activated in primary mediastinal large B-cell lymphoma. Blood 101:2756-2761.
DeRisi, J., et al. 1996. Use of a cDNA microarray to analyze gene expression patterns in human cancer. Nat Genet 14:457-60.
Dudoit, S., Fridlyand, J., Speed, T.P. 2002. Comparison of discrimination methods for the classification of tumors using gene expression data. J Am Stat Assoc 97:77-87.

Golub, T.R., et al. 1999. Molecular classification of cancer: class discovery and class prediction by gene expression monitoring, Science 286:531-537.
Radmacher, M.D., McShane, L.M., Simon, R. 2002. A paradigm for class prediction using gene expression profiles. J Comput Biol 9:505-511.
Ramaswamy, S., et al. 2001. Multiclass cancer diagnosis using tumor gene expression signatures. Proc Natl Acad Sci USA 98:15149-15154.
Rosenwald, A., et al. 2002. The use of molecular profiling to predict survival after chemotherapy for diffuse large-B-cell lymphoma. New Engl J Med 346:1937-1947.
Rosenwald, A., et al. 2003. The proliferation gene expression signature is a quantitative integrator of oncogenic events that predicts survival in mantle cell lymphoma. Cancer Cell 3:185-197.
Tibshirani, R., Hastie, T., Narasimhan, B., Chu, G. 2002. Diagnosis of multiple cancer types by shrunken centroids of gene expression. Proc Natl Acad Sci USA 99:6567-6572.
Wright, G., et al. 2003. A gene expression-based method to diagnose clinically distinct subgroups of diffuse large B cell lymphoma. Proc Natl Acad Sci USA 100:9991-9996.
Alizadeh et al., Distinct Types of Diffuse Large B-cell Lymphoma Identified by Gene Expression Profiling. Nature, Feb. 2000, vol. 403, pp. 503-511.
Ando et al., Fuzzy Neural Network Applied to Gene Expression Profiling for Predicting the Prognosis of Diffuse Large B-cll Lymphoma. Jpn. J. Cancer Res., Nov. 2002, vol, 93, pp. 1207-1212.
Eisen et al., Cluster Analysis and Display of Genome-wide Expression Patterns. Proc. Natl. Acad. Ci. USA, Dec. 1998, vol. 95, pp. 14863-14868.
Khan et al., Classification and Diagnostic Prediction of Cancers Using Gene Expression Profiling and Artificial Neural Networks, Nature Medicine, Jun. 2001, vol. 7, pp. 673-679.
Shipp et al., Diffuse Large B-cell Lymphoma Outcome Prediction by Gene-Expression Profiling and Supervised Machine Learning. Nature Medicine, Jan. 2002, vol. 8, pp. 68-74.
Bea et al., *Blood*, 106(9): 3183-3190 (Nov. 1, 2005).
Dave et al., *N. England J. Med.*, 354(23): 2431-2442 (Jun. 8, 2006).
Fu et al., *Blood*, 106(13): 4315-4321 (Dec. 15, 2005).
Andreasson et al., *Cancer Genet. Cytogenet.*, 102: 81-82 (1998).
Basso et al., *Blood*, 104: 4088-4096 (2004).
Bea et al., *Blood*, 93: 4365-4374 (1999).

(Continued)

*Primary Examiner*—Shubo (Joe) Zhou
(74) *Attorney, Agent, or Firm*—Leydig, Voit & Mayer, Ltd.

(57) ABSTRACT

Gene expression data provides a basis for more accurate identification and diagnosis of lymphoproliferative disorders. In addition, gene expression data can be used to develop more accurate predictors of survival. The present invention discloses methods for identifying, diagnosing, and predicting survival in a lymphoma or lymphoproliferative disorder on the basis of gene expression patterns. The invention discloses a novel microarray, the Lymph Dx microarray, for obtaining gene expression data from a lymphoma sample. The invention also discloses a variety of methods for utilizing lymphoma gene expression data to determine the identity of a particular lymphoma and to predict survival in a subject diagnosed with a particular lymphoma. This information will be useful in developing the therapeutic approach to be used with a particular subject.

29 Claims, 28 Drawing Sheets

OTHER PUBLICATIONS

Bea et al., *J. Clin. Oncol.*, 22: 3498-3506 (2004).
Berglund et al., *Mod. Pathol.*, 15: 807-816 (2002).
Bergsagel et al., *Immunol. Rev.*, 194: 96-104 (2003).
Bishop et al., *Cancer Invest.*, 18: 574-583 (2000).
Boxer et al., *Oncogene*, 20: 5595-5610 (2001).
Chiarle et al., *Blood*, 95: 619-626 (2000).
Cigudosa et al., *Genes Chromosomes Cancer*, 25: 123-133 (1999).
Dave et al., *Cancer Genet. Cytogenet.*, 132: 125-132 (2002).
Delmer et al., *Blood*, 85: 2870-2876 (1995).
Doglioni et al., *J. Pathol.*, 185: 159-166 (1998).
Feuerhake et al., *Blood*, 106: 1392-1399 (2005).
Gerbitz et al., *Oncogene*, 18: 1745-1753 (1999).
Goff et al., *Br. J. Haematol.*, 111: 618-625 (2000).
Gress et al., *Oncogene*, 13: 1819-1830 (1996).
Haralambieva et al., *Am. J. Surg. Pathol.*, 29: 1086-1094 (2005).
Huang et al., *Blood*, 99: 2285-2290 (2002).
Hyman et al., *Cancer Res.*, 62: 6240-6245 (2002).
Iqbal et al., *Am. J. Pathol.*, 165: 159-166 (2004).
Jares et al., *Am. J. Pathol.*, 148: 1591-1600 (1996).
Kramer et al., *Blood*, 92: 3152-3162 (1998).
Monni et al., *Blood*, 87: 5269-5278 (1996).
Li, *Bioinformatics*, 22: 466-471 (2006).
Neri et al., *Proc. Natl. Acad. Sci. USA*, 85: 2748-2752 (1988).
Orsetti et al., *Cancer Res.*, 64: 6453-6460 (2004).
Ott et al., *Blood*, 90: 3154-3159 (1997).
Pruneri et al., *J. Pathol.*, 200: 596-601 (2003).
Quintanilla-Martinez et al., *Am. J. Pathol.*, 153: 175-182 (1998).
Ransohoff, *Nat. Rev. Cancer*, 4: 309-314 (2004).
Rao et al., *Blood*, 92: 234-240 (1998).
Rosenwald et al., *J. Exp. Med.*, 198: 851-862 (2003).
Savage et al., *Blood*, 102: 3871-3879 (2003).
Sonoki et al., *Blood*, 98: 2837-2844 (2001).
Yatabe et al., *Blood*, 95: 2253-2261 (2000).
Ye et al., *Blood*, 102: 1012-1018 (2003).
Zeller et al., *Genome Biol.*, 4: R69 (2003).
Supplementary European Search Report, European Patent Office, Jul. 10, 2008.

Figure 16

| | Model Prediction | | | | | |
|---|---|---|---|---|---|---|
| | ABC | MCL | GCB | MCL | SLL | MCL |
| ABC | 42 | 0 | | | | |
| MCL | 0 | 46 | | | | |
| GCB | | | 67 | 0 | | |
| MCL | | | 0 | 46 | | |
| SLL | | | | | 11 | 0 |
| MCL | | | | | 0 | 46 |

Training Set

| | ABC | MCL | GCB | MCL | SLL | MCL |
|---|---|---|---|---|---|---|
| ABC | 41 | 0 | | | | |
| MCL | 1 | 45 | | | | |
| GCB | | | 66 | 0 | | |
| MCL | | | 0 | 46 | | |
| SLL | | | | | 11 | 0 |
| MCL | | | | | 0 | 46 |

Validation Set

MCL vs. ABC Model  
MCL vs. GCB Model  
MCL vs. SLL Model

Lymphoma Subtype

Error score = 4*(Error Rate) + Unclassified Rate

METHODS FOR DIAGNOSING LYMPHOMA TYPES

RELATED APPLICATIONS

The present utility application claims priority to provisional patent application U.S. Ser. No. 60/500,377 (Staudt et al.), filed Sep. 3, 2003, the disclosure of which is incorporated by reference herein in its entirety, including but not limited to the electronic data submitted on 21 CD-ROMs accompanying the provisional application.

FIELD OF THE INVENTION

The present invention relates to the field of diagnosing, identifying, and predicting survival in lymphoproliferative disorders.

REFERENCE TO TABLES SUBMITTED ON COMPACT DISC

Tables 2-1723 and 1725-2358 are contained on 21 CD-ROMs provided herewith. These CD-ROMs are numbered 1-21 of 22. Each CD-ROM is provided in two copies, 15 for a total of 44 CD-ROMs. The name, size, and date of creation for each file is presented in the List of Materials Submitted by Compact Disc at the end of this specification and in the file entitled "Tableofcontents.txt," located on CD number 21 of 22. The name of each file incorporates the number of the corresponding table. Any reference to a table or file should be considered an incorporation by reference of the contents of the table and/or file at that particular place in the specification.

REFERENCE TO COMPUTER PROGRAM LISTING APPENDIX SUBMITTED ON COMPACT DISC

A computer program listing appendix is contained on one CD-ROM provided herewith. Three copies of this CD-ROM, numbered 22 of 22, are provided. The computer program listing appendix contains files related to the implementation of an algorithm for determining lymphoma type. The name, size, and date of creation for each file in the computer program listing appendix is presented in the file entitled "Table_of_contents.txt," located on CD-ROM 22. Any reference to a file contained in the computer program listing appendix should be considered an incorporation by reference of the contents of that file at that particular place in the specification.

BACKGROUND OF INVENTION

A variety of systems for identifying and classifying lymphomas have been proposed over the last 20 years. In the 1980's, the Working Formulation was introduced as a method of classifying lymphomas based on morphological and clinical characteristics. In the 1990's, the Revised European-American Lymphoma (REAL) system was introduced in an attempt to take into account immunophenotypic and genetic characteristics in classifying lymphomas (Harris 1994). The most recent standard, set forth by the World Health Organization (WHO), attempts to build on these previous systems (Jaffe 2001). The WHO classification of lymphomas is based on several factors, including tumor morphology, immunophenotype, recurrent genetic abnormalities, and clinical features. Table 1, below, contains a list of the B and T cell neoplasms that have been recognized by the WHO classification. Each malignancy is listed according to its WHO classification nomenclature, followed by a WHO classification number.

TABLE 1

| Category | Name | WHO ID # |
|---|---|---|
| | B-cell neoplasms | |
| Precursor B-cell neoplasms | Precursor B-cell lymphoblastic leukemia | 9835/3 |
| | Precursor B-cell lymphoblastic lymphoma | 9728/3 |
| Mature B-cell neoplasms | Chronic lymphocytic leukemia | 9823/3 |
| | Small lymphocytic lymphoma | 9670/3 |
| | B-cell prolymphocytic leukemia | 9833/3 |
| | Lymphoplasmacytic lymphoma | 9671/3 |
| | Splenic marginal zone lymphoma | 9689/3 |
| | Hairy cell leukemia | 9940/3 |
| | Plasma cell myeloma | 9732/3 |
| | Solitary plasmacytoma of bone | 9731/3 |
| | Extraosseous plasmacytoma | 9734/3 |
| | Extranodal marginal zone B-cell lymphoma of mucosa-associated lymphoid tissue (MALT lymphoma) | 9699/3 |
| | Nodal marginal zone B-cell lymphoma | 9699/3 |
| | Follicular lymphoma (Grade 1, 2, 3a, 3b) | 9690/3 |
| | Mantle cell lymphoma | 9673/3 |
| | Diffuse large B-cell lymphoma | 9680/3 |
| | Mediastinal (thymic) large B-cell lymphoma | 9679/3 |
| | Intravascular large B-cell lymphoma | 9680/3 |
| | Primary effusion lymphoma | 9678/3 |
| | Burkitt lymphoma | 9687/3 |
| | Burkitt leukemia | 9826/3 |
| B-cell proliferations of uncertain malignant potential | Lymphomatoid granulomatosis | 9766/1 |
| | Post-transplant lymphoproliferative disorder, polymorphic | 9970/1 |
| | T-cell and NK-cell neoplasms | |
| Precursor T-cell and NK-cell neoplasms | Precursor T lymphoblastic leukemia | 9837/3 |
| | Precursor T lymphoblastic lymphoma | 9729/3 |
| | Blastic NK-cell lymphoma | 9727/3 |
| Mature T-cell and NK-cell neoplasms | T-cell prolymphocytic leukemia | 9834/3 |
| | T-cell large granular lymphocytic leukemia | 9831/3 |
| | Aggressive NK-cell leukemia | 9948/3 |
| | Adult T-cell leukemia/lymphoma | 9827/3 |
| | Extranodal NK-/T-cell lymphoma, nasal type | 9719/3 |
| | Enteropathy-type T-cell lymphoma | 9717/3 |
| | Hepatosplenic T-cell lymphoma | 9716/3 |
| | Subcutaneous panniculitis-like T-cell lymphoma | 9708/3 |
| | Mycosis fungoides | 9700/3 |
| | Sezary syndrome (9701/3) | 9701/3 |
| | Primary cutaneous anaplastic large cell lymphoma (C-ALCL) | 9718/3 |
| | Peripheral T-cell lymphoma, unspecified | 9702/3 |
| | Angioimmunoblastic T-cell lymphoma | 9705/3 |
| | Anaplastic large cell lymphoma | 9714/3 |
| T-cell proliferation of uncertain malignant potential | Lymphomatoid papulosis | 9718/3 |

TABLE 1-continued

| Category | Name | WHO ID # |
|---|---|---|
| Hodgkin lymphoma | Nodular lymphocyte predominant Hodgkin lymphoma | 9659/3 |
| | Classical Hodgkin lymphoma | 9650/3 |
| | Classical Hodgkin lymphoma, nodular sclerosis | 9663/3 |
| | Classical Hodgkin lymphoma, lymphocyte-rich | 9651/3 |
| | Classical Hodgkin lymphoma, mixed cellularity | 9652/3 |
| | Classical Hodgkin lymphoma, lymphocyte depleted | 9653/3 |

Other diagnoses that have not been given WHO diagnostic numbers include HIV-associated lymphoma, germinal center B cell-like subtype of diffuse large B cell lymphoma, activated B cell-like subtype of diffuse large B-cell lymphoma, follicular hyperplasia (non-malignant), and infectious mononucleosis (non-malignant).

Although the WHO classification has proven useful in patient management and treatment, patients assigned to the same WHO diagnostic category often have noticeably different clinical outcomes. In many cases, these different outcomes appear to be due to molecular differences between tumors that cannot be readily observed by analyzing tumor morphology. More precise methods are needed for identifying and classifying lymphomas based on their molecular characteristics.

SUMMARY OF THE INVENTION

Accurate identification of lymphoma type or subtype in a subject suffering from a lymphoproliferative disorder is important for developing an appropriate therapeutic strategy. Previous attempts have been made to identify lymphomas using gene expression data obtained using a microarray. However, there is a need in the art for more accurate and predictive methods of analyzing this gene expression data. In addition, there is a need for more specific and efficient methods of obtaining gene expression data.

The present invention discloses a novel microarray for obtaining gene expression data to be used in identifying lymphoma types and predicting survival in a subject. The present invention further discloses a variety of methods for analyzing gene expression data obtained from a lymphoma sample, and specific algorithms for predicting survival and clinical outcome in a subject suffering from a lymphoma.

One embodiment of the present invention provides a composition comprising the set of probes listed in Table 2, contained in the file entitled "Table_0002_LymphDx_Probe_List.txt." Preferably, this composition comprises a microarray.

In another embodiment, the present invention provides a method of generating a survival predictor for a particular lymphoma type. In this method, one or more biopsy samples that have been diagnosed as belonging to a particular lymphoma type are obtained. Gene expression data is obtained for these samples, and genes with expression patterns associated with longer or shorter survival are identified. Hierarchical clustering is performed to group these genes into gene expression signatures, and the expression of all genes within each signature are averaged to obtain a gene expression signature value for each signature. These gene expression signature values are then used to generate a multivariate survival predictor.

In another embodiment, the present invention provides a method for predicting survival in a follicular lymphoma (FL) subject. In this method, a biopsy sample is obtained from the subject and gene expression data is obtained from the biopsy sample. The expression level of those genes belonging to an immune response-1 or immune response-2 gene expression signature are averaged to generate gene expression signature values for each signature. A survival predictor score is then calculated using an equation: [2.71*(immune response-2 gene expression signature value)]−[2.36*(immune response-1 gene expression signature value)]. A higher survival predictor score is associated with a less favorable outcome. In one embodiment, the gene expression data used in this method is obtained using a microarray.

In another embodiment, the present invention provides another method for predicting survival in a follicular lymphoma (FL) subject. In this method, a biopsy sample is obtained from the subject and gene expression data is obtained from the biopsy sample. The expression level of those genes belonging to a B cell differentiation, T-cell, or macrophage gene expression signature are averaged to generate gene expression signature values for each signature. A survival predictor score is then calculated using an equation: [2.053*(macrophage gene expression signature value)]−[2.344*(T-cell gene expression signature value)]−[0.729*(B-cell gene expression signature value)]. A higher survival predictor score is associated with a less favorable outcome. In one embodiment, the gene expression data used in this method is obtained using a microarray.

In another embodiment, the present invention provides yet another method for predicting survival in a follicular lymphoma (FL) subject. In this method, a biopsy sample is obtained from the subject and gene expression data is obtained from the biopsy sample. The expression level of those genes belonging to a macrophage, T-cell, or B-cell differentiation gene expression signature are averaged to generate gene expression signature values for each signature. A survival predictor score is then calculated using an equation: [1.51*(macrophage gene expression signature value)]−[2.11*(T-cell gene expression signature value)]−[0.505*(B-cell differentiation gene expression signature value)]. A higher survival predictor score is associated with a less favorable outcome. In one embodiment, the gene expression data used in this method is obtained using a microarray.

In another embodiment, the present invention provides a method for predicting survival in a diffuse large B cell lymphoma (DLBCL) subject. In this method, a biopsy sample is obtained from the subject and gene expression data is obtained from the biopsy sample. The expression level of those genes belonging to an ABC DLBCL high, lymph node, or MHC class II gene expression signature are averaged to generate gene expression signature values for each signature. A survival predictor score is then calculated using an equation: [0.586*(ABC DLBCL high gene expression signature value)]−[0.468*(lymph node gene expression signature value)]−[0.336*(MHC class II gene expression signature value)]. A higher survival predictor score is associated with a less favorable outcome. In one embodiment, the gene expression data used in this method is obtained using a microarray.

In another embodiment, the present invention provides another method for predicting survival in a diffuse large B cell lymphoma (DLBCL) subject. In this method, a biopsy sample is obtained from the subject and gene expression data is obtained from the biopsy sample. The expression level of those genes belonging to a lymph node, germinal B cell, proliferation, or MHC class II gene expression signature are averaged to generate gene expression signature values for each signature. A survival predictor score is then calculated using an equation: [−0.4337*(lymph node gene expression signature)]+[0.09*(proliferation gene expression signature)]−[0.4144*(germinal center B-cell gene expression signature)]−[0.2006*(MHC class II gene expression signature)]. A higher survival predictor score is associated with a less favorable outcome. In one embodiment, the gene expression data used in this method is obtained using a microarray.

In another embodiment, the present invention provides yet another method for predicting survival in a diffuse large B cell lymphoma (DLBCL) subject. In this method, a biopsy sample is obtained from the subject and gene expression data is obtained from the biopsy sample. The expression level of those genes belonging to a lymph node, germinal B cell, or MHC class II gene expression signature are averaged to generate gene expression signature values for each signature. A survival predictor score is then calculated using an equation: [−0.32*(lymph node gene expression signature)]−[0.176*(germinal B cell gene expression signature)]−[0.206*(MHC class II gene expression signature)]. A higher survival predictor score is associated with a less favorable outcome. In one embodiment, the gene expression data used in this method is obtained using a microarray. In another embodiment, the gene expression data is obtained using RT-PCR.

In another embodiment, the present invention provides a method for predicting survival in a mantle cell lymphoma (MCL) subject. In this method, a biopsy sample is obtained from the subject and gene expression data is obtained from the biopsy sample. The expression level of those genes belonging to a proliferation gene expression signature are averaged to generate a gene expression signature value. A survival predictor score is then calculated using an equation: [1.66*(proliferation gene expression signature value)]. A higher survival predictor score is associated with a less favorable outcome. In one embodiment, the gene expression data used in this method is obtained using a microarray.

In another embodiment, the present invention provides a method for determining the probability that a sample X belongs to a first lymphoma type or a second lymphoma type. In this method, a set of genes is identified that is differentially expressed between the two lymphoma types in question, and a set of scale factors representing the difference in expression between the lymphoma types for each of these genes are calculated. A series of linear predictor scores are generated for samples belonging to either of the two lymphoma types based on expression of these genes. Gene expression data is then obtained for sample X, and a linear predictor score is calculated for this sample. The probability that sample X belongs to the first lymphoma type is calculated using an equation that incorporates the linear predictor score of sample X and the mean and variance of the linear predictor scores for the known samples of either lymphoma type.

In another embodiment, the present invention provides a method for determining the lymphoma type of a sample X. In this method, a set of genes is identified that is differentially expressed between a first lymphoma type and a second lymphoma type, and a set of scale factors representing the difference in expression of each of these genes between the two lymphoma types are calculated. A series of linear predictor scores are generated for samples belonging to either of the two lymphoma types based on expression of these genes. Gene expression data is then obtained for sample X, and a linear predictor score is calculated for this sample. The probability that sample X belongs to the first lymphoma type is calculated using an equation that incorporates the linear predictor score of sample X and the mean and variance of the linear predictor scores for the known samples of either lymphoma type. This entire process is then repeated with various lymphoma types being substituted for the first lymphoma type, the second lymphoma type, or both.

In another embodiment, the present invention provides another method for determining the lymphoma type of a sample X. In this method, a series of lymphoma type pairs are created, with each pair consisting of a first lymphoma type and a second lymphoma type. For each type pair, gene expression data is obtained for a set of genes, and a series of scale factors representing the difference in expression of each of these genes between the two lymphoma types are calculated. A subset of z genes with the largest scale factors are identified, and a series of linear predictor scores are generated for samples belonging to either of the two lymphoma types. Linear predictor scores are calculated for anywhere from 1 to z of these genes. The number of genes from 1 to z that results in the largest difference in linear predictor scores between the two lymphoma types is selected, and gene expression data for these genes is obtained for sample X. A linear predictor score is generated for sample X, and the probability that the sample belongs to the first lymphoma type is calculated using an equation that incorporates the linear predictor score for sample X and the mean and variance of the linear predictor scores for the known samples of either lymphoma type.

In another embodiment, the present invention provides another method for determining the lymphoma type of a sample X. In this method, a series of lymphoma type pairs are created, with each pair consisting of a first lymphoma type and a second lymphoma type. For each type pair, gene expression data is obtained for a set of genes, and a series of scale factors representing the difference in expression of each of these genes between the two lymphoma types are calculated. The set of genes is divided into gene-list categories indicating correlation with a gene expression signature. Within each gene-list category, a subset of z genes with the largest scale factors are identified, and a series of linear predictor scores are generated for samples belonging to either of the two lymphoma types. Linear predictor scores are calculated for anywhere from 1 to z of these genes. The number of genes from 1 to z that results in the largest difference in linear predictor scores between the two lymphoma types is selected, and gene expression data for these genes is obtained for sample X. A linear predictor score is generated for sample X, and the probability q that the sample belongs to the first lymphoma type is calculated using an equation that incorporates the linear predictor score for sample X and the mean and variance of the linear predictor scores for the known samples of either lymphoma type. A high probability q indicates that sample X belongs to the first lymphoma type, a low probability q indicates that sample X belongs to the second lymphoma type, and a middle probability q indicates that sample X belongs to neither lymphoma type. The cut-off point between high, middle, and low probability values is determined by ranking samples of known lymphoma type according to their probability values, then analyzing every possible cut-off point between adjacent samples using the equation: 3.99*[(% of first lymphoma type misidentified as second lymphoma type)+(% of second lymphoma type misidentified as a first lymphoma type)]+[(% of first lymphoma type identified as belonging to neither lymphoma type)+(% of second lymphoma type identified as belonging to neither lymphoma type)]. The final cut-off points are those that minimize the value of this equation.

[(2.71*immune response-2 gene expression signature value)]−[(2.36×immune response-1 gene expression signature value)].

Figure 6:
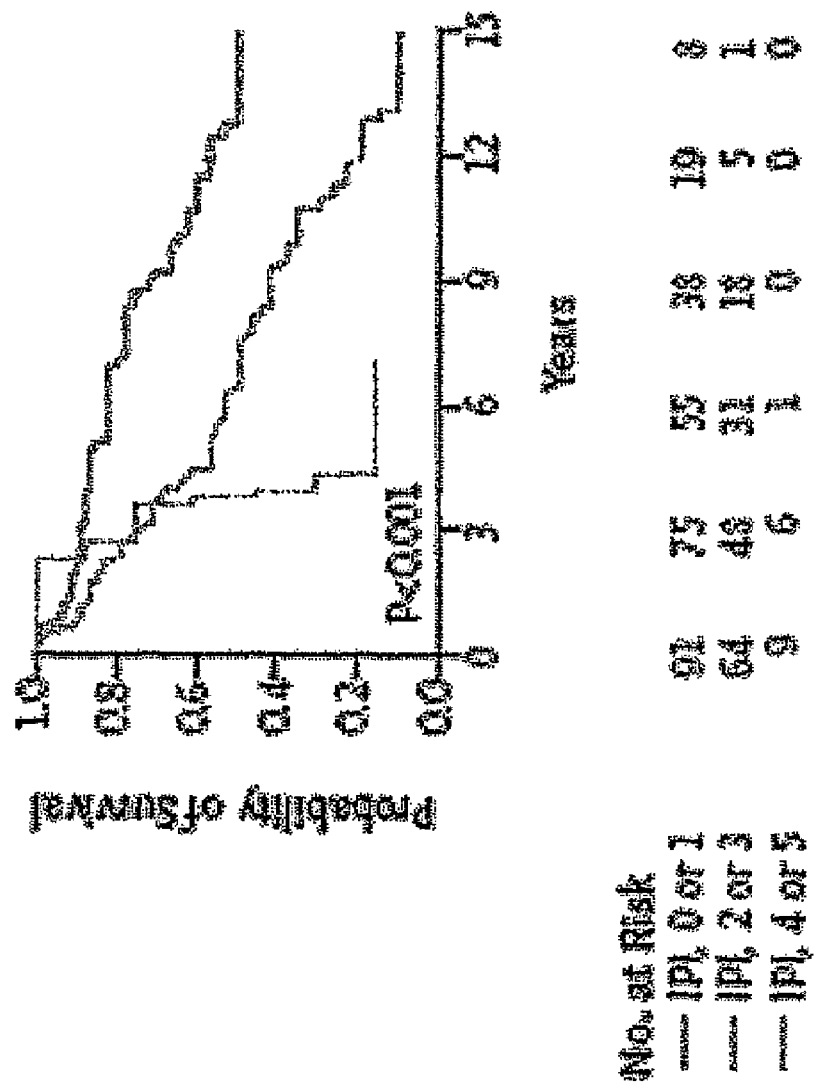

FIG. 6: Kaplan-Meier plot of survival in FL samples based on IPI score. 96 FL samples were divided into three groups based on their IPI scores.

Figure 7:
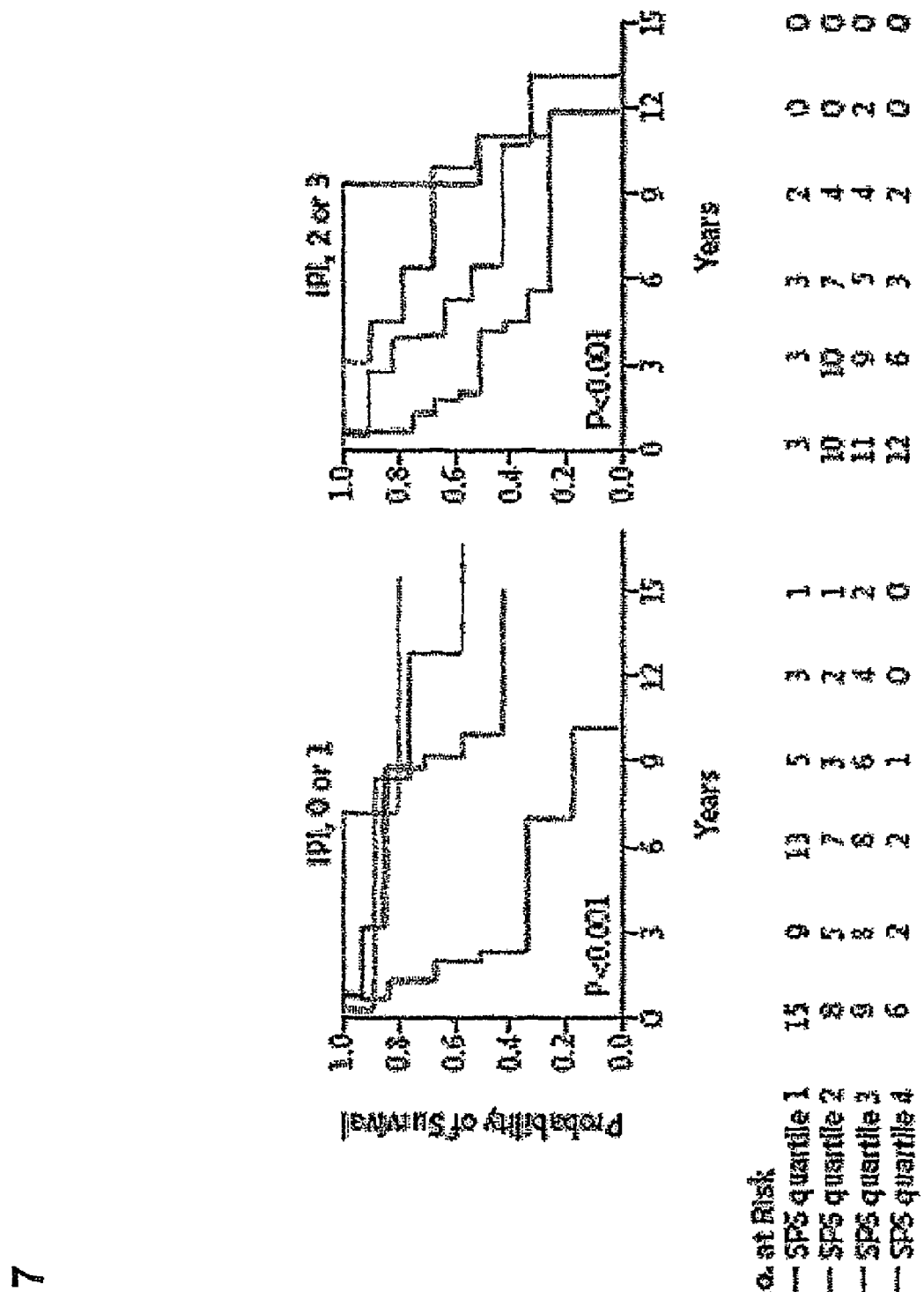

FIG. 7: Kaplan-Meier plot of survival in FL samples with low or high risk IPI scores based on survival predictor scores. 96 FL samples with low risk (left panel) or intermediate risk (right panel) IPI scores were divided into quartiles based on their survival predictor scores. The survival predictor scores were calculated using the equation: [(2.71*immune response-2 gene expression signature value)]−[(2.36×immune response-1 gene expression signature value)].

Figure 8:
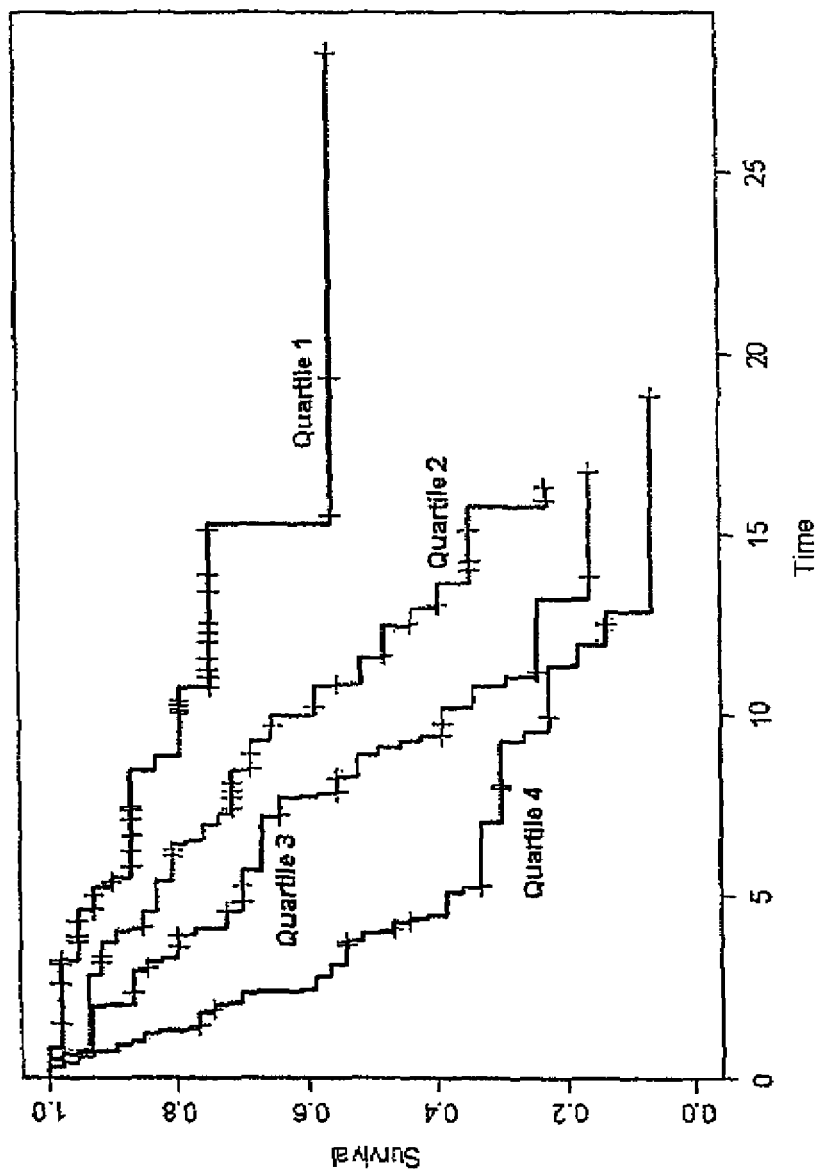

FIG. 8: Kaplan-Meier plot of survival in FL samples based on survival predictor scores. 191 FL samples were divided into quartiles based on their survival predictor scores. The survival predictor scores were calculated using the equation:

[2.053*(macrophage gene expression signature value)]−[2.344*(T-cell gene expression signature value)]−[0.729*(B-cell differentiation gene expression signature value)].

Figure 9:
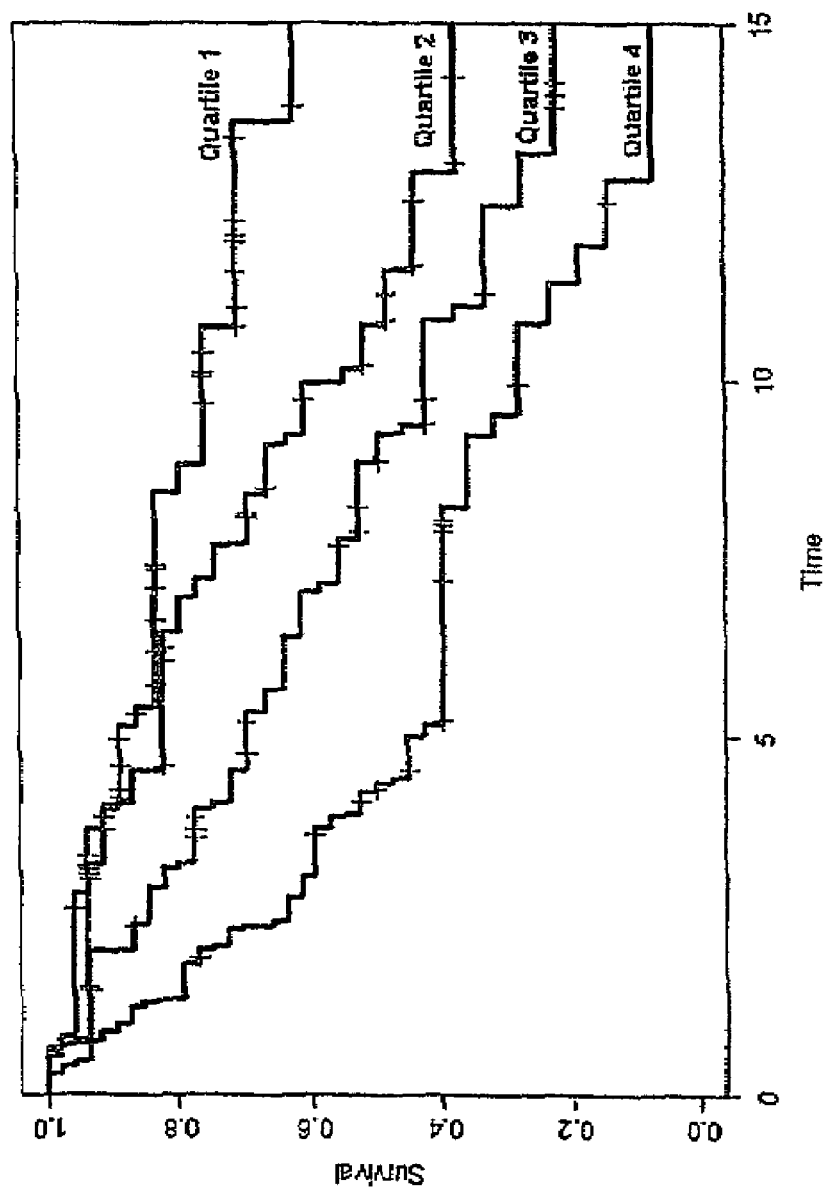

FIG. 9: Kaplan-Meier plot of survival in FL samples based on survival predictor scores. 191 FL samples were divided into quartiles based on their survival predictor scores. The survival predictor scores were calculated using the equation:

[1.51*(macrophage gene expression signature value)]−[2.11*(T-cell gene expression signature value)]−[0.505*(B-cell differentiation gene expression signature value)].

Figure 10:
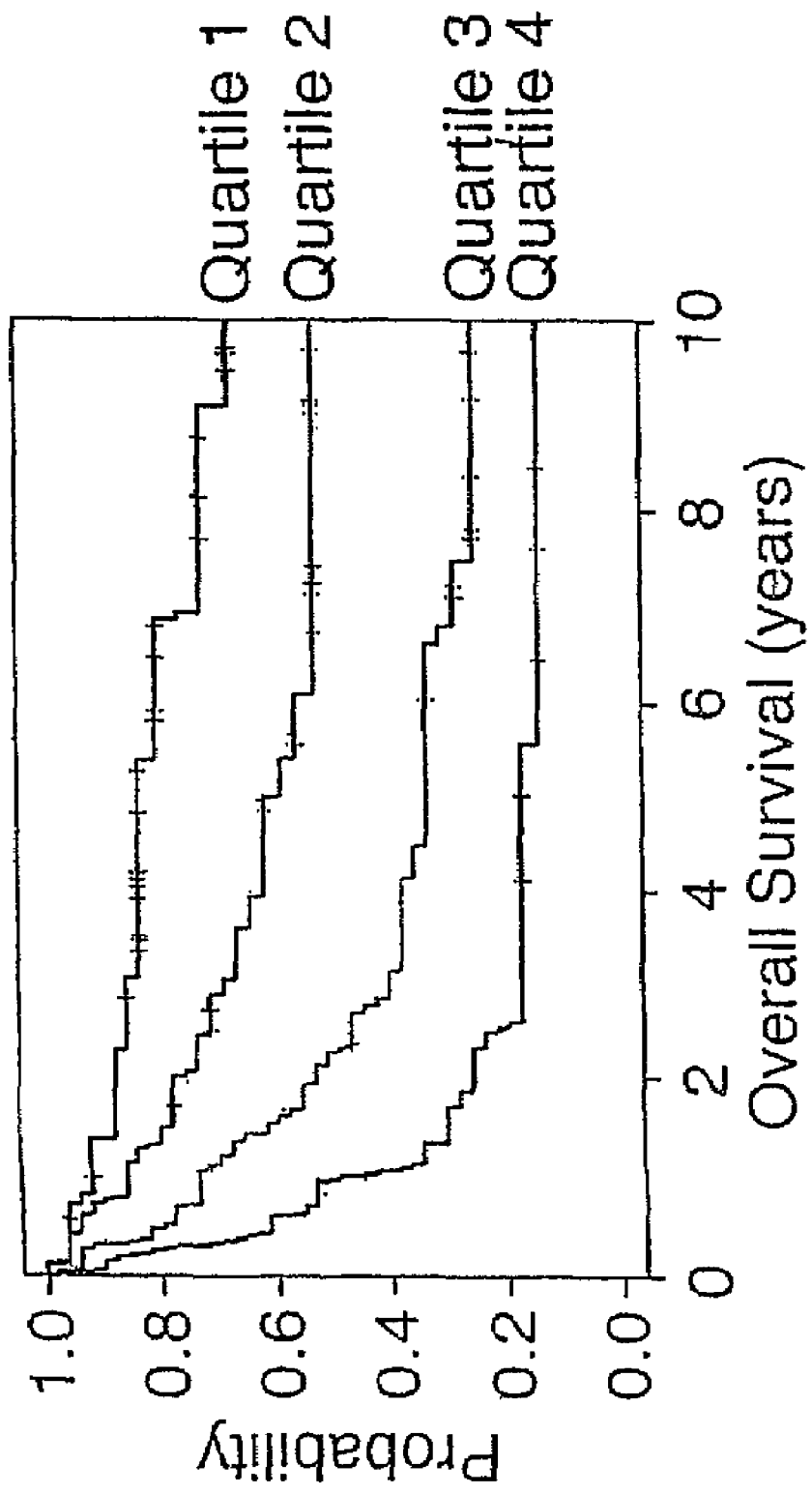

FIG. 10: Kaplan-Meier plot of survival in DLBCL samples based on survival predictor scores. 231 DLBCL samples were divided into quartiles based on their survival predictor scores. The survival predictor scores were calculated using the equation: [0.586*(ABC DLBCL high gene expression signature value)]−[0.468*(lymph node gene expression signature value)]−[(0.336*MHC Class II gene expression signature value)].

Figure 11:
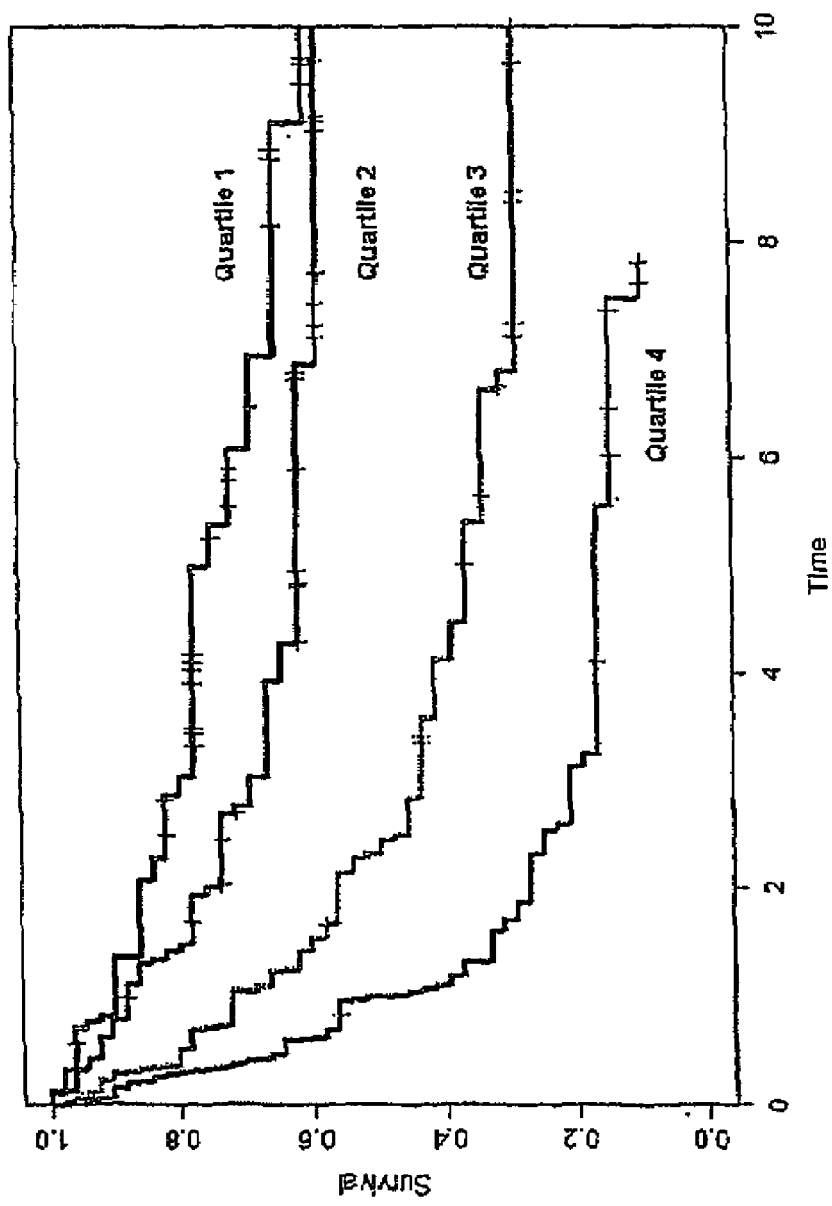

FIG. 11: Kaplan-Meier plot of survival in DLBCL samples based on survival predictor scores. 200 DLBCL samples were divided into quartiles based on their survival predictor scores. The survival predictor scores were calculated using the equation: [−0.4337*(lymph node gene expression signature value)]+[0.09*(proliferation gene expression signature value)]−[0.4144*(germinal center B-cell gene expression signature value)]−[0.2006*(MHC class II gene expression signature value)].

Figure 12:
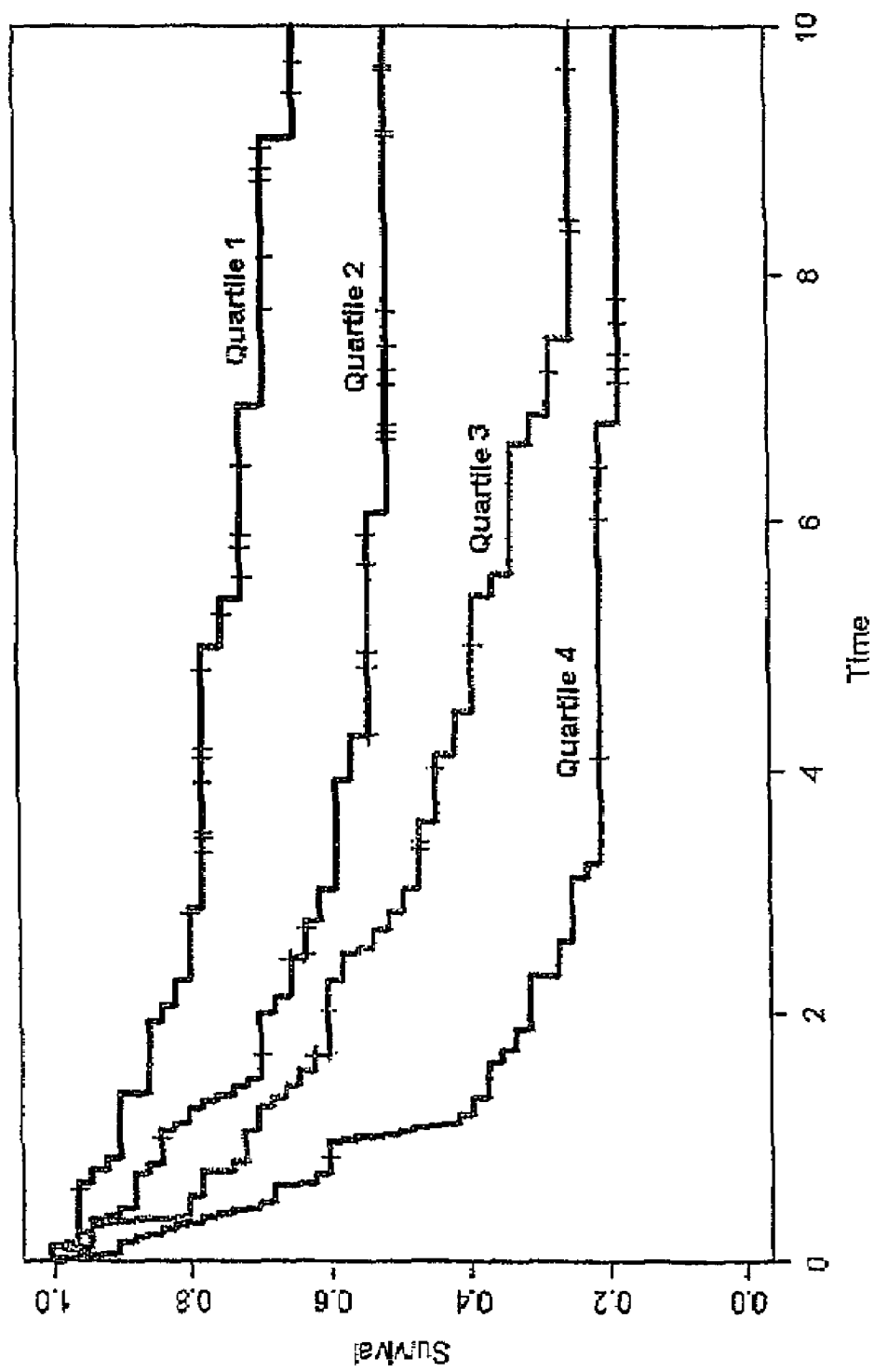

FIG. 12: Kaplan-Meier plot of survival in DLBCL samples based on survival predictor scores. 200 DLBCL samples were divided into quartiles based on their survival predictor scores. The survival predictor scores were calculated using the equation: [−0.32*(lymph node gene expression signature value)]−[0.176*(germinal center B-cell gene expression signature value)]−[0.206*(MHC class II gene expression signature value)].

Figure 13:
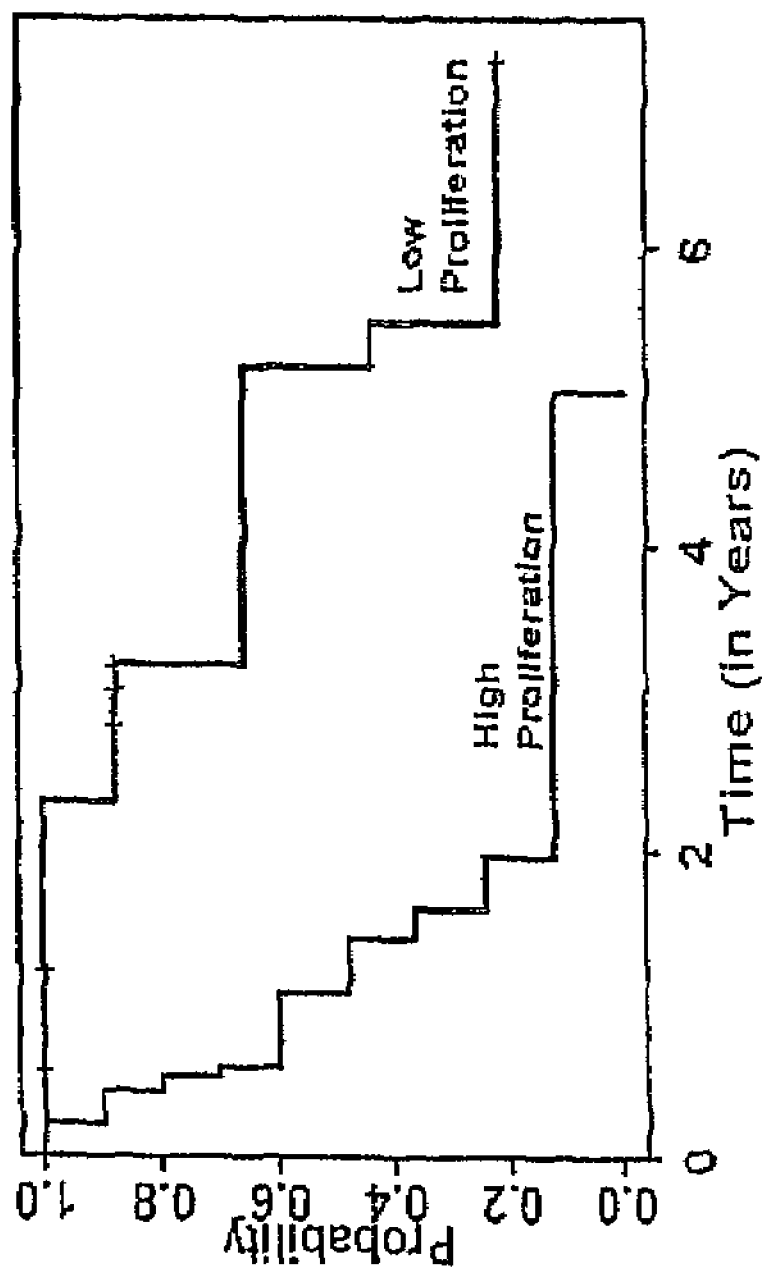

FIG. 13: Kaplan-Meier plot of survival in MCL samples based on survival predictor scores. 21 MCL samples were divided into two equivalent groups based on their survival predictor scores. The survival predictor scores were calculated using the equation: 1.66*(proliferation gene expression signature value).

Figure 14:
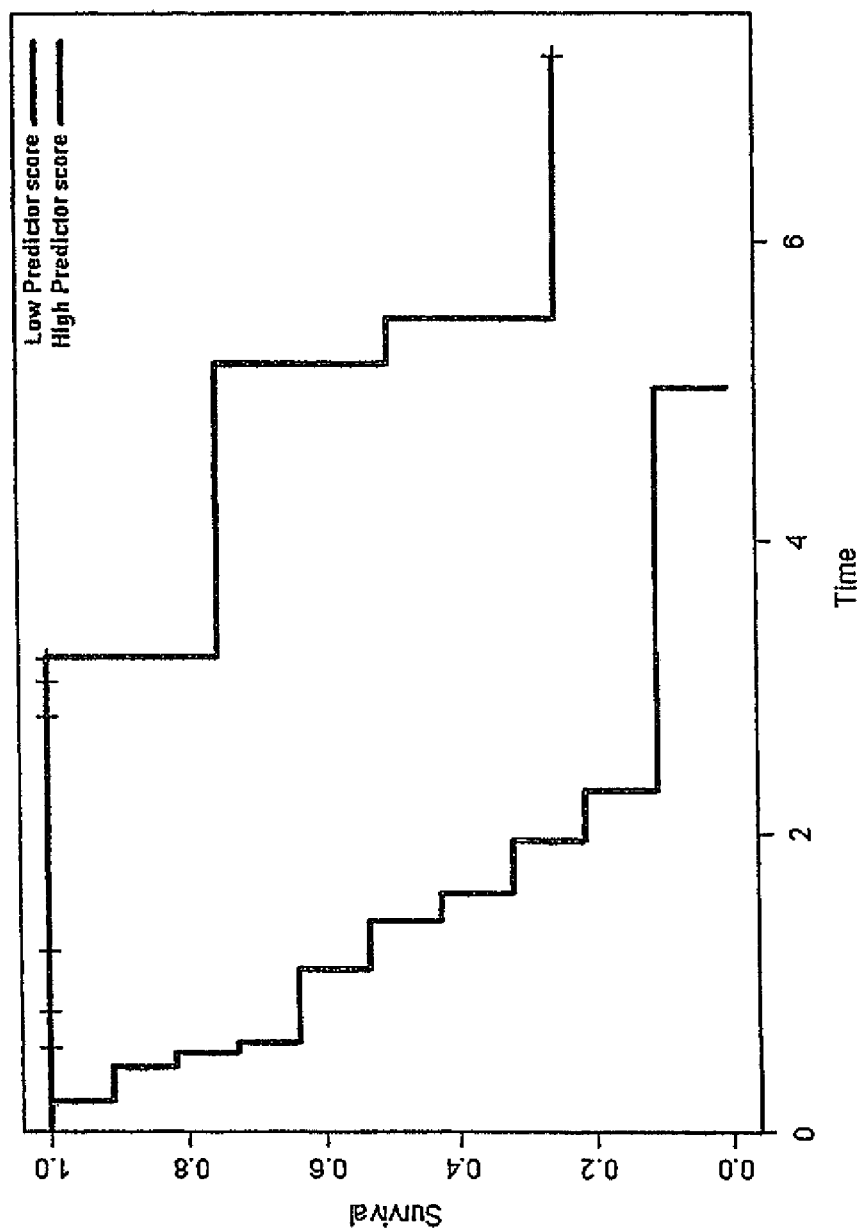

FIG. 14: Kaplan-Meier plot of survival in MCL samples based on survival predictor scores. 21 MCL samples were divided into two equivalent groups based on their survival predictor scores. The survival predictor scores were calculated using the equation: 1.66*(proliferation gene expression signature value).

Figure 15:
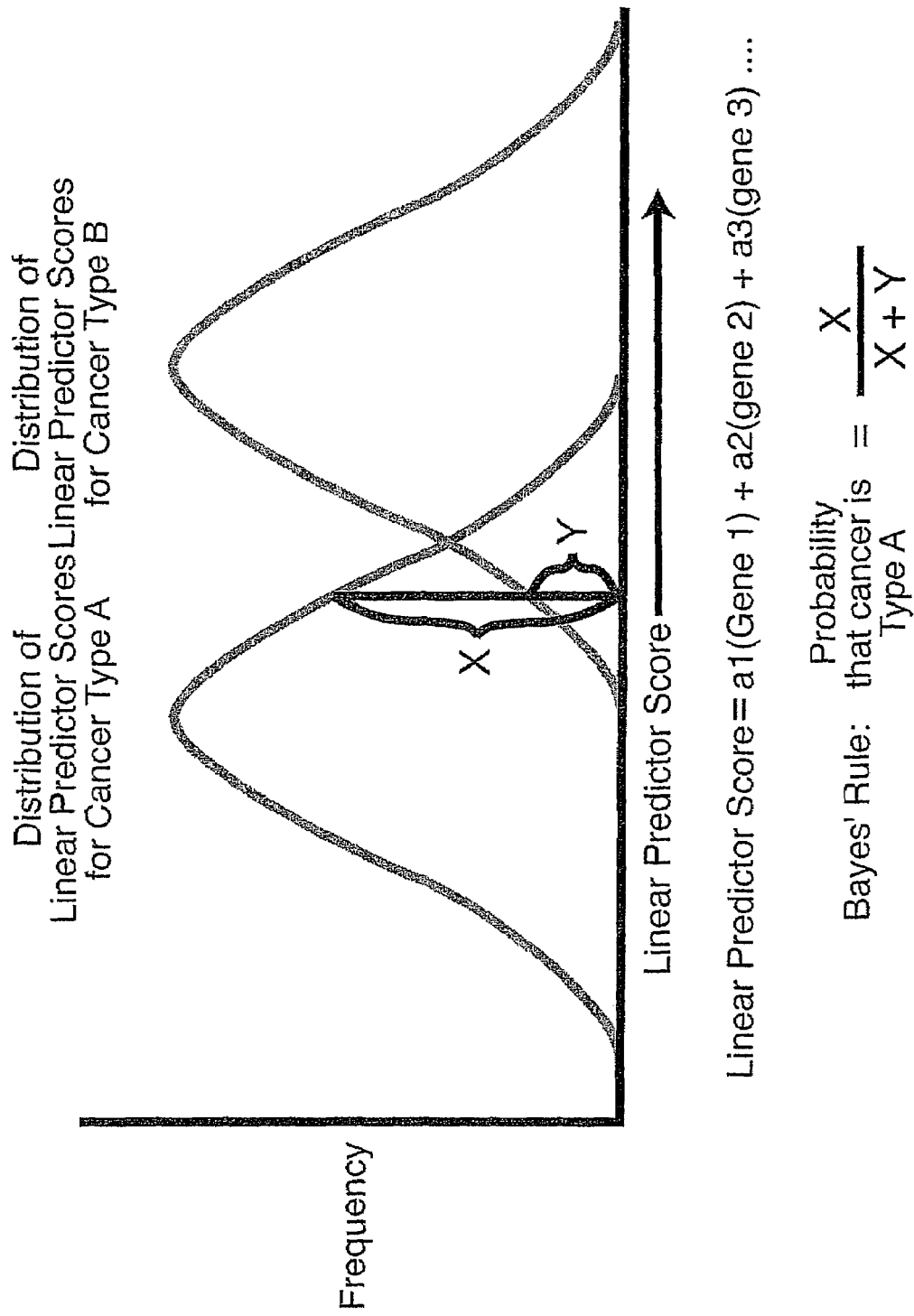

FIG. 15: Predicting lymphoma type using Bayesian analysis. Bayes' rule can be used to determine the probability that an unknown sample belongs to a first lymphoma type rather than a second lymphoma type. A linear predictor score is generated for the sample, and the probability that the sample belongs to the first lymphoma type is determined based on the distribution of linear predictor scores within the first and second lymphoma type.

FIG. 16: Performance of MCL predictor model. Results of the gene-expression based predictor model for MCL are shown for three models (MCL vs. ABC, MCL vs. GCB, MCL vs. SLL). Performance is shown for both the training set and the validation set.

Figure 17:
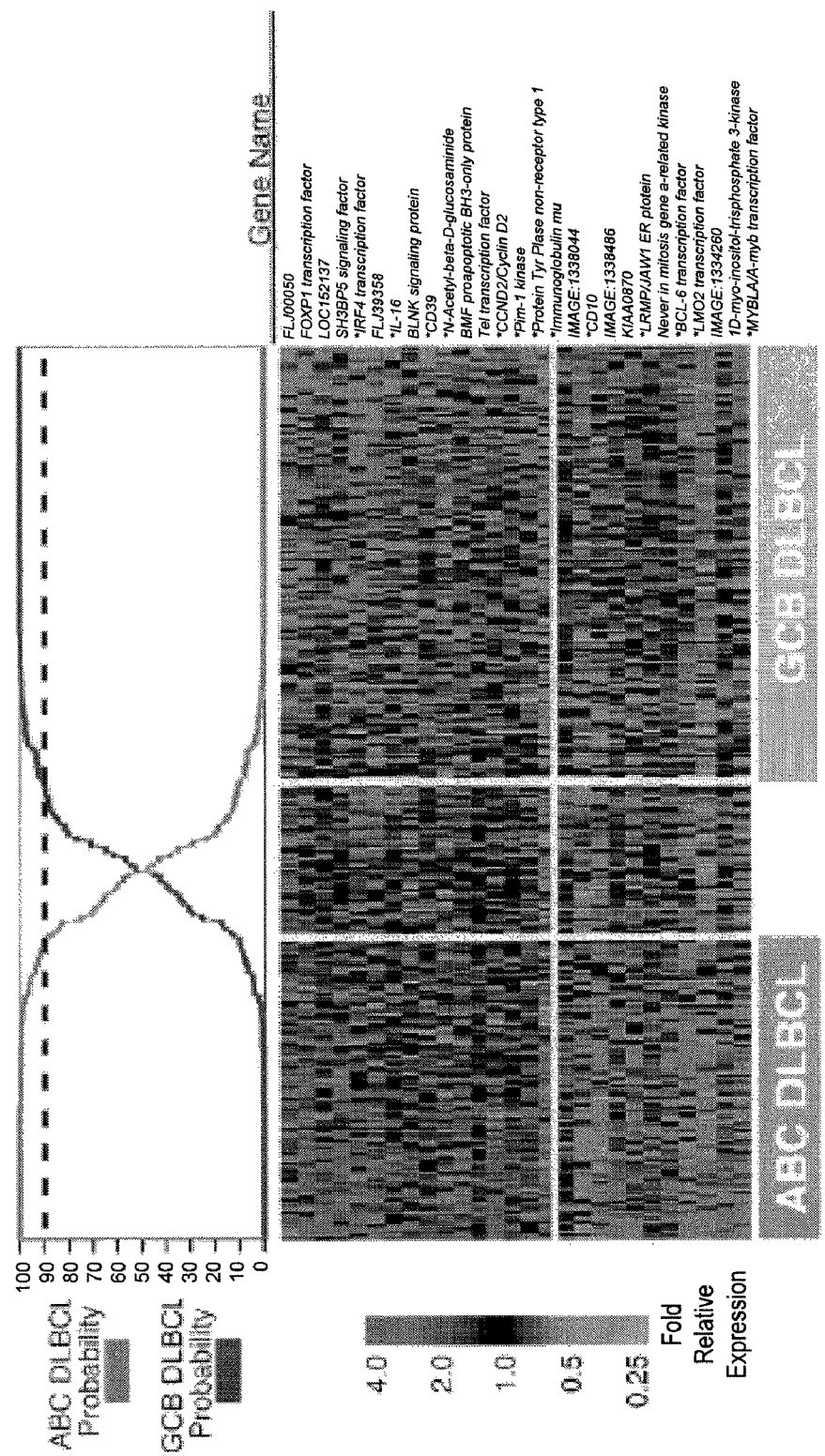

FIG. 17: Gene expression-based identification of DLBCL. Expression levels for 27 genes in a subgroup predictor are shown for 274 DLBCL samples. Expression levels are depicted according to the scale shown at the left. The 14 genes used to predict the DLBCL subgroups in the Affymetrix data set are indicated with asterisks. The probabilities that the DLBCL samples belong to the ABC or GCB subtypes are graphed at the top, and the DLBCL cases are arranged accordingly. Cases belonging to either ABC or GCB with 90% or greater probability are indicated.

Figure 18:
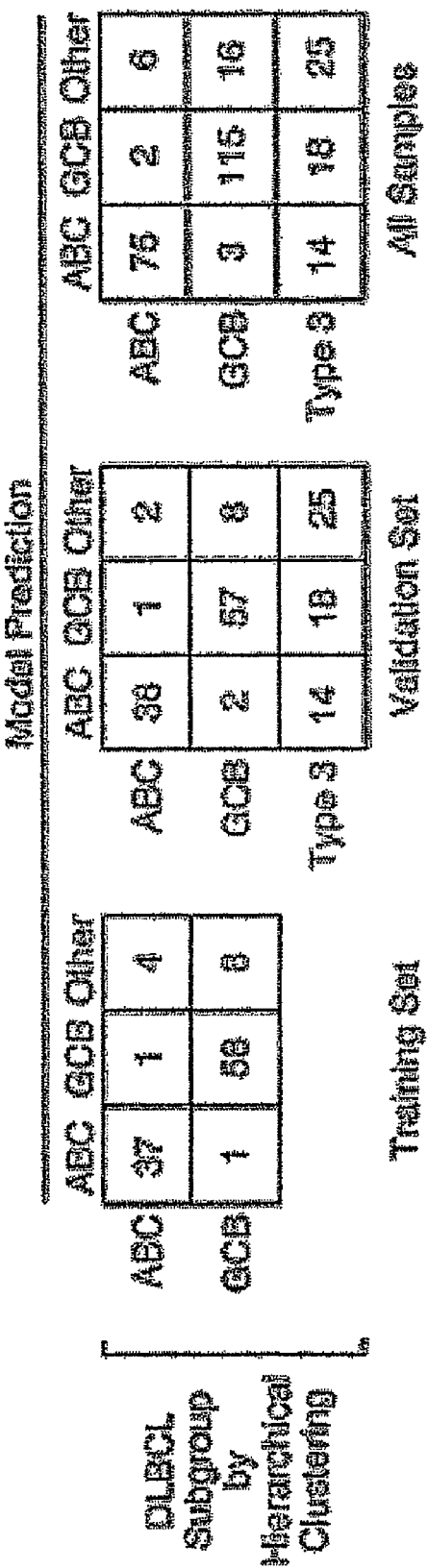

FIG. 18: Performance of DLBCL subtype predictor model. Assignments of DLBCL samples to the ABC or GCB subtypes based on hierarchical clustering vs. the predictor model disclosed herein are compared within the training, validation, and total set of samples.

Figure 19:
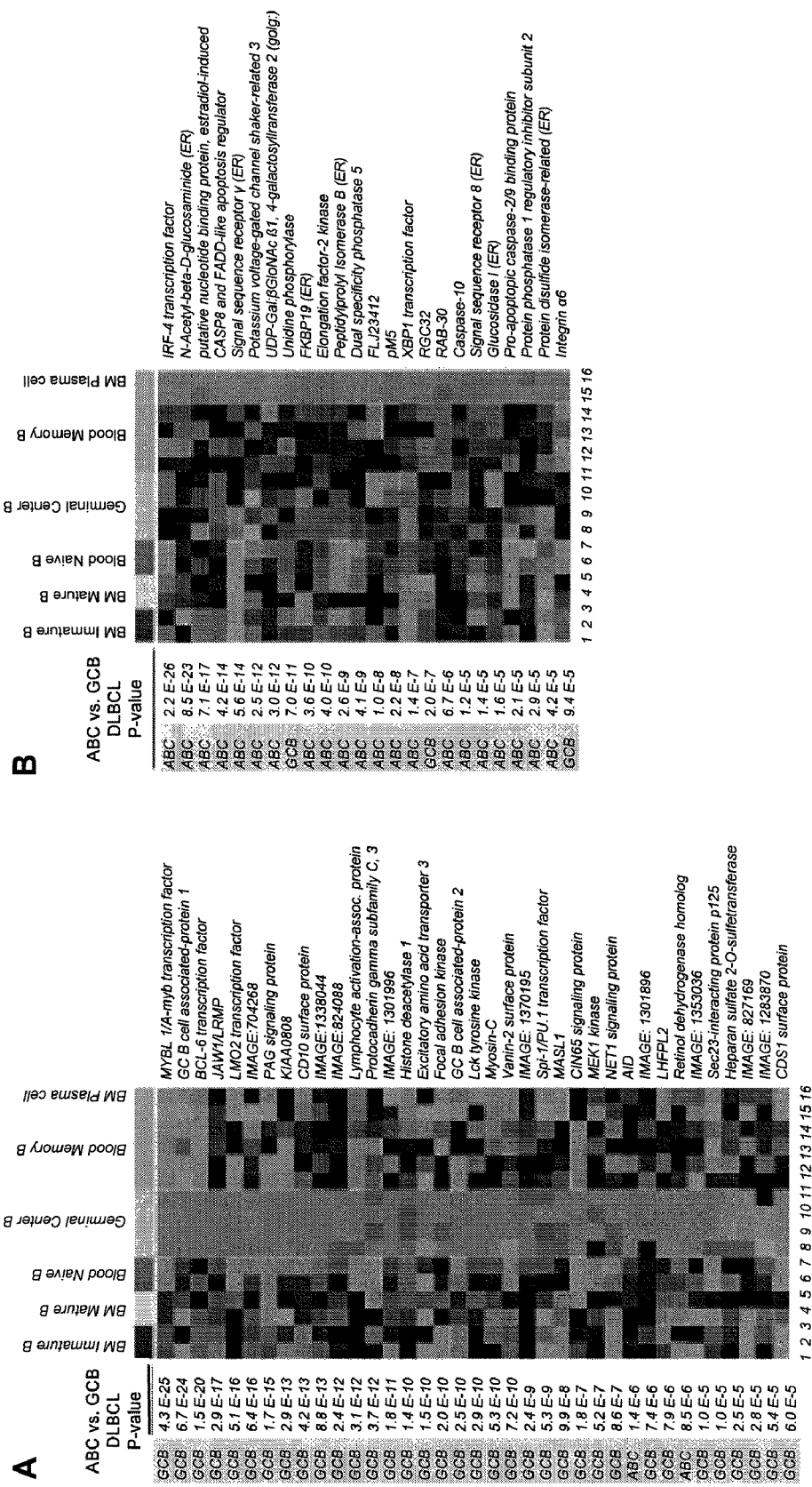

FIG. 19: Relationship of gene expression in normal B cell subpopulations to DLBCL subtypes. Relative gene expression in the indicated purified B cell populations is depicted according to the scale in FIG. 17. The P value of the difference in expression of these genes between the GCB and ABC DLBCL subtypes is shown, and the subtype with the higher expression is shown is indicated (blue, ABC; orange, GCB).

A. DLBCL subtype distinction genes that are more highly expressed in germinal center B cells than at other B cell differentiation stages. B. DLBCL subtype distinction genes that are more highly expressed in plasma cells than at other B cell differentiation stages.

Figure 20:
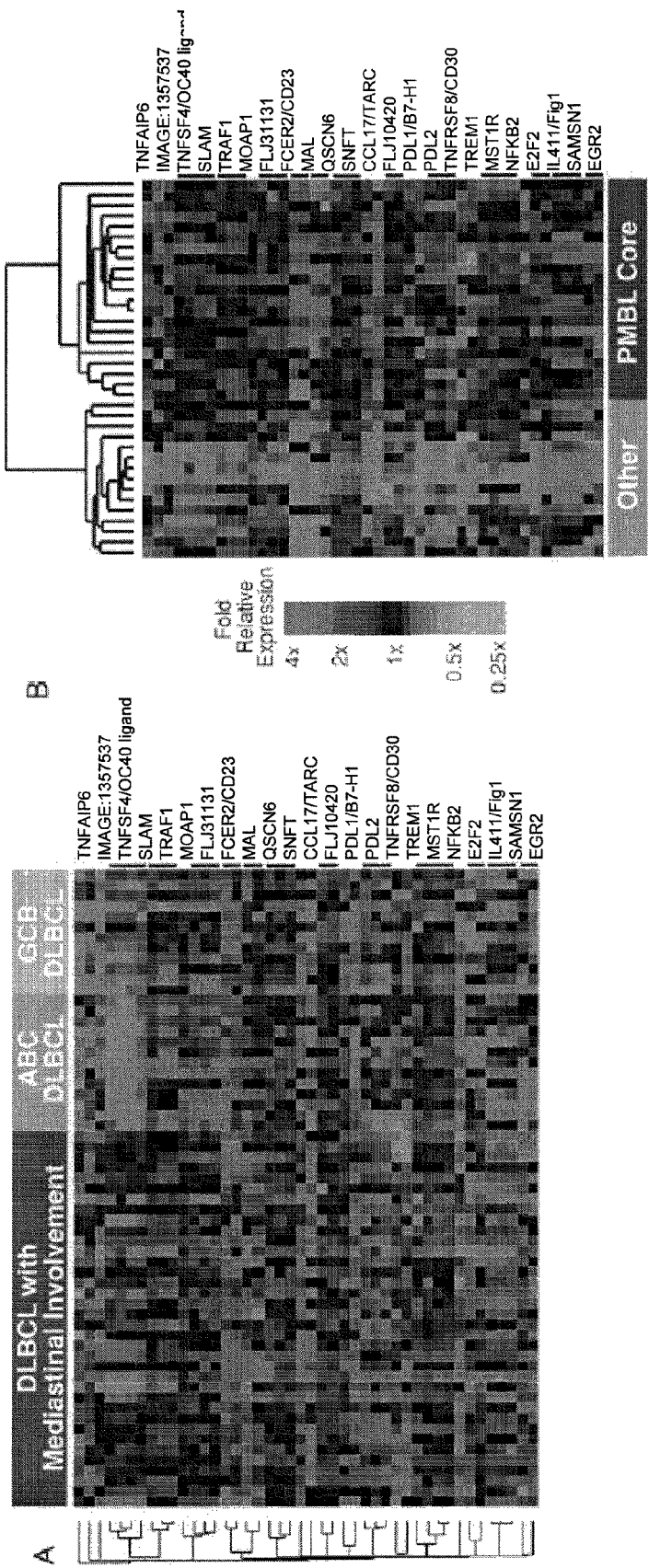

FIG. 20: Identification of a PMBL gene expression signature. A. Hierarchical clustering identified a set of 23 PMBL signature genes that were more highly expressed in most lymphomas with a clinical diagnosis of PMBL than in lymphomas assigned to the GCB or ABC subtypes. Each row presents gene expression measurements from a single Lymphochip microarray feature representing the genes indicated. Each column represents a single lymphoma biopsy sample. Relative gene expression is depicted according to the scale shown. B. Hierarchical clustering of the lymphoma biopsy samples based on expression of the PMBL signature genes identified in (A). A "core" cluster of lymphoma cases was identified that highly expressed the PMBL signature genes.

Figure 21:
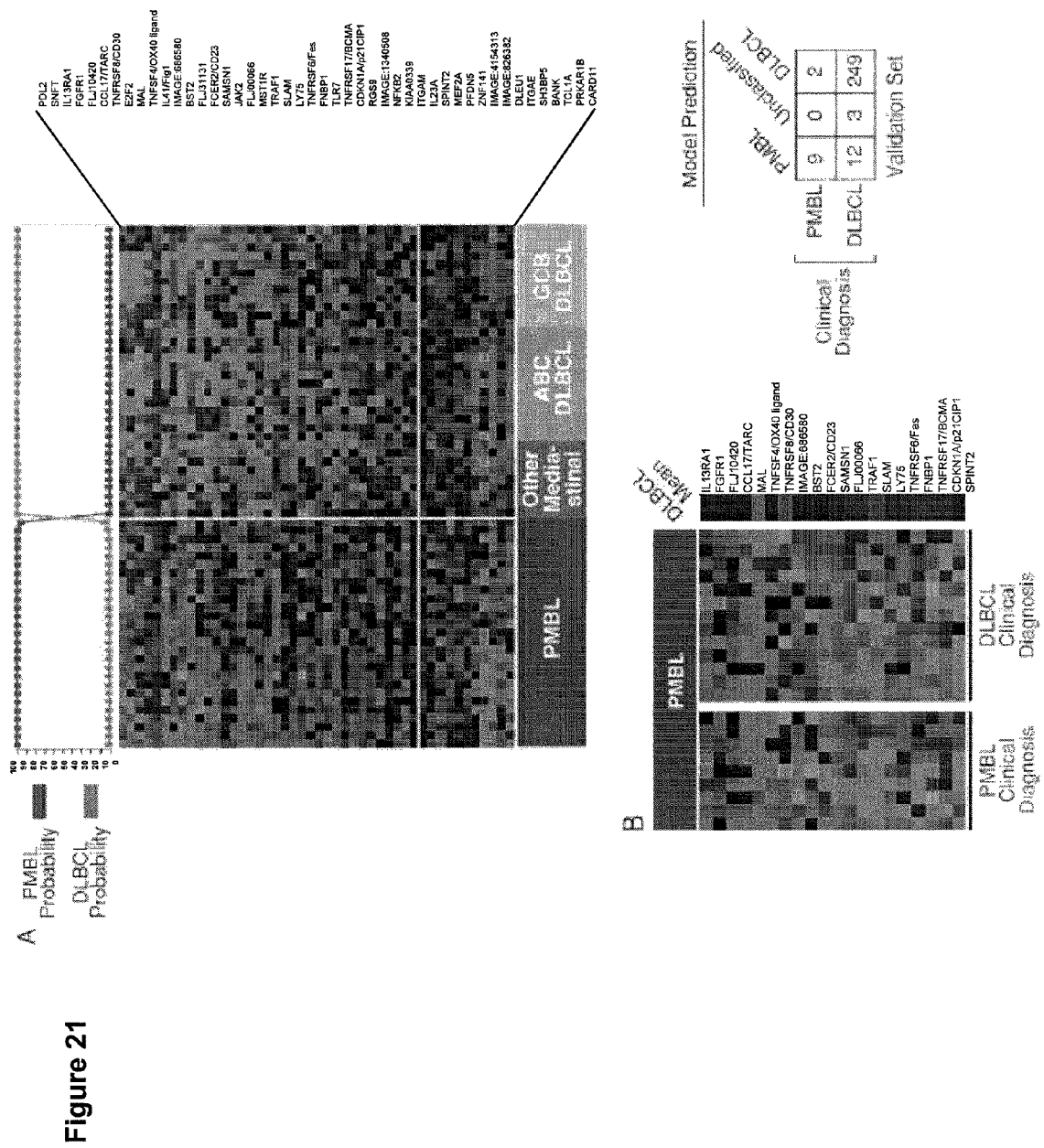

FIG. 21: Development of a gene expression-based molecular diagnosis of PMBL. A. A PMBL predictor was created based on expression of the 46 genes shown. Relative gene expression for each lymphoma biopsy sample is presented according to the scale shown in FIG. 20. The probability that each sample is PMBL or DLBCL based on gene expression is shown at the top. B. The PMBL predictor was used to classify 274 lymphoma samples as PMBL or DLBCL. Prediction results are summarized on the right, and the relative gene expression for each case that was classified by the predictor as PMBL is shown on the left. Average expression of each gene in samples classified as DLBCL is also shown. The 20 genes listed are those represented on the Lymphochip that were more highly expressed in PMBL than in DLBCL. Not shown are eight genes from the PMBL predictor that were more highly expressed in DLBCL than in PMBL.

Figure 22:
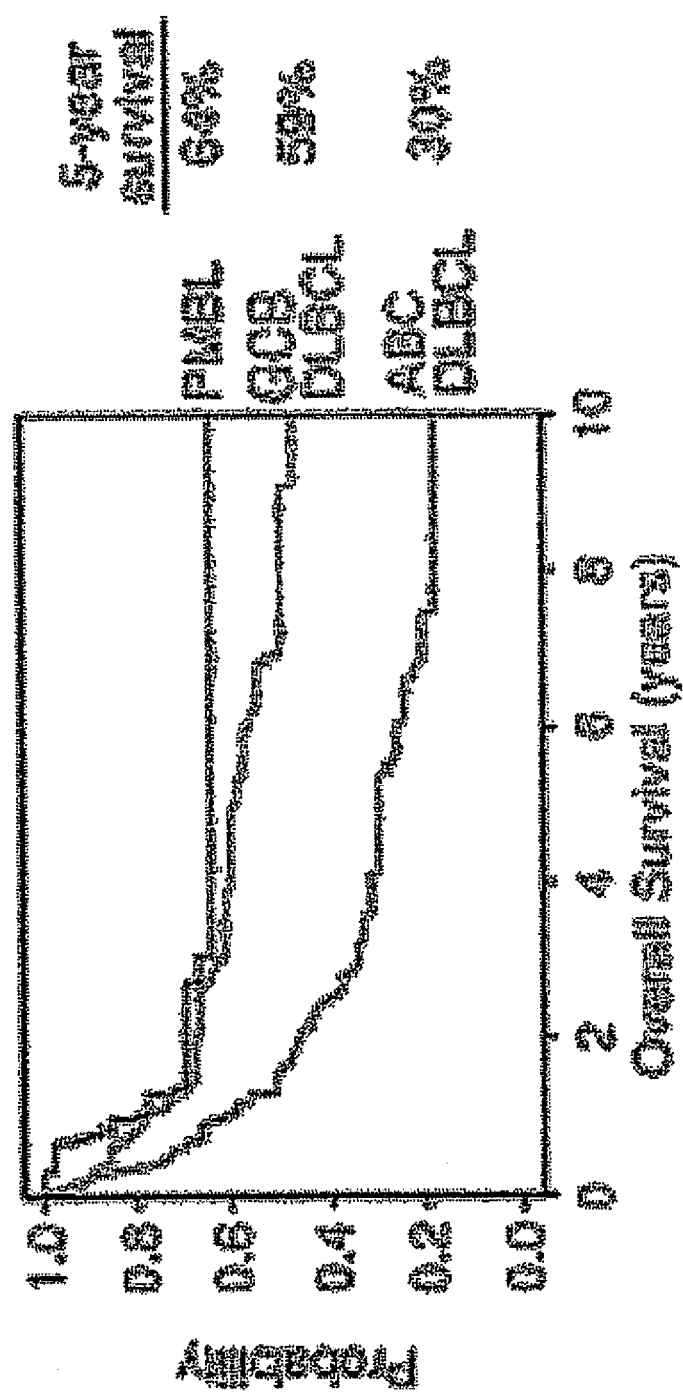

FIG. 22: Clinical characteristics of PMBL patients. Kaplan-Meier plot of overall survival in PMBL, GCB, and ABC patients after chemotherapy.

Figure 23:
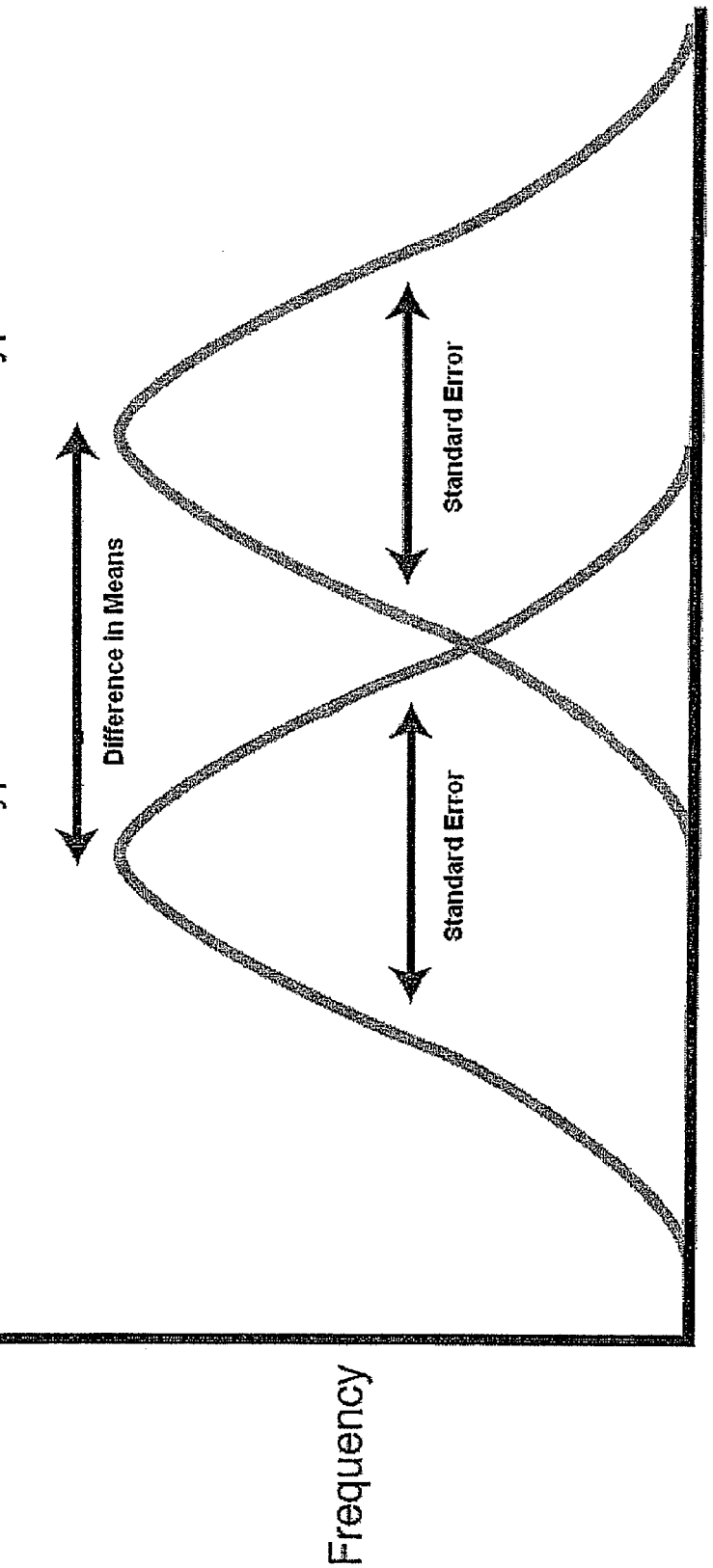

FIG. 23: Optimization of gene number in lymphoma predictor. The optimal number of genes for inclusion in the lymphoma type predictor model is that number which generates a maximum t-statistic when comparing the LPS of two samples from different lymphoma types.

Figure 24:
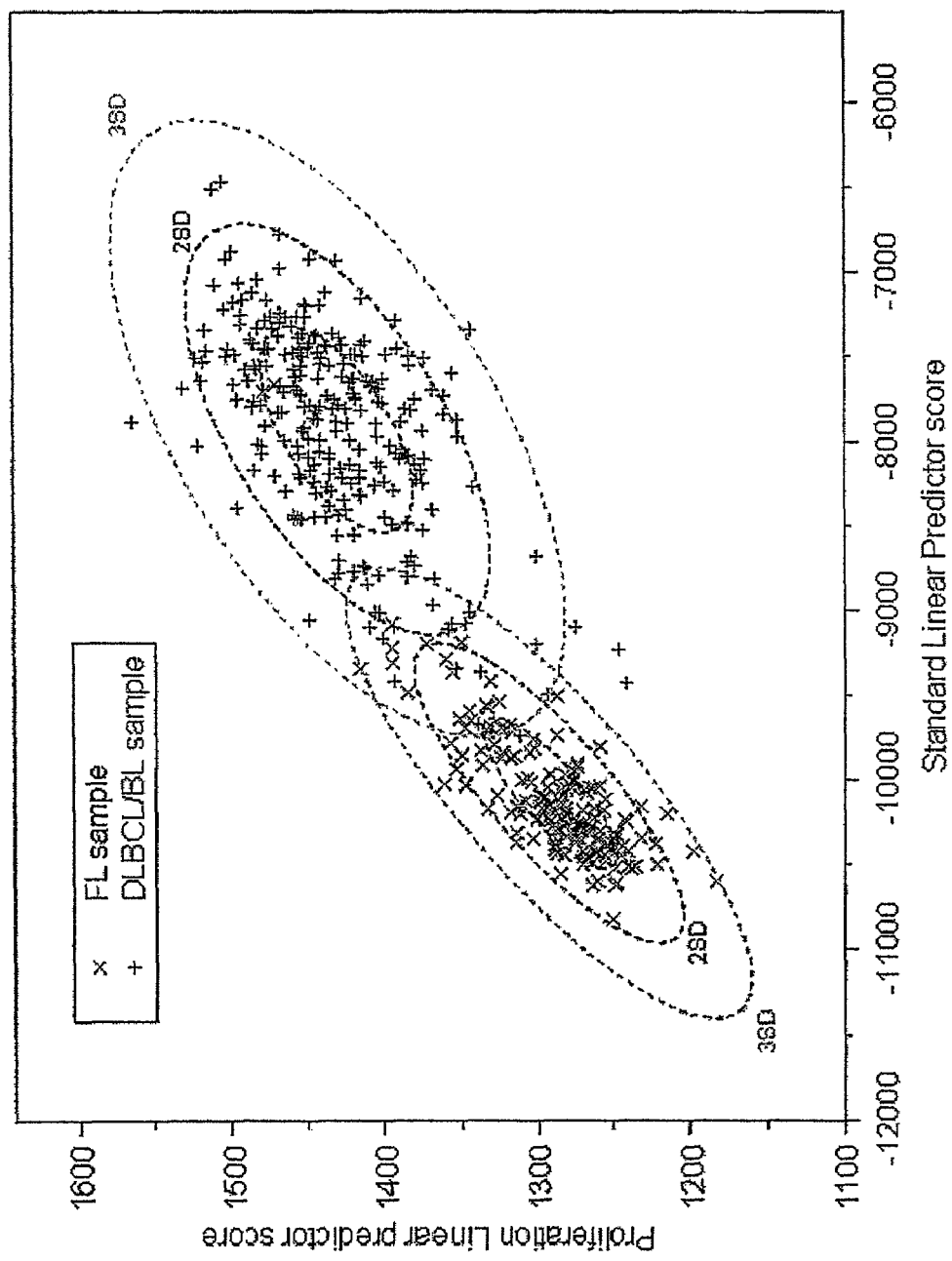

FIG. 24: LPS distribution among FL and DLBCL/BL samples. Standard and proliferation LPSs for FL (x) and DLBCL/BL (+) samples. Dotted lines indicate standard deviations from the fitted multivariate normal distributions.

Figure 25:
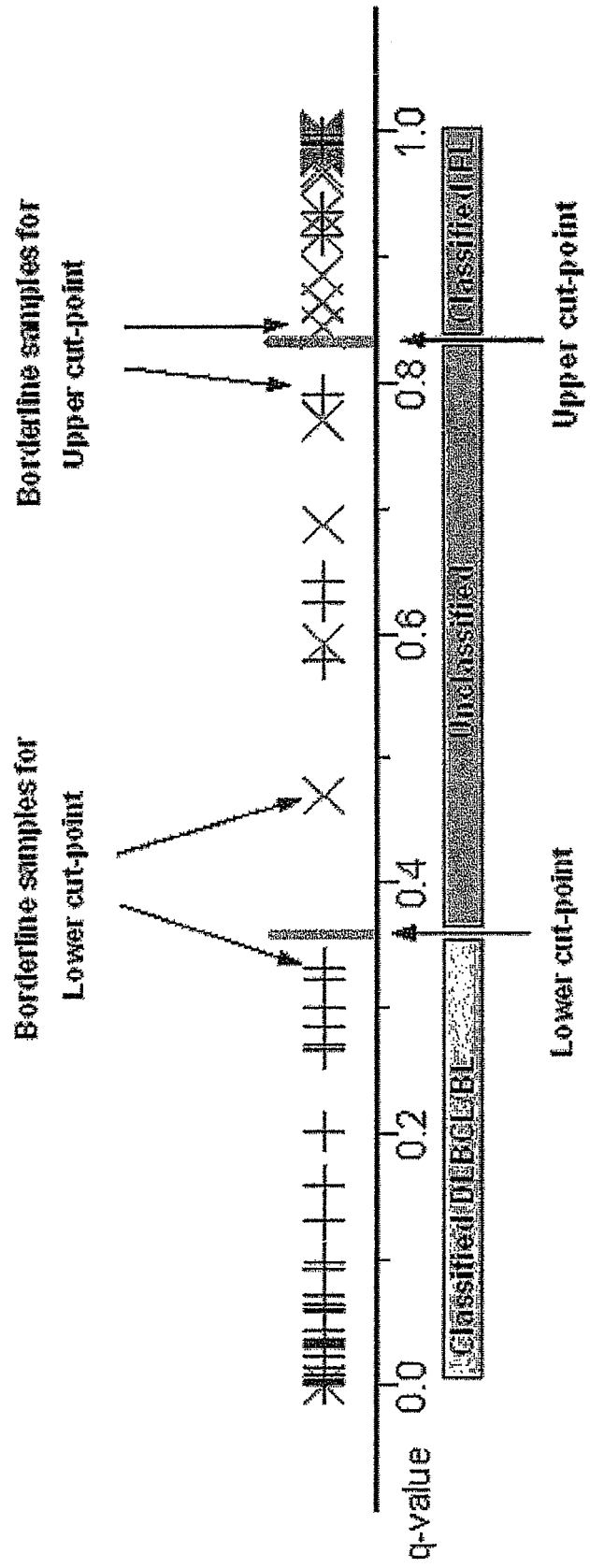

FIG. 25: Determination of cut-off points for lymphoma classification. The cut-off points between samples classified as DLBCL/BL, FL, or unclassified were optimized to minimize the number of samples classified as the wrong lymphoma type. The optimal lower cut-off point was at q=0.49, while the optimal upper cut-off point was at q=0.84.

Figure 26:
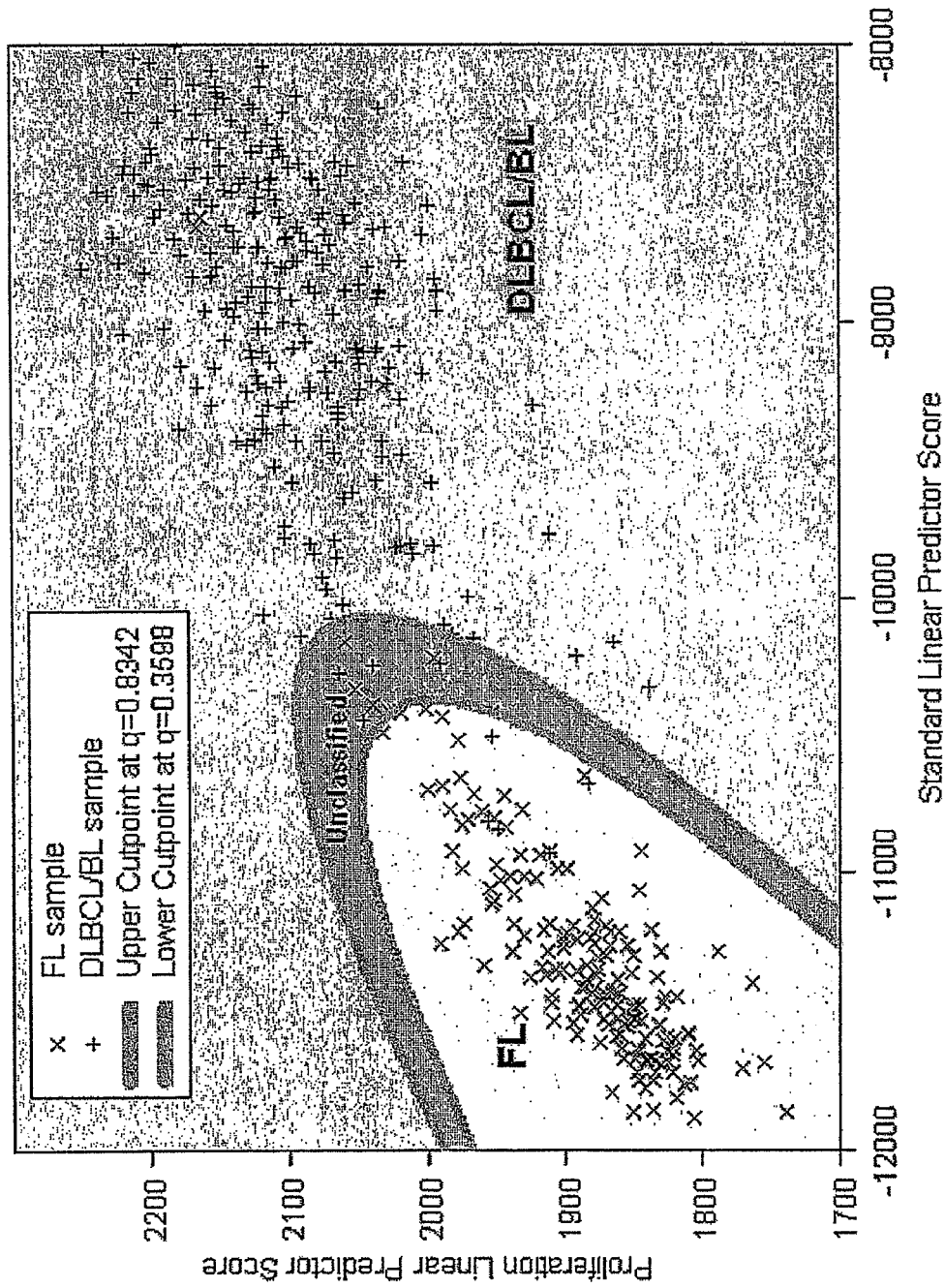

FIG. 26: Division of LPSs among FL and DLBCL/FL samples. Illustration of how the cut-off points described in FIG. 25 divided the space between the LPSs of FL (x) and DLBCL/BL (+) samples.

Figure 27:
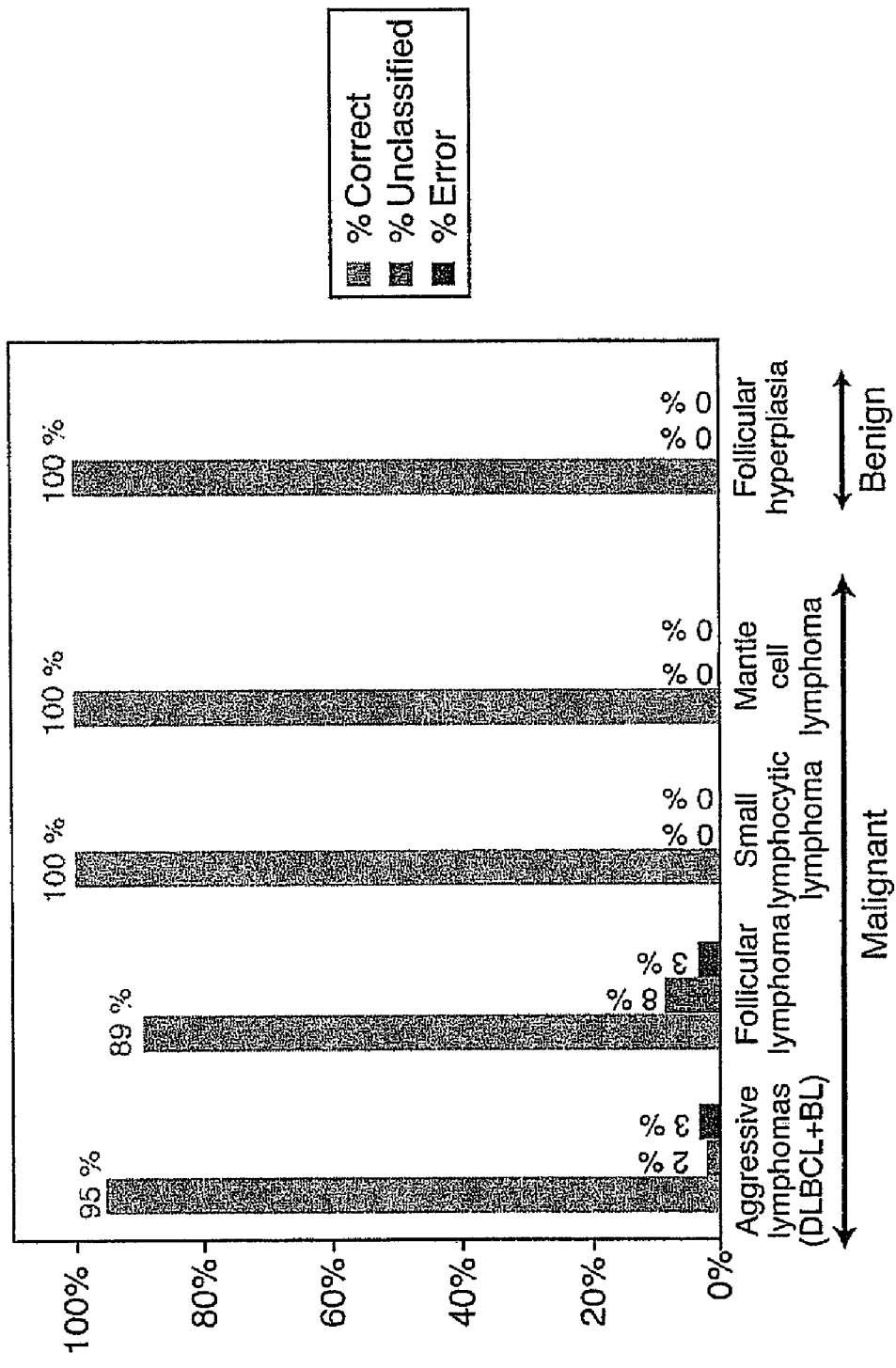

FIG. 27: Lymphoma classification results. Results of lymphoma classification based on gene expression. 100% of SLL, MCL, and FH samples were classified correctly, and only 3% of DLBCL/BL and FL samples were classified incorrectly.

Figure 28:
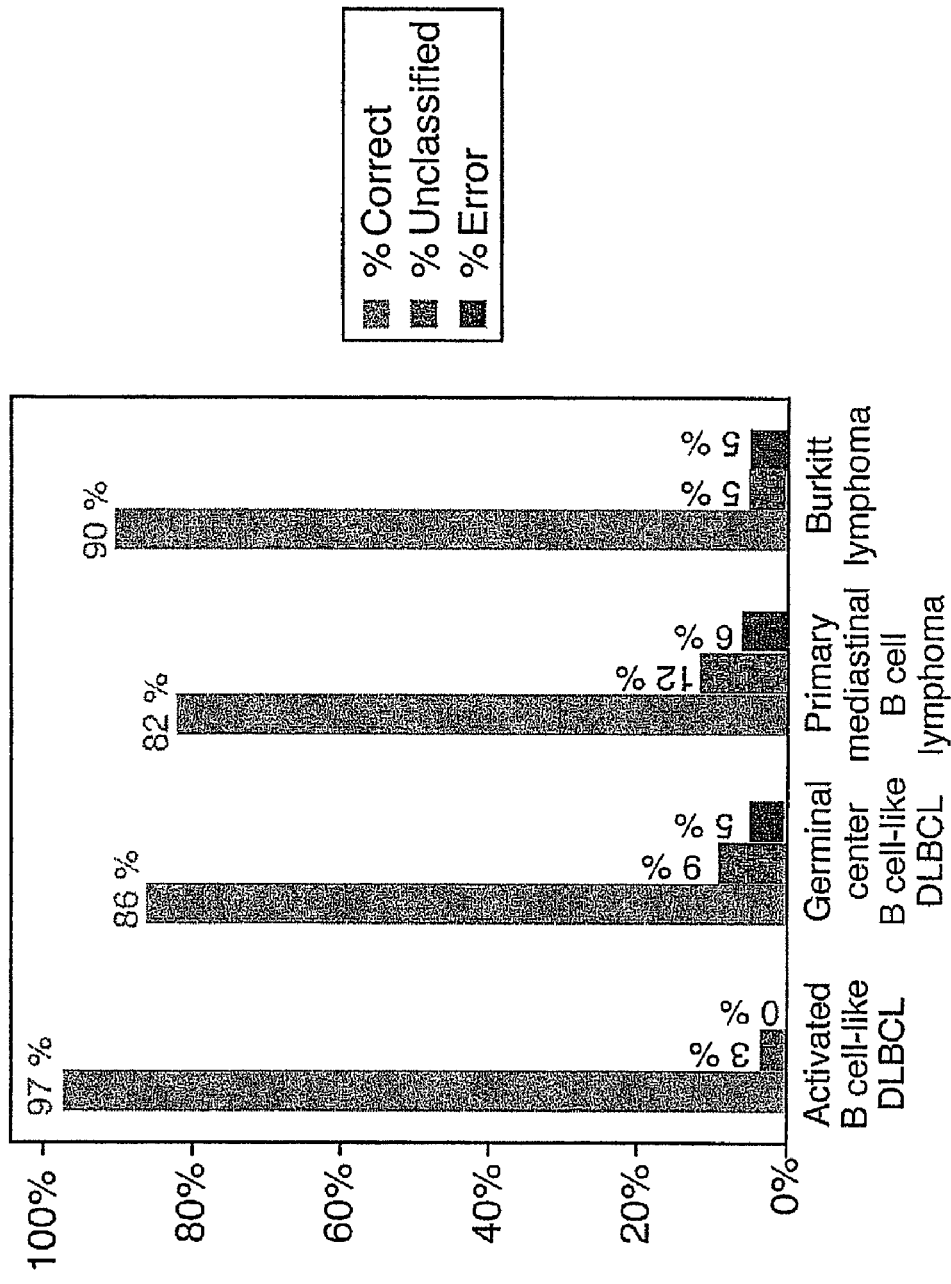

FIG. 28: DLBCL classification results. Results of DLBCL subtype classification based on gene expression. None of the ABC samples were classified as the wrong subtype, while only one of the BL samples was classified incorrectly. Of the GCB and PMBL samples, only 5% and 6%, respectively, were classified incorrectly.

DETAILED DESCRIPTION

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it us understood that such equivalent embodiments are to be included herein.

Gene expression profiling of a cancer cell or biopsy reflects the molecular phenotype of a cancer at the time of diagnosis. As a consequence, the detailed picture provided by the genomic expression pattern provides the basis for a new systematic classification of cancers and more accurate predictors of survival and response to treatment. The present invention discloses methods for identifying, diagnosing, and/or classifying a lymphoma, lymphoid malignancy, or lymphoproliferative disorder based on its gene expression patterns. The present invention also discloses methods for predicting survival in a subject diagnosed with a particular lymphoma type or subtype using gene expression data. The information obtained using these methods will be useful in evaluating the optimal therapeutic approach to be employed with regards to a particular subject.

The term "lymphoproliferative disorder" as used herein refers to any tumor of lymphocytes, and may refer to both malignant and benign tumors. The terms "lymphoma" and "lymphoid malignancy" as used herein refer specifically to malignant tumors derived from lymphocytes and lymphoblasts. Examples of lymphomas include, but are not limited to, follicular lymphoma (FL), Burkitt lymphoma (BL), mantle cell lymphoma (MCL), follicular hyperplasia (FH), small cell lymphocytic lymphoma (SLL), mucosa-associated lymphoid tissue lymphoma (MALT), splenic lymphoma, multiple myeloma, lymphoplasmacytic lymphoma, posttransplant lymphoproliferative disorder (PTLD), lymphoblastic lymphoma, nodal marginal zone lymphoma (NMZ), germinal center B cell-like diffuse large B cell lymphoma (GCB), activated B cell-like diffuse large B cell lymphoma (ABC) and primary mediastinal B cell lymphoma (PMBL).

The phrase "lymphoma type" (or simply "type") as used herein refers to a diagnostic classification of a lymphoma. The phrase may refer to a broad lymphoma class (e.g., DLBCL, FL, MCL, etc.) or to a subtype or subgroup falling within a broad lymphoma class (e.g., GCB DLBCL, ABC DLBCL).

The phrase "gene expression data" as used herein refers to information regarding the relative or absolute level of expression of a gene or set of genes in a cell or group of cells. The level of expression of a gene may be determined based on the level of RNA, such as mRNA, encoded by the gene. Alternatively, the level of expression may be determined based on the level of a polypeptide or fragment thereof encoded by the gene. "Gene expression data" may be acquired for an individual cell, or for a group of cells such as a tumor or biopsy sample.

The term "microarray," "array," or "chip" refers to a plurality of nucleic acid probes coupled to the surface of a substrate in different known locations. The substrate is preferably solid. Microarrays have been generally described in the art in, for example, U.S. Pat. No. 5,143,854 (Pirrung), U.S. Pat. No. 5,424,186 (Fodor), U.S. Pat. No. 5,445,934 (Fodor), U.S. Pat. No. 5,677,195 (Winkler), U.S. Pat. No. 5,744,305 (Fodor), U.S. Pat. No. 5,800,992 (Fodor), U.S. Pat. No. 6,040,193 (Winkler), and Fodor et al. 1991. Light-directed, spatially addressable parallel chemical synthesis. Science, 251:767-777. Each of these references is incorporated by reference herein in their entirety.

The term "gene expression signature" or "signature" as used herein refers to a group of coordinately expressed genes. The genes making up this signature may be expressed in a specific cell lineage, stage of differentiation, or during a particular biological response. The genes can reflect biological aspects of the tumors in which they are expressed, such as the cell of origin of the cancer, the nature of the non-malignant cells in the biopsy, and the oncogenic mechanisms responsible for the cancer (Shaffer 2001). Examples of gene expression signatures include lymph node (Shaffer 2001), proliferation (Rosenwald 2002), MHC class II, ABC DLBCL high, B-cell differentiation, T-cell, macrophage, immune response-1, immune response-2, and germinal center B cell.

The phrase "survival predictor score" as used herein refers to a score generated by a multivariate model used to predict survival based on gene expression. A subject with a higher survival predictor score is predicted to have poorer survival than a subject with a lower survival predictor score.

The term "survival" as used herein may refer to the probability or likelihood of a subject surviving for a particular period of time. Alternatively, it may refer to the likely term of survival for a subject, such as expected mean or median survival time for a subject with a particular gene expression pattern.

The phrase "linear predictor score" or "LPS" as used herein refers to a score that denotes the probability that a sample belongs to a particular lymphoma type. An LPS may be calculated using an equation such as:

$$LPS(S) = \sum_{j \in G} t_j S_j,$$

where $S_j$ is the expression of gene j from gene set G in a sample S, and $t_j$ is a scale factor representing the difference in expression of gene j between a first lymphoma type and a second lymphoma type. Alternatively, a linear predictor score may be generated by other methods including but not limited to linear discriminant analysis (Dudoit 2002), support vector machines (Furey 2000), or shrunken centroids (Tibshirani 2002)

The phrase "scale factor" as used herein refers to a factor that defines the relative difference in expression of a particular gene between two samples. An example of a scale factor is a t-score generated by a Student's t-test.

The phrase "lymphoma subject," wherein "lymphoma" is a specific lymphoma type (e.g., "follicular lymphoma subject"), may refer to a subject that has been diagnosed with a particular lymphoma by any method known in the art or discussed herein. This phrase may also refer to a subject with a known or suspected predisposition or risk of developing a particular lymphoma type.

The pattern of expression of a particular gene is closely connected to the biological role and effect of its gene product. For this reason, the systematic study of variations in gene expression provides an alternative approach for linking specific genes with specific diseases and for recognizing heritable gene variations that are important for immune function. For example, allelic differences in the regulatory region of a gene may influence the expression levels of that gene. An appreciation for such quantitative traits in the immune system may help elucidate the genetics of autoimmune diseases and lymphoproliferative disorders.

Genes that encode components of the same multi-subunit protein complex are often coordinately regulated. Coordinate regulation is also observed among genes whose products function in a common differentiation program or in the same physiological response pathway. Recent application of gene expression profiling to the immune system has shown that lymphocyte differentiation and activation are accompanied by parallel changes in expression among hundreds of genes. Gene expression databases may be used to interpret the pathological changes in gene expression that accompany autoimmunity, immune deficiencies, cancers of immune cells and of normal immune responses.

Scanning and interpreting large bodies of relative gene expression data is a formidable task. This task is greatly facilitated by algorithms designed to organize the data in a way that highlights systematic features, and by visualization tools that represent the differential expression of each gene as varying intensities and hues of color (Eisen 1998). The development of microarrays, which are capable of generating massive amounts of expression data in a single experiment, has greatly increased the need for faster and more efficient methods of analyzing large-scale expression data sets. In order to effectively utilize microarray gene expression data for the identification and diagnosis of lymphoma and for the prediction of survival in lymphoma patients, new algorithms must be developed to identify important information and convert it to a more manageable format. In addition, the microarrays used to generate this data should be streamlined to incorporate probe sets that are useful for diagnosis and survival prediction. Embodiments of the present invention disclose methods and compositions that address both of these considerations.

The mathematical analysis of gene expression data is a rapidly evolving science based on a rich mathematics of pattern recognition developed in other contexts (Kohonen 1997). Mathematical analysis of gene expression generally has three goals. First, it may be used to identify groups of genes that are coordinately regulated within a biological system. Second, it may be used to recognize and interpret similarities between biological samples on the basis of similarities in gene expression patterns. Third, it may be used to recognize and identify those features of a gene expression pattern that are related to distinct biological processes or phenotypes.

Mathematical analysis of gene expression data often begins by establishing the expression pattern for each gene on an array across n experimental samples. The expression pattern of each gene can be represented by a point in n-dimensional space, with each coordinate specified by an expression measurement in one of the n samples (Eisen 1998). A clustering algorithm that uses distance metrics can then be applied to locate clusters of genes in this n-dimensional space. These clusters indicate genes with similar patterns of variation in expression over a series of experiments. Clustering methods that have been applied to microarray data in the past include hierarchical clustering (Eisen 1998), self-organizing maps (SOMs) (Tamayo 1999), k-means (Tavazoie 1999), and deterministic annealing (Alon 1999). A variety of different algorithms, each emphasizing distinct orderly features of the data, may be required to glean the maximal biological insight from a set of samples (Alizadeh 1998). One such algorithm, hierarchical clustering, begins by determining the gene expression correlation coefficients for each pair of the n genes studied. Genes with similar gene expression correlation coefficients are grouped next to one another in a hierarchical fashion. Generally, genes with similar expression patterns under a particular set of conditions encode protein products that play related roles in the physiological adaptation to those conditions. Novel genes of unknown function that are clustered with a large group of functionally related genes are likely to participate in the same biological process. Likewise, the other clustering methods mentioned herein may also group genes together that encode proteins with related biological function.

Gene expression maps may be constructed by organizing the gene expression data from multiple samples using any of the various clustering algorithms outlined herein. The ordered tables of data may then be displayed graphically in a way that allows researchers and clinicians to assimilate both the choreography of gene expression on a broad scale and the fine distinctions in expression of individual genes.

In such a gene expression map, genes that are clustered together reflect a particular biological function, and are termed gene expression signatures (Shaffer 2001). One general type of gene expression signature includes genes that are characteristically expressed in a particular cell type or at a particular stage of cellular differentiation or activation. Another general type of gene expression signature includes genes that are regulated in their expression by a particular biological process such as proliferation, or by the activity of a particular transcription factor or signaling pathway.

The pattern of gene expression in a biological sample provides a distinctive and accessible molecular picture of its functional state and identity (DeRisi 1997; Cho 1998; Chu 1998; Holstege 1998; Spellman 1998). Each cell transduces variation in its environment, internal state, and developmental state into readily measured and recognizable variation in gene expression patterns. Two different samples that have related gene expression patterns are therefore likely to be biologically and functionally similar to one another. Some biological processes are reflected by the expression of genes in a gene expression signature, as described above. The expression of gene expression signatures in a particular sample can provide important biological insights regarding its cellular composition and the function of various intracellular pathways within the cells.

The present invention discloses a variety of gene expression signatures related to the clinical outcome of lymphoma patients. While several of these signatures share a name with a previously disclosed signature, each of the gene expression signatures disclosed herein comprises a novel combination of genes. For example, the lymph node signature disclosed herein includes genes encoding extracellular matrix components and genes that are characteristically expressed in macrophage, NK, and T cells (e.g., α-Actinin, collagen type III α 1, connective tissue growth factor, fibronectin, KIAA0233, urokinase plasminogen activator). The proliferation signature includes genes that are characteristically expressed by cells that are rapidly multiplying or proliferating (e.g., c-myc, E21G3, NPM3, BMP6). The MHC class II signature includes genes that interact with lymphocytes in order to allow the recognition of foreign antigens (e.g., HLA-DPα, HLA-DQα, HLA-DRα, HLA-DRβ). The immune response-1 signature includes genes encoding T cell markers (e.g., CD7, CD8B1, ITK, LEF1, STAT4), as well as genes that are highly expressed in macrophages (e.g., ACTN1, TNFSF13B). The immune response-2 signature includes genes known to be preferentially expressed in macrophages and/or dendritic cells (e.g., TLR5, FCGR1A, SEPT10, LGMN, C3AR1). The germinal center B cell signature includes genes known to be overexpressed at this stage of B cell differentiation (e.g., MME, MEF2C, BCL6, LMO2, PRSPAP2, MBD4, EBF, MYBL1.

Databases of gene expression signatures have proven quite useful in elucidating the complex gene expression patterns of various cancers. For example, expression of genes from the germinal center B-cell signature in a lymphoma biopsy suggests that the lymphoma is derived from this stage of B cell differentiation. In the same lymphoma-biopsy, the expression of genes from the T cell signature can be used to estimate the degree of infiltration of the tumor by host T cells, while the expression of genes from the proliferation signature can be used to quantitate the tumor cell proliferation rate. In this manner, gene expression signatures provide an "executive summary" of the biological properties of a tumor specimen. Gene expression signatures can also be helpful in interpreting the results of a supervised analysis of gene expression data. Supervised analysis generates a long list of genes with expression patterns that are correlated with survival. Gene expression signatures can be useful in assigning these "predictive" genes to functional categories. In building a multivariate model of survival based on gene expression data, this functional categorization helps to limit the inclusion of multiple genes in the model that measure the same aspect of tumor biology.

Gene expression profiles can be used to create multivariate models for predicting survival. The methods for creating these models are called "supervised" because they use clinical data to guide the selection of genes to be used in the prognostic classification. For example, a supervised method might identify genes with expression patterns that correlate with the length of overall survival following chemotherapy. The general method used to create a multivariate model for predicting survival may utilize the following steps:

1. Identify genes with expression patterns that are univariately associated with a particular clinical outcome using a Cox proportional hazards model. Generally, a univariate p-value of <0.01 is considered the cut-off for significance. These genes are termed "predictor" genes.
2. Within a set of predictor genes, identify gene expression signatures.
3. For each gene expression signature that is significantly associated with survival, average the expression of the component genes within this signature to generate a gene expression signature value.
4. Build a multivariate Cox model of clinical outcome using the gene expression signature values.
5. If possible, include additional genes in the model that do not belong to a gene expression signature but which add to the statistical power of the model.

This approach has been utilized in the present invention to create novel survival prediction models for FL, DLBCL, and MCL. Each of these models generates a survival predictor score, with a higher score being associated with worse clinical outcome. Each of these models may be used separately to predict survival. Alternatively, these models may be used in conjunction with one or more other models, disclosed herein or in other references, to predict survival.

A first FL survival predictor was generated using gene expression data obtained using Affymetrix U133A and U133B microarrays. This predictor incorporated immune response-1 and immune response-2 gene expression signatures. Fitting the Cox proportional hazards model to the gene expression signature values obtained from these signatures resulted in the following model:

Survival predictor score=[(2.71*immune response-2 gene expression signature value)]−[(2.36×immune response-1 gene expression signature value)].

A second FL survival predictor was generated using gene expression data obtained using Affymetrix U133A and U133B microarrays. This predictor incorporated macrophage, T-cell, and B-cell differentiation gene expression signatures. Fitting the Cox proportional hazards model to the gene expression signature values obtained from these signatures resulted in the following model:

> Survival predictor score=[2.053*(macrophage gene expression signature value)]−[2.344*(T-cell gene expression signature value)]−[0.729*(B-cell differentiation gene expression signature value)].

A third FL survival predictor was generated using gene expression data obtained using the Lymph Dx microarray. This predictor incorporated macrophage, T-cell, and B-cell differentiation gene expression signatures. Fitting the Cox proportional hazards model to the gene expression signature values obtained from these signatures resulted in the following model:

> Survival predictor score=[1.51*(macrophage gene expression signature value)]−[2.11*(T-cell gene expression signature value)]−[0.505*(B-cell differentiation gene expression signature value)].

A first DLBCL survival predictor was generated using gene expression data obtained using Affymetrix U133A and U133B microarrays. This predictor incorporated ABC DLBCL high, lymph node, and MHC class II gene expression signatures. Fitting the Cox proportional hazards model to the gene expression signature values obtained from these signatures resulted in the following model:

> Survival predictor score=[0.586*(ABC DLBCL high gene expression signature value)]−[0.468* (lymph node gene expression signature value)]− [0.336*(MHC class II gene expression signature value)].

A second DLBCL survival predictor was generated using gene expression data obtained using the Lymph Dx microarray. This predictor incorporated lymph node, proliferation, germinal center B-cell, and MHC class II gene expression signatures. Fitting the Cox proportional hazards model to the gene expression signature values obtained from these signatures resulted in the following model:

> Survival predictor score=[−0.4337*(lymph node gene expression signature value)]+[0.09*(proliferation gene expression signature value)]−[0.4144*(germinal center B-cell gene expression signature value)]−[0.2006*(MHC class II gene expression signature value)].

A third DLBCL survival predictor was generated using gene expression data obtained using the Lymph Dx microarray. This predictor incorporated lymph node, germinal center B cell, and MHC class II gene expression signatures. Fitting the Cox proportional hazards model to the gene expression signature values obtained from these signatures resulted in the following model:

> Survival predictor score=[−0.32*(lymph node gene expression signature value)]−[0.176*(germinal center B-cell gene expression signature value)]− [0.206*(MHC class II gene expression signature value)].

An MCL survival predictor was generated using gene expression data obtained using Affymetrix U133A, Affymetrix U133B, and Lymph Dx microarrays. This predictor incorporated a proliferation gene expression signature. Fitting the Cox proportional hazards model to the gene expression signature values obtained from these signatures resulted in the following model:

> Survival predictor score=[1.66*(proliferation gene expression signature value)].

Gene expression data can also be used to diagnose and identify lymphoma types. In an embodiment of the present invention, a statistical method based on Bayesian analysis was developed to classify lymphoma specimens according to their gene expression profiles. This method does not merely assign a tumor to a particular lymphoma type, but also determines the probability that the tumor belongs to that lymphoma type. Many different methods have been formulated to predict cancer subgroups (Golub 1999; Ramaswamy 2001; Dudoit 2002; Radmacher 2002). These methods assign tumors to one of two subgroups based on expression of a set of differentially expressed genes. However, they do not provide a probability of membership in a subgroup. By contrast, the method disclosed herein used Bayes' rule to estimate this probability, thus allowing one to vary the probability cut-off for assignment of a tumor to a particular subgroup. In tumor types in which unknown additional subgroups may exist, the present method allows samples that do not meet the gene expression criteria of known subgroups to fall into an unclassified group with intermediate probability. A cancer subgroup predictor of the type described herein may be used clinically to provide quantitative diagnostic information for an individual cancer patient. This information can in turn be used to provide a predictor of treatment outcome for a particular cancer patient.

For any two lymphoma types A and B, there is a set of genes with significantly higher expression in type A than type B, and a set of genes with significantly lower expression in type A than in type B. By observing the expression of these genes in an unknown sample, it is possible to determine to which of the two types the sample belongs. Evaluating the likelihood that a particular sample belongs to one or the other lymphoma type by Bayesian analysis may be done using the following steps:

1) Identify those genes that are most differentially expressed between the two lymphoma types. This can be done by selecting those genes with the largest t-statistic between the two lymphoma types. The genes in this step may be subdivided into gene expression signatures in certain cases, with genes from each signature analyzed separately.
2) Create a series of linear predictor score (LPS) for samples belonging to either lymphoma type.
3) Evaluate the LPS for each sample in a training set, and estimate the distribution of these scores within each lymphoma type according to a normal distribution.
4) Use Bayes' rule to evaluate the probability that each subsequent sample belongs to one or the other lymphoma type.

If only two types of lymphoma are being distinguished, then a single probability score is sufficient to discriminate between the two types. However, if more than two lymphoma types are being distinguished, multiple scores will be needed to highlight specific differences between the types.

In an embodiment of the present invention, a novel microarray entitled the Lymph Dx microarray was developed for the identification and diagnosis of lymphoma types. The Lymph Dx microarray contains cDNA probes corresponding to approximately 2,653 genes, fewer than the number seen on microarrays that have been used previously for lymphoma diagnosis. The reduced number of probes on the Lymph Dx microarray is the result of eliminating genes that are less useful for the identification of lymphoma types and predicting clinical outcome. This reduction allows for simplified analysis of gene expression data. The genes represented on the Lymph Dx microarray can be divided into four broad categories: 1,101 lymphoma predictor genes identified previously using the Affymetrix U133 microarray, 171 outcome predictor genes, 167 new genes not found on the Affymetrix U133 microarray, and 1,121 named genes. A list of the probe sets on the Lymph Dx microarray is presented in Table 2, contained in the file "Table_0002_LymphDx_Probe_List.txt."

Figure 1:
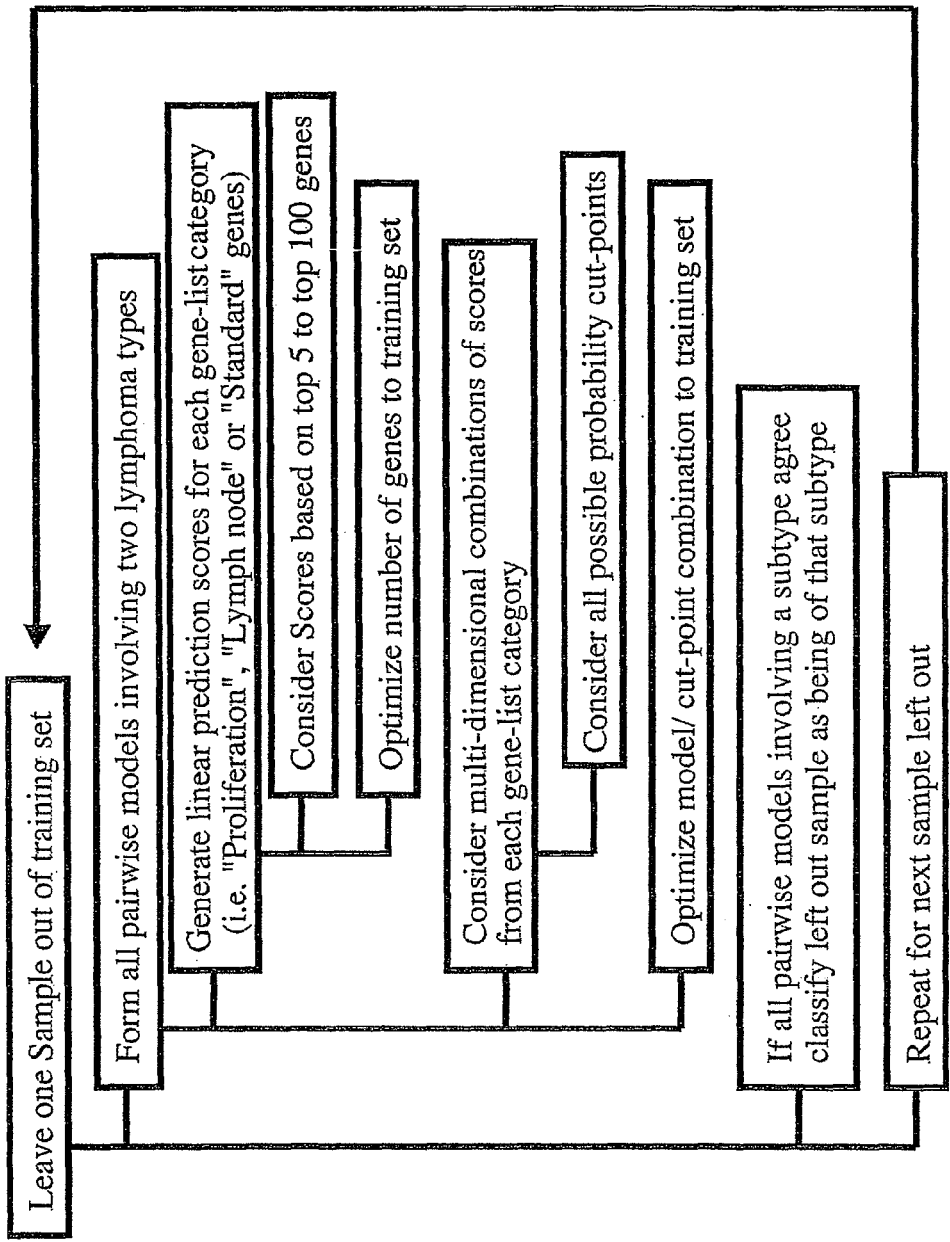
FIG. 1: Method for identifying lymphoma type. Flow chart depicts a general method for identifying lymphoma type using gene expression data.

In an embodiment of the present invention, gene expression data obtained using the Lymph Dx microarray was used to identify and classify lymphomas using Bayesian analysis. This method was similar to that outlined above, but included additional steps designed to optimize the number of genes used and the cut-off points between lymphoma types. A general overview of this method is presented in FIG. 1. Each gene represented on the Lymph Dx microarray was placed into one of three gene-list categories based on its correlation with the lymph node or proliferation gene expression signatures: lymph node, proliferation, or standard. These signatures were identified by clustering of the DLBCL cases using hierarchical clustering and centroid-correlation of 0.35. Standard genes were those with expression patterns that did not correlate highly with expression of the lymph node or proliferation signatures. Lymph Dx gene expression data was first used to identify samples as FL, MCL, SLL, FH, or DLBCL/BL, then to identify DLBCL/BL samples as ABC, GCB, PMBL, or BL. For each stage, a series of pair-wise models was created, with each model containing a different pair of lymphoma types (e.g., FL vs. MCL, SLL vs. FH, etc.). For each pair, the difference in expression of each gene on the microarray was measured, and a t-statistic was generated representing this difference. Genes from each gene-list category were ordered based on their t-statistic, and those with the largest t-statistics were used to generate a series of LPSs for samples belonging to either lymphoma type. The number of genes used to generate the LPSs was optimized by repeating the calculation using between five and 100 genes from each gene-list category. The number of genes from each category used in the final LPS calculation was that which gave rise to the largest difference in LPS between the two lymphoma types. Once the number of genes in each gene-list category was optimized, four different LPSs were calculated for each sample. The first included genes from the standard gene-list category only, the second included genes from the proliferation and standard gene-list categories, the third included genes from the lymph node and standard gene-list categories, and the fourth included genes from all three categories. The probability q that a sample X belongs to the first lymphoma type of a pair-wise model can then be calculated using an equation:

$$q = \frac{\phi(LPS(X); \hat{\mu}_1, \hat{\sigma}_1)}{\phi(LPS(X); \hat{\mu}_1, \hat{\sigma}_1) + \phi(LPS(X); \hat{\mu}_2, \hat{\sigma}_2)}$$

LPS(X) is the LPS for sample X, $\phi(x; \mu, \sigma)$ is the normal density function with mean $\mu$ and standard deviation $\sigma$, $\hat{\mu}_1$ and $\hat{\sigma}_1$ are the mean and variance of the LPSs for samples belonging to the first lymphoma type, and $\hat{\mu}_2$ and $\hat{\sigma}_2$ are the mean and variance of the LPSs for samples belonging to the second lymphoma type. Samples with high q values were classified as the first lymphoma type, samples with low q values were classified as the second lymphoma type, and samples with middle range q values were deemed unclassified. To determine the proper cut-off point between high, low, and middle q values, every possible cut-off point between adjacent samples was analyzed by an equation:

3.99*[(% of type 1 misidentified as type 2)+(% of type 2 misidentified as type 1)]+[(% of type 1 unclassified)+(% of type 2 misidentified)].

This equation was used to favor the assignment of a sample to an "unclassified" category rather than to an incorrect lymphoma type. The final cut-off points were those which minimized this equation. The coefficient of 3.99 was chosen arbitrarily to allow an additional classification error only if the adjustment resulted in four or more unclassified samples becoming correctly classified. The coefficient can be varied to achieve a different set of trade-offs between the number of unclassified and misidentified samples.

To ensure that the accuracy of the model was not a result of overfitting, each model was validated by leave-one-out cross-validation. This entailed removing each sample of known lymphoma type from the data one at a time, and then determining whether the model could predict the missing sample. This process confirmed the accuracy of the prediction method.

The classification of a lymphoproliferative disorder in accordance with embodiments of the present invention may be used in combination with any other effective classification feature or set of features. For example, a disorder may be classified by a method of the present invention in conjunction with WHO suggested guidelines, morphological properties, histochemical properties, chromosomal structure, genetic mutation, cellular proliferation rates, immunoreactivity, clinical presentation, and/or response to chemical, biological, or other agents. Embodiments of the present invention may be used in lieu of or in conjunction with other methods for lymphoma diagnosis, such as immunohistochemistry, flow cytometry, FISH for translocations, or viral diagnostics.

Accurate determination of lymphoma type in a subject allows for better selection and application of therapeutic methods. Knowledge about the exact lymphoma affecting a subject allows a clinician to select therapies or treatments that are most appropriate and useful for that subject, while avoiding therapies that are nonproductive or even counterproductive. For example, CNS prophylaxis may be useful for treating BL but not DLBCL, CHOP treatment may be useful for treating DLBCL but not blastic MCL (Fisher 1993; Khouri 1998), and subjects with follicular lymphoma frequently receive treatment while subjects with follicular hyperplasia do not. In each of these situations, the lymphoma types or subtypes in question can be difficult to distinguish using prior art diagnostic methods. The diagnostic and identification methods of the present invention allow for more precise delineation between these lymphomas, which simplifies the decision of whether to pursue a particular therapeutic option. Likewise, the survival prediction methods disclosed in the present invention also allow for better selection of therapeutic options. A subject with a very low survival predictor score (i.e., very good prognosis) may not receive treatment, but may instead be subjected to periodic check-ups and diligent observation. As survival predictor scores increase (i.e., prognosis gets worse), subjects may receive more intensive treatments. Those subjects with the highest survival predictor scores (i.e., very poor prognosis) may receive experimental treatments or treatments with novel agents. Accurate survival prediction using the methods disclosed herein provides an improved tool for selecting treatment options and for predicting the likely clinical outcome of those options.

Any effective method of quantifying the expression of at least one gene, gene set, or group of gene sets may be used to acquire gene expression data for use in embodiments of the present invention. For example, gene expression data may be measured or estimated using one or more microarrays. The microarrays may be of any effective type, including but not limited to nucleic acid based or antibody based. Gene expression may also be measured by a variety of other techniques, including but not limited to PCR, quantitative RT-PCR, real-time PCR, RNA amplification, in situ hybridization, immunohistochemistry, immunocytochemistry, FACS, serial analysis of gene expression (SAGE) (Velculescu 1995), Northern blot hybridization, or western blot hybridization.

Nucleic acid microarrays generally comprise nucleic acid probes derived from individual genes and placed in an ordered array on a support. This support may be, for example, a glass slide, a nylon membrane, or a silicon wafer. Gene expression patterns in a sample are obtained by hybridizing the microarray with the gene expression product from the sample. This gene expression product may be, for example, total cellular mRNA, rRNA, or cDNA obtained by reverse transcription of total cellular mRNA. The gene expression product from a sample is labeled with a radioactive, fluorescent, or other label to allow for detection. Following hybridization, the microarray is washed, and hybridization of gene expression product to each nucleic acid probe on the microarray is detected and quantified using a detection device such as a phosphorimager or scanning confocal microscope.

There are two broad classes of microarrays: cDNA and oligonucleotide arrays. cDNA arrays consist of hundreds or thousands of cDNA probes immobilized on a solid support. These cDNA probes are usually 100 nucleotides or greater in size. There are two commonly used designs for cDNA arrays. The first is the nitrocellulose filter array, which is generally prepared by robotic spotting of purified DNA fragments or lysates of bacteria containing cDNA clones onto a nitrocellulose filter (Southern 1992; Southern 1994; Gress 1996; Pietu 1996). The other commonly used cDNA arrays is fabricated by robotic spotting of PCR fragments from cDNA clones onto glass microscope slides (Schena 1995; DeRisi 1996; Schena 1996; Shalon 1996; DeRisi 1997; Heller 1997; Lashkari 1997). These cDNA microarrays are simultaneously hybridized with two fluorescent cDNA probes, each labeled with a different fluorescent dye (typically Cy3 or Cy5). In this format, the relative mRNA expression in two samples is directly compared for each gene on the microarray. Oligonucleotide arrays differ from cDNA arrays in that the probes are 20- to 25-mer oligonucleotides. Oligonucleotide arrays are generally produced by in situ oligonucleotide synthesis in conjunction with photolithographic masking techniques (Pease 1994; Lipshutz 1995; Chee 1996; Lockhart 1996; Wodicka 1997). The solid support for oligonucleotide arrays is typically a glass or silicon surface.

Methods and techniques applicable to array synthesis and use have been described in, for example, U.S. Pat. No. 5,143,854 (Pirrung), U.S. Pat. No. 5,242,974 (Holmes), U.S. Pat. No. 5,252,743 (Barrett), U.S. Pat. No. 5,324,633 (Fodor), U.S. Pat. No. 5,384,261 (Winkler), U.S. Pat. No. 5,424,186 (Fodor), U.S. Pat. No. 5,445,934 (Fodor), U.S. Pat. No. 5,451,683 (Barrett), U.S. Pat. No. 5,482,867 (Barrett), U.S. Pat. No. 5,491,074 (Aldwin), U.S. Pat. No. 5,527,681 (Holmes), U.S. Pat. No. 5,550,215 (Holmes), U.S. Pat. No. 5,571,639 (Hubbell), U.S. Pat. No. 5,578,832 (Trulson), U.S. Pat. No. 5,593,839 (Hubbell), U.S. Pat. No. 5,599,695 (Pease), U.S. Pat. No. 5,624,711 (Sundberg), U.S. Pat. No. 5,631,734 (Stern), U.S. Pat. No. 5,795,716 (Chee), U.S. Pat. No. 5,831,070 (Pease), U.S. Pat. No. 5,837,832 (Chee), U.S. Pat. No. 5,856,101 (Hubbell), U.S. Pat. No. 5,858,659 (Sapolsky), U.S. Pat. No. 5,936,324 (Montagu), U.S. Pat. No. 5,968,740 (Fodor), U.S. Pat. No. 5,974,164 (Chee), U.S. Pat. No. 5,981,185 (Matson), U.S. Pat. No. 5,981,956 (Stern), U.S. Pat. No. 6,025,601 (Trulson), U.S. Pat. No. 6,033,860 (Lockhart), U.S. Pat. No. 6,040,193 (Winkler), U.S. Pat. No. 6,090,555 (Fiekowsky), and U.S. Pat. No. 6,410,229 (Lockhart), and U.S. Patent Application Publication No. 20030104411 (Fodor). Each of the above patents and applications is incorporated by reference herein in its entirety.

Microarrays may generally be produced using a variety of techniques, such as mechanical or light directed synthesis methods that incorporate a combination of photolithographic methods and solid phase synthesis methods. Techniques for the synthesis of microarrays using mechanical synthesis methods are described in, for example, U.S. Pat. No. 5,384,261 (Winkler) and U.S. Pat. No. 6,040,193 (Winkler). Although a planar array surface is preferred, the microarray may be fabricated on a surface of virtually any shape, or even on a multiplicity of surfaces. Microarrays may be nucleic acids on beads, gels, polymeric surfaces, fibers such as fiber optics, glass or any other appropriate substrate. See, for example, U.S. Pat. No. 5,708,153 (Dower); U.S. Pat. No. 5,770,358 (Dower); U.S. Pat. No. 5,789,162 (Dower); U.S. Pat. No. 5,800,992 (Fodor); and U.S. Pat. No. 6,040,193 (Winkler), each of which is incorporated by reference herein in its entirety.

Microarrays may be packaged in such a manner as to allow for diagnostic use, or they can be an all-inclusive device. See, for example, U.S. Pat. No. 5,856,174 (Lipshutz) and U.S. Pat. No. 5,922,591 (Anderson), both of which are incorporated by reference herein in their entirety.

Microarrays directed to a variety of purposes are commercially available from Affymetrix (Affymetrix, Santa Clara, Calif.). For instance, these microarrays may be used for genotyping and gene expression monitoring for a variety of eukaryotic and prokaryotic species.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1

Collection and Analysis of Gene Expression Data Using Affymetrix U133A and U133B Microarrays 568 cell samples representing various forms of human lymphoid malignancies were obtained by biopsy using known methods described in the literature. The samples were reviewed by a panel of hematopathologists and classified into the following lymphoma types based on current diagnostic criteria:

231 diffuse large B cell lymphomas (DLBCL)
191 follicular lymphomas (FL)
26 Burkitt lymphomas (BL)
21 mantle cell lymphoma (MCL)
18 follicular hyperplasias (FH)
17 small cell lymphocytic lymphomas (SLL)
16 mucosa-associated lymphoid tissue lymphomas (MALT)
13 splenic lymphomas (Splenic)
10 cyclin-D1 negative lymphomas with MCL morphology (CD1negMCL)

9 multiple myeloma (Mult_Myeloma)
6 lymphoplasmacytic lymphomas (LPC)
4 post-transplant lymphoproliferative disorders (PTLD)
3 lymphoblastic lymphomas (Lymbl)
3 nodal marginal zone lymphomas (NMZ)

The 231 DLBCL samples were subdivided into the following lymphoma types based on gene expression (see below):
  88 germinal center B cell-like (GCB)
  78 activated B cell-like (ABC)
  33 primary mediastinal B cell lymphoma (PMBL)
  32 samples for which the subtype could not be determined (UC_DLBCL)

The 16 MALT samples were subdivided into the following four group based on tumor origin:
  9 from the gastric region (MALT_gastric)
  1 from the salivary gland (MALT_salivary)
  1 from the lung (MALT_lung)
  1 from the tonsil (MALT_tonsil)
  4 of unknown origin (MALT_unk)

Each of the 568 cell samples was given a unique sample ID number consisting of the lymphoma type followed by a unique numerical identifier. For example, "ABC_304" refers to an ABC DLBCL sample numbered 304. Cells were purified and RNA was isolated from the purified cells according to known methods described in the literature.

Aliquots of RNA from each sample were applied to Affymetrix U133A and Affymetrix U133B microarrays according to standard Affymetrix protocol. The U133A and U133B microarrays are divided into probe sets, with each probe set consisting of up to 69 oligonucleotide probes 25 nucleotides in length. Each probe set represents a distinct human gene. Information pertaining to these microarrays is available at the Affymetrix company web site. Each microarray was scanned using an Affymetrix scanner, which records signal intensity for every probe on the microarray. This information can be transformed into summary signal values for each probe set using a number of different algorithms, including MAS 5.0, D-chip (Li 2001), or Bioconductor's RMA algorithms (Irizarry 2003). The images produced by the scanner were evaluated by Affymetrix MAS 5.0 software and stored as tables in .txt format. Since each sample was scanned on both microarrays, there are two .txt files for each sample. Each .txt file was given a unique name consisting of the table number, sample ID number (discussed above), and a letter denoting the microarray used. For example, Table_0588_ABC_304_A.txt is the .txt file for Table 588, which contains data for sample ID number ABC_304 from the U133A array. The data for each sample tested is contained in Tables 3-1138.

The signal value for each probe on the U133A and U133B microarrays was normalized to a target value of 500, and the base-2 log of the normalized values was used for the following analyses. Log-signal values for each probe set are presented in Tables 1139-1706, contained in files with the title format "Table_No._NAME_log_signal.txt," where NAME refers to the sample ID number (e.g., ABC_304). The first column provides the UNIQID for the probe set, while the second column provides the log-signal value.

Log-signal files were statistically analyzed using S+ software and the S+ subtype predictor script contained in the file entitled "Subtype_Predictor.txt," located in the computer program listing appendix contained on CD number 22 of 22. Although the log-signal values were analyzed using S+ software and the above algorithm, any effective software/algorithm combination may be used. Tables 1707-1721 provide descriptive statistical characteristics for each of the lymphoma types tested except for CD1negMCL, non-gastric MALT, and UC_DLBCL. Table 1722 provides statistical characteristics for all MALT samples combined, while Table 1723 does likewise for all DLBCL samples.

The files containing Tables 1707-1723 have the title format "Table_No._TYPE_Stats.txt," where TYPE refers to the lymphoma type. Each row of these tables represents a particular probe set. The first column of each table provides the UNIQID for the probe set, while the second column provides the average log-signal for the probe set over all samples of a particular lymphoma type. The third column provides the log-fold change in expression of the probe set between the lymphoma type in question and a second lymphoma type. For example, if logfold.ABC.vs.GCB is −0.21 for gene X, expression of gene X in the ABC DLBCL samples is, on average, 0.86 (i.e., $2^{-0.21}$) times greater than expression of gene X in the GCB DLBCL samples. The fourth column provides a two-sided P-value derived from a t-test of the log signals of the two lymphoma types compared in column three. If, for example, P.value.ABC.vs.GCB was 0.00001 for gene X, this would indicate that the observed difference in expression of gene X between ABC DLBCL and GCB DLBCL would only occur approximately one time in 100,000 if there was no actual difference in gene X expression between the two lymphoma types. The remainder of the columns can be read as pairs that repeat the pattern of columns three and four, presenting the log-fold change and P-value of the difference in expression of the probe set for the lymphoma type in question versus all other lymphoma types being tested. Tables 1710, 1715, and 1723 (corresponding to FL, MCL, and DLBCL, respectively) contain two additional columns entitled "TYPE_Cox coefficient" and "TYPE_Cox_P_value." The content of these columns is discussed in the following examples.

Example 2

Collection of Gene Expression Data Using the Novel Lymph Dx Microarray

The novel Lymph Dx microarray contains cDNA probes corresponding to approximately 2,734 genes. 174 of these are "housekeeping" genes present for quality control, since they represent genes that are most variably expressed across all lymphoma samples. Other genes represented on the microarray were selected for their utility in identifying particular lymphoma samples and predicting survival in those samples. The genes represented on the Lymph Dx microarray can be divided into four broad categories: 1,101 lymphoma predictor genes identified previously using the Affymetrix U133 microarray, 171 outcome predictor genes identified using the Affymetrix U133 microarray, 167 genes not found on the Affymetrix U133 microarray but represented on the Lymphochip microarray (Alizadeh 1999), and 1,121 named genes. The types of genes making up each of these broad categories are summarized in Table 1724, below, while the specific genes represented on the Lymph Dx microarray are listed in Table 2, contained in the file "Table_0002_LymphDx_Probe_List.txt."

TABLE 1724

| Gene type | Number of genes |
|---|---|
| Lymphoma predictor genes | 1101 |
| Subtype specific | 763 |

TABLE 1724-continued

| Gene type | Number of genes |
| --- | --- |
| Lymph node signature | 178 |
| Proliferation signature | 160 |
| Outcome predictor genes | 171 |
| DLBCL | 79 |
| FL | 81 |
| MCL | 11 |
| New genes not on U133 | 167 |
| Lymphochip lymphoma predictor genes | 84 |
| EBV and HHV8 viral genes | 18 |
| BCL-2/cyclin D1/INK4a specialty probes | 14 |
| Named genes missing from U133 | 51 |
| Named genes | 1121 |
| Protein kinase | 440 |
| Interleukin | 35 |
| Interleukin receptor | 29 |
| Chemokine | 51 |
| Chemokine receptor | 29 |
| TNF family | 26 |
| TNF receptor family | 51 |
| Adhesion | 45 |
| Surface marker | 264 |
| Oncogene/tumor suppressor | 49 |
| Apoptosis | 46 |
| Drug target | 10 |
| Regulatory | 46 |

Cell samples representing various forms of human lymphoid malignancy were obtained by biopsy using known methods described in the literature. These 634 biopsy samples were reviewed by a panel of hematopathologists and classified into the following lymphoma types based on current diagnostic criteria:
- 201 diffuse large B-cell lymphomas (DLBCL)
- 191 follicular lymphomas (FL)
- 60 Burkitt lymphomas (BL)
- 21 mantle cell lymphomas (MCL)
- 30 primary mediastinal B cell lymphoma (PMBL)
- 18 follicular hyperplasias (FH)
- 18 small cell lymphocytic lymphomas (SLL)
- 17 mucosa-associated lymphoid tissue lymphomas (MALT), including 9 gastric MALTs (GMALT)
- 16 chronic lymphocytic leukemias (CLL)
- 13 splenic lymphomas (SPL)
- 11 lymphoplasmacytic lymphomas (LPC)
- 11 transformed DLBCL (trDLBCL) (DLBCL that arose from an antecedent FL)
- 10 cyclin D1 negative lymphomas with MCL morphology (CD1N)
- 6 peripheral T-cell lymphoma (PTCL)
- 4 post-transplant lymphoproliferative disorders (PTLD)
- 4 nodal marginal zone lymphomas (NMZ)
- 3 lymphoblastic lymphomas (LBL)

Each of the 634 samples was given a unique sample ID number consisting of the lymphoma type followed by a unique numerical identifier. For example, "BL__2032__52748" refers to a Burkitt lymphoma sample with the numerical identifier 2032__52748. Cells were purified and RNA was isolated from the purified cells according to known methods described in the literature.

Aliquots of purified RNA from each sample was applied to the Lymph Dx microarrays according to standard Affymetrix microarray protocol. Each microarray was scanned on an Affymetrix scanner. This scanner produced an image of the microarray, which was then evaluated by Affymetrix MAS 5.0 software. This information was stored in tables in .txt format. Each of these .txt files was given a unique name consisting of the table number, the sample ID number (discussed above), and the UNIQID for identifying the array data in the National Cancer Institute Database. For example, Table__1725_BL__2032__52748.txt is the .txt file for Table 1725, which contains data for sample ID number BL__2032. The data for each sample analyzed is contained in Tables 1725-2358. The signal intensity for each probe on the microarray can be transformed into summary signal values for each probe set through a number of different algorithms, including but not limited to MAS 5.0, D-chip (Li 2001), or Bioconductor's RMA algorithms (Irizarry 2003).

Example 3

Figure 2:
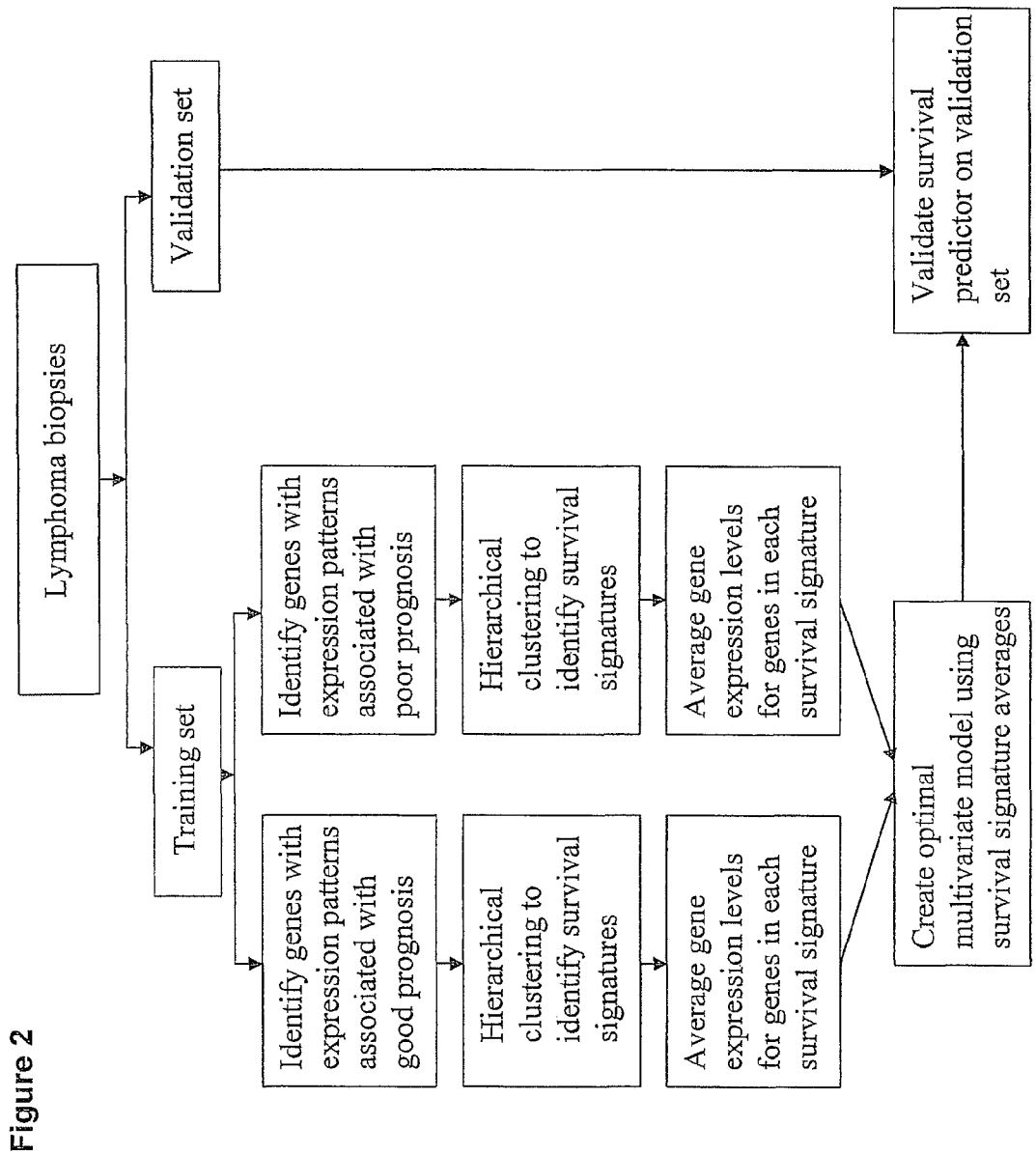
FIG. 2: Survival signature analysis. Flow chart depicts method for developing a lymphoma survival predictor based on gene expression patterns.

Development of a First FL Survival Predictor Using Gene Expression Data from Affymetrix U133A and U133B Microarrays An analytical method entitled Survival Signature Analysis was developed to create survival prediction models for lymphoma. This method is summarized in FIG. 2. The key feature of this method is the identification of gene expression signatures. Survival Signature Analysis begins by identifying genes whose expression patterns are statistically associated with survival. A hierarchical clustering algorithm is then used to identify subsets of these genes with correlated expression patterns across the lymphoma samples. These subsets are operationally defined as "survival-associated signatures." Evaluating a limited number of survival-associated signatures mitigates the multiple comparison problems that are inherent in the use of large-scale gene expression data sets to create statistical models of survival (Ransohoff 2004).

Figure 3:
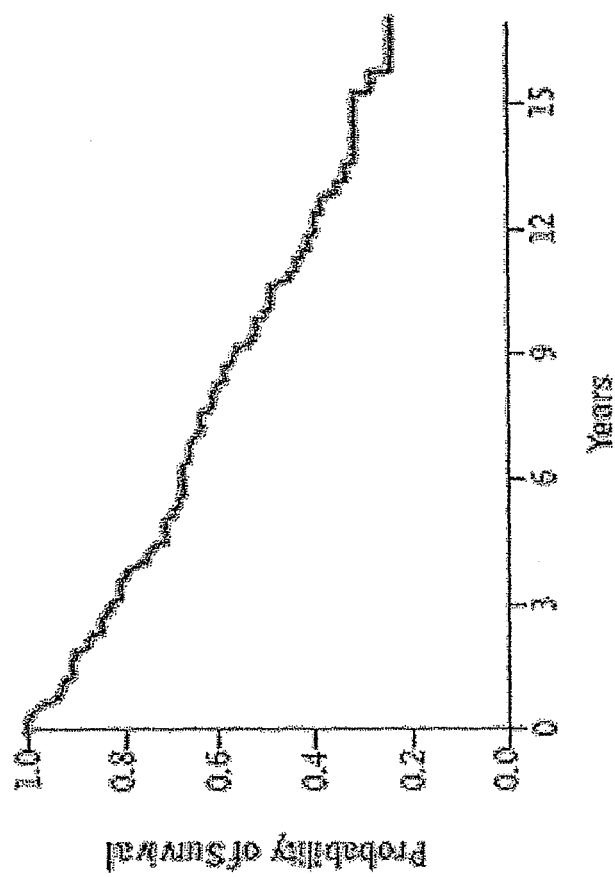
FIG. 3: FL survival data. Survival data for 191 subjects diagnosed with FL. Median age at diagnosis was 51 years (ranging from 23 to 81 years), and the subjects had a median follow-up of 6.6 years (8.1 years for survivors, with a range of <1 to 28.2 years).
Figure 4:
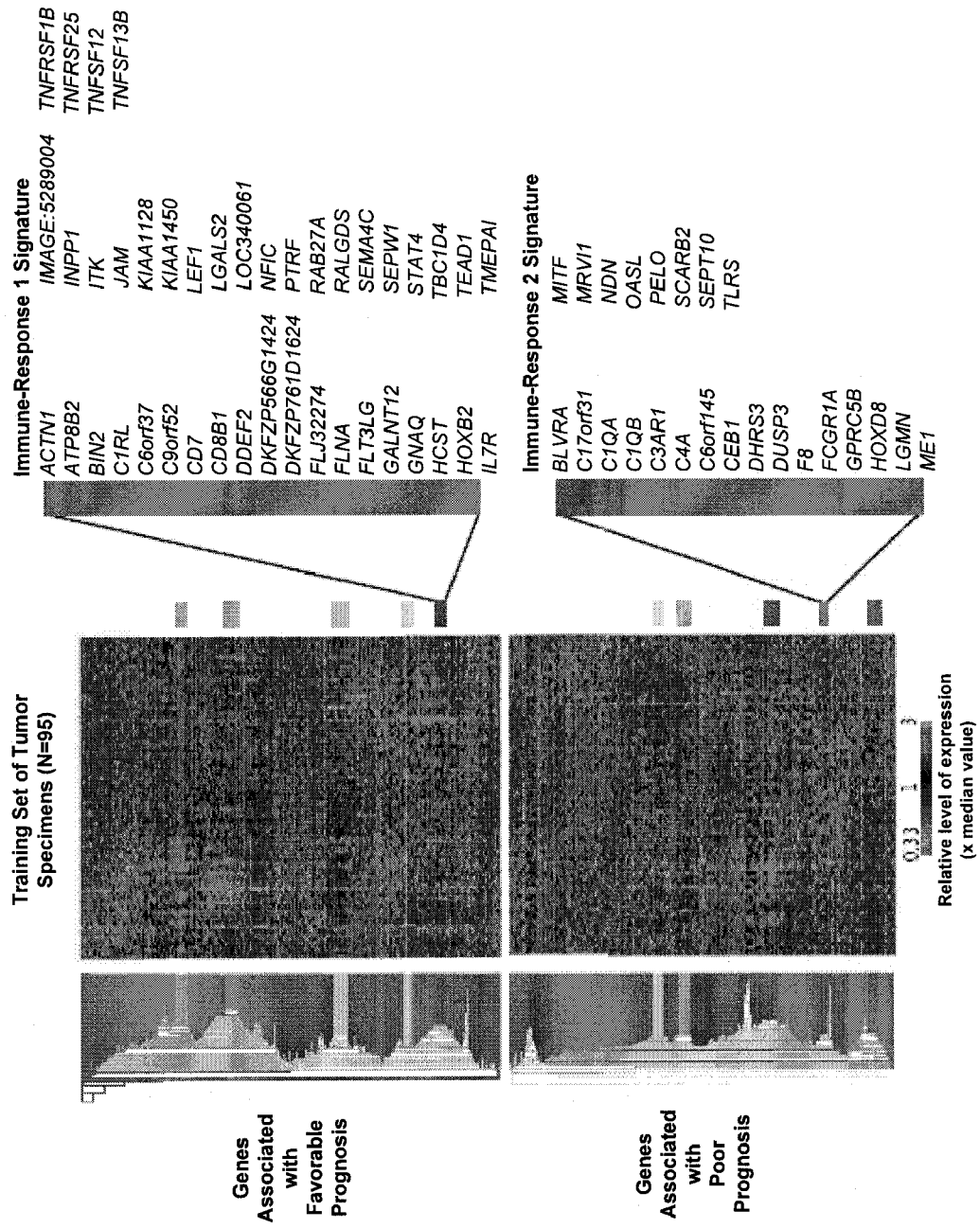
FIG. 4: Hierarchical clustering of survival associated genes in FL samples. Each column represents a single FL sample, while each row represents a single gene. Relative gene expression is depicted according to the scale at the bottom of the figure. The dendrogram to the left indicates the degree to which the expression pattern of each gene is correlated with that of the other genes. The bars indicate sets of coordinately regulated genes defined as gene expression signatures. Genes comprising the immune response-1 and immune response-2 gene expression signature are listed on the right.

FL samples were divided into two equivalent groups: a training set (95 samples) for developing the survival prediction model, and a validation set (96 samples) for evaluating the reproducibility of the model. The overall survival of this cohort is depicted in FIG. 3. The median age at diagnosis was 51 years (ranging from 23 to 81 years), and the patients had a median follow-up of 6.6 years (8.1 years for survivors, with a range of <1 to 28.2 years). Gene expression data from Affymetrix U133A and U133B microarrays was obtained for each sample. Within the training set, a Cox proportional hazards model was used to identify "survival predictor" genes, which were genes whose expression levels were associated with long survival (good prognosis genes) or short survival (poor prognosis genes). A hierarchical clustering algorithm (Eisen 1998) was used to identify gene expression signatures within the good and poor prognosis genes according to their expression pattern across all samples. Ten gene expression signatures were observed within either the good prognosis or poor prognosis gene sets (FIG. 4). The expression level of every component gene in each of these ten gene expression signatures was averaged to create a gene expression signature value.

To create a multivariate model of survival, different combinations of the ten gene expression signature values were generated and evaluated for their ability to predict survival within the training set. Among models consisting of two signatures, an exceptionally strong statistical synergy was observed between one signature from the good prognosis group and one signature from the poor prognosis group. These signatures were deemed "immune response-1" and "immune response-2," respectively; based on the biological function of certain genes within each signature. The immune response-1 gene expression signature included genes encoding T cell markers (e.g., CD7, CD8B1, ITK, LEF1, STAT4) and .genes that are highly expressed in macrophaqes (e.g., ACTN1, TNFSF13B). The immune response-1 signature is not merely a surrogate for the number of T cells in the FL biopsy sample because many other standard T cell genes (e.g., CD2, CD4, LAT, TRIM, SH2D1A) were not associated with survival. The immune response-2 gene expression signature included genes known to be preferentially expressed in macrophages and/or dendritic cells (e.g., TLR5, FCGR1A, SEPT10, LGMN, C3AR1). Table 2359 lists the genes that were used to generate the gene expression signature values for the immune response-1 and immune response-2 signatures. The Unigene ID Build database referenced in the following tables is hosted by the hosted by the National Center for Biotechnology Information (NCBI) web site.

TABLE 2359

| Signature | UNIQID | Unigene ID Build 167 | Gene symbol |
| --- | --- | --- | --- |
| Immune response-1 | 1095985 | 83883 | TMEPAI |
| Immune response-1 | 1096579 | 117339 | HCST |
| Immune response-1 | 1097255 | 380144 | |
| Immune response-1 | 1097307 | 379754 | LOC340061 |
| Immune response-1 | 1097329 | 528675 | TEAD1 |
| Immune response-1 | 1097561 | 19221 | C20orf112 |
| Immune response-1 | 1098152 | 377588 | KIAA1450 |
| Immune response-1 | 1098405 | 362807 | IL7R |
| Immune response-1 | 1098548 | 436639 | NFIC |
| Immune response-1 | 1098893 | 43577 | ATP8B2 |
| Immune response-1 | 1099053 | 376041 | |
| Immune response-1 | 1100871 | 48353 | |
| Immune response-1 | 1101004 | 2969 | SKI |
| Immune response-1 | 1103303 | 49605 | C9orf52 |
| Immune response-1 | 1107713 | 171806 | |
| Immune response-1 | 1115194 | 270737 | TNFSF13B |
| Immune response-1 | 1119251 | 433941 | SEPW1 |
| Immune response-1 | 1119838 | 469951 | GNAQ |
| Immune response-1 | 1119924 | 32309 | INPP1 |
| Immune response-1 | 1120196 | 173802 | TBC1D4 |
| Immune response-1 | 1120267 | 256278 | TNFRSF1B |
| Immune response-1 | 1121313 | 290432 | HOXB2 |
| Immune response-1 | 1121406 | NA | TNFSF12 |
| Immune response-1 | 1121720 | 80642 | STAT4 |
| Immune response-1 | 1122956 | 113987 | LGALS2 |
| Immune response-1 | 1123038 | 119000 | ACTN1 |
| Immune response-1 | 1123092 | 437191 | PTRF |
| Immune response-1 | 1123875 | 428 | FLT3LG |
| Immune response-1 | 1124760 | 419149 | JAM3 |
| Immune response-1 | 1128356 | 415792 | C1RL |
| Immune response-1 | 1128395 | 7188 | SEMA4C |
| Immune response-1 | 1132104 | 173802 | TBC1D4 |
| Immune response-1 | 1133408 | 12802 | DDEF2 |
| Immune response-1 | 1134069 | 405667 | CD8B1 |
| Immune response-1 | 1134751 | 106185 | RALGDS |
| Immune response-1 | 1134945 | 81897 | KIAA1128 |
| Immune response-1 | 1135743 | 299558 | TNFRSF25 |
| Immune response-1 | 1135968 | 119000 | ACTN1 |
| Immune response-1 | 1136048 | 299558 | TNFRSF25 |
| Immune response-1 | 1136087 | 211576 | ITK |
| Immune response-1 | 1137137 | 195464 | FLNA |
| Immune response-1 | 1137289 | 36972 | CD7 |
| Immune response-1 | 1137534 | 36972 | CD7 |
| Immune response-1 | 1139339 | 47099 | GALNT12 |
| Immune response-1 | 1139461 | 14770 | BIN2 |
| Immune response-1 | 1140391 | 44865 | LEF1 |
| Immune response-1 | 1140524 | 10784 | C6orf37 |
| Immune response-1 | 1140759 | 298530 | RAB27A |
| Immune response-2 | 1118755 | 127826 | EPOR |
| Immune response-2 | 1118966 | 19196 | LOC51619 |
| Immune response-2 | 1121053 | 1690 | FGFBP1 |
| Immune response-2 | 1121267 | 334629 | SLN |
| Immune response-2 | 1121331 | 8980 | TESK2 |
| Immune response-2 | 1121766 | 396566 | MPP3 |
| Immune response-2 | 1121852 | 421391 | LECT1 |
| Immune response-2 | 1122624 | 126378 | ABCG4 |
| Immune response-2 | 1122679 | 232770 | ALOXE3 |
| Immune response-2 | 1122770 | 66578 | CRHR2 |
| Immune response-2 | 1123767 | 1309 | CD1A |
| Immune response-2 | 1123841 | 389 | ADH7 |

TABLE 2359-continued

| Signature | UNIQID | Unigene ID Build 167 | Gene symbol |
| --- | --- | --- | --- |
| Immune response-2 | 1126097 | 498015 | |
| Immune response-2 | 1126380 | 159408 | |
| Immune response-2 | 1126628 | 254321 | CTNNA1 |
| Immune response-2 | 1126836 | 414410 | NEK1 |
| Immune response-2 | 1127277 | 121494 | SPAM1 |
| Immune response-2 | 1127519 | NA | |
| Immune response-2 | 1127648 | 285050 | |
| Immune response-2 | 1128483 | 444359 | SEMA4G |
| Immune response-2 | 1128818 | 115830 | HS3ST2 |
| Immune response-2 | 1129012 | 95497 | SLC2A9 |
| Immune response-2 | 1129582 | 272236 | C21orf77 |
| Immune response-2 | 1129658 | 58356 | PGLYRP4 |
| Immune response-2 | 1129705 | 289368 | ADAM19 |
| Immune response-2 | 1129867 | 283963 | G6PC2 |
| Immune response-2 | 1130003 | 432799 | |
| Immune response-2 | 1130388 | 19196 | LOC51619 |
| Immune response-2 | 1131837 | 156114 | PTPNS1 |
| Immune response-2 | 1133843 | 6682 | SLC7A11 |
| Immune response-2 | 1133949 | 502092 | PSG9 |
| Immune response-2 | 1134447 | 417628 | CRHR1 |
| Immune response-2 | 1135117 | 512646 | PSG6 |
| Immune response-2 | 1136017 | 1645 | CYP4A11 |
| Immune response-2 | 1137478 | 315235 | ALDOB |
| Immune response-2 | 1137745 | 26776 | NTRK3 |
| Immune response-2 | 1137768 | 479985 | |
| Immune response-2 | 1138476 | 351874 | HLA-DOA |
| Immune response-2 | 1138529 | 407604 | CRSP2 |
| Immune response-2 | 1138601 | 149473 | PRSS7 |
| Immune response-2 | 1139862 | 251383 | CHST4 |
| Immune response-2 | 1140189 | 287369 | IL22 |
| Immune response-2 | 1140389 | 22116 | CDC14B |

Although the immune response-1 and immune response-2 gene expression signatures taken individually were not ideal predictors of survival, the binary model formed by combining the two was more predictive of survival in the training set than any other binary model (p<0.001). Using this binary model as an anchor, other signatures were added to the model using a step up procedure (Drapner 1966). Of the remaining eight signatures, only one signature contributed significantly to the model in the training set (p<0.01), resulting in a three-variable model for survival. This model was associated with survival in a highly statistically significant fashion in both the training (p<0.001) and validation sets (p=0.003). However, only the immune response-1 and immune response-2 gene expression signatures contributed to the predictive power of the model in both the training set and the validation set. The predictive power of each of these signatures is summarized in Table 2360.

TABLE 2360

| Gene expression signature | Contribution of signature to model in validation set (p-value) | Relative risk of death among patients in validation set (95% C.I.) | Effect of increased expression on survival |
| --- | --- | --- | --- |
| Immune response-1 | <0.001 | 0.15 (0.05-0.46) | Favorable |
| Immune response-2 | <0.001 | 9.35 (3.02-28.9) | Poor |

Based on this information, the third signature was removed from the model and the two-signature model was used to generate a survival predictor score using the following equation:

Survival predictor score=[(2.71*immune response-2 gene expression signature value)]−[(2.36×immune response-1 gene expression signature value)].

A higher survival predictor score was associated with worse outcome. The two-signature model was associated with survival in a statistically significant fashion in both the training set (p<0.001) and the validation set (p<0.001), which demonstrated that the model was reproducible. For the 187 FL samples with available clinical data, the survival predictor score had a mean of 1.6 and a standard deviation of 0.894, with each unit increase in the predictor score corresponding to a 2.5 fold increase in the relative risk of death. Data for all 191 samples is shown in Table 2361.

TABLE 2361

| Sample ID # | Set | Length of follow-up (years) | Status at follow-up | Immune response-1 signature value | Immune response-2 signature value | Survival predictor score |
| --- | --- | --- | --- | --- | --- | --- |
| FL__1073 | Training | 7.68 | Dead | 9.20 | 8.67 | 1.77 |
| FL__1074 | Training | 4.52 | Dead | 9.10 | 8.57 | 1.74 |
| FL__1075 | Validation | 4.52 | Dead | 8.97 | 8.69 | 2.38 |
| FL__1076 | Training | 3.22 | Dead | 9.20 | 8.55 | 1.44 |
| FL__1077 | Training | 7.06 | Alive | 9.80 | 8.46 | −0.20 |
| FL__1078 | Training | 4.95 | Alive | 9.32 | 8.23 | 0.30 |
| FL__1080 | Training | 6.05 | Alive | 9.45 | 8.94 | 1.93 |
| FL__1081 | Validation | 6.61 | Alive | 9.00 | 8.22 | 1.05 |
| FL__1083 | Training | 10.01 | Alive | 9.82 | 8.72 | 0.47 |
| FL__1085 | Validation | 8.84 | Alive | 9.31 | 8.58 | 1.29 |
| FL__1086 | Validation | 1.98 | Dead | 9.49 | 9.09 | 2.22 |
| FL__1087 | Training | 8.19 | Alive | 9.98 | 9.27 | 1.57 |
| FL__1088 | Validation | 5.30 | Alive | 9.22 | 8.47 | 1.20 |
| FL__1089 | Training | 10.72 | Alive | 9.42 | 8.35 | 0.40 |
| FL__1090 | Validation | 10.20 | Alive | 9.27 | 8.37 | 0.82 |
| FL__1097 | Validation | 8.79 | Dead | 9.87 | 8.92 | 0.87 |
| FL__1098 | Validation | 5.34 | Dead | 9.33 | 8.81 | 1.87 |
| FL__1099 | Training | 7.65 | Alive | 9.73 | 9.04 | 1.54 |
| FL__1102 | Validation | 13.20 | Dead | 9.45 | 8.89 | 1.79 |
| FL__1104 | Training | 8.42 | Dead | 9.30 | 8.27 | 0.48 |
| FL__1106 | Validation | 7.94 | Alive | 9.13 | 9.19 | 3.36 |
| FL__1107 | Training | 5.01 | Dead | 9.41 | 9.32 | 3.07 |
| FL__1183 | Training | 11.56 | Dead | 9.31 | 8.53 | 1.16 |
| FL__1184 | Training | 6.93 | Dead | 9.66 | 8.83 | 1.13 |
| FL__1185 | Validation | 7.02 | Dead | 9.23 | 9.09 | 2.86 |
| FL__1186 | Training | 1.34 | Dead | 9.01 | 8.84 | 2.68 |
| FL__1416 | Validation | 6.21 | Alive | 9.50 | 8.67 | 1.08 |
| FL__1417 | Training | 2.40 | Dead | 8.47 | 8.39 | 2.73 |
| FL__1418 | Validation | 3.59 | Alive | 8.94 | 8.42 | 1.72 |
| FL__1419 | Training | 3.85 | Alive | 9.82 | 8.56 | 0.03 |
| FL__1422 | Training | 5.72 | Alive | 9.46 | 8.49 | 0.68 |
| FL__1425 | Validation | 4.26 | Alive | 8.93 | 8.50 | 1.98 |
| FL__1426 | Training | 7.32 | Alive | 9.08 | 8.26 | 0.97 |
| FL__1427 | Training | 5.22 | Alive | 8.57 | 8.28 | 2.22 |
| FL__1428 | Validation | 5.41 | Dead | 9.22 | 8.44 | 1.10 |
| FL__1432 | Training | 3.66 | Alive | 9.22 | 8.95 | 2.51 |
| FL__1436 | Training | 9.08 | Dead | 9.48 | 8.63 | 1.02 |
| FL__1440 | Training | 7.85 | Alive | 9.07 | 8.35 | 1.22 |
| FL__1445 | Training | 9.24 | Dead | 8.67 | 8.66 | 3.01 |
| FL__1450 | Validation | 0.65 | Dead | 9.83 | 9.99 | 3.86 |
| FL__1472 | Validation | 16.72 | Alive | 8.85 | 8.49 | 2.10 |
| FL__1473 | Training | 15.07 | Alive | 9.75 | 8.50 | 0.02 |
| FL__1474 | Validation | 2.75 | Dead | 9.34 | 9.10 | 2.62 |
| FL__1476 | Validation | 4.08 | Dead | 9.51 | 8.87 | 1.60 |
| FL__1477 | Training | 0.59 | Dead | 9.64 | 9.06 | 1.83 |
| FL__1478 | Training | 12.47 | Dead | 9.60 | 8.87 | 1.39 |
| FL__1479 | Training | 2.29 | Dead | 8.71 | 9.07 | 4.01 |
| FL__1480 | Training | 16.29 | Alive | 9.40 | 8.67 | 1.30 |
| FL__1579 | Training | 8.22 | Dead | 8.81 | 8.44 | 2.10 |
| FL__1580 | Training | 19.30 | Alive | 9.58 | 8.52 | 0.49 |
| FL__1581 | Training | 9.52 | Dead | 9.08 | 9.02 | 3.00 |
| FL__1582 | Validation | 1.30 | Dead | 8.40 | 8.18 | 2.36 |
| FL__1583 | Training | 15.26 | Dead | 9.47 | 8.79 | 1.48 |
| FL__1584 | Training | 15.73 | Dead | 9.44 | 8.55 | 0.89 |
| FL__1585 | Validation | 0.01 | Alive | 8.96 | 8.53 | 1.96 |
| FL__1586 | Validation | 3.11 | Alive | 9.38 | 8.55 | 1.03 |
| FL__1588 | Training | 0.49 | Dead | 9.52 | 9.06 | 2.08 |
| FL__1589 | Training | 3.15 | Alive | 9.72 | 8.74 | 0.72 |
| FL__1591 | Training | 11.22 | Alive | 9.49 | 8.62 | 0.97 |
| FL__1594 | Validation | 11.19 | Alive | 9.25 | 8.59 | 1.47 |
| FL__1595 | Training | 8.03 | Alive | 9.75 | 9.60 | 3.01 |
| FL__1598 | Validation | 2.80 | Dead | 8.81 | 8.33 | 1.79 |
| FL__1599 | Validation | 6.17 | Alive | 9.48 | 8.65 | 1.06 |
| FL__1603 | Training | 5.17 | Dead | 9.66 | 9.75 | 3.63 |

TABLE 2361-continued

| Sample ID # | Set | Length of follow-up (years) | Status at follow-up | Immune response-1 signature value | Immune response-2 signature value | Survival predictor score |
|---|---|---|---|---|---|---|
| FL__1604 | Training | 3.98 | Dead | 9.24 | 8.86 | 2.20 |
| FL__1606 | Validation | 4.22 | Dead | 9.45 | 9.18 | 2.57 |
| FL__1607 | Validation | 8.12 | Alive | 9.40 | 8.60 | 1.13 |
| FL__1608 | Validation | 9.70 | Alive | 8.92 | 8.41 | 1.72 |
| FL__1610 | Validation | 2.05 | Dead | 9.33 | 9.35 | 3.32 |
| FL__1611 | Validation | 10.15 | Alive | 9.42 | 8.69 | 1.31 |
| FL__1616 | Training | 2.36 | Dead | 9.38 | 8.82 | 1.78 |
| FL__1617 | Validation | 7.85 | Alive | 8.96 | 8.49 | 1.87 |
| FL__1619 | Validation | 9.24 | Dead | 9.43 | 8.56 | 0.94 |
| FL__1620 | Validation | 9.36 | Dead | 9.14 | 8.35 | 1.04 |
| FL__1622 | Training | 14.01 | Alive | 9.23 | 8.53 | 1.33 |
| FL__1623 | Training | 9.72 | Alive | 9.67 | 8.93 | 1.38 |
| FL__1624 | Validation | 3.98 | Dead | 9.05 | 8.50 | 1.70 |
| FL__1625 | Validation | 11.16 | Alive | 8.98 | 8.47 | 1.75 |
| FL__1626 | Validation | 6.47 | Dead | 8.59 | 8.14 | 1.76 |
| FL__1628 | Validation | 0.82 | Dead | 9.80 | 8.72 | 0.51 |
| FL__1637 | Validation | 18.81 | Alive | 9.95 | 9.58 | 2.48 |
| FL__1638 | Validation | 4.06 | Alive | 9.13 | 8.88 | 2.51 |
| FL__1639 | Training | 4.75 | Alive | 9.53 | 8.89 | 1.62 |
| FL__1643 | Training | 0.77 | Dead | 9.73 | 9.06 | 1.58 |
| FL__1644 | Validation | 3.84 | Alive | 9.55 | 8.68 | 0.98 |
| FL__1645 | Training | 3.56 | Alive | 9.49 | 8.70 | 1.18 |
| FL__1646 | Training | 1.97 | Dead | 9.25 | 8.61 | 1.50 |
| FL__1647 | Training | 1.22 | Dead | 9.12 | 8.89 | 2.55 |
| FL__1648 | Training | 11.01 | Alive | 9.13 | 8.12 | 0.46 |
| FL__1652 | Training | 3.72 | Dead | 9.50 | 9.14 | 2.35 |
| FL__1654 | Validation | 0.30 | Dead | 8.74 | 8.28 | 1.82 |
| FL__1655 | Training | 8.45 | Alive | 9.51 | 8.85 | 1.53 |
| FL__1656 | Validation | 9.36 | Alive | 9.06 | 8.58 | 1.87 |
| FL__1657 | Training | 10.09 | Alive | 9.53 | 8.46 | 0.44 |
| FL__1660 | Training | 2.32 | Alive | 8.81 | 8.38 | 1.91 |
| FL__1661 | Validation | 1.48 | Alive | 9.86 | 8.90 | 0.85 |
| FL__1662 | Validation | 0.74 | Dead | 9.57 | 9.15 | 2.21 |
| FL__1664 | Validation | 4.53 | Dead | 9.34 | 8.62 | 1.31 |
| FL__1669 | Training | 4.40 | Dead | 8.87 | 8.58 | 2.30 |
| FL__1670 | Training | 1.88 | Alive | 9.64 | 9.45 | 2.86 |
| FL__1675 | Training | 4.57 | Alive | 9.36 | 8.46 | 0.84 |
| FL__1681 | Validation | 4.23 | Alive | 9.52 | 8.63 | 0.91 |
| FL__1683 | Validation | 4.03 | Dead | 9.95 | 9.10 | 1.19 |
| FL__1684 | Training | 2.88 | Dead | 9.53 | 8.73 | 1.18 |
| FL__1716 | Validation | 9.69 | Alive | 8.95 | 8.35 | 1.50 |
| FL__1717 | Validation | 2.01 | Dead | 9.35 | 8.88 | 1.98 |
| FL__1718 | Training | 10.35 | Alive | 9.23 | 8.13 | 0.26 |
| FL__1719 | Validation | 7.70 | Dead | 9.13 | 8.50 | 1.49 |
| FL__1720 | Training | 3.91 | Dead | 8.78 | 8.88 | 3.33 |
| FL__1729 | Training | 8.06 | Alive | 9.35 | 8.65 | 1.39 |
| FL__1732 | Validation | 0.71 | Dead | 7.81 | 8.59 | 4.86 |
| FL__1761 | Validation | 10.83 | Alive | 9.31 | 8.55 | 1.22 |
| FL__1764 | Training | 0.42 | Dead | 9.25 | 8.87 | 2.21 |
| FL__1768 | Training | 13.04 | Alive | 9.42 | 8.47 | 0.72 |
| FL__1771 | Training | 9.26 | Dead | 9.09 | 8.67 | 2.06 |
| FL__1772 | Validation | 13.64 | Dead | 9.49 | 8.49 | 0.61 |
| FL__1788 | Training | 1.00 | Dead | 9.09 | 9.13 | 3.29 |
| FL__1790 | Training | 1.42 | Alive | 9.85 | 9.40 | 2.22 |
| FL__1792 | Validation | 2.01 | Dead | 9.33 | 8.72 | 1.61 |
| FL__1795 | Training | 0.71 | Dead | 10.19 | 9.27 | 1.08 |
| FL__1797 | Validation | 7.17 | Alive | 9.34 | 8.92 | 2.14 |
| FL__1799 | Training | 14.18 | Alive | 9.32 | 8.63 | 1.38 |
| FL__1810 | Validation | 9.91 | Alive | 8.66 | 8.41 | 2.35 |
| FL__1811 | Validation | 3.04 | Alive | 9.38 | 8.27 | 0.29 |
| FL__1825 | Training | 2.98 | Alive | 9.46 | 9.07 | 2.25 |
| FL__1827 | Training | 3.66 | Alive | 9.80 | 8.84 | 0.83 |
| FL__1828 | Validation | 11.51 | Alive | 8.99 | 8.09 | 0.72 |
| FL__1829 | Validation | 4.11 | Alive | 9.57 | 8.73 | 1.08 |
| FL__1830 | Validation | 5.65 | Dead | 9.01 | 8.68 | 2.25 |
| FL__1833 | Training | 11.95 | Alive | 9.74 | 8.67 | 0.51 |
| FL__1834 | Validation | 15.92 | Alive | 9.22 | 8.72 | 1.88 |
| FL__1835 | Validation | 12.49 | Alive | 9.26 | 8.83 | 2.10 |
| FL__1836 | Validation | 12.24 | Alive | 9.55 | 8.64 | 0.85 |
| FL__1837 | Validation | 0.55 | Dead | 9.47 | 8.84 | 1.62 |
| FL__1838 | Validation | 2.54 | Alive | 9.90 | 9.12 | 1.34 |
| FL__1839 | Training | 4.48 | Alive | 8.56 | 8.32 | 2.34 |

TABLE 2361-continued

| Sample ID # | Set | Length of follow-up (years) | Status at follow-up | Immune response-1 signature value | Immune response-2 signature value | Survival predictor score |
|---|---|---|---|---|---|---|
| FL_1841 | Training | 0.88 | Dead | 9.32 | 9.10 | 2.66 |
| FL_1842 | Validation | 4.56 | Alive | 9.73 | 8.87 | 1.07 |
| FL_1844 | Validation | 13.39 | Alive | 9.41 | 8.55 | 0.98 |
| FL_1845 | Training | 12.92 | Dead | 9.89 | 9.04 | 1.16 |
| FL_1846 | Validation | 1.80 | Dead | 9.79 | 9.61 | 2.93 |
| FL_1848 | Training | 12.52 | Alive | 9.76 | 8.81 | 0.82 |
| FL_1851 | Training | 4.08 | Dead | 9.43 | 9.01 | 2.18 |
| FL_1853 | Validation | 12.50 | Alive | 9.28 | 8.54 | 1.25 |
| FL_1854 | Validation | 13.81 | Alive | 9.32 | 8.84 | 1.98 |
| FL_1855 | Validation | 9.96 | Dead | 9.31 | 8.39 | 0.75 |
| FL_1857 | Validation | 8.39 | Dead | 9.80 | 9.14 | 1.65 |
| FL_1861 | Validation | 3.19 | Dead | 9.47 | 8.57 | 0.88 |
| FL_1862 | Validation | 7.22 | Dead | 8.96 | 8.33 | 1.44 |
| FL_1863 | Validation | 10.77 | Dead | 9.31 | 8.85 | 2.00 |
| FL_1864 | Training | 14.25 | Alive | 9.98 | 9.12 | 1.17 |
| FL_1866 | Training | 10.72 | Dead | 9.93 | 8.94 | 0.79 |
| FL_1870 | Validation | 6.41 | Dead | 10.01 | 9.22 | 1.36 |
| FL_1873 | Training | 7.78 | Dead | 9.39 | 8.66 | 1.30 |
| FL_1874 | Validation | 3.15 | Dead | 9.38 | 8.74 | 1.53 |
| FL_1876 | Validation | 15.07 | Alive | 9.59 | 8.72 | 0.98 |
| FL_1879 | Training | 7.13 | Dead | 9.25 | 8.62 | 1.53 |
| FL_1880 | Validation | 12.84 | Dead | 8.82 | 8.35 | 1.82 |
| FL_1882 | Training | 8.84 | Dead | 9.43 | 8.76 | 1.49 |
| FL_1884 | Validation | 11.92 | Dead | 9.48 | 9.14 | 2.41 |
| FL_1885 | Validation | 15.49 | Alive | 9.70 | 8.85 | 1.11 |
| FL_1887 | Training | 5.14 | Dead | 9.47 | 8.57 | 0.87 |
| FL_1888 | Training | 15.08 | Alive | 9.83 | 8.97 | 1.11 |
| FL_1890 | Training | 3.03 | Dead | 9.29 | 9.05 | 2.60 |
| FL_1894 | Training | 11.37 | Dead | 9.01 | 8.64 | 2.13 |
| FL_1896 | Training | 12.03 | Alive | 9.80 | 8.56 | 0.08 |
| FL_1897 | Training | 9.63 | Alive | 9.02 | 8.33 | 1.29 |
| FL_1898 | Training | 5.20 | Alive | 8.82 | 8.25 | 1.54 |
| FL_1900 | Validation | 7.38 | Alive | 9.13 | 8.26 | 0.85 |
| FL_1903 | Validation | 28.25 | Alive | 9.07 | 8.46 | 1.54 |
| FL_1904 | Validation | 7.36 | Alive | 9.16 | 8.53 | 1.50 |
| FL_1905 | Validation | 3.68 | Dead | 9.25 | 8.38 | 0.87 |
| FL_1906 | Training | 2.35 | Dead | 8.04 | 8.69 | 4.56 |
| FL_1907 | Validation | 2.35 | Dead | 8.11 | 8.21 | 3.11 |
| FL_1910 | Training | 13.84 | Alive | 9.36 | 8.72 | 1.56 |
| FL_1912 | Validation | 0.73 | Dead | 9.30 | 9.21 | 3.02 |
| FL_1913 | Training | 2.57 | Alive | 9.77 | 8.51 | 0.01 |
| FL_1916 | Validation | 11.61 | Alive | 9.22 | 8.49 | 1.24 |
| FL_1918 | Validation | 9.95 | Dead | 9.54 | 8.77 | 1.26 |
| FL_1919 | Training | 10.84 | Dead | 9.51 | 8.81 | 1.44 |
| FL_735 | Validation | 11.05 | Dead | 8.81 | 8.23 | 1.53 |
| FL_738 | Validation | 10.15 | Dead | 9.19 | 8.79 | 2.13 |
| FL_739 | Training | 10.80 | Dead | 9.29 | 8.77 | 1.85 |
| FL_878 | Validation | 3.87 | Dead | 8.85 | 8.54 | 2.26 |
| FL_879 | Training | 4.34 | Dead | 8.95 | 8.74 | 2.56 |
| FL_886 | Validation | 3.29 | Alive | 9.43 | 8.72 | 1.40 |
| FL_888 | Validation | 1.32 | Dead | 8.76 | 8.49 | 2.34 |
| FL_1627 | Training | NA | NA | 9.60 | 8.51 | 0.40 |
| FL_1429 | Training | NA | NA | 8.69 | 8.28 | 1.93 |
| FL_1850 | Validation | NA | NA | 9.75 | 8.83 | 0.92 |
| FL_1735 | Validation | NA | NA | 7.32 | 8.30 | 5.24 |

Figure 5:
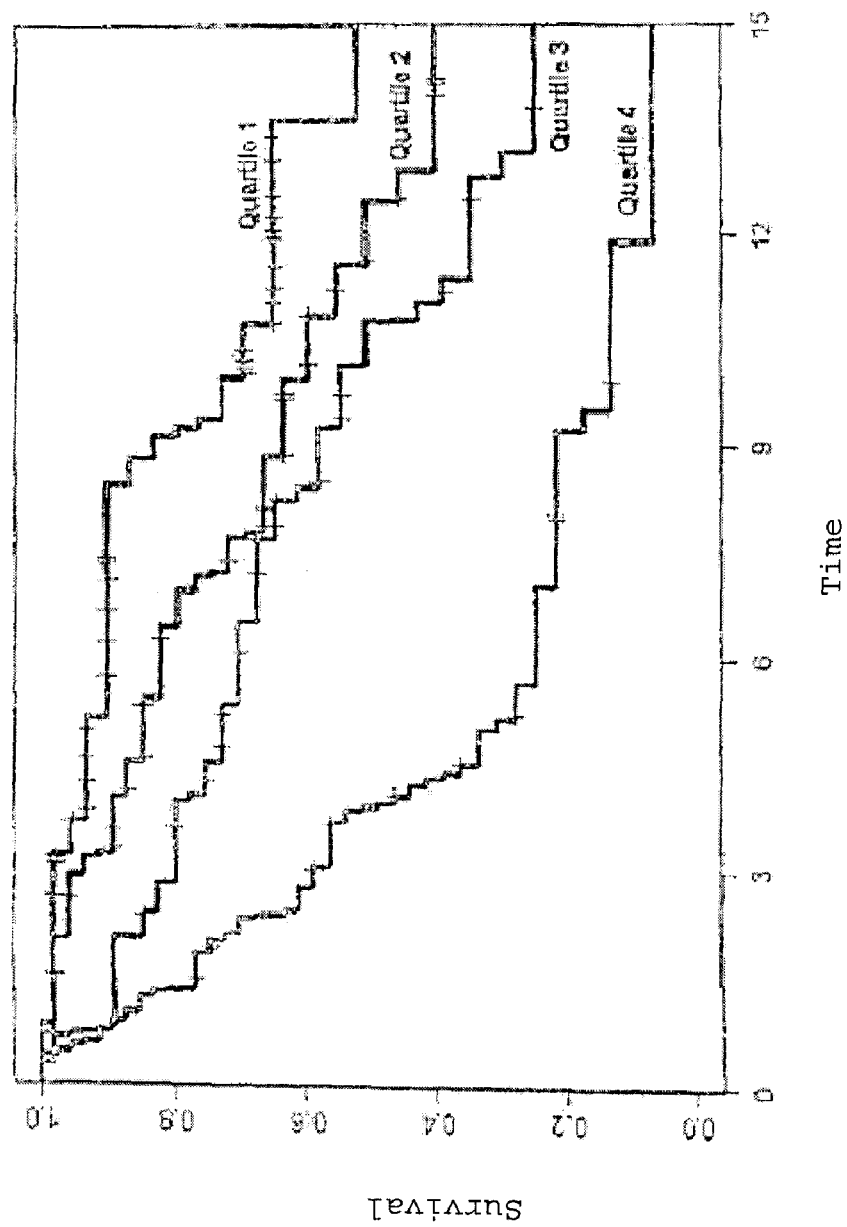
FIG. 5: Kaplan-Meier plot of survival in FL samples based on survival predictor scores. 191 FL samples were divided into quartiles based on their survival predictor scores. The survival predictor scores were calculated using the equation.

In order to visualize the predictive power of the model, the FL samples were ranked according to their survival predictor scores and divided into four quartiles. Kaplan-Meier plots of overall survival showed clear differences in survival rate in the validation set (FIG. 5). The median survival for each of the four quartiles is set forth in Table 2362.

TABLE 2362

| Quartile | Median survival (years) |
|---|---|
| 1 | 13.6 |
| 2 | 11.1 |
| 3 | 10.8 |
| 4 | 3.9 |

Various clinical variables were found to be significantly associated with survival, including the IPI and some of its components and the presence of B-symptoms. The gene expression-based model was independent of each of these variables at predicting survival. These clinical variables and the relative risk of death associated with each are summarized in Table 2363.

TABLE 2363

| Clinical variable | Criteria | % of patients[1] Training set | % of patients[1] Validation set | Univariate (clinical variable only) relative risk of death among patients in validation set | | Multivariate (clinical variable + survival predictor score) relative risk of death among patients in validation set | |
|---|---|---|---|---|---|---|---|
| | | | | RR[2] (95% C.I.) | p-value | RR[2] (95% C.I.) | p-value |
| Age | 60 | 64.5 | 70.2 | 1.90 (1.02-3.56) | 0.044 | 2.21 (1.48-3.29) | <0.001 |
| | >60 | 35.5 | 29.8 | | | | |
| Stage | I-II | 33.3 | 25 | 1.31 (0.65-2.64) | 0.447 | 2.31 (1.51-3.52) | <0.001 |
| | III-IV | 66.7 | 75 | | | | |
| Extranodal sites (#) | 2 | 5.4 | 20.2 | 1.58 (0.83-2.99) | 0.163 | 2.21 (1.48-3.30) | <0.001 |
| | <2 | 94.6 | 79.8 | | | | |
| LDH | Normal | 77.1 | 66.2 | 1.77 (0.97-3.24) | 0.065 | 2.40 (1.57-3.67) | <0.001 |
| | Greater than normal | 22.9 | 33.8 | | | | |
| ECOG performance status | 2 | 9.4 | 12.5 | 2.05 (0.89-4.71) | 0.090 | 2.17 (1.40-3.35) | <0.001 |
| | <2 | 90.6 | 87.5 | | | | |
| Gender | Male | 42 | 65 | 1.62 (0.90-2.90) | 0.105 | 2.17 (1.45-3.25) | <0.001 |
| | Female | 58 | 35 | | | | |
| B-symptoms | Present | 17.2 | 21.3 | 2.05 (1.08-3.89) | 0.029 | 2.10 (1.37-3.23) | <0.001 |
| | Absent | 82.8 | 78.7 | | | | |
| Grade[3] | 1 | 45 | 43.4 | N/A | 0.118 | 2.55 (1.63-3.99) | <0.001 |
| | 2 | 34.8 | 33.3 | 2.03 (1.04-3.96) | | | |
| | 3 | 20.2 | 23.3 | 1.39 (0.65-2.98) | | | |
| Int'l. Prognostic Index[4] | Scores 0-1 | 63.1 | 47.5 | N/A | 0.029 | 2.28 (1.46-3.57) | <0.001 |
| | Scores 2-3 | 33.3 | 45 | 2.07 (1.07-4.00) | | | |
| | Scores 4-5 | 3.6 | 7.5 | 3.73 (1.18-11.18) | | | |

[1] Due to rounding, percentages may not total 100
[2] Relative risk of death (RR) based on 2-fold increase in expression
[3] RR for grades 2 and 3 calculated with respect to risk of death for grade 1. The p-value is calculated for all grades.
[4] RR for scores 2-3 and 4-5 calculated with respect to risk of death for scores 0-1. The p-value is calculated for all grades.

The samples in the validation set were divided into three groups based on their IPI score, and the relationship between survival and IPI score was visualized by Kaplan-Meier plot (FIG. 6). Among validation set samples from the low-risk (IPI 0-1) and intermediate risk (IPI 2-3) IPI groups, the gene-expression-based survival predictor could stratify patients into groups differing by more than 5 years with regards to median survival (FIG. 7). The high-risk IPI group (IPI 4-5) comprised less than 5% of the samples, and was omitted from this analysis. These results demonstrate that the gene expression-based model is not merely acting as a surrogate for clinical variables that are known to predict survival in FL, but rather it identifies distinct biological attributes of the tumors that are associated with survival.

Example 4

Development of a Second FL Survival Predictor Using Gene Expression Data from Affymetrix U133A and U133B Microarrays 191 FL were divided into two equivalent groups: a training set (95 samples) for developing the survival prediction model, and a validation set (96 samples) for evaluating the reproducibility of the model. Gene expression data from Affymetrix U133A and U133B microarrays was obtained for each of the samples. A Cox proportional hazards model was used to identify survival predictor genes whose expression levels were associated with long survival (good prognosis genes) or short survival (poor prognosis genes) in the training set. The correlation between expression and survival for each gene on the microarrays is provided in the final two columns of Table 1710. The first of these two columns ("FL_Cox_coefficient") provides a Cox coefficient indicating the extent to which a 2-fold increase in expression of a particular gene affects mortality. A positive Cox coefficient indicates increasing mortality with increasing expression of the gene, while a negative Cox coefficient indicates decreasing mortality with increasing expression of the gene. The second of these two columns provides a Cox p-value indicating the estimated probability that the increase or decrease in survival associated with the gene would occur by chance if there was no connection between the expression of the gene and survival.

A hierarchical clustering algorithm (Eisen 1998) was used to identify gene expression signatures within the good and poor prognosis genes according to their expression pattern across all samples. Eight clusters of coordinately regulated genes were observed within the good prognosis gene set and six clusters were observed in the poor prognosis gene sets. The expression level of every component gene in each of these gene expression signatures was averaged to create a gene expression signature value. After averaging, only ten of the gene expression signatures were found to be significantly associated with survival in the training set (p<0.01). To create a multivariate model of survival, different combinations of these ten gene expression signature averages were generated and evaluated for their ability to predict survival within the training set. Among models consisting of two signatures, an exceptionally strong statistical synergy was noted between one signature from the good prognosis group and one from the poor prognosis group. These gene expression signatures were termed "T-cell" and "macrophage" based on the biological function of certain genes within each signature. The T-cell gene expression signature included genes that were typically expressed in T-cells, while the macrophage gene expression signature included a number of genes typically expressed in macrophages. Although these two signatures taken individually were not the best predictors of survival, the binary model formed by combining the two was more predictive than any combination of three signatures that did not contain these two signatures. Using these two signatures as an anchor, other signatures were added to the model using a step up procedure (Drapner 1966). Only one of the remaining eight signatures, termed the B-cell differentiation signature, contributed significantly to the model in the training set (p=0.054). The B-cell differentiation signature included a number of genes that appear to be involved in B-cell signal transduction. Table 2364 lists the genes that were used to generate the gene expression signature values for the T-cell, macrophage, and B-cell differentiation gene expression signatures.

TABLE 2364

| Signature | UNIQID | Unigene ID Build 167 | Gene symbol |
|---|---|---|---|
| B-cell differentiation | 1119350 | 331141 | ALDH2 |
| B-cell differentiation | 1130922 | 459987 | ANP32B |
| B-cell differentiation | 1130923 | 459987 | ANP32B |
| B-cell differentiation | 1099291 | 130774 | C9orf105 |
| B-cell differentiation | 1102859 | 446195 | FLJ42418 |
| B-cell differentiation | 1120976 | 245644 | GCHFR |
| B-cell differentiation | 1098862 | 303669 | MGC26694 |
| B-cell differentiation | 1111070 | 202201 | |
| B-cell differentiation | 1105935 | | |
| B-cell differentiation | 1139017 | 274424 | NANS |
| B-cell differentiation | 1108988 | 3532 | NLK |
| B-cell differentiation | 1114726 | 3532 | NLK |
| B-cell differentiation | 1097897 | 266175 | PAG |
| B-cell differentiation | 1097901 | 266175 | PAG |
| B-cell differentiation | 1119813 | 155342 | PRKCD |
| B-cell differentiation | 1123298 | 20191 | SIAH2 |
| B-cell differentiation | 1101439 | 63335 | TERF2 |
| B-cell differentiation | 1120316 | 63335 | TERF2 |
| B-cell differentiation | 1096035 | 105794 | UGCGL1 |
| T-cell | 1134945 | 81897 | KIAA1128 |
| T-cell | 1134069 | 405667 | CD8B1 |
| T-cell | 1137809 | 405667 | CD8B1 |
| T-cell | 1119251 | 433941 | SEPW1 |
| T-cell | 1096579 | 117339 | HCST |
| T-cell | 1101004 | 2969 | SKI |
| T-cell | 1137137 | 195464 | FLNA |
| T-cell | 1100871 | 48353 | |
| T-cell | 1139461 | 14770 | BIN2 |
| T-cell | 1128395 | 7188 | SEMA4C |
| T-cell | 1119880 | 442844 | FMOD |
| T-cell | 1130676 | 194431 | KIAA0992 |
| T-cell | 1130668 | 194431 | KIAA0992 |
| T-cell | 1135968 | 119000 | ACTN1 |
| T-cell | 1097329 | 528675 | TEAD1 |
| T-cell | 1098548 | 436639 | NFIC |
| T-cell | 1123038 | 119000 | ACTN1 |
| T-cell | 1128356 | 415792 | C1RL |
| T-cell | 1133408 | 12802 | DDEF2 |
| T-cell | 1140524 | 10784 | C6orf37 |
| T-cell | 1119838 | 469951 | GNAQ |
| T-cell | 1097255 | 380144 | |
| T-cell | 1098152 | 377588 | KIAA1450 |

TABLE 2364-continued

| Signature | UNIQID | Unigene ID Build 167 | Gene symbol |
|---|---|---|---|
| T-cell | 1115194 | 270737 | TNFSF13B |
| T-cell | 1124760 | 419149 | JAM3 |
| T-cell | 1120267 | 256278 | TNFRSF1B |
| T-cell | 1137289 | 36972 | CD7 |
| T-cell | 1137534 | 36972 | CD7 |
| T-cell | 1097307 | 379754 | LOC340061 |
| T-cell | 1123613 | 97087 | CD3Z |
| T-cell | 1121720 | 80642 | STAT4 |
| T-cell | 1120196 | 173802 | TBC1D4 |
| T-cell | 1136087 | 211576 | ITK |
| T-cell | 1132104 | 173802 | TBC1D4 |
| T-cell | 1140391 | 44865 | LEF1 |
| T-cell | 1098405 | 362807 | IL7R |
| T-cell | 1135743 | 299558 | TNFRSF25 |
| T-cell | 1136048 | 299558 | TNFRSF25 |
| T-cell | 1123875 | 428 | FLT3LG |
| T-cell | 1098893 | 43577 | ATP8B2 |
| T-cell | 1097561 | 19221 | C20orf112 |
| T-cell | 1122956 | 113987 | LGALS2 |
| T-cell | 1121406 | | TNFSF12 |
| T-cell | 1125532 | | |
| T-cell | 1138538 | 2014 | TRD |
| T-cell | 1103303 | 49605 | C9orf52 |
| T-cell | 1119924 | 32309 | INPP1 |
| Macrophage | 1123682 | 114408 | TLR5 |
| Macrophage | 1099124 | 355455 | SEPT10 |
| Macrophage | 1123401 | 50130 | NDN |
| Macrophage | 1134379 | 150833 | C4A |
| Macrophage | 1137481 | 150833 | C4A |
| Macrophage | 1132220 | 448805 | GPRC5B |
| Macrophage | 1119400 | 181046 | DUSP3 |
| Macrophage | 1131119 | 349656 | SCARB2 |
| Macrophage | 1123566 | 155935 | C3AR1 |
| Macrophage | 1138443 | 77424 | FCGR1A |
| Macrophage | 1127943 | 9641 | C1QA |
| Macrophage | 1119998 | 8986 | C1QB |
| Macrophage | 1132433 | 14732 | ME1 |
| Macrophage | 1119260 | 18069 | LGMN |
| Macrophage | 1098278 | 166017 | MITF |

The three signatures were used to generate a survival predictor score using the following equation:

Survival predictor score=[2.053*(macrophage gene expression signature value)]−[2.344*(T-cell gene expression signature value)]−[0.729*(B-cell differentiation gene expression signature value)].

A higher survival predictor score was associated with worse outcome. According to a likelihood ratio test adjusted for the number of variables included, this model was significant in predicting survival in both the training set ($p=1.8 \times 10^{-8}$) and the validation set ($p=2.0 \times 10^{-5}$). For the 187 FL samples with available clinical data, the survival predictor score had a mean of −11.9 and a standard deviation of 0.9418, with each unit increase in the predictor score corresponding to a 2.5 fold increase in the relative risk of death. Data for all 191 samples is shown in Table 2365.

TABLE 2365

| Sample ID # | Set | B cell differentiation signature value | T-cell signature value | Macrophage signature value | Survival predictor score |
|---|---|---|---|---|---|
| FL__1073 | Training | 9.70 | 9.14 | 8.58 | −10.89 |
| FL__1074 | Training | 11.11 | 9.06 | 8.52 | −11.84 |
| FL__1075 | Validation | 11.23 | 8.92 | 8.75 | −11.15 |
| FL__1076 | Training | 10.02 | 9.21 | 8.59 | −11.25 |
| FL__1077 | Training | 9.94 | 9.77 | 8.44 | −12.82 |
| FL__1078 | Training | 10.67 | 9.32 | 8.21 | −12.76 |

TABLE 2365-continued

| Sample ID # | Set | B cell differentiation signature value | T-cell signature value | Macrophage signature value | Survival predictor score |
|---|---|---|---|---|---|
| FL_1080 | Training | 10.62 | 9.44 | 8.88 | −11.64 |
| FL_1081 | Validation | 10.38 | 9.00 | 8.09 | −12.04 |
| FL_1083 | Training | 10.29 | 9.77 | 8.74 | −12.47 |
| FL_1085 | Validation | 9.87 | 9.24 | 8.43 | −11.55 |
| FL_1086 | Validation | 10.03 | 9.50 | 9.02 | −11.06 |
| FL_1087 | Training | 9.83 | 9.98 | 9.37 | −11.31 |
| FL_1088 | Validation | 10.57 | 9.21 | 8.29 | −12.27 |
| FL_1089 | Training | 10.30 | 9.38 | 8.27 | −12.53 |
| FL_1090 | Validation | 9.74 | 9.24 | 8.20 | −11.93 |
| FL_1097 | Validation | 9.57 | 9.82 | 8.80 | −11.93 |
| FL_1098 | Validation | 11.08 | 9.40 | 8.97 | −11.69 |
| FL_1099 | Training | 10.23 | 9.70 | 9.12 | −11.46 |
| FL_1102 | Validation | 9.66 | 9.46 | 8.90 | −10.93 |
| FL_1104 | Training | 10.72 | 9.19 | 8.20 | −12.53 |
| FL_1106 | Validation | 11.11 | 9.17 | 9.57 | −9.96 |
| FL_1107 | Training | 9.70 | 9.42 | 9.55 | −9.54 |
| FL_1183 | Training | 9.85 | 9.25 | 8.44 | −11.54 |
| FL_1184 | Training | 10.12 | 9.57 | 8.86 | −11.63 |
| FL_1185 | Validation | 10.75 | 9.21 | 9.13 | −10.68 |
| FL_1186 | Training | 9.76 | 8.88 | 8.83 | −9.80 |
| FL_1416 | Validation | 9.94 | 9.45 | 8.59 | −11.77 |
| FL_1417 | Training | 10.12 | 8.53 | 8.43 | −10.08 |
| FL_1418 | Validation | 9.35 | 8.86 | 8.27 | −10.59 |
| FL_1419 | Training | 10.20 | 9.76 | 8.53 | −12.81 |
| FL_1422 | Training | 10.22 | 9.48 | 8.40 | −12.43 |
| FL_1425 | Validation | 9.61 | 8.89 | 8.58 | −10.23 |
| FL_1426 | Training | 10.80 | 9.06 | 8.13 | −12.41 |
| FL_1427 | Training | 10.27 | 8.56 | 8.13 | −10.87 |
| FL_1428 | Validation | 10.76 | 9.25 | 8.38 | −12.32 |
| FL_1432 | Training | 10.51 | 9.17 | 9.04 | −10.59 |
| FL_1436 | Training | 9.69 | 9.40 | 8.61 | −11.42 |
| FL_1440 | Training | 9.82 | 9.04 | 8.21 | −11.50 |
| FL_1445 | Training | 9.24 | 8.69 | 8.62 | −9.41 |
| FL_1450 | Validation | 9.70 | 9.88 | 10.37 | −8.93 |
| FL_1472 | Validation | 10.78 | 8.96 | 8.51 | −11.40 |
| FL_1473 | Training | 9.99 | 9.70 | 8.41 | −12.75 |
| FL_1474 | Validation | 10.21 | 9.27 | 9.05 | −10.59 |
| FL_1476 | Validation | 9.82 | 9.44 | 8.78 | −11.27 |
| FL_1477 | Training | 9.32 | 9.61 | 9.03 | −10.78 |
| FL_1478 | Validation | 10.19 | 9.60 | 8.81 | −11.83 |
| FL_1479 | Training | 10.69 | 8.78 | 9.09 | −9.71 |
| FL_1480 | Training | 10.10 | 9.42 | 8.70 | −11.57 |
| FL_1579 | Training | 10.15 | 8.82 | 8.24 | −11.15 |
| FL_1580 | Training | 10.31 | 9.59 | 8.50 | −12.54 |
| FL_1581 | Training | 9.91 | 8.96 | 9.05 | −9.66 |
| FL_1582 | Validation | 9.73 | 8.31 | 8.06 | −10.03 |
| FL_1583 | Training | 10.95 | 9.45 | 8.86 | −11.95 |
| FL_1584 | Training | 9.98 | 9.38 | 8.46 | −11.89 |
| FL_1585 | Validation | 10.53 | 8.88 | 8.46 | −11.11 |
| FL_1586 | Validation | 10.00 | 9.30 | 8.42 | −11.81 |
| FL_1588 | Training | 9.59 | 9.41 | 8.94 | −10.68 |
| FL_1589 | Training | 10.29 | 9.68 | 8.73 | −12.27 |
| FL_1591 | Training | 10.44 | 9.45 | 8.56 | −12.18 |
| FL_1594 | Validation | 10.01 | 9.25 | 8.56 | −11.41 |
| FL_1595 | Training | 9.61 | 9.75 | 9.65 | −10.07 |
| FL_1598 | Validation | 11.18 | 8.80 | 8.31 | −11.71 |
| FL_1599 | Validation | 10.55 | 9.48 | 8.60 | −12.24 |
| FL_1603 | Training | 9.40 | 9.60 | 9.77 | −9.31 |
| FL_1604 | Training | 9.92 | 9.21 | 8.90 | −10.54 |
| FL_1606 | Validation | 9.87 | 9.45 | 9.17 | −10.52 |
| FL_1607 | Validation | 9.76 | 9.37 | 8.50 | −11.63 |
| FL_1608 | Validation | 9.92 | 8.90 | 8.39 | −10.85 |
| FL_1610 | Validation | 10.02 | 9.38 | 9.74 | −9.30 |
| FL_1611 | Validation | 10.18 | 9.41 | 8.69 | −11.64 |
| FL_1616 | Training | 9.62 | 9.33 | 8.85 | −10.71 |
| FL_1617 | Validation | 9.90 | 8.95 | 8.39 | −10.98 |
| FL_1619 | Validation | 9.98 | 9.37 | 8.47 | −11.85 |
| FL_1620 | Validation | 9.43 | 8.95 | 8.12 | −11.19 |
| FL_1622 | Validation | 9.84 | 9.15 | 8.31 | −11.56 |
| FL_1623 | Training | 9.95 | 9.61 | 8.97 | −11.37 |
| FL_1624 | Validation | 10.55 | 9.06 | 8.43 | −11.61 |
| FL_1625 | Validation | 10.00 | 8.89 | 8.23 | −11.22 |
| FL_1626 | Validation | 11.05 | 8.62 | 8.10 | −11.62 |
| FL_1628 | Validation | 10.08 | 9.81 | 8.66 | −12.57 |
| FL_1637 | Validation | 9.77 | 9.95 | 9.59 | −10.76 |
| FL_1638 | Validation | 10.25 | 9.20 | 9.07 | −10.41 |
| FL_1639 | Training | 10.29 | 9.52 | 8.99 | −11.35 |
| FL_1643 | Training | 9.80 | 9.72 | 9.00 | −11.46 |
| FL_1644 | Validation | 9.51 | 9.46 | 8.61 | −11.43 |
| FL_1645 | Training | 9.39 | 9.46 | 8.70 | −11.15 |
| FL_1646 | Training | 9.90 | 9.25 | 8.52 | −11.42 |
| FL_1647 | Training | 9.51 | 9.12 | 8.95 | −9.92 |
| FL_1648 | Training | 10.02 | 9.18 | 7.86 | −12.67 |
| FL_1652 | Training | 9.62 | 9.39 | 9.19 | −10.16 |
| FL_1654 | Validation | 10.32 | 8.59 | 8.10 | −11.02 |
| FL_1655 | Training | 10.12 | 9.53 | 8.75 | −11.74 |
| FL_1656 | Validation | 10.54 | 9.08 | 8.55 | −11.42 |
| FL_1657 | Training | 10.53 | 9.53 | 8.55 | −12.46 |
| FL_1660 | Training | 10.24 | 8.75 | 8.27 | −10.99 |
| FL_1661 | Validation | 10.08 | 9.85 | 9.00 | −11.97 |
| FL_1662 | Validation | 9.85 | 9.56 | 9.49 | −10.11 |
| FL_1664 | Validation | 10.16 | 9.35 | 8.48 | −11.92 |
| FL_1669 | Validation | 9.48 | 8.76 | 8.28 | −10.45 |
| FL_1670 | Training | 9.76 | 9.66 | 9.66 | −9.92 |
| FL_1675 | Training | 10.57 | 9.28 | 8.41 | −12.18 |
| FL_1681 | Validation | 10.48 | 9.52 | 8.66 | −12.19 |
| FL_1683 | Validation | 9.88 | 9.92 | 9.07 | −11.83 |
| FL_1684 | Training | 9.64 | 9.53 | 8.85 | −11.20 |
| FL_1716 | Validation | 9.90 | 8.91 | 8.22 | −11.23 |
| FL_1717 | Validation | 9.87 | 9.34 | 8.95 | −10.71 |
| FL_1718 | Training | 10.00 | 9.21 | 7.98 | −12.49 |
| FL_1719 | Validation | 9.87 | 9.06 | 8.42 | −11.14 |
| FL_1720 | Training | 10.70 | 8.77 | 8.92 | −10.05 |
| FL_1729 | Training | 10.50 | 9.23 | 8.65 | −11.53 |
| FL_1732 | Validation | 9.91 | 7.68 | 8.54 | −7.69 |
| FL_1761 | Validation | 9.81 | 9.22 | 8.39 | −11.54 |
| FL_1764 | Training | 9.81 | 9.24 | 8.77 | −10.80 |
| FL_1768 | Training | 10.12 | 9.36 | 8.50 | −11.86 |
| FL_1771 | Training | 9.92 | 9.12 | 8.68 | −10.79 |
| FL_1772 | Validation | 9.72 | 9.42 | 8.43 | −11.87 |
| FL_1788 | Training | 9.65 | 9.05 | 9.12 | −9.51 |
| FL_1790 | Training | 9.58 | 9.83 | 9.48 | −10.56 |
| FL_1792 | Validation | 9.79 | 9.29 | 8.67 | −11.11 |
| FL_1795 | Training | 9.58 | 10.18 | 9.33 | −11.69 |
| FL_1797 | Validation | 9.93 | 9.26 | 8.79 | −10.90 |
| FL_1799 | Training | 10.49 | 9.28 | 8.64 | −11.65 |
| FL_1810 | Validation | 10.06 | 8.55 | 8.21 | −10.52 |
| FL_1811 | Validation | 9.84 | 9.37 | 8.08 | −12.56 |
| FL_1825 | Training | 10.49 | 9.44 | 9.03 | −11.24 |
| FL_1827 | Training | 10.06 | 9.76 | 8.84 | −12.08 |
| FL_1828 | Validation | 10.55 | 8.93 | 7.67 | −12.87 |
| FL_1829 | Validation | 9.85 | 9.58 | 8.65 | −11.87 |
| FL_1830 | Validation | 10.80 | 8.99 | 8.67 | −11.15 |
| FL_1833 | Training | 10.41 | 9.83 | 8.82 | −12.52 |
| FL_1834 | Validation | 10.81 | 9.25 | 8.63 | −11.85 |
| FL_1835 | Validation | 9.36 | 9.25 | 8.91 | −10.21 |
| FL_1836 | Validation | 10.58 | 9.58 | 8.61 | −12.50 |
| FL_1837 | Validation | 10.22 | 9.47 | 8.76 | −11.68 |
| FL_1838 | Validation | 10.51 | 9.89 | 9.19 | −11.98 |
| FL_1839 | Training | 10.79 | 8.54 | 8.19 | −11.09 |
| FL_1841 | Training | 10.32 | 9.31 | 9.18 | −10.48 |
| FL_1842 | Validation | 10.36 | 9.69 | 8.92 | −11.95 |
| FL_1844 | Validation | 10.92 | 9.43 | 8.49 | −12.65 |
| FL_1845 | Training | 9.87 | 9.87 | 9.06 | −11.73 |
| FL_1846 | Validation | 9.66 | 9.81 | 8.70 | −9.63 |
| FL_1848 | Training | 9.82 | 9.74 | 8.70 | −12.14 |
| FL_1851 | Training | 9.89 | 9.47 | 9.03 | −10.87 |
| FL_1853 | Validation | 9.96 | 9.28 | 8.54 | −11.49 |
| FL_1854 | Validation | 9.97 | 9.29 | 8.73 | −11.12 |
| FL_1855 | Validation | 9.95 | 9.33 | 8.42 | −11.85 |
| FL_1857 | Validation | 10.35 | 9.81 | 9.28 | −11.50 |
| FL_1861 | Validation | 9.73 | 9.46 | 8.43 | −11.96 |
| FL_1862 | Validation | 10.42 | 8.94 | 8.22 | −11.69 |
| FL_1863 | Validation | 10.79 | 9.29 | 8.82 | −11.54 |
| FL_1864 | Training | 9.67 | 9.97 | 9.07 | −11.80 |
| FL_1866 | Training | 10.19 | 9.88 | 8.89 | −12.33 |
| FL_1870 | Validation | 9.78 | 10.07 | 9.30 | −11.63 |
| FL_1873 | Training | 10.09 | 9.41 | 8.77 | −11.40 |

TABLE 2365-continued

| Sample ID # | Set | B cell differentiation signature value | T-cell signature value | Macrophage signature value | Survival predictor score |
|---|---|---|---|---|---|
| FL__1874 | Validation | 10.05 | 9.33 | 8.69 | −11.37 |
| FL__1876 | Validation | 10.15 | 9.59 | 8.67 | −12.08 |
| FL__1879 | Training | 9.73 | 9.21 | 8.58 | −11.06 |
| FL__1880 | Validation | 10.02 | 8.79 | 8.35 | −10.77 |
| FL__1882 | Training | 9.59 | 9.44 | 8.80 | −11.05 |
| FL__1884 | Validation | 9.76 | 9.51 | 9.26 | −10.38 |
| FL__1885 | Validation | 10.48 | 9.66 | 8.75 | −12.32 |
| FL__1887 | Training | 9.98 | 9.42 | 8.47 | −11.96 |
| FL__1888 | Training | 9.73 | 9.83 | 8.99 | −11.67 |
| FL__1890 | Training | 10.06 | 9.33 | 8.98 | −10.76 |
| FL__1894 | Training | 9.85 | 8.99 | 8.75 | −10.29 |
| FL__1896 | Training | 10.21 | 9.80 | 8.51 | −12.94 |
| FL__1897 | Training | 10.67 | 8.99 | 8.26 | −11.90 |
| FL__1898 | Training | 9.59 | 8.77 | 8.21 | −10.68 |
| FL__1900 | Validation | 10.12 | 9.10 | 8.10 | −12.08 |
| FL__1903 | Validation | 11.08 | 8.99 | 8.39 | −11.93 |
| FL__1904 | Validation | 10.20 | 9.16 | 8.30 | −11.87 |
| FL__1905 | Validation | 9.73 | 9.21 | 8.22 | −11.80 |
| FL__1906 | Training | 9.95 | 8.15 | 8.44 | −9.01 |
| FL__1907 | Validation | 10.12 | 7.95 | 7.99 | −9.62 |
| FL__1910 | Training | 11.03 | 9.38 | 8.74 | −12.10 |
| FL__1912 | Validation | 9.83 | 9.38 | 9.36 | −9.95 |
| FL__1913 | Training | 9.81 | 9.75 | 8.43 | −12.69 |
| FL__1916 | Validation | 9.83 | 9.18 | 8.40 | −11.43 |
| FL__1918 | Validation | 9.86 | 9.52 | 8.79 | −11.45 |
| FL__1919 | Training | 9.87 | 9.53 | 8.79 | −11.48 |
| FL__735 | Validation | 10.48 | 8.73 | 8.23 | −11.20 |
| FL__738 | Validation | 11.05 | 9.10 | 8.75 | −11.43 |
| FL__739 | Training | 9.66 | 9.25 | 8.74 | −10.78 |
| FL__878 | Validation | 10.61 | 8.92 | 8.65 | −10.89 |
| FL__879 | Training | 9.92 | 8.94 | 8.78 | −10.14 |
| FL__886 | Validation | 10.16 | 9.41 | 8.63 | −11.73 |
| FL__888 | Validation | 9.35 | 8.76 | 8.38 | −10.15 |
| FL__1627 | Training | 9.82 | 9.48 | 8.49 | −11.94 |
| FL__1429 | Training | 10.06 | 8.70 | 8.14 | −11.01 |
| FL__1850 | Validation | 9.58 | 9.73 | 8.70 | −11.93 |
| FL__1735 | Validation | 9.60 | 7.46 | 8.42 | −7.19 |

In order to visualize the predictive power of the model, the FL samples were ranked according to their survival predictor scores and divided into four quartiles. Kaplan-Meier plots of overall survival showed clear differences in survival rate in the validation set (FIG. 8). The median survival for each of the four quartiles is set forth in Table 2366.

TABLE 2366

| Quartile | Median survival (yrs.) | 5-year survival | 10-year survival |
|---|---|---|---|
| 1 | NR | 94% | 79% |
| 2 | 11.6 | 82% | 62% |
| 3 | 8.8 | 69% | 39% |
| 4 | 3.9 | 38% | 22% |

Example 5

Development of a Third FL Survival Predictor Using Gene Expression Data from the Lymph Dx Microarray 191 FL samples were divided into two equivalent groups: a training set for developing the survival prediction model, and a validation set for evaluating the reproducibility of the model. Gene expression data from the Lymph Dx microarray was obtained for those genes listed in Table 2364, above. This gene expression data was used to calculate gene expression signature values for the macrophage, T-cell, and B-cell differentiation gene expression signatures, and these signature values were used to generate a survival predictor score using the following equation:

Survival predictor score=[1.51*(macrophage gene expression signature value)]−[2.11*(T-cell gene expression signature value)]−[0.505*(B-cell differentiation gene expression signature value)].

A higher survival predictor score was associated with worse outcome. For the 187 FL samples with available clinical data, the survival predictor score had a mean of −10.1 and a standard deviation of 0.69, with each unit increase in the predictor score corresponding to a 2.7 fold increase in the relative risk of death. Data for all 191 samples is shown in Table 2367.

TABLE 2367

| Sample ID # | Set | B cell differentiation signature value | T-cell signature value | Macrophage signature value | Survival predictor score |
|---|---|---|---|---|---|
| FL__1073 | Training | 8.26 | 8.17 | 7.36 | −10.30 |
| FL__1074 | Training | 9.53 | 8.12 | 7.56 | −10.53 |
| FL__1075 | Validation | 9.81 | 8.00 | 7.99 | −9.77 |
| FL__1076 | Training | 8.46 | 8.10 | 7.62 | −9.86 |
| FL__1077 | Training | 8.45 | 8.66 | 7.32 | −11.49 |
| FL__1078 | Training | 9.23 | 8.32 | 7.32 | −11.18 |
| FL__1080 | Training | 9.18 | 8.37 | 7.86 | −10.42 |
| FL__1081 | Validation | 8.96 | 8.01 | 6.94 | −10.96 |
| FL__1083 | Training | 8.72 | 8.65 | 7.89 | −10.75 |
| FL__1085 | Validation | 8.34 | 8.17 | 7.54 | −10.07 |
| FL__1086 | Validation | 8.50 | 8.35 | 7.94 | −9.94 |
| FL__1087 | Training | 8.02 | 8.88 | 8.48 | −10.00 |
| FL__1088 | Validation | 9.10 | 8.15 | 7.38 | −10.65 |
| FL__1089 | Training | 8.76 | 8.31 | 7.35 | −10.86 |
| FL__1090 | Validation | 8.18 | 8.23 | 7.43 | −10.28 |
| FL__1097 | Validation | 8.07 | 8.81 | 7.90 | −10.73 |
| FL__1098 | Training | 9.53 | 8.30 | 8.09 | −10.11 |
| FL__1099 | Training | 8.44 | 8.56 | 8.26 | −9.86 |
| FL__1102 | Validation | 7.92 | 8.43 | 7.94 | −9.80 |
| FL__1104 | Training | 9.17 | 8.07 | 7.21 | −10.78 |
| FL__1106 | Validation | 9.71 | 8.15 | 8.77 | −8.85 |
| FL__1107 | Training | 8.16 | 8.44 | 8.60 | −8.95 |
| FL__1183 | Training | 8.49 | 8.15 | 7.23 | −10.56 |
| FL__1184 | Training | 8.81 | 8.49 | 7.91 | −10.43 |
| FL__1185 | Validation | 9.31 | 8.19 | 8.06 | −9.80 |
| FL__1186 | Training | 8.43 | 7.87 | 7.83 | −9.04 |
| FL__1416 | Validation | 8.42 | 8.34 | 7.63 | −10.34 |
| FL__1417 | Training | 8.65 | 7.51 | 7.05 | −9.58 |
| FL__1418 | Validation | 7.96 | 7.82 | 7.22 | −9.62 |
| FL__1419 | Training | 8.80 | 8.71 | 7.55 | −11.43 |
| FL__1422 | Training | 8.63 | 8.35 | 7.39 | −10.83 |
| FL__1425 | Validation | 8.21 | 7.92 | 7.62 | −9.36 |
| FL__1426 | Training | 9.39 | 8.09 | 7.15 | −11.01 |
| FL__1427 | Training | 8.66 | 7.51 | 7.00 | −9.65 |
| FL__1428 | Validation | 9.33 | 8.18 | 7.39 | −10.81 |
| FL__1432 | Training | 8.98 | 8.17 | 7.93 | −9.81 |
| FL__1436 | Training | 8.04 | 8.17 | 7.35 | −10.20 |
| FL__1440 | Training | 8.29 | 7.82 | 7.15 | −9.89 |
| FL__1445 | Training | 8.04 | 7.78 | 7.63 | −8.94 |
| FL__1450 | Validation | 8.25 | 8.81 | 9.52 | −8.39 |
| FL__1472 | Validation | 9.29 | 7.88 | 7.33 | −10.26 |
| FL__1473 | Training | 8.49 | 8.57 | 7.52 | −11.03 |
| FL__1474 | Validation | 8.59 | 8.09 | 8.53 | −8.54 |
| FL__1476 | Validation | 8.25 | 8.39 | 7.71 | −10.23 |
| FL__1477 | Training | 7.94 | 8.57 | 7.88 | −10.21 |
| FL__1478 | Training | 8.57 | 8.40 | 7.88 | −10.16 |
| FL__1479 | Training | 9.15 | 7.83 | 7.87 | −9.27 |
| FL__1480 | Training | 8.25 | 8.38 | 7.44 | −10.63 |
| FL__1579 | Training | 8.70 | 7.73 | 7.43 | −9.48 |
| FL__1580 | Training | 8.86 | 8.46 | 7.64 | −10.79 |
| FL__1581 | Training | 8.41 | 7.89 | 8.08 | −8.69 |
| FL__1582 | Validation | 8.20 | 7.42 | 6.99 | −9.24 |
| FL__1583 | Training | 9.34 | 8.34 | 7.94 | −10.32 |
| FL__1584 | Training | 8.50 | 8.33 | 7.75 | −10.17 |
| FL__1585 | Validation | 9.08 | 7.96 | 7.72 | −9.72 |

TABLE 2367-continued

| Sample ID # | Set | B cell differentiation signature value | T-cell signature value | Macrophage signature value | Survival predictor score |
|---|---|---|---|---|---|
| FL__1586 | Validation | 8.52 | 8.25 | 7.36 | −10.61 |
| FL__1588 | Training | 7.97 | 8.35 | 7.73 | −9.98 |
| FL__1589 | Training | 8.85 | 8.48 | 7.76 | −10.66 |
| FL__1591 | Training | 8.92 | 8.36 | 7.77 | −10.42 |
| FL__1594 | Validation | 8.54 | 8.22 | 7.74 | −9.96 |
| FL__1595 | Training | 8.05 | 8.82 | 8.68 | −9.57 |
| FL__1598 | Validation | 9.74 | 7.81 | 6.97 | −10.88 |
| FL__1599 | Validation | 9.13 | 8.42 | 7.69 | −10.77 |
| FL__1603 | Training | 7.97 | 8.66 | 8.90 | −8.86 |
| FL__1604 | Training | 8.47 | 8.14 | 7.75 | −9.75 |
| FL__1606 | Validation | 8.34 | 8.32 | 8.11 | −9.51 |
| FL__1607 | Validation | 8.33 | 8.30 | 7.39 | −10.57 |
| FL__1608 | Validation | 8.35 | 7.88 | 6.98 | −10.31 |
| FL__1610 | Validation | 8.48 | 8.35 | 8.86 | −8.52 |
| FL__1611 | Validation | 8.54 | 8.33 | 7.64 | −10.37 |
| FL__1616 | Training | 8.03 | 8.39 | 7.67 | −10.18 |
| FL__1617 | Validation | 8.30 | 7.85 | 7.52 | −9.40 |
| FL__1619 | Validation | 8.53 | 8.31 | 7.64 | −10.32 |
| FL__1620 | Validation | 8.09 | 7.99 | 7.17 | −10.11 |
| FL__1622 | Training | 8.14 | 8.10 | 7.36 | −10.09 |
| FL__1623 | Training | 8.45 | 8.52 | 8.15 | −9.93 |
| FL__1624 | Validation | 9.13 | 8.12 | 7.46 | −10.49 |
| FL__1625 | Validation | 8.53 | 7.94 | 7.17 | −10.23 |
| FL__1626 | Validation | 9.63 | 7.67 | 7.17 | −10.22 |
| FL__1628 | Validation | 8.63 | 8.76 | 7.95 | −10.86 |
| FL__1637 | Validation | 8.07 | 8.81 | 8.79 | −9.38 |
| FL__1638 | Validation | 8.52 | 8.18 | 8.19 | −9.18 |
| FL__1639 | Training | 8.70 | 8.33 | 7.89 | −10.06 |
| FL__1643 | Training | 8.26 | 8.62 | 8.01 | −10.26 |
| FL__1644 | Validation | 8.28 | 8.33 | 7.77 | −10.02 |
| FL__1645 | Training | 7.84 | 8.32 | 7.68 | −9.91 |
| FL__1646 | Training | 8.40 | 8.26 | 7.71 | −10.01 |
| FL__1647 | Training | 8.10 | 8.04 | 7.92 | −9.10 |
| FL__1648 | Training | 8.33 | 8.08 | 6.87 | −10.90 |
| FL__1652 | Training | 8.15 | 8.33 | 8.37 | −9.07 |
| FL__1654 | Validation | 8.67 | 7.62 | 7.03 | −9.85 |
| FL__1655 | Training | 8.53 | 8.41 | 7.75 | −10.36 |
| FL__1656 | Validation | 9.09 | 8.09 | 7.62 | −10.16 |
| FL__1657 | Training | 8.95 | 8.44 | 7.58 | −10.89 |
| FL__1660 | Training | 8.82 | 7.79 | 7.26 | −9.93 |
| FL__1661 | Validation | 8.56 | 8.79 | 8.17 | −10.53 |
| FL__1662 | Validation | 8.30 | 8.47 | 8.69 | −8.93 |
| FL__1664 | Validation | 8.62 | 8.23 | 7.56 | −10.31 |
| FL__1669 | Validation | 7.89 | 7.67 | 7.39 | −9.02 |
| FL__1670 | Training | 8.01 | 8.54 | 8.64 | −9.03 |
| FL__1675 | Training | 9.00 | 8.21 | 7.36 | −10.76 |
| FL__1681 | Validation | 8.83 | 8.39 | 7.59 | −10.72 |
| FL__1683 | Validation | 8.14 | 8.85 | 7.97 | −10.74 |
| FL__1684 | Validation | 7.99 | 8.42 | 7.84 | −9.97 |
| FL__1716 | Validation | 8.28 | 7.90 | 7.26 | −9.88 |
| FL__1717 | Validation | 8.27 | 8.21 | 7.89 | −9.60 |
| FL__1718 | Training | 8.50 | 8.17 | 7.15 | −10.75 |
| FL__1719 | Validation | 8.35 | 8.02 | 7.21 | −10.26 |
| FL__1720 | Training | 9.03 | 7.65 | 8.01 | −8.61 |
| FL__1729 | Training | 8.97 | 8.27 | 7.69 | −10.37 |
| FL__1732 | Validation | 8.49 | 6.82 | 7.71 | −7.02 |
| FL__1761 | Validation | 8.36 | 8.19 | 7.29 | −10.49 |
| FL__1764 | Training | 8.52 | 8.24 | 7.94 | −9.69 |
| FL__1768 | Training | 8.70 | 8.25 | 7.63 | −10.28 |
| FL__1771 | Training | 8.55 | 8.19 | 7.65 | −10.04 |
| FL__1772 | Validation | 8.30 | 8.38 | 7.41 | −10.71 |
| FL__1788 | Training | 8.14 | 8.06 | 8.11 | −8.87 |
| FL__1790 | Training | 7.95 | 8.69 | 8.36 | −9.74 |
| FL__1792 | Validation | 8.16 | 8.20 | 7.64 | −9.88 |
| FL__1795 | Training | 7.94 | 9.08 | 8.37 | −10.54 |
| FL__1797 | Validation | 8.17 | 8.21 | 7.87 | −9.57 |
| FL__1799 | Training | 9.02 | 8.21 | 7.77 | −10.14 |
| FL__1810 | Validation | 8.43 | 7.52 | 7.06 | −9.47 |
| FL__1811 | Validation | 8.33 | 8.24 | 7.07 | −10.93 |
| FL__1825 | Training | 8.90 | 8.39 | 7.97 | −10.18 |
| FL__1827 | Training | 8.47 | 8.77 | 7.96 | −10.76 |
| FL__1828 | Validation | 9.13 | 7.87 | 6.76 | −11.01 |
| FL__1829 | Validation | 8.34 | 8.51 | 7.59 | −10.71 |
| FL__1830 | Validation | 9.26 | 8.04 | 7.62 | −10.13 |
| FL__1833 | Training | 8.82 | 8.86 | 7.88 | −11.26 |
| FL__1834 | Validation | 9.25 | 8.17 | 7.62 | −10.39 |
| FL__1835 | Validation | 7.71 | 8.16 | 8.01 | −9.02 |
| FL__1836 | Validation | 9.06 | 8.52 | 7.59 | −11.09 |
| FL__1837 | Validation | 8.57 | 8.33 | 7.37 | −10.79 |
| FL__1838 | Validation | 8.78 | 8.72 | 8.04 | −10.69 |
| FL__1839 | Training | 9.27 | 7.36 | 7.37 | −9.08 |
| FL__1841 | Training | 8.66 | 8.35 | 8.17 | −9.64 |
| FL__1842 | Validation | 8.62 | 8.50 | 8.02 | −10.19 |
| FL__1844 | Validation | 9.37 | 8.40 | 7.47 | −11.18 |
| FL__1845 | Training | 8.33 | 8.84 | 8.30 | −10.32 |
| FL__1846 | Validation | 8.11 | 8.75 | 9.06 | −8.89 |
| FL__1848 | Training | 8.19 | 8.60 | 7.91 | −10.33 |
| FL__1851 | Training | 8.37 | 8.50 | 8.15 | −9.84 |
| FL__1853 | Validation | 8.37 | 8.14 | 7.43 | −10.19 |
| FL__1854 | Validation | 8.50 | 8.29 | 7.96 | −9.78 |
| FL__1855 | Validation | 8.63 | 8.34 | 7.54 | −10.58 |
| FL__1857 | Validation | 8.73 | 8.82 | 8.45 | −10.26 |
| FL__1861 | Validation | 8.21 | 8.50 | 7.50 | −10.77 |
| FL__1862 | Validation | 8.98 | 7.96 | 7.31 | −10.28 |
| FL__1863 | Validation | 9.30 | 8.22 | 7.86 | −10.18 |
| FL__1864 | Training | 8.13 | 8.93 | 8.27 | −10.46 |
| FL__1866 | Training | 8.62 | 8.78 | 7.91 | −10.93 |
| FL__1870 | Validation | 8.16 | 8.97 | 8.52 | −10.18 |
| FL__1873 | Training | 8.55 | 8.30 | 8.00 | −9.74 |
| FL__1874 | Validation | 8.43 | 8.20 | 7.59 | −10.10 |
| FL__1876 | Validation | 8.48 | 8.52 | 7.70 | −10.64 |
| FL__1879 | Training | 8.29 | 8.21 | 7.66 | −9.94 |
| FL__1880 | Validation | 8.56 | 7.76 | 7.34 | −9.61 |
| FL__1882 | Training | 8.02 | 8.40 | 7.71 | −10.14 |
| FL__1884 | Validation | 8.14 | 8.46 | 8.42 | −9.24 |
| FL__1885 | Validation | 8.88 | 8.57 | 7.78 | −10.81 |
| FL__1887 | Training | 8.38 | 8.39 | 7.38 | −10.78 |
| FL__1888 | Training | 8.14 | 8.74 | 8.07 | −10.37 |
| FL__1890 | Training | 8.45 | 8.24 | 8.11 | −9.41 |
| FL__1894 | Validation | 8.38 | 7.97 | 7.82 | −9.25 |
| FL__1896 | Training | 8.63 | 8.71 | 7.52 | −11.37 |
| FL__1897 | Training | 9.01 | 7.91 | 6.93 | −10.78 |
| FL__1898 | Training | 8.08 | 7.75 | 7.09 | −9.74 |
| FL__1900 | Validation | 8.61 | 7.94 | 6.84 | −10.77 |
| FL__1903 | Validation | 9.63 | 7.96 | 7.30 | −10.64 |
| FL__1904 | Validation | 8.79 | 8.14 | 7.15 | −10.82 |
| FL__1905 | Validation | 8.22 | 8.24 | 7.36 | −10.43 |
| FL__1906 | Training | 8.40 | 7.40 | 7.24 | −8.93 |
| FL__1907 | Validation | 8.61 | 7.11 | 6.59 | −9.40 |
| FL__1910 | Training | 9.47 | 8.28 | 7.63 | −10.73 |
| FL__1912 | Validation | 8.32 | 8.45 | 8.52 | −9.18 |
| FL__1913 | Training | 8.24 | 8.60 | 7.23 | −11.41 |
| FL__1916 | Validation | 8.31 | 8.04 | 7.27 | −10.19 |
| FL__1918 | Validation | 8.30 | 8.49 | 7.78 | −10.37 |
| FL__1919 | Training | 8.05 | 8.42 | 8.00 | −9.75 |
| FL__735 | Validation | 9.03 | 7.83 | 7.41 | −9.88 |
| FL__738 | Validation | 9.54 | 8.07 | 7.65 | −10.30 |
| FL__739 | Training | 8.14 | 8.09 | 7.69 | −9.57 |
| FL__878 | Validation | 9.17 | 7.91 | 7.70 | −9.69 |
| FL__879 | Training | 8.37 | 7.96 | 7.67 | −9.45 |
| FL__886 | Validation | 8.59 | 8.38 | 7.67 | −10.44 |
| FL__888 | Validation | 7.85 | 7.71 | 7.07 | −9.56 |
| FL__1627 | Training | 8.26 | 8.17 | 7.36 | −10.30 |
| FL__1429 | Training | 9.53 | 8.12 | 7.56 | −10.53 |
| FL__1850 | Validation | 9.81 | 8.00 | 7.99 | −9.77 |
| FL__1735 | Validation | 8.46 | 8.10 | 7.62 | −9.86 |

In order to visualize the predictive power of the model, the FL samples were ranked according to their survival predictor scores and divided into four quartiles. Kaplan-Meier plots of overall survival showed clear differences in survival rate in the validation set (FIG. 9).

Example 6

Development of a First DLBCL Survival Predictor Using Gene Expression Data from Affymetrix U133A and U133B Microarrays Gene expression data from Affymetrix U133A and U133B microarrays was obtained for 231 DLBCL samples. The follow-up time and status at follow-up for each of the subjects from whom these samples were acquired is listed in Table 2368. Table 2368 also indicates which samples were used in creating the survival predictor.

TABLE 2368

| Sample ID # | Length of follow-up (years) | Status at follow-up | Used in creating survival predictor? |
| --- | --- | --- | --- |
| ABC_1000 | 0.69 | Dead | Yes |
| ABC_1002 | 0.28 | Dead | Yes |
| ABC_1023 | 5.57 | Dead | Yes |
| ABC_1027 | 0.25 | Dead | Yes |
| ABC_1031 | 6.64 | Dead | Yes |
| ABC_1034 | 2.31 | Dead | Yes |
| ABC_1038 | 0.71 | Dead | Yes |
| ABC_1043 | 2.31 | Dead | Yes |
| ABC_1045 | 2.26 | Dead | Yes |
| ABC_1055 | 7.81 | Alive | Yes |
| ABC_1057 | 2.13 | Dead | Yes |
| ABC_1059 | 2.00 | Dead | Yes |
| ABC_1061 | 1.04 | Dead | Yes |
| ABC_1946 | 0.68 | Dead | No |
| ABC_1994 | 1.21 | Dead | No |
| ABC_2001 | 1.32 | Dead | No |
| ABC_304 | 1.31 | Dead | Yes |
| ABC_305 | 0.82 | Alive | Yes |
| ABC_309 | 2.80 | Alive | Yes |
| ABC_413 | 0.60 | Dead | Yes |
| ABC_428 | 11.38 | Alive | Yes |
| ABC_432 | 0.38 | Dead | Yes |
| ABC_446 | 2.82 | Dead | Yes |
| ABC_462 | 7.49 | Dead | Yes |
| ABC_477 | 1.70 | Dead | Yes |
| ABC_481 | 10.75 | Alive | Yes |
| ABC_482 | 7.72 | Alive | Yes |
| ABC_538 | 0.34 | Dead | Yes |
| ABC_541 | 4.11 | Alive | Yes |
| ABC_544 | 1.31 | Dead | Yes |
| ABC_547 | 0.05 | Dead | Yes |
| ABC_577 | 1.65 | Alive | Yes |
| ABC_616 | 0.99 | Dead | Yes |
| ABC_626 | 2.49 | Dead | Yes |
| ABC_633 | 2.02 | Alive | Yes |
| ABC_642 | 0.34 | Dead | Yes |
| ABC_644 | 0.31 | Dead | Yes |
| ABC_645 | 6.08 | Dead | Yes |
| ABC_646 | 2.59 | Dead | Yes |
| ABC_651 | 2.34 | Alive | Yes |
| ABC_652 | 0.01 | Dead | Yes |
| ABC_660 | 0.20 | Dead | Yes |
| ABC_663 | 0.62 | Dead | Yes |
| ABC_668 | 6.44 | Alive | Yes |
| ABC_676 | 1.00 | Dead | Yes |
| ABC_678 | 0.06 | Dead | Yes |
| ABC_687 | 0.94 | Dead | Yes |
| ABC_689 | 2.54 | Dead | Yes |
| ABC_692 | 10.53 | Alive | Yes |
| ABC_694 | 4.83 | Alive | Yes |
| ABC_700 | 5.40 | Dead | Yes |
| ABC_702 | 4.13 | Dead | Yes |
| ABC_704 | 9.67 | Alive | Yes |
| ABC_709 | 0.47 | Dead | Yes |
| ABC_712 | 3.26 | Dead | Yes |
| ABC_714 | 2.45 | Dead | Yes |
| ABC_717 | 0.42 | Dead | Yes |
| ABC_725 | 0.96 | Dead | Yes |
| ABC_726 | 7.62 | Alive | Yes |
| ABC_730 | 1.03 | Dead | Yes |
| ABC_753 | 0.04 | Dead | Yes |
| ABC_756 | 7.21 | Alive | Yes |
| ABC_771 | 6.80 | Dead | Yes |
| ABC_779 | 0.35 | Dead | Yes |
| ABC_800 | 0.33 | Dead | Yes |
| ABC_807 | 0.31 | Dead | Yes |
| ABC_809 | 0.51 | Dead | Yes |
| ABC_816 | 1.86 | Dead | Yes |
| ABC_820 | 1.59 | Dead | Yes |
| ABC_823 | 0.16 | Dead | Yes |
| ABC_835 | 1.22 | Dead | Yes |
| ABC_839 | 0.29 | Dead | Yes |
| ABC_841 | 10.14 | Alive | Yes |
| ABC_858 | 3.58 | Dead | Yes |
| ABC_872 | 5.00 | Alive | Yes |
| ABC_875 | 8.45 | Alive | Yes |
| ABC_912 | 16.79 | Alive | Yes |
| ABC_996 | 0.21 | Dead | Yes |
| GCB_1005 | 5.77 | Alive | Yes |
| GCB_1008 | 6.46 | Alive | Yes |
| GCB_1009 | 9.68 | Alive | Yes |
| GCB_1021 | 14.59 | Alive | Yes |
| GCB_1025 | 2.86 | Dead | Yes |
| GCB_1026 | 6.94 | Dead | Yes |
| GCB_1037 | 0.23 | Dead | Yes |
| GCB_1039 | 2.05 | Dead | Yes |
| GCB_1049 | 1.33 | Dead | Yes |
| GCB_1051 | 0.12 | Dead | Yes |
| GCB_1058 | 0.42 | Dead | Yes |
| GCB_1060 | 6.45 | Alive | Yes |
| GCB_1990 | 0.06 | Dead | No |
| GCB_1991 | 1.01 | Dead | No |
| GCB_2017 | 0.08 | Dead | No |
| GCB_2018 | 0.17 | Dead | No |
| GCB_2095 | 0.97 | Alive | No |
| GCB_412 | 12.12 | Alive | Yes |
| GCB_415 | 5.38 | Dead | Yes |
| GCB_421 | 1.24 | Dead | Yes |
| GCB_424 | 10.62 | Dead | Yes |
| GCB_433 | 0.76 | Dead | Yes |
| GCB_434 | 10.53 | Alive | Yes |
| GCB_438 | 8.15 | Alive | Yes |
| GCB_459 | 9.65 | Alive | Yes |
| GCB_470 | 11.17 | Alive | Yes |
| GCB_479 | 7.24 | Alive | Yes |
| GCB_492 | 11.29 | Alive | Yes |
| GCB_517 | 3.03 | Dead | Yes |
| GCB_523 | 8.36 | Alive | Yes |
| GCB_524 | 5.88 | Alive | Yes |
| GCB_529 | 1.06 | Dead | Yes |
| GCB_533 | 0.71 | Dead | Yes |
| GCB_537 | 4.99 | Dead | Yes |
| GCB_543 | 3.47 | Alive | Yes |
| GCB_545 | 1.10 | Dead | Yes |
| GCB_549 | 2.68 | Dead | Yes |
| GCB_550 | 21.78 | Alive | Yes |
| GCB_553 | 0.82 | Dead | Yes |
| GCB_565 | 9.11 | Dead | Yes |
| GCB_572 | 14.24 | Alive | Yes |
| GCB_617 | 5.88 | Alive | Yes |
| GCB_618 | 5.65 | Alive | Yes |
| GCB_619 | 8.76 | Alive | Yes |
| GCB_623 | 2.43 | Alive | Yes |
| GCB_627 | 1.27 | Dead | Yes |
| GCB_654 | 7.37 | Alive | Yes |
| GCB_661 | 0.56 | Alive | Yes |
| GCB_669 | 7.11 | Alive | Yes |

TABLE 2368-continued

| Sample ID # | Length of follow-up (years) | Status at follow-up | Used in creating survival predictor? |
|---|---|---|---|
| GCB_672 | 6.78 | Alive | Yes |
| GCB_674 | 7.22 | Alive | Yes |
| GCB_675 | 6.02 | Alive | Yes |
| GCB_681 | 9.70 | Alive | Yes |
| GCB_688 | 0.33 | Dead | Yes |
| GCB_695 | 0.15 | Dead | Yes |
| GCB_698 | 3.88 | Alive | Yes |
| GCB_701 | 3.90 | Alive | Yes |
| GCB_710 | 1.08 | Dead | Yes |
| GCB_711 | 3.93 | Dead | Yes |
| GCB_722 | 3.32 | Alive | Yes |
| GCB_724 | 1.40 | Dead | Yes |
| GCB_731 | 10.18 | Alive | Yes |
| GCB_742 | 4.09 | Alive | Yes |
| GCB_744 | 8.86 | Alive | Yes |
| GCB_745 | 1.33 | Dead | Yes |
| GCB_747 | 15.41 | Alive | Yes |
| GCB_749 | 10.40 | Alive | Yes |
| GCB_758 | 1.10 | Dead | Yes |
| GCB_772 | 2.48 | Alive | Yes |
| GCB_777 | 4.27 | Dead | Yes |
| GCB_792 | 5.53 | Alive | Yes |
| GCB_795 | 3.43 | Alive | Yes |
| GCB_797 | 6.87 | Dead | Yes |
| GCB_803 | 1.45 | Dead | Yes |
| GCB_810 | 11.72 | Alive | Yes |
| GCB_817 | 2.76 | Dead | Yes |
| GCB_818 | 0.10 | Dead | Yes |
| GCB_819 | 0.72 | Dead | Yes |
| GCB_821 | 9.47 | Alive | Yes |
| GCB_832 | 4.01 | Alive | Yes |
| GCB_836 | 4.29 | Alive | Yes |
| GCB_840 | 3.40 | Alive | Yes |
| GCB_847 | 4.16 | Alive | Yes |
| GCB_860 | 3.03 | Dead | Yes |
| GCB_871 | 0.41 | Dead | Yes |
| GCB_874 | 0.12 | Dead | Yes |
| GCB_995 | 6.65 | Alive | Yes |
| PMBL_1006 | 7.12 | Alive | Yes |
| PMBL_1024 | 19.83 | Alive | Yes |
| PMBL_1048 | 7.70 | Alive | Yes |
| PMBL_1053 | 1.04 | Dead | Yes |
| PMBL_1920 | 1.97 | Alive | No |
| PMBL_1921 | 4.16 | Alive | No |
| PMBL_1923 | 1.60 | Alive | No |
| PMBL_1924 | 6.11 | Alive | No |
| PMBL_1935 | 12.42 | Alive | No |
| PMBL_1941 | 0.71 | Alive | No |
| PMBL_1942 | 0.88 | Alive | No |
| PMBL_1943 | 8.96 | Alive | No |
| PMBL_1945 | 0.84 | Dead | No |
| PMBL_1948 | 7.96 | Alive | No |
| PMBL_1949 | 4.28 | Alive | No |
| PMBL_1989 | 1.33 | Dead | No |
| PMBL_1992 | 1.00 | Dead | No |
| PMBL_1993 | 1.33 | Dead | No |
| PMBL_2002 | 6.62 | Alive | No |
| PMBL_2019 | 0.99 | Dead | No |
| PMBL_2020 | 2.08 | Alive | No |
| PMBL_2092 | 1.27 | Alive | No |
| PMBL_484 | 1.40 | Dead | Yes |
| PMBL_546 | 0.78 | Dead | Yes |
| PMBL_570 | 14.40 | Alive | Yes |
| PMBL_621 | 8.14 | Alive | Yes |
| PMBL_638 | 0.70 | Dead | Yes |
| PMBL_691 | 0.32 | Dead | Yes |
| PMBL_791 | 1.33 | Dead | Yes |
| PMBL_824 | 12.24 | Alive | Yes |
| PMBL_906 | 16.80 | Alive | Yes |
| PMBL_994 | 4.79 | Alive | Yes |
| PMBL_998 | 9.11 | Alive | Yes |
| UC_DLBCL_1001 | 0.33 | Dead | Yes |
| UC_DLBCL_1004 | 6.72 | Alive | Yes |
| UC_DLBCL_1007 | 2.26 | Dead | Yes |
| UC_DLBCL_1018 | 0.03 | Dead | Yes |
| UC_DLBCL_1041 | 3.13 | Dead | Yes |
| UC_DLBCL_1054 | 12.34 | Alive | Yes |
| UC_DLBCL_306 | 2.69 | Alive | Yes |
| UC_DLBCL_310 | 0.97 | Alive | Yes |
| UC_DLBCL_449 | 9.16 | Alive | Yes |
| UC_DLBCL_452 | 9.17 | Alive | Yes |
| UC_DLBCL_458 | 1.18 | Dead | Yes |
| UC_DLBCL_460 | 9.02 | Alive | Yes |
| UC_DLBCL_491 | 4.47 | Dead | Yes |
| UC_DLBCL_528 | 1.64 | Alive | Yes |
| UC_DLBCL_615 | 4.94 | Alive | Yes |
| UC_DLBCL_625 | 5.24 | Alive | Yes |
| UC_DLBCL_664 | 0.62 | Dead | Yes |
| UC_DLBCL_671 | 3.35 | Alive | Yes |
| UC_DLBCL_682 | 0.11 | Dead | Yes |
| UC_DLBCL_683 | 7.42 | Alive | Yes |
| UC_DLBCL_684 | 1.92 | Dead | Yes |
| UC_DLBCL_748 | 1.01 | Dead | Yes |
| UC_DLBCL_751 | 9.99 | Alive | Yes |
| UC_DLBCL_808 | 0.37 | Dead | Yes |
| UC_DLBCL_831 | 11.02 | Dead | Yes |
| UC_DLBCL_834 | 1.64 | Dead | Yes |
| UC_DLBCL_838 | 0.00 | Dead | Yes |
| UC_DLBCL_851 | 0.05 | Dead | Yes |
| UC_DLBCL_854 | 1.51 | Dead | Yes |
| UC_DLBCL_855 | 1.67 | Alive | Yes |
| UC_DLBCL_856 | 0.60 | Dead | Yes |

The correlation between expression of each gene represented on the microarrays and survival was estimated using a Cox proportional hazards model. The results of this survival analysis are provided in the final two columns of Table 1723. The first of these two columns ("DLBCL_Cox_coefficient") provides a Cox coefficient indicating the extent to which a 2-fold increase in expression of a particular gene affects mortality. A positive Cox coefficient indicates increasing mortality with increasing expression of the gene, while a negative Cox coefficient indicates decreasing mortality with increasing expression of the gene. The second of these two columns ("DLBCL_Cox_P_value") provides a Cox p-value indicating the estimated probability that the increase or decrease in survival associated with the gene would occur by chance if there was no connection between the expression of the gene and survival.

Genes that were significantly correlated with survival ($p<0.001$) were grouped into gene expression signatures using a hierarchical clustering algorithm. The expression level of every component gene in each of these gene expression signatures was averaged for each sample to create a gene expression signature value. A step-up procedure (Drapner 1966) was applied to determine the optimal number of gene signatures to use in the survival predictor model. First, the gene expression signature that was most significantly associated with survival was included in the model. Next, the gene expression signature with the second highest association with survival was added to the model to form a two-component model. This procedure was repeated until there was no gene expression signature to add to the model with a p-value of $<0.05$.

The final prediction model incorporated gene expression signature values from three gene expression signatures. The first gene expression signature added to the model was termed "ABC DLBCL high," because it included genes that were more highly expressed in ABC than in GCB (Rosenwald 2002). The second gene expression signature added to the model was termed "lymph node," because it reflected the response of non-tumor cells in the lymph node to the malignant lymphoma cells. The final gene expression signature added to the model was termed "MHC class II," because it included all of the genes encoding the MHC class II alpha and beta chains. Table 2369 shows the genes that were averaged to form each of these signatures.

TABLE 2369

| Signature | UNIQID | Gene symbol | Survival p-value |
|---|---|---|---|
| ABC DLBCL high | 1134271 | POU5F1 | 3.09E−05 |
| ABC DLBCL high | 1121564 | DRIL1 | 4.06E−05 |
| ABC DLBCL high | 1119889 | PDCD4 | 7.28E−05 |
| ABC DLBCL high | 1133300 | CTH | 1.23E−04 |
| ABC DLBCL high | 1106030 | MGC: 50789 | 1.70E−04 |
| ABC DLBCL high | 1139301 | FLJ20150 | 4.49E−04 |
| ABC DLBCL high | 1122131 | CHST7 | 5.18E−04 |
| ABC DLBCL high | 1114824 | LIMD1 | 5.20E−04 |
| ABC DLBCL high | 1100161 | LOC142678 | 6.24E−04 |
| ABC DLBCL high | 1120129 | TLE1 | 6.95E−04 |
| Lymph node | 1097126 | TEM8 | 5.14E−09 |
| Lymph node | 1120880 | LTBP2 | 9.80E−07 |
| Lymph node | 1098898 | FLJ31066 | 1.09E−06 |
| Lymph node | 1123376 | RARRES2 | 1.68E−06 |
| Lymph node | 1128945 | SLC12A8 | 2.90E−06 |
| Lymph node | 1130994 | DPYSL3 | 3.37E−06 |
| Lymph node | 1124429 | SULF1 | 3.53E−06 |
| Lymph node | 1099358 | FLJ39971 | 4.09E−06 |
| Lymph node | 1130509 | SPARC | 6.23E−06 |
| Lymph node | 1095985 | TMEPAI | 7.07E−06 |
| Lymph node | 1123038 | ACTN1 | 7.90E−06 |
| Lymph node | 1133700 | CDH11 | 8.20E−06 |
| Lymph node | 1122101 | TFEC | 9.66E−06 |
| Lymph node | 1124296 | SDC2 | 9.99E−06 |
| MHC Class II | 1123127 | HLA-DRA | 1.21E−06 |
| MHC Class II | 1136777 | HLA-DQA1 | 3.45E−06 |
| MHC Class II | 1137771 | HLA-DRB1 | 3.95E−06 |
| MHC Class II | 1134281 | HLA-DRB4 | 2.70E−05 |
| MHC Class II | 1136573 | HLA-DPA1 | 2.92E−05 |
| MHC Class II | 1132710 | HLA-DRB3 | 7.09E−05 |

Fitting the Cox proportional hazards model to the three gene expression signature values resulted in the following model:

Survival predictor score=[0.586*(ABC DLBCL high gene expression signature value)]−[0.468* (lymph node gene expression signature value)]− [0.336*(MHC Class II gene expression signature value)].

A higher survival predictor score was associated with worse outcome. According to a likelihood ratio test adjusted for the number of variables included, this model was significant in predicting survival at $p=2.13\times10^{-13}$. In order to visualize the predictive power of the model, the 205 samples used to create the model were ranked according to their survival predictor scores and divided into four quartiles. Kaplan-Meier plots of overall survival probability show clear differences in survival rate between these four quartiles (FIG. 10). The five-year survival probabilities for each quartile are set forth in Table 2370.

TABLE 2370

| Quartile | 5-year survival |
|---|---|
| 1 | 83% |
| 2 | 59% |
| 3 | 33% |
| 4 | 17% |

Example 7

Development of a Second DLBCL Survival Predictor Using Gene Expression Data from the Lymph Dx Microarray A DLBCL survival model based on gene expression had been developed previously using proliferation, germinal center B-cell, lymph node, and MHC class II gene expression signatures and the expression of the single gene BMP-6 (Rosenwald 2002). BMP-6 expression was poorly measured on the Lymph Dx microarray, but genes associated with each of these four gene expression signatures exhibited associations with survival similar to those observed using Lymphochip microarrays. DLBCL samples were divided into two groups: a training set (100 samples) for developing the survival prediction model, and a validation set (100 samples) for evaluating the reproducibility of the model. Gene expressed in the training set samples were clustered, and lymph node, germinal center B-cell, MHC class II, and proliferation gene expression signatures were identified. Within each signature, expression of genes that were associated with survival (p<0.01) was averaged to generate a gene expression signature value for each signature. Table 2371 lists the genes that were used to generate the gene expression signature value for each signature.

TABLE 2371

| Signature | UNIQID | Unigene ID Build 167 | Gene symbol |
|---|---|---|---|
| Germinal center B-cell | 1099686 | 117721 | |
| Germinal center B-cell | 1099711 | 243596 | |
| Germinal center B-cell | 1103390 | 271752 | BPNT1 |
| Germinal center B-cell | 1106025 | 49500 | KIAA0746 |
| Germinal center B-cell | 1128287 | 300063 | ASB13 |
| Germinal center B-cell | 1132520 | 283063 | LMO2 |
| Germinal center B-cell | 1138192 | 126608 | NR3C1 |
| Germinal center B-cell | 1529318 | 291954 | |
| Germinal center B-cell | 1529344 | 317970 | SERPINA11 |
| Germinal center B-cell | 1529352 | 446195 | |
| Germinal center B-cell | 1096570 | 409813 | ANUBL1 |
| Germinal center B-cell | 1097897 | 266175 | PAG |
| Germinal center B-cell | 1097901 | 266175 | PAG |
| Germinal center B-cell | 1098611 | 433611 | PDK1 |
| Germinal center B-cell | 1100581 | 155024 | BCL6 |
| Germinal center B-cell | 1115034 | 387222 | NEK6 |
| Germinal center B-cell | 1120090 | 155024 | BCL6 |
| Germinal center B-cell | 1120946 | 25209 | MAPK10 |
| Germinal center B-cell | 1121248 | 54089 | BARD1 |
| Germinal center B-cell | 1123105 | 434281 | PTK2 |
| Germinal center B-cell | 1125456 | 300592 | MYBL1 |
| Germinal center B-cell | 1128694 | 171466 | ELL3 |
| Germinal center B-cell | 1128787 | 114611 | C7orf10 |
| Germinal center B-cell | 1132122 | 307734 | MME |
| Germinal center B-cell | 1136269 | 101474 | MAST2 |
| Germinal center B-cell | 1136702 | 155584 | KIAA0121 |
| Germinal center B-cell | 1139230 | 29724 | PLEKHF2 |
| Germinal center B-cell | 1529292 | NA | |
| Germinal center B-cell | 1529295 | 116441 | |
| Lymph node | 1097126 | 274520 | ANTXR1 |
| Lymph node | 1099028 | 334838 | FNDC1 |
| Lymph node | 1099358 | 93135 | |
| Lymph node | 1101478 | 146246 | MGC45780 |
| Lymph node | 1103497 | 50115 | |
| Lymph node | 1121029 | 412999 | CSTA |
| Lymph node | 1124429 | 409602 | SULF1 |
| Lymph node | 1135068 | 71719 | PDLIM3 |
| Lymph node | 1136051 | 520937 | CSF2RA |
| Lymph node | 1136172 | 38084 | SULT1C1 |
| MHC class II | 1136777 | 387679 | HLA-DQA1 |
| MHC class II | 1136877 | 409934 | HLA-DQB1 |
| Proliferation | 1096903 | 437460 | FLJ10385 |
| Proliferation | 1120583 | 153768 | RNU3IP2 |
| Proliferation | 1123289 | 5409 | POLR1C |
| Proliferation | 1131808 | 75447 | RALBP1 |

TABLE 2371-continued

| Signature | UNIQID | Unigene ID Build 167 | Gene symbol |
|---|---|---|---|
| Proliferation | 1133102 | 360041 | FRDA |
| Proliferation | 1136595 | 404814 | VDAC1 |

Table 2372 lists p-values for the association of each signature with survival in the training set, the validation set, and overall.

TABLE 2372

| Signature | Training set | Validation set | Overall |
|---|---|---|---|
| Lymph node | $4.0 \times 10^{-5}$ | $2.3 \times 10^{-6}$ | $6.8 \times 10^{-10}$ |
| Proliferation | $8.1 \times 10^{-5}$ | $3.4 \times 10^{-3}$ | $2.1 \times 10^{-6}$ |
| Germinal center B-cell | $6.2 \times 10^{-6}$ | $2.1 \times 10^{-3}$ | $5.0 \times 10^{-8}$ |
| MHC class II | $2.4 \times 10^{-2}$ | $2.7 \times 10^{-3}$ | $3.1 \times 10^{-4}$ |

The four gene expression signatures were used to generate a survival predictor score using the following equation:

Survival predictor score=[−0.4337*(lymph node gene expression signature value)]+[0.09*(proliferation gene expression signature value)]−[0.4144*(germinal center B-cell gene expression signature value)]−[0.2006*(MHC class II gene expression signature value)].

A higher survival predictor score was associated with worse outcome. For the 200 DLBCL samples used to generate the model, the survival predictor score had a mean of 5.7 and a standard deviation of 0.78, with each unit increase in the predictor score corresponding to an approximately 2.7 fold increase in the relative risk of death. Data for all 200 samples is presented in Table 2373.

TABLE 2373

| Sample ID # | Set | Lymph node signature value | Proliferation signature value | Germinal center B-cell signature value | MHC class II signature value | Survival predictor score |
|---|---|---|---|---|---|---|
| ABC_1000 | Validation | 6.50 | 8.92 | 7.60 | 11.50 | −5.08 |
| ABC_1002 | Validation | 7.00 | 8.58 | 7.27 | 12.54 | −5.50 |
| ABC_1023 | Validation | 7.43 | 8.99 | 6.80 | 11.42 | −5.05 |
| ABC_1027 | Training | 5.68 | 9.00 | 6.87 | 12.31 | −4.70 |
| ABC_1031 | Validation | 8.02 | 9.00 | 7.17 | 11.68 | −5.53 |
| ABC_1034 | Validation | 6.06 | 9.61 | 6.72 | 11.83 | −4.58 |
| ABC_1038 | Training | 6.83 | 8.97 | 7.17 | 12.30 | −5.23 |
| ABC_1043 | Training | 6.96 | 9.01 | 6.77 | 12.29 | −5.11 |
| ABC_1045 | Validation | 8.18 | 8.21 | 6.77 | 12.07 | −5.66 |
| ABC_1055 | Validation | 5.58 | 9.16 | 7.30 | 13.05 | −4.76 |
| ABC_1057 | Training | 7.33 | 8.94 | 7.74 | 12.05 | −5.53 |
| ABC_1059 | Validation | 9.02 | 8.46 | 7.15 | 11.35 | −6.08 |
| ABC_1061 | Training | 7.13 | 9.18 | 7.09 | 12.28 | −5.21 |
| ABC_304 | Validation | 5.92 | 8.80 | 6.76 | 12.76 | −4.84 |
| ABC_305 | Training | 5.92 | 8.74 | 7.50 | 11.89 | −4.91 |
| ABC_309 | Validation | 8.86 | 8.39 | 7.62 | 12.53 | −6.46 |
| ABC_413 | Validation | 6.45 | 9.32 | 6.55 | 9.04 | −4.16 |
| ABC_428 | Training | 7.52 | 9.19 | 7.98 | 10.25 | −5.51 |
| ABC_432 | Validation | 6.48 | 9.33 | 7.45 | 9.56 | −4.56 |
| ABC_446 | Training | 7.91 | 9.42 | 7.41 | 10.55 | −5.46 |
| ABC_462 | Validation | 6.41 | 8.85 | 6.67 | 13.36 | −5.03 |
| ABC_477 | Validation | 6.26 | 9.02 | 6.69 | 12.45 | −4.89 |
| ABC_481 | Training | 8.18 | 8.30 | 7.35 | 11.98 | −5.91 |
| ABC_482 | Training | 8.59 | 9.01 | 7.66 | 12.35 | −6.16 |
| ABC_538 | Validation | 8.06 | 8.84 | 7.17 | 11.83 | −5.69 |
| ABC_541 | Training | 6.14 | 8.52 | 7.42 | 10.59 | −4.71 |
| ABC_544 | Training | 6.91 | 9.03 | 6.82 | 11.87 | −4.89 |
| ABC_547 | Validation | 5.80 | 8.96 | 7.14 | 11.38 | −4.60 |
| ABC_577 | Validation | 7.84 | 8.65 | 8.16 | 11.95 | −5.94 |
| ABC_616 | Validation | 6.03 | 9.05 | 7.36 | 12.64 | −4.84 |
| ABC_626 | Validation | 7.48 | 9.22 | 7.25 | 11.11 | −5.27 |
| ABC_633 | Training | 7.74 | 8.35 | 7.39 | 12.45 | −5.80 |
| ABC_642 | Training | 5.71 | 8.82 | 6.41 | 13.80 | −4.62 |
| ABC_644 | Validation | 6.64 | 9.15 | 7.05 | 13.28 | −5.20 |
| ABC_645 | Training | 8.44 | 8.81 | 7.93 | 13.39 | −6.43 |
| ABC_646 | Validation | 5.94 | 9.11 | 6.71 | 11.60 | −4.63 |
| ABC_652 | Validation | 5.87 | 8.85 | 6.88 | 12.73 | −4.77 |
| ABC_660 | Training | 5.19 | 9.34 | 6.64 | 10.17 | −3.86 |
| ABC_663 | Training | 5.69 | 9.02 | 7.33 | 12.82 | −4.91 |
| ABC_668 | Validation | 7.12 | 9.28 | 7.03 | 10.57 | −4.91 |
| ABC_676 | Training | 4.95 | 8.90 | 7.09 | 13.32 | −4.61 |
| ABC_678 | Training | 5.84 | 9.11 | 7.34 | 11.26 | −4.41 |
| ABC_687 | Validation | 5.15 | 9.89 | 6.56 | 10.46 | −3.76 |
| ABC_689 | Training | 6.49 | 8.86 | 7.10 | 12.56 | −4.88 |
| ABC_692 | Validation | 7.32 | 8.96 | 7.25 | 11.57 | −5.32 |
| ABC_694 | Validation | 8.28 | 9.21 | 8.01 | 12.41 | −6.23 |
| ABC_700 | Training | 7.29 | 8.97 | 7.55 | 12.10 | −5.48 |

TABLE 2373-continued

| Sample ID # | Set | Lymph node signature value | Proliferation signature value | Germinal center B-cell signature value | MHC class II signature value | Survival predictor score |
|---|---|---|---|---|---|---|
| ABC_702 | Validation | 7.60 | 8.66 | 6.86 | 12.55 | −5.45 |
| ABC_704 | Training | 7.07 | 8.92 | 7.03 | 12.83 | −5.35 |
| ABC_709 | Validation | 5.92 | 8.58 | 6.37 | 13.40 | −4.66 |
| ABC_712 | Validation | 5.79 | 9.12 | 6.34 | 12.02 | −4.23 |
| ABC_714 | Training | 7.49 | 8.88 | 7.49 | 11.97 | −5.54 |
| ABC_717 | Training | 7.17 | 9.45 | 7.01 | 11.34 | −5.05 |
| ABC_725 | Training | 6.71 | 9.01 | 6.52 | 12.76 | −4.86 |
| ABC_726 | Validation | 6.91 | 8.72 | 6.71 | 11.91 | −4.90 |
| ABC_730 | Validation | 6.28 | 9.22 | 7.28 | 12.14 | −4.88 |
| ABC_753 | Training | 6.84 | 9.64 | 7.05 | 13.00 | −5.22 |
| ABC_756 | Training | 7.67 | 8.45 | 7.59 | 12.48 | −5.85 |
| ABC_771 | Training | 6.98 | 8.76 | 6.91 | 12.20 | −5.18 |
| ABC_779 | Training | 6.73 | 9.32 | 6.78 | 9.82 | −4.44 |
| ABC_800 | Validation | 8.75 | 8.31 | 7.45 | 11.91 | −6.04 |
| ABC_807 | Training | 5.50 | 9.53 | 6.92 | 7.56 | −3.79 |
| ABC_809 | Training | 7.40 | 8.70 | 7.68 | 10.83 | −5.50 |
| ABC_816 | Training | 5.20 | 9.91 | 7.65 | 10.64 | −4.14 |
| ABC_820 | Training | 6.71 | 8.94 | 6.55 | 11.98 | −4.85 |
| ABC_823 | Validation | 5.58 | 9.26 | 6.44 | 10.09 | −3.97 |
| ABC_835 | Validation | 6.95 | 8.68 | 8.04 | 12.31 | −5.59 |
| ABC_839 | Training | 6.63 | 9.17 | 7.23 | 11.89 | −5.04 |
| ABC_841 | Validation | 6.35 | 9.51 | 7.52 | 13.19 | −5.28 |
| ABC_858 | Training | 7.63 | 8.51 | 7.12 | 11.74 | −5.42 |
| ABC_872 | Training | 6.78 | 8.73 | 7.41 | 12.47 | −5.44 |
| ABC_875 | Training | 7.59 | 8.81 | 7.20 | 11.26 | −5.25 |
| ABC_912 | Validation | 7.01 | 8.55 | 7.45 | 12.79 | −5.64 |
| ABC_996 | Validation | 5.00 | 9.53 | 6.70 | 10.02 | −3.94 |
| GCB_1005 | Validation | 8.28 | 8.67 | 9.11 | 13.27 | −6.98 |
| GCB_1008 | Training | 8.17 | 8.59 | 9.83 | 12.83 | −7.06 |
| GCB_1009 | Training | 6.63 | 9.02 | 10.07 | 12.28 | −6.19 |
| GCB_1021 | Validation | 6.44 | 8.83 | 9.34 | 13.20 | −6.15 |
| GCB_1025 | Validation | 7.87 | 8.48 | 9.27 | 12.37 | −6.57 |
| GCB_1026 | Training | 7.71 | 8.30 | 9.81 | 13.52 | −6.85 |
| GCB_1037 | Training | 4.95 | 8.83 | 9.35 | 12.57 | −5.22 |
| GCB_1039 | Training | 7.63 | 8.65 | 9.01 | 13.28 | −6.47 |
| GCB_1049 | Validation | 8.54 | 8.61 | 8.12 | 12.60 | −6.41 |
| GCB_1051 | Validation | 6.26 | 9.09 | 9.48 | 12.76 | −5.97 |
| GCB_1058 | Validation | 7.12 | 8.89 | 8.34 | 12.80 | −5.85 |
| GCB_1060 | Validation | 8.27 | 8.84 | 8.94 | 12.96 | −6.75 |
| GCB_412 | Training | 7.22 | 8.33 | 8.50 | 13.09 | −6.09 |
| GCB_415 | Training | 9.01 | 8.62 | 8.38 | 11.99 | −6.47 |
| GCB_421 | Training | 7.59 | 7.89 | 7.49 | 12.20 | −5.80 |
| GCB_424 | Training | 9.29 | 8.42 | 8.51 | 12.44 | −6.79 |
| GCB_433 | Training | 8.45 | 8.34 | 8.02 | 12.64 | −6.54 |
| GCB_434 | Training | 8.46 | 8.55 | 9.17 | 12.54 | −6.98 |
| GCB_438 | Validation | 8.14 | 8.71 | 9.13 | 12.51 | −6.67 |
| GCB_459 | Validation | 8.98 | 8.39 | 8.42 | 11.37 | −6.49 |
| GCB_470 | Validation | 7.72 | 8.57 | 8.67 | 12.23 | −6.12 |
| GCB_479 | Validation | 6.86 | 8.25 | 7.13 | 13.07 | −5.35 |
| GCB_492 | Training | 8.01 | 8.61 | 9.51 | 12.34 | −6.63 |
| GCB_517 | Validation | 8.57 | 8.73 | 7.99 | 12.76 | −6.48 |
| GCB_523 | Training | 5.96 | 8.56 | 8.74 | 12.77 | −5.72 |
| GCB_524 | Training | 8.51 | 8.09 | 8.76 | 12.51 | −6.57 |
| GCB_529 | Training | 5.12 | 9.17 | 8.88 | 10.77 | −4.86 |
| GCB_533 | Training | 8.88 | 8.81 | 8.36 | 12.44 | −6.60 |
| GCB_537 | Validation | 7.42 | 8.19 | 9.73 | 13.29 | −6.68 |
| GCB_543 | Validation | 8.49 | 8.02 | 8.66 | 12.06 | −6.45 |
| GCB_545 | Training | 8.65 | 8.28 | 6.90 | 12.90 | −6.13 |
| GCB_549 | Validation | 6.87 | 8.24 | 8.65 | 12.15 | −6.00 |
| GCB_550 | Validation | 8.98 | 8.29 | 8.76 | 12.24 | −6.94 |
| GCB_553 | Validation | 8.51 | 8.64 | 8.62 | 12.63 | −6.69 |
| GCB_565 | Validation | 7.97 | 8.79 | 9.79 | 13.42 | −6.98 |
| GCB_572 | Training | 7.61 | 8.60 | 9.39 | 12.58 | −6.42 |
| GCB_617 | Validation | 8.31 | 7.89 | 7.54 | 13.17 | −6.12 |
| GCB_618 | Training | 5.66 | 8.97 | 9.20 | 13.32 | −5.54 |
| GCB_619 | Validation | 7.83 | 8.65 | 9.34 | 12.12 | −6.36 |
| GCB_623 | Training | 7.16 | 8.88 | 9.26 | 12.35 | −6.21 |
| GCB_627 | Validation | 8.13 | 8.83 | 8.62 | 11.85 | −6.31 |
| GCB_654 | Training | 6.30 | 9.60 | 8.45 | 10.00 | −4.88 |
| GCB_661 | Validation | 8.46 | 8.51 | 8.18 | 12.66 | −6.33 |
| GCB_669 | Training | 7.88 | 8.65 | 8.59 | 12.32 | −6.19 |
| GCB_672 | Training | 8.29 | 8.61 | 8.14 | 12.41 | −6.21 |
| GCB_674 | Validation | 8.36 | 8.62 | 7.76 | 12.33 | −6.14 |

TABLE 2373-continued

| Sample ID # | Set | Lymph node signature value | Proliferation signature value | Germinal center B-cell signature value | MHC class II signature value | Survival predictor score |
|---|---|---|---|---|---|---|
| GCB_675 | Validation | 6.01 | 9.52 | 8.90 | 10.12 | −5.09 |
| GCB_681 | Training | 9.25 | 8.72 | 8.72 | 12.59 | −6.89 |
| GCB_688 | Validation | 6.97 | 9.01 | 9.90 | 9.94 | −5.99 |
| GCB_695 | Validation | 8.80 | 8.73 | 9.23 | 12.45 | −6.84 |
| GCB_698 | Validation | 9.27 | 8.35 | 8.85 | 11.99 | −6.96 |
| GCB_701 | Training | 7.77 | 7.93 | 8.68 | 13.10 | −6.33 |
| GCB_710 | Validation | 6.12 | 8.78 | 7.65 | 13.19 | −5.24 |
| GCB_711 | Training | 7.57 | 8.80 | 8.43 | 11.44 | −5.84 |
| GCB_722 | Training | 7.78 | 8.31 | 8.93 | 12.61 | −6.51 |
| GCB_724 | Training | 7.88 | 9.08 | 8.74 | 11.53 | −6.21 |
| GCB_731 | Validation | 7.72 | 8.92 | 9.08 | 12.20 | −6.46 |
| GCB_742 | Validation | 8.33 | 8.55 | 8.58 | 12.95 | −6.70 |
| GCB_744 | Training | 8.02 | 8.64 | 9.36 | 11.85 | −6.52 |
| GCB_745 | Training | 8.47 | 8.34 | 8.93 | 11.95 | −6.67 |
| GCB_747 | Validation | 7.64 | 8.48 | 8.32 | 13.06 | −6.27 |
| GCB_749 | Training | 7.57 | 8.61 | 9.40 | 12.55 | −6.56 |
| GCB_758 | Validation | 5.66 | 8.77 | 7.89 | 12.51 | −4.63 |
| GCB_772 | Validation | 8.52 | 7.81 | 7.95 | 12.25 | −6.34 |
| GCB_777 | Validation | 7.52 | 8.65 | 8.57 | 11.69 | −6.10 |
| GCB_792 | Training | 8.14 | 8.64 | 9.21 | 12.08 | −6.65 |
| GCB_795 | Validation | 9.19 | 8.17 | 8.81 | 11.60 | −6.92 |
| GCB_797 | Validation | 7.50 | 8.62 | 8.08 | 12.84 | −6.09 |
| GCB_803 | Validation | 6.19 | 8.65 | 9.49 | 13.18 | −6.11 |
| GCB_810 | Training | 8.46 | 8.32 | 8.10 | 13.13 | −6.50 |
| GCB_817 | Training | 6.93 | 8.51 | 9.49 | 11.09 | −6.04 |
| GCB_818 | Training | 7.18 | 8.96 | 8.08 | 12.23 | −5.76 |
| GCB_819 | Validation | 7.16 | 8.97 | 8.06 | 13.22 | −5.79 |
| GCB_821 | Validation | 8.13 | 8.59 | 8.90 | 12.41 | −6.61 |
| GCB_832 | Training | 7.83 | 8.35 | 8.71 | 12.47 | −6.37 |
| GCB_836 | Validation | 7.84 | 8.99 | 8.50 | 11.46 | −5.85 |
| GCB_840 | Training | 8.24 | 7.75 | 7.40 | 11.74 | −5.77 |
| GCB_847 | Training | 7.82 | 8.17 | 8.97 | 12.55 | −6.51 |
| GCB_860 | Training | 7.12 | 8.39 | 9.34 | 11.54 | −6.10 |
| GCB_871 | Training | 5.59 | 9.60 | 7.28 | 11.16 | −4.23 |
| GCB_874 | Training | 8.53 | 9.14 | 8.95 | 11.65 | −6.47 |
| GCB_995 | Validation | 6.98 | 8.68 | 8.54 | 12.22 | −5.76 |
| PMBL_1006 | Validation | 7.34 | 8.51 | 7.66 | 10.94 | −5.33 |
| PMBL_1024 | Validation | 7.62 | 8.48 | 8.56 | 10.89 | −5.96 |
| PMBL_1048 | Validation | 8.68 | 8.16 | 7.23 | 12.18 | −6.08 |
| PMBL_1053 | Training | 7.02 | 8.28 | 8.24 | 11.12 | −5.31 |
| PMBL_484 | Training | 7.15 | 8.45 | 7.01 | 13.62 | −5.41 |
| PMBL_546 | Validation | 8.19 | 7.88 | 7.66 | 11.73 | −6.06 |
| PMBL_570 | Training | 9.34 | 8.21 | 8.48 | 12.70 | −6.86 |
| PMBL_621 | Training | 8.08 | 8.60 | 9.14 | 12.96 | −6.72 |
| PMBL_638 | Training | 7.56 | 8.26 | 8.00 | 11.37 | −5.75 |
| PMBL_691 | Validation | 6.48 | 8.92 | 8.40 | 10.17 | −5.04 |
| PMBL_791 | Validation | 7.72 | 8.65 | 8.94 | 11.56 | −6.16 |
| PMBL_824 | Validation | 8.06 | 8.01 | 7.76 | 13.28 | −6.11 |
| PMBL_994 | Training | 9.15 | 8.36 | 7.46 | 12.43 | −6.29 |
| PMBL_998 | Training | 6.70 | 8.35 | 9.24 | 13.19 | −6.20 |
| UC_DLBCL_1001 | Validation | 6.74 | 8.43 | 7.10 | 12.76 | −5.31 |
| UC_DLBCL_1004 | Validation | 7.54 | 8.75 | 8.01 | 13.09 | −6.10 |
| UC_DLBCL_1007 | Training | 9.97 | 8.44 | 7.64 | 12.97 | −6.85 |
| UC_DLBCL_1018 | Training | 6.42 | 8.38 | 6.97 | 12.71 | −5.03 |
| UC_DLBCL_1041 | Validation | 5.76 | 8.69 | 6.78 | 13.38 | −4.71 |
| UC_DLBCL_1054 | Training | 8.92 | 8.65 | 8.51 | 11.48 | −6.59 |
| UC_DLBCL_306 | Validation | 7.85 | 8.90 | 8.31 | 12.36 | −6.23 |
| UC_DLBCL_310 | Training | 8.14 | 8.80 | 7.63 | 12.27 | −6.03 |
| UC_DLBCL_449 | Validation | 9.03 | 8.48 | 7.07 | 12.17 | −6.01 |
| UC_DLBCL_458 | Training | 5.92 | 8.53 | 8.28 | 9.60 | −4.96 |
| UC_DLBCL_460 | Validation | 7.92 | 9.08 | 8.30 | 12.29 | −6.13 |
| UC_DLBCL_491 | Training | 7.65 | 8.33 | 7.35 | 12.39 | −5.53 |
| UC_DLBCL_528 | Validation | 6.99 | 8.56 | 7.36 | 11.63 | −5.35 |
| UC_DLBCL_615 | Validation | 7.11 | 8.32 | 8.77 | 12.80 | −6.10 |
| UC_DLBCL_625 | Training | 8.93 | 7.78 | 7.85 | 12.62 | −6.46 |
| UC_DLBCL_664 | Training | 7.62 | 8.15 | 8.17 | 12.72 | −6.04 |
| UC_DLBCL_671 | Training | 8.09 | 8.48 | 7.61 | 11.53 | −5.78 |
| UC_DLBCL_682 | Training | 7.38 | 8.35 | 7.14 | 12.33 | −5.43 |
| UC_DLBCL_683 | Training | 7.91 | 8.36 | 7.78 | 12.57 | −6.02 |
| UC_DLBCL_684 | Validation | 8.06 | 8.63 | 8.29 | 12.76 | −6.29 |
| UC_DLBCL_748 | Validation | 5.38 | 8.57 | 7.45 | 9.55 | −4.23 |
| UC_DLBCL_751 | Training | 6.33 | 8.65 | 8.88 | 13.14 | −5.74 |
| UC_DLBCL_808 | Training | 7.42 | 9.01 | 7.44 | 13.09 | −5.63 |

TABLE 2373-continued

| Sample ID # | Set | Lymph node signature value | Proliferation signature value | Germinal center B-cell signature value | MHC class II signature value | Survival predictor score |
|---|---|---|---|---|---|---|
| UC_DLBCL_831 | Validation | 8.33 | 8.30 | 7.46 | 11.58 | −5.84 |
| UC_DLBCL_834 | Training | 6.98 | 9.09 | 8.61 | 11.77 | −5.66 |
| UC_DLBCL_838 | Validation | 7.25 | 8.40 | 7.23 | 12.56 | −5.36 |
| UC_DLBCL_851 | Validation | 6.28 | 9.05 | 6.78 | 8.19 | −4.10 |
| UC_DLBCL_854 | Validation | 7.36 | 8.50 | 7.39 | 12.59 | −5.53 |
| UC_DLBCL_855 | Training | 8.31 | 7.94 | 7.49 | 12.08 | −6.07 |
| UC_DLBCL_856 | Validation | 5.65 | 9.01 | 8.52 | 9.32 | −4.68 |

In order to visualize the predictive power of the model, the 200 samples were ranked according to their survival predictor scores and divided into four quartiles. Kaplan-Meier plots of overall survival probability show clear differences in survival rate between these four quartiles (FIG. 11).

Example 8

Development of a Third DLBCL Survival Predictor Using Gene Expression Data from the Lymph Dx Microarray The number of genes used to generate the DLBCL survival predictor in Example 7 were reduced in order to create a survival predictor compatible with RT-PCR. The list of genes from the lymph node and germinal center B-cell gene expression signatures was narrowed to those three genes from each signature that were most closely correlated with the lymph node and germinal center B-cell gene expression signature values, respectively. The genes from the proliferation gene expression signature did not add significantly to the reduced gene survival prediction model, so they were removed entirely. The expression of the genes within each signature was averaged on the $\log_2$ scale to generate a gene expression signature value for each signature. Table 2374 lists the genes that were used to generate these gene expression signature values.

TABLE 2374

| Signature | UNIQID | Unigene ID Build 167 | Gene symbol |
|---|---|---|---|
| Germinal center B-cell | 1099686 | 117721 | |
| Germinal center B-cell | 1529318 | 291954 | |
| Germinal center B-cell | 1529344 | 317970 | SERPINA11 |
| Lymph node | 1097126 | 274520 | ANTXR1 |

TABLE 2374-continued

| Signature | UNIQID | Unigene ID Build 167 | Gene symbol |
|---|---|---|---|
| Lymph node | 1099358 | 93135 | |
| Lymph node | 1121029 | 412999 | CSTA |
| MHC class II | 1136777 | 387679 | HLA-DQA1 |
| MHC class II | 1136877 | 409934 | HLA-DQB1 |

Table 2375 lists p-values for the association of each signature with survival in the training set, the validation set, and overall.

TABLE 2375

| Signature | Training set | Validation set | Overall |
|---|---|---|---|
| Lymph node | $6.1 \times 10^{-6}$ | 0.0021 | $2.1 \times 10^{-17}$ |
| Germinal center B-cell | $3.5 \times 10^{-4}$ | 0.0099 | $2.7 \times 10^{-5}$ |
| MHC class II | 0.024 | 0.0026 | 0.00031 |

The three gene expression signatures were used to generate a survival predictor score using the following equation:

Survival predictor score=[−0.32*(lymph node gene expression signature value)]−[0.176*(germinal center B-cell gene expression signature value)]−[0.206*(MHC class II gene expression signature value)].

A higher survival predictor score was associated with worse outcome. For the 200 DLBCL samples used to generate the model, the survival predictor score had a mean of 6.54 and a standard deviation of 0.69, with each unit increase in the predictor score corresponding to an approximately 2.7 fold increase in the relative risk of death. Data for all 200 samples is presented in Table 2376.

TABLE 2376

| Sample ID # | Set | Lymph node signature value | Germinal center B-cell signature value | MHC class II signature value | Survival predictor score |
|---|---|---|---|---|---|
| ABC_1000 | Validation | 8.08 | 5.68 | 11.50 | −5.96 |
| ABC_1002 | Validation | 8.32 | 6.06 | 12.54 | −6.31 |
| ABC_1023 | Validation | 9.36 | 4.74 | 11.42 | −6.18 |
| ABC_1027 | Training | 7.41 | 4.90 | 12.31 | −5.77 |
| ABC_1031 | Validation | 9.40 | 5.23 | 11.68 | −6.33 |
| ABC_1034 | Validation | 7.47 | 4.92 | 11.83 | −5.69 |
| ABC_1038 | Training | 7.89 | 5.84 | 12.30 | −6.09 |
| ABC_1043 | Training | 7.84 | 4.66 | 12.29 | −5.86 |

TABLE 2376-continued

| Sample ID # | Set | Lymph node signature value | Germinal center B-cell signature value | MHC class II signature value | Survival predictor score |
|---|---|---|---|---|---|
| ABC_1045 | Validation | 9.31 | 4.66 | 12.07 | −6.29 |
| ABC_1055 | Validation | 6.46 | 6.38 | 13.05 | −5.88 |
| ABC_1057 | Training | 9.13 | 7.93 | 12.05 | −6.80 |
| ABC_1059 | Validation | 10.93 | 4.82 | 11.35 | −6.68 |
| ABC_1061 | Training | 8.18 | 5.04 | 12.28 | −6.04 |
| ABC_304 | Validation | 7.31 | 6.47 | 12.76 | −6.10 |
| ABC_305 | Training | 7.02 | 6.60 | 11.89 | −5.86 |
| ABC_309 | Validation | 10.47 | 7.00 | 12.53 | −7.16 |
| ABC_413 | Validation | 7.99 | 4.80 | 9.04 | −5.26 |
| ABC_428 | Training | 9.43 | 7.59 | 10.25 | −6.47 |
| ABC_432 | Validation | 7.29 | 8.16 | 9.56 | −5.74 |
| ABC_446 | Training | 9.49 | 5.46 | 10.55 | −6.17 |
| ABC_462 | Validation | 7.72 | 4.97 | 13.36 | −6.10 |
| ABC_477 | Validation | 7.16 | 3.69 | 12.45 | −5.51 |
| ABC_481 | Training | 9.75 | 6.89 | 11.98 | −6.80 |
| ABC_482 | Training | 10.51 | 7.64 | 12.35 | −7.25 |
| ABC_538 | Validation | 8.79 | 5.00 | 11.83 | −6.13 |
| ABC_541 | Training | 7.70 | 5.80 | 10.59 | −5.67 |
| ABC_544 | Training | 8.90 | 3.98 | 11.87 | −5.99 |
| ABC_547 | Validation | 7.05 | 5.18 | 11.38 | −5.51 |
| ABC_577 | Validation | 9.93 | 8.05 | 11.95 | −7.06 |
| ABC_616 | Validation | 7.34 | 4.54 | 12.64 | −5.75 |
| ABC_626 | Validation | 8.78 | 6.77 | 11.11 | −6.29 |
| ABC_633 | Training | 9.63 | 5.02 | 12.45 | −6.53 |
| ABC_642 | Training | 7.31 | 4.95 | 13.80 | −6.05 |
| ABC_644 | Validation | 7.72 | 5.35 | 13.28 | −6.15 |
| ABC_645 | Training | 9.77 | 6.21 | 13.39 | −6.98 |
| ABC_646 | Validation | 7.39 | 3.75 | 11.60 | −5.41 |
| ABC_652 | Validation | 7.51 | 4.53 | 12.73 | −5.82 |
| ABC_660 | Training | 5.85 | 3.55 | 10.17 | −4.59 |
| ABC_663 | Training | 7.04 | 5.06 | 12.82 | −5.78 |
| ABC_668 | Validation | 8.00 | 5.65 | 10.57 | −5.73 |
| ABC_676 | Training | 6.53 | 4.29 | 13.32 | −5.59 |
| ABC_678 | Training | 6.87 | 7.48 | 11.26 | −5.83 |
| ABC_687 | Validation | 6.39 | 3.78 | 10.46 | −4.87 |
| ABC_689 | Training | 8.29 | 5.07 | 12.56 | −6.13 |
| ABC_692 | Validation | 8.10 | 5.26 | 11.57 | −5.90 |
| ABC_694 | Validation | 9.67 | 8.15 | 12.41 | −7.09 |
| ABC_700 | Training | 8.37 | 6.75 | 12.10 | −6.36 |
| ABC_702 | Validation | 8.44 | 4.59 | 12.55 | −6.09 |
| ABC_704 | Training | 8.51 | 4.34 | 12.83 | −6.13 |
| ABC_709 | Validation | 7.47 | 4.54 | 13.40 | −5.95 |
| ABC_712 | Validation | 7.12 | 3.99 | 12.02 | −5.46 |
| ABC_714 | Training | 9.57 | 7.03 | 11.97 | −6.77 |
| ABC_717 | Training | 8.33 | 5.54 | 11.34 | −5.98 |
| ABC_725 | Training | 8.04 | 4.40 | 12.76 | −5.97 |
| ABC_726 | Validation | 7.79 | 4.18 | 11.91 | −5.68 |
| ABC_730 | Validation | 8.13 | 7.36 | 12.14 | −6.40 |
| ABC_753 | Training | 9.24 | 6.60 | 13.00 | −6.80 |
| ABC_756 | Training | 9.51 | 5.21 | 12.48 | −6.53 |
| ABC_771 | Training | 8.08 | 4.74 | 12.20 | −5.93 |
| ABC_779 | Training | 8.11 | 4.09 | 9.82 | −5.34 |
| ABC_800 | Validation | 10.34 | 4.83 | 11.91 | −6.61 |
| ABC_807 | Training | 6.58 | 4.44 | 7.56 | −4.44 |
| ABC_809 | Training | 9.29 | 5.72 | 10.83 | −6.21 |
| ABC_816 | Training | 6.36 | 6.36 | 10.64 | −5.35 |
| ABC_820 | Training | 8.10 | 4.79 | 11.98 | −5.90 |
| ABC_823 | Validation | 6.63 | 4.85 | 10.09 | −5.05 |
| ABC_835 | Validation | 9.17 | 7.78 | 12.31 | −6.84 |
| ABC_839 | Training | 8.06 | 4.97 | 11.89 | −5.90 |
| ABC_841 | Validation | 8.05 | 6.24 | 13.19 | −6.39 |
| ABC_858 | Training | 9.02 | 4.86 | 11.74 | −6.16 |
| ABC_872 | Training | 8.67 | 5.85 | 12.47 | −6.37 |
| ABC_875 | Training | 9.60 | 5.59 | 11.26 | −6.37 |
| ABC_912 | Validation | 7.99 | 7.74 | 12.79 | −6.56 |
| ABC_996 | Validation | 6.89 | 6.23 | 10.02 | −5.36 |
| GCB_1005 | Validation | 9.02 | 9.56 | 13.27 | −7.30 |
| GCB_1008 | Training | 9.27 | 10.49 | 12.83 | −7.46 |
| GCB_1009 | Training | 7.80 | 10.09 | 12.28 | −6.80 |
| GCB_1021 | Validation | 8.73 | 9.20 | 13.20 | −7.13 |
| GCB_1025 | Validation | 9.94 | 9.97 | 12.37 | −7.49 |
| GCB_1026 | Training | 9.54 | 10.20 | 13.52 | −7.63 |
| GCB_1037 | Training | 6.34 | 8.79 | 12.57 | −6.17 |
| GCB_1039 | Training | 8.71 | 9.94 | 13.28 | −7.27 |

TABLE 2376-continued

| Sample ID # | Set | Lymph node signature value | Germinal center B-cell signature value | MHC class II signature value | Survival predictor score |
|---|---|---|---|---|---|
| GCB_1049 | Validation | 10.53 | 8.18 | 12.60 | −7.41 |
| GCB_1051 | Validation | 7.63 | 10.18 | 12.76 | −6.86 |
| GCB_1058 | Validation | 8.61 | 9.04 | 12.80 | −6.98 |
| GCB_1060 | Validation | 10.23 | 9.38 | 12.96 | −7.59 |
| GCB_412 | Training | 8.79 | 7.92 | 13.09 | −6.90 |
| GCB_415 | Training | 10.72 | 8.57 | 11.99 | −7.41 |
| GCB_421 | Training | 9.23 | 5.26 | 12.20 | −6.39 |
| GCB_424 | Training | 11.14 | 8.46 | 12.44 | −7.62 |
| GCB_433 | Training | 9.26 | 8.52 | 12.64 | −7.07 |
| GCB_434 | Training | 9.73 | 10.13 | 12.54 | −7.48 |
| GCB_438 | Validation | 9.60 | 9.99 | 12.51 | −7.41 |
| GCB_459 | Validation | 10.51 | 7.75 | 11.37 | −7.07 |
| GCB_470 | Validation | 9.56 | 6.63 | 12.23 | −6.74 |
| GCB_479 | Validation | 7.77 | 4.71 | 13.07 | −6.01 |
| GCB_492 | Training | 8.82 | 9.52 | 12.34 | −7.04 |
| GCB_517 | Validation | 9.92 | 6.96 | 12.76 | −7.03 |
| GCB_523 | Training | 6.59 | 9.17 | 12.77 | −6.35 |
| GCB_524 | Training | 10.00 | 7.83 | 12.51 | −7.16 |
| GCB_529 | Training | 5.61 | 7.93 | 10.77 | −5.41 |
| GCB_533 | Training | 9.55 | 5.54 | 12.44 | −6.59 |
| GCB_537 | Validation | 8.25 | 10.25 | 13.29 | −7.18 |
| GCB_543 | Validation | 9.92 | 8.85 | 12.06 | −7.21 |
| GCB_545 | Training | 9.69 | 4.91 | 12.90 | −6.62 |
| GCB_549 | Validation | 7.86 | 8.88 | 12.15 | −6.58 |
| GCB_550 | Validation | 10.64 | 9.53 | 12.24 | −7.60 |
| GCB_553 | Validation | 10.14 | 9.05 | 12.63 | −7.44 |
| GCB_565 | Validation | 9.08 | 10.80 | 13.42 | −7.57 |
| GCB_572 | Training | 8.93 | 10.03 | 12.58 | −7.21 |
| GCB_617 | Validation | 9.27 | 7.80 | 13.17 | −7.05 |
| GCB_618 | Training | 7.23 | 9.11 | 13.32 | −6.66 |
| GCB_619 | Validation | 9.63 | 9.63 | 12.12 | −7.27 |
| GCB_623 | Training | 8.94 | 9.07 | 12.35 | −7.00 |
| GCB_627 | Validation | 9.72 | 8.33 | 11.85 | −7.02 |
| GCB_654 | Training | 7.04 | 5.60 | 10.00 | −5.30 |
| GCB_661 | Validation | 10.27 | 7.92 | 12.66 | −7.29 |
| GCB_669 | Training | 9.15 | 9.29 | 12.32 | −7.10 |
| GCB_672 | Training | 9.69 | 7.36 | 12.41 | −6.95 |
| GCB_674 | Validation | 9.93 | 6.23 | 12.33 | −6.81 |
| GCB_675 | Validation | 7.48 | 8.46 | 10.12 | −5.97 |
| GCB_681 | Training | 10.77 | 9.52 | 12.59 | −7.72 |
| GCB_688 | Validation | 8.01 | 10.17 | 9.94 | −6.40 |
| GCB_695 | Validation | 10.58 | 9.38 | 12.45 | −7.60 |
| GCB_698 | Validation | 10.44 | 9.00 | 11.99 | −7.39 |
| GCB_701 | Training | 9.38 | 9.27 | 13.10 | −7.33 |
| GCB_710 | Validation | 6.96 | 5.59 | 13.19 | −5.93 |
| GCB_711 | Training | 9.28 | 8.49 | 11.44 | −6.82 |
| GCB_722 | Training | 8.93 | 9.51 | 12.61 | −7.13 |
| GCB_724 | Training | 9.51 | 8.39 | 11.53 | −6.90 |
| GCB_731 | Validation | 8.82 | 9.19 | 12.20 | −6.95 |
| GCB_742 | Validation | 9.95 | 9.37 | 12.95 | −7.50 |
| GCB_744 | Training | 10.23 | 10.11 | 11.85 | −7.49 |
| GCB_745 | Training | 10.29 | 9.71 | 11.95 | −7.46 |
| GCB_747 | Validation | 9.83 | 9.79 | 13.06 | −7.56 |
| GCB_749 | Training | 8.57 | 10.27 | 12.55 | −7.14 |
| GCB_758 | Validation | 6.88 | 5.69 | 12.51 | −5.78 |
| GCB_772 | Validation | 9.92 | 7.28 | 12.25 | −6.98 |
| GCB_777 | Validation | 9.03 | 9.63 | 11.69 | −6.99 |
| GCB_792 | Training | 9.49 | 9.06 | 12.08 | −7.12 |
| GCB_795 | Validation | 11.12 | 9.02 | 11.60 | −7.54 |
| GCB_797 | Validation | 8.42 | 5.90 | 12.84 | −6.38 |
| GCB_803 | Validation | 7.33 | 10.11 | 13.18 | −6.84 |
| GCB_810 | Training | 10.00 | 8.22 | 13.13 | −7.35 |
| GCB_817 | Training | 8.60 | 10.16 | 11.09 | −6.82 |
| GCB_818 | Training | 9.14 | 7.78 | 12.23 | −6.81 |
| GCB_819 | Validation | 9.08 | 8.63 | 13.22 | −7.15 |
| GCB_821 | Validation | 10.05 | 9.81 | 12.41 | −7.50 |
| GCB_832 | Training | 8.83 | 6.91 | 12.47 | −6.61 |
| GCB_836 | Validation | 9.49 | 7.86 | 11.46 | −6.78 |
| GCB_840 | Training | 9.45 | 5.02 | 11.74 | −6.33 |
| GCB_847 | Training | 9.41 | 8.77 | 12.55 | −7.14 |
| GCB_860 | Training | 9.02 | 6.66 | 11.54 | −6.43 |
| GCB_871 | Training | 6.60 | 4.46 | 11.16 | −5.20 |
| GCB_874 | Training | 10.39 | 9.13 | 11.65 | −7.33 |
| GCB_995 | Validation | 8.52 | 9.35 | 12.22 | −6.89 |

TABLE 2376-continued

| Sample ID # | Set | Lymph node signature value | Germinal center B-cell signature value | MHC class II signature value | Survival predictor score |
|---|---|---|---|---|---|
| PMBL_1006 | Validation | 8.72 | 4.67 | 10.94 | −5.86 |
| PMBL_1024 | Validation | 9.30 | 8.47 | 10.89 | −6.71 |
| PMBL_1048 | Validation | 10.30 | 4.98 | 12.18 | −6.68 |
| PMBL_1053 | Training | 8.75 | 9.78 | 11.12 | −6.81 |
| PMBL_484 | Training | 8.25 | 4.96 | 13.62 | −6.32 |
| PMBL_546 | Validation | 9.66 | 6.07 | 11.73 | −6.57 |
| PMBL_570 | Training | 10.58 | 8.54 | 12.70 | −7.50 |
| PMBL_621 | Training | 9.39 | 9.94 | 12.96 | −7.43 |
| PMBL_638 | Training | 9.81 | 8.35 | 11.37 | −6.95 |
| PMBL_691 | Validation | 8.37 | 7.51 | 10.17 | −6.10 |
| PMBL_791 | Validation | 9.29 | 8.65 | 11.56 | −6.88 |
| PMBL_824 | Validation | 9.87 | 7.19 | 13.28 | −7.16 |
| PMBL_994 | Training | 11.27 | 6.73 | 12.43 | −7.35 |
| PMBL_998 | Training | 7.92 | 8.34 | 13.19 | −6.72 |
| UC_DLBCL_1001 | Validation | 8.25 | 5.63 | 12.76 | −6.26 |
| UC_DLBCL_1004 | Validation | 9.01 | 7.01 | 13.09 | −6.81 |
| UC_DLBCL_1007 | Training | 11.42 | 6.73 | 12.97 | −7.51 |
| UC_DLBCL_1018 | Training | 7.77 | 4.58 | 12.71 | −5.91 |
| UC_DLBCL_1041 | Validation | 7.90 | 4.33 | 13.38 | −6.05 |
| UC_DLBCL_1054 | Training | 10.41 | 8.72 | 11.48 | −7.23 |
| UC_DLBCL_306 | Validation | 9.42 | 6.54 | 12.36 | −6.71 |
| UC_DLBCL_310 | Training | 9.97 | 5.50 | 12.27 | −6.69 |
| UC_DLBCL_449 | Validation | 10.01 | 5.37 | 12.17 | −6.65 |
| UC_DLBCL_458 | Training | 7.50 | 5.79 | 9.60 | −5.40 |
| UC_DLBCL_460 | Validation | 10.26 | 8.27 | 12.29 | −7.27 |
| UC_DLBCL_491 | Training | 9.43 | 4.73 | 12.39 | −6.40 |
| UC_DLBCL_528 | Validation | 8.42 | 6.19 | 11.63 | −6.18 |
| UC_DLBCL_615 | Validation | 8.44 | 9.01 | 12.80 | −6.92 |
| UC_DLBCL_625 | Training | 10.43 | 8.27 | 12.62 | −7.39 |
| UC_DLBCL_664 | Training | 9.80 | 8.74 | 12.72 | −7.29 |
| UC_DLBCL_671 | Training | 9.42 | 5.26 | 11.53 | −6.32 |
| UC_DLBCL_682 | Training | 9.01 | 4.73 | 12.33 | −6.26 |
| UC_DLBCL_683 | Training | 8.85 | 8.23 | 12.57 | −6.87 |
| UC_DLBCL_684 | Validation | 9.62 | 8.78 | 12.76 | −7.25 |
| UC_DLBCL_748 | Validation | 7.60 | 5.79 | 9.55 | −5.42 |
| UC_DLBCL_751 | Training | 6.40 | 9.91 | 13.14 | −6.50 |
| UC_DLBCL_808 | Training | 9.44 | 7.01 | 13.09 | −6.95 |
| UC_DLBCL_831 | Validation | 9.45 | 5.81 | 11.58 | −6.43 |
| UC_DLBCL_834 | Training | 8.52 | 7.66 | 11.77 | −6.50 |
| UC_DLBCL_838 | Validation | 8.49 | 4.60 | 12.56 | −6.11 |
| UC_DLBCL_851 | Validation | 7.50 | 4.82 | 8.19 | −4.94 |
| UC_DLBCL_854 | Validation | 8.35 | 5.82 | 12.59 | −6.29 |
| UC_DLBCL_855 | Training | 9.56 | 5.44 | 12.08 | −6.51 |
| UC_DLBCL_856 | Validation | 6.81 | 7.49 | 9.32 | −5.42 |

In order to visualize the predictive power of the model, the 200 samples were ranked according to their survival predictor scores and divided into four quartiles. Kaplan-Meier plots of overall survival probability show clear differences in survival rate between these four quartiles (FIG. 12).

Example 9

Development of an MCL Survival Predictor Using Gene Expression Data from Affymetrix U133A and U133B Microarrays The connection between higher expression of proliferation genes and worse survival in MCL had previously been documented and validated (Rosenwald 2003). A cluster of proliferation genes had been identified in the DLBCL samples used to create the DLBCL survival predictor described in Example 7. By averaging the expression of these genes, a proliferation gene expression signature value had been developed for the DLBCL samples. The correlation of this signature with each probe set on the U133A and U133B microarrays was determined, and the 22 genes for which the correlation was greater than 0.5 were labeled proliferation genes. The correlation between expression of these proliferation genes and survival in 21 MCL samples was estimated using the Cox proportional hazards model. Table 2377 lists these 21 MCL samples.

TABLE 2377

| Sample ID # | Length of follow-up (years) | Status at follow-up | Used in creating survival predictor? |
|---|---|---|---|
| MCL_1012 | 3.19 | Alive | Yes |
| MCL_1091 | 3.03 | Alive | Yes |
| MCL_1114 | 0.59 | Dead | Yes |
| MCL_1128 | 0.43 | Dead | Yes |
| MCL_1150 | 3.21 | Dead | Yes |
| MCL_1162 | 0.78 | Alive | Yes |
| MCL_1166 | 0.53 | Dead | Yes |
| MCL_1194 | 0.55 | Alive | Yes |
| MCL_885 | 1.19 | Alive | Yes |
| MCL_918 | 1.95 | Dead | Yes |
| MCL_924 | 5.48 | Dead | Yes |
| MCL_925 | 7.23 | Alive | Yes |
| MCL_926 | 5.18 | Dead | Yes |
| MCL_936 | 2.80 | Alive | Yes |
| MCL_939 | 1.07 | Dead | Yes |
| MCL_953 | 2.31 | Dead | Yes |

TABLE 2377-continued

| Sample ID # | Length of follow-up (years) | Status at follow-up | Used in creating survival predictor? |
|---|---|---|---|
| MCL__956 | 1.40 | Dead | Yes |
| MCL__964 | 0.75 | Alive | Yes |
| MCL__966 | 0.21 | Dead | Yes |
| MCL__968 | 1.59 | Dead | Yes |
| MCL__970 | 5.02 | Dead | Yes |

Out of the 22 proliferation genes, 11 were significant at a 0.001 level. The expression level of these 11 genes in each of the 21 MCL samples was averaged to generate a proliferation gene expression signature value. No other genes represented on the U133A or U133B microarrays correlated with MCL survival to an extent greater than would be expected by chance, so the final model included only proliferation genes. The 11 genes used to generate the model are presented in Table 2378.

TABLE 2378

| Signature | UNIQID | Gene Symbol |
|---|---|---|
| Proliferation | 1097290 | CIRH1A |
| Proliferation | 1101295 | FLJ40629 |
| Proliferation | 1119729 | TK1 |
| Proliferation | 1120153 | LMNB1 |
| Proliferation | 1120494 | CDC6 |
| Proliferation | 1124745 | KIAA0056 |
| Proliferation | 1126148 | DKFZp586E1120 |
| Proliferation | 1130618 | TPI1 |
| Proliferation | 1134753 | WHSC1 |
| Proliferation | 1139654 | ECT2 |
| Proliferation | 1140632 | IMAGE:52707 |

A survival predictor score for MCL was generated using the following equation:

Survival predictor score=1.66*(proliferation gene expression signature value).

This model was associated with survival in a statistically significant manner (p=0.00018). To illustrate the significance of the model in predicting survival, the 21 MCL samples were divided into two equivalent groups based on their survival predictor scores. Those samples with survival predictor scores above the median were placed in the high proliferation group, while those with survival predictor scores below the median were placed in the low proliferation group. FIG. 13 illustrates the Kaplan Meier survival estimates for these two groups. Median survival for the high proliferation group was 1.07 years, while median survival for the low proliferation group was 5.18 years.

Example 10

Development of an MCL Survival Predictor Using Gene Expression Data from the Lymph Dx Microarray A set of 21 genes associated with proliferation and poor prognosis in MCL had been identified previously (Rosenwald 2003). Of these 21 genes, only four were represented on the Lymph Dx microarray. In order to find a larger set of genes on the Lymph Dx microarray associated with survival in MCL, Lymphochip expression data (Rosenwald 2003) was re-analyzed and another set of proliferation genes whose expression levels were correlated with poor survival in MCL were identified. Thirteen of these genes were represented on the Lymph Dx microarray (median expression>6 on $\log_2$ scale). These 13 genes are listed in Table 2379.

TABLE 2379

| Signature | UNIQID | Unigene ID Build 167 | Gene symbol |
|---|---|---|---|
| Proliferation | 1119294 | 156346 | TOP2A |
| Proliferation | 1119729 | 164457 | TK1 |
| Proliferation | 1120153 | 89497 | LMNB1 |
| Proliferation | 1121276 | 24529 | CHEK1 |
| Proliferation | 1123358 | 442658 | AURKB |
| Proliferation | 1124178 | 446579 | HSPCA |
| Proliferation | 1124563 | 249441 | WEE1 |
| Proliferation | 1130799 | 233952 | PSMA7 |
| Proliferation | 1131274 | 374378 | CKS1B |
| Proliferation | 1131778 | 396393 | UBE2S |
| Proliferation | 1132449 | 250822 | STK6 |
| Proliferation | 1135229 | 367676 | DUT |
| Proliferation | 1136585 | 80976 | MKI67 |

The expression levels of the 13 genes listed in Table 2379 on the Lymph Dx microarray were transformed into the $\log_2$ scale and averaged to form a proliferation gene expression signature value. This was used to generate a survival predictor score using the following equation:

Survival predictor score=1.66*(proliferation gene expression signature value)

For the 21 MCL samples analyzed, the survival predictor score had a mean of 14.85 and a standard deviation of 1.13. Even in this limited sample set, the survival predictor score was significantly associated with prognosis (p=0.0049), with each unit increase in the score corresponding to a 2.7 fold increase in the relative risk of death. Data for all 21 samples is shown in Table 2380.

TABLE 2380

| Sample ID # | Proliferation signature value | Survival predictor score |
|---|---|---|
| MCL__1012 | 8.83 | 14.658 |
| MCL__1091 | 8.81 | 14.625 |
| MCL__1114 | 10.39 | 17.247 |
| MCL__1128 | 10.12 | 16.799 |
| MCL__1150 | 8.33 | 13.828 |
| MCL__1162 | 8.15 | 13.529 |
| MCL__1166 | 9.40 | 15.604 |
| MCL__1194 | 7.44 | 12.350 |
| MCL__885 | 8.68 | 14.409 |
| MCL__918 | 9.33 | 15.488 |
| MCL__924 | 8.35 | 13.861 |
| MCL__925 | 8.86 | 14.708 |
| MCL__926 | 8.14 | 13.512 |
| MCL__936 | 8.56 | 14.21 |
| MCL__939 | 9.14 | 15.172 |
| MCL__953 | 9.25 | 15.355 |
| MCL__956 | 9.35 | 15.521 |
| MCL__964 | 9.74 | 16.168 |
| MCL__966 | 8.76 | 14.542 |
| MCL__968 | 9.10 | 15.106 |
| MCL__970 | 9.27 | 15.388 |

To illustrate the significance of the model in predicting survival, the 21 MCL samples were divided into two equivalent groups based on their survival predictor scores. Those samples with survival predictor scores above the median were placed in the high proliferation group, while those with survival predictor scores below the median were placed in the

Example 11

Identification of Lymphoma Samples as MCL Based on Bayesian Analysis of Gene Expression Data from Affymetrix U133A and U133B Microarrays A statistical method based on Bayesian analysis was developed to distinguish MCL samples from samples belonging to other lymphoma types based on gene expression profiling. This method was developed using the gene expression data obtained in Example 1 for the following lymphoma types: ABC, GCB, PMBL, BL, FH, FL, MALT, MCL, PTLD, SLL, and splenic marginal zone lymphoma (splenic). Tables 1707-1741 (discussed in Example 1) provide gene expression data for samples within each of these lymphoma types, including the expression level of each gene and the difference in expression of each gene between types. Tables 1710, 1715, and 1723 (corresponding to FL, MCL, and DLBCL, respectively) include the correlation between expression of each gene and survival.

To determine the lymphoma type of a sample, a series of predictor models are generated. Each predictor model calculates the probability that the sample belongs to a first lymphoma type rather than a second lymphoma type. A method was developed to determine whether a sample was MCL, or one of the following lymphoma types: ABC, BL, FH, FL, GCB, MALT, PMBL, PTLD, SLL, or splenic. This method required ten different predictor models, each designed to determine whether the sample belonged to MCL or one of the other ten lymphoma types (e.g., MCL vs. ABC, MCL vs. BL, etc.).

Several of the lymphoma samples analyzed displayed a tendency towards elevated or reduced expression of genes from the lymph node and proliferation gene expression signatures. These genes are likely to be highly differentially expressed between the lymphoma types, but they do not serve as good predictor genes because they are often variably expressed within a single lymphoma type. For this reason, any gene that displayed a correlation with the proliferation or lymph node signatures was eliminated from consideration.

For each lymphoma type pair (e.g., MCL vs. ABC, MCL vs. FL, etc.), 20 genes were identified that exhibited the greatest difference in expression between MCL and the second lymphoma type according to a Student's t-test. The choice to use 20 genes was arbitrary. For each sample X, the 20 genes were used to generate a linear predictor score (LPS) according to the following formula:

$$LPS(X) = \sum_{j=1}^{20} t_j X_j,$$

where $X_j$ is the expression of gene j in sample X and $t_j$ is the t-statistic for the difference in expression of gene j between a first lymphoma type and a second lymphoma type. This is merely one method for generating an LPS. Others methods include linear discriminant analysis (Dudoit 2002), support vector machines (Furey 2000), or shrunken centroids (Tibshirani 2002). In addition, there is no requirement that a t-statistic be used as the scaling factor.

After an LPS had been formulated for each lymphoma sample, the mean and standard deviation of these LPS's was calculated for each lymphoma type. For a new sample X, Bayes' rule can be used to estimate the probability that the sample belongs to a first lymphoma type rather than a second lymphoma type (FIG. 15). In this example, Bayes' rule was used to calculate the probability q that sample X was MCL rather than a second lymphoma type using the following equation:

$$q(X \text{ is type } 1) = \frac{\phi(LPS(X); \hat{\mu}_1, \hat{\sigma}_1)}{\phi(LPS(X); \hat{\mu}_1, \hat{\sigma}_1) + \phi(LPS(X); \hat{\mu}_2, \hat{\sigma}_2)}$$

where type 1 is MCL, type 2 is one of the other nine lymphoma types, $\phi(x; \mu, \sigma)$ is the normal density function with mean $\mu$ and standard deviation $\sigma$, $\hat{\mu}_1$ and $\hat{\sigma}_1$ are the sample mean and variance of the LPS values for lymphoma type 1, and $\hat{\mu}_2$ and $\hat{\sigma}_2$ are the sample mean and variance of the LPS values for lymphoma type 2.

This method was used to develop ten predictor models, one for each pairing of MCL and a second lymphoma type. A sample was classified as MCL if each of the ten predictors generated at least a 90% probability that the sample was MCL. If any of the ten predictors indicated a probability of less than 90%, the sample was classified as non-MCL.

The 10 sets of 20 genes that were included in these models and the t-statistics for each gene are presented in Tables 2381-2490.

TABLE 2381

MCL vs. ABC predictor genes

| UNIQID | Gene symbol | gi | GENBANK Accession | Affymetrix probe set ID | Scale Factor |
|---|---|---|---|---|---|
| 1103711 |  | 10433184 | AK021895.1 | 232478_at | 17.88496416 |
| 1133111 | PDE9A | 48762717 | NM_001001567.1 | 205593_s_at | 17.61579873 |
| 1137987 | PLXNB1 | 41152087 | NM_002673.3 | 215807_s_at | 17.47030156 |
| 1132835 | SOX11 | 30581115 | NM_003108.3 | 204915_s_at | 16.89404131 |
| 1109505 | MGC39372 | 19263721 | BC025340.1 | 239186_at | 15.78111902 |
| 1139054 | ZBED5 | 49574209 | NM_021211.2 | 218263_s_at | 15.77800815 |
| 1119361 | TIA1 | 11863160 | NM_022037.1 | 201448_at | 15.68070962 |
| 1115226 | KIAA1683 | 144922706 | NM_025249.2 | 223600_s_at | 15.67954057 |
| 1101211 | STRBP | 21361744 | NM_018387.2 | 229513_at | 15.4183527 |
| 1118963 |  | 11084506 | BF196503.1 | 65472_at | 15.36802586 |
| 1096503 | C9orf45 | 12005727 | AF251293.1 | 223522_at | 14.64776335 |
| 1127849 | SNN | 83627728 | NM_003498.4 | 218032_at | 14.54859775 |
| 1099204 |  | 5817123 | AL110204.1 | 227121_at | 14.32724822 |
| 1098840 | CCDC50 | 41281910 | NM_178335.1 | 226713_at | 14.10346944 |

TABLE 2381-continued

MCL vs. ABC predictor genes

| UNIQID | Gene symbol | gi | GENBANK Accession | Affymetrix probe set ID | Scale Factor |
|---|---|---|---|---|---|
| 1139444 | RABL2B | 51317348 | NM_001003789.1 | 219151_s_at | 14.10016196 |
| 1106855 | KIAA1909 | 148529024 | NM_052909.3 | 236255_at | 13.9504946 |
| 1126695 | LOC730273 | 113419660 | XM_001124203.1 | 216000_at | 13.92285415 |
| 1120137 | FCGBP | 154146261 | NM_003890.2 | 203240_at | 13.86147896 |
| 1133011 | TMSL8 | 72255577 | NM_021992.2 | 205347_s_at | 13.74377784 |
| 1133192 | RASGRP3 | 24762238 | NM_170672.1 | 205801_s_at | −17.09085725 |

TABLE 2382

MCL vs. BL predictor genes

| UNIQID | Gene symbol | gi | GENBANK Accession | Affymetrix probe set ID | Scale Factor |
|---|---|---|---|---|---|
| 1120900 | EPHB6 | 56119211 | NM_004445.2 | 204718_at | 13.43582327 |
| 1112061 | SDK2 | 48255893 | NM_019064.3 | 242064_at | 12.73065392 |
| 1109505 | MGC39372 | 19263721 | BC025340.1 | 239186_at | 12.63674985 |
| 1133099 | DNASE1L3 | 58331226 | NM_004944.2 | 205554_s_at | 12.43333984 |
| 1106855 | KIAA1909 | 148529024 | NM_052909.3 | 236255_at | 12.32623489 |
| 1110070 |  | 8168250 | AW977010.1 | 239803_at | 12.05416064 |
| 1121739 | ZNF135 | 34419632 | NM_003436.2 | 206142_at | 11.90460363 |
| 1098840 | CCDC50 | 41281910 | NM_178335.1 | 226713_at | 11.90309143 |
| 1132833 | SOX11 | 30581115 | NM_003108.3 | 204913_s_at | 11.60864812 |
| 1121693 | PLCH2 | 78499632 | NM_014638.2 | 206080_at | 11.33634052 |
| 1123760 | LILRA4 | 47519952 | NM_012276.3 | 210313_at | 11.18744726 |
| 1125964 | TMEM63A | 7662307 | NM_014698.1 | 214833_at | 11.14762675 |
| 1112306 |  | 6139540 | AW135407.1 | 242354_at | 11.02434114 |
| 1096070 | DNMT3A | 28559066 | NM_022552.3 | 222640_at | 10.98991879 |
| 1129943 | ZNF506 | 149944539 | NM_001099269.1 | 221626_at | 10.72494956 |
| 1118749 |  | 11125347 | AJ296290.1 | 39313_at | 10.64623382 |
| 1098954 | MOBKL2B | 41350329 | NM_024761.3 | 226844_at | 10.46164401 |
| 1134749 | ZMYND8 | 34335265 | NM_012408.3 | 209049_s_at | 10.40948157 |
| 1131860 | BIN1 | 21536381 | NM_004305.2 | 202931_x_at | 10.31084561 |
| 1123148 | TGFBR2 | 133908632 | NM_001024847.2 | 208944_at | 10.2956213 |

TABLE 2383

MCL vs. FH predictor genes

| UNIQID | Gene symbol | gi | GENBANK Accession | Affymetrix probe set ID | Scale Factor |
|---|---|---|---|---|---|
| 1132834 | SOX11 | 30581115 | NM_003108.3 | 204914_s_at | 24.3531072 |
| 1100873 | WNT3 | 21536426 | NM_030753.3 | 229103_at | 16.83342764 |
| 1109603 |  | 4971784 | AI694444.1 | 239292_at | 13.02401995 |
| 1139411 | OSBPL10 | 23111057 | NM_017784.3 | 219073_s_at | 12.54369577 |
| 1106855 | KIAA1909 | 148529024 | NM_052909.3 | 236255_at | 12.10316361 |
| 1125193 | CNR1 | 38683843 | NM_016083.3 | 213436_at | 12.070579 |
| 1137450 | ALOX5 | 62912458 | NM_000698.2 | 214366_s_at | 11.74571823 |
| 1100258 | KLHL14 | 55741642 | NM_020805.1 | 228377_at | 11.60998697 |
| 1133167 | ZNF107 | 62243639 | NM_001013746.1 | 205739_x_at | 11.52931491 |
| 1136831 | PPFIBP2 | 57163846 | NM_003621.1 | 212841_s_at | 11.50062692 |
| 1138222 | CD24 | 73623396 | NM_013230.2 | 216379_x_at | 10.99674674 |
| 1099437 | PTPRJ | 148728159 | NM_001098503.1 | 227396_at | 10.90797288 |
| 1140236 | FCRL2 | 74048626 | NM_138738.2 | 221239_s_at | 10.77082801 |
| 1114109 | CLECL1 | 40548404 | NM_172004.2 | 244413_at | 10.65867119 |
| 1098277 | PRICKLE1 | 23308518 | NM_153026.1 | 226065_at | 10.55457068 |
| 1135138 | CD24 | 73623396 | NM_013230.2 | 209771_x_at | 10.41999962 |
| 1103304 | LOC439949 | 113421296 | XM_001128367.1 | 232001_at | −10.46625233 |
| 1128460 | PITPNC1 | 32307139 | NM_012417.2 | 219155_at | −10.91106245 |
| 1121953 | KIAA0125 | 20302136 | NM_014792.2 | 206478_at | −11.22466255 |
| 1129281 | FAM30A | 6841343 | AF161538.1 | 220377_at | −15.54465448 |

TABLE 2384

MCL vs. FL predictor genes

| UNIQID | Gene symbol | gi | GENBANK Accession | Affymetrix probe set ID | Scale Factor |
|---|---|---|---|---|---|
| 1132835 | SOX11 | 30581115 | NM_003108.3 | 204915_s_at | 22.14208817 |
| 1096070 | DNMT3A | 28559066 | NM_022552.3 | 222640_at | 20.53740132 |
| 1103711 | | 10433184 | AK021895.1 | 232478_at | 20.49880004 |
| 1137987 | PLXNB1 | 41152087 | NM_002673.3 | 215807_s_at | 18.38081568 |
| 1109505 | MGC39372 | 19263721 | BC025340.1 | 239186_at | 17.17812448 |
| 1098840 | CCDC50 | 41281910 | NM_178335.1 | 226713_at | 16.32703666 |
| 1130926 | C5orf13 | 4758865 | NM_004772.1 | 201310_s_at | 15.34261878 |
| 1096396 | SPG3A | 74024913 | NM_015915.3 | 223340_at | 14.75437736 |
| 1132734 | COL9A3 | 119508425 | NM_001853.3 | 204724_s_at | 14.684583 |
| 1139393 | OPN3 | 71999130 | NM_014322.2 | 219032_x_at | 14.39118445 |
| 1115537 | CNFN | 26024194 | NM_032488.2 | 224329_s_at | 14.18446144 |
| 1102215 | PRICKLE1 | 23308518 | NM_003105.3 | 230708_at | 14.16246426 |
| 1124585 | SORL1 | 18379347 | NM_003105.3 | 212560_at | −14.33315955 |
| 1137561 | HOXA1 | 84697023 | NM_005522.4 | 214639_s_at | −15.38404642 |
| 1100581 | BCL6 | 21040323 | NM_001706.2 | 228758_at | −15.91666634 |
| 1124646 | RFTN1 | 41872576 | NM_015150.1 | 212646_at | −16.40577696 |
| 1114543 | | 5395779 | A1809213.1 | 244887_at | −17.60167863 |
| 1120090 | BCL6 | 21040323 | NM_001706.2 | 203140_at | −17.63091181 |
| 1123731 | RGS13 | 21464137 | NM_170672.1 | 210258_at | −22.41602151 |
| 1133192 | RASGRP3 | 24762238 | NM_170672.1 | 205801_s_at | −27.28308723 |

TABLE 2385

MCL vs. GCB predictor genes

| UNIQID | Gene symbol | gi | GENBANK Accession | Affymetrix probe set ID | Scale Factor |
|---|---|---|---|---|---|
| 1098840 | CCDC50 | 41281910 | NM_178335.1 | 226713_at | 22.26488562 |
| 1132835 | SOX11 | 30581115 | NM_003108.3 | 204915_s_at | 17.76179754 |
| 1137987 | PLXNB1 | 41152087 | NM_002673.3 | 215807_s_at | 16.86845147 |
| 1098954 | MOBKL2B | 41350329 | NM_024761.3 | 226844_at | 16.65023669 |
| 1103711 | | 10433184 | AK021895.1 | 232478_at | 15.64719784 |
| 1096070 | DNMT3A | 28559066 | NM_022552.3 | 222640_at | 15.22540494 |
| 1139393 | OPN3 | 71999130 | NM_014322.2 | 219032_x_at | 14.64030565 |
| 1127849 | SNN | 83627728 | NM_003498.4 | 218032_at | 14.28242206 |
| 1098156 | MAP3K1 | 153945764 | NM_005921.1 | 225927_at | 14.00049272 |
| 1128845 | SIDT1 | 116812583 | NM_017699.2 | 219734_at | 13.96064416 |
| 1129943 | ZNF506 | 149944539 | NM_001099269.1 | 221626_at | 13.85404507 |
| 1140116 | ARHGAP24 | 111154091 | NM_001025616.2 | 221030_s_at | 13.81464172 |
| 1106855 | KIAA1909 | 148529024 | NM_052909.3 | 236255_at | 13.74521849 |
| 1120900 | EPHB6 | 56119211 | NM_004445.2 | 204718_at | 13.46567004 |
| 1127371 | | 4372199 | A1479031.1 | 217164_at | 13.45735668 |
| 1119361 | TIA1 | 11863160 | NM_022037.1 | 201448_at | 13.37376559 |
| 1120854 | EDG1 | 87196352 | NM_001400.3 | 204642_at | 13.1047657 |
| 1098277 | PRICKLE1 | 23308518 | NM_153026.1 | 226065_at | 13.04993076 |
| 1140127 | TRIM6-TRIM34 | 51477689 | NM_001003819.1 | 221044_s_at | 12.66260609 |
| 1100581 | BCL6 | 21040323 | NM_001706.2 | 228758_at | −12.81251689 |

TABLE 2386

MCL vs. MALT predictor genes

| UNIQID | Gene symbol | gi | GENBANK Accession | Affymetrix probe set ID | Scale Factor |
|---|---|---|---|---|---|
| 1132834 | SOX11 | 30581115 | NM_003108.3 | 204914_s_at | 20.7489202 |
| 1101987 | K1AA1909 | 148529024 | NM_052909.3 | 230441_at | 10.78991326 |
| 1100873 | WNT3 | 21536426 | NM_030753.3 | 229103_at | 10.11845036 |
| 1130764 | HNRNPA0 | 52426775 | NM_006805.3 | 201055_s_at | 9.432459453 |
| 1102178 | H2BFXP | 115432116 | NR_003238.1 | 230664_at | 9.035605572 |
| 1098277 | PRICKLE1 | 23308518 | NM_153026.1 | 226065_at | 9.003360784 |
| 1130926 | C5orf13 | 4758865 | NM_004772.1 | 201310_s_at | 8.712830747 |
| 1098694 | SBK1 | 67906173 | NM_001024401.2 | 226548_at | 8.309789856 |
| 1103711 | | 10433184 | AK021895.1 | 232478_at | 8.248526605 |
| 1138099 | FADS3 | 34304362 | NM_021727.3 | 216080_s_at | 8.107440225 |
| 1120854 | EDG1 | 87196352 | NM_001400.3 | 204642_at | 8.045872672 |
| 1102215 | PRICKLE1 | 23308518 | NM_153026.1 | 230708_at | 8.032351578 |
| 1121739 | ZNF135 | 34419632 | NM_003436.2 | 206142_at | 8.020919565 |

| UNIQID | Gene symbol | gi | GENBANK Accession | Affymetrix probe set ID | Scale Factor |
|---|---|---|---|---|---|
| 1096070 | DNMT3A | 28559066 | NM_022552.3 | 222640_at | 7.964477216 |
| 1101211 | STRBP | 21361744 | NM_018387.2 | 229513_at | 7.738742472 |
| 1120825 | CHL1 | 27894375 | NM_006614.2 | 204591_at | 7.516130116 |
| 1099437 | PTPRJ | 148728159 | NM_001098503.1 | 227396_at | 7.209041652 |
| 1096503 | C9orf45 | 12005727 | AF251293.1 | 223522_at | 7.171540413 |
| 1135927 | LILRA2 | 5803067 | NM_006866.1 | 211102_s_at | 7.134470829 |
| 1120645 | FADS3 | 34304362 | NM_021727.3 | 204257_at | 7.039952979 |

TABLE 2387

MCL vs. PMBL predictor genes

| UNIQID | Gene symbol | gi | GENBANK Accession | Affymetrix probe set ID | Scale Factor |
|---|---|---|---|---|---|
| 1132834 | SOX11 | 30581115 | NM_003108.3 | 204914_s_at | 28.17593839 |
| 1100873 | WNT3 | 21536426 | NM_030753.3 | 229103_at | 17.90004832 |
| 1096503 | C9orf45 | 12005727 | AF251293.1 | 223522_at | 17.43982729 |
| 1098840 | CCDC50 | 41281910 | NM_178335.1 | 226713_at | 17.37421052 |
| 1124734 | ZNF238 | 45439300 | NM_006352.3 | 212774_at | 16.73821457 |
| 1135102 | PRKCB1 | 47157320 | NM_002738.5 | 209685_s_at | 16.67436366 |
| 1103711 | | 10433184 | AK021895.1 | 232478_at | 16.57202026 |
| 1140416 | FAIM3 | 34147517 | NM_005449.3 | 221601_s_at | 15.64802242 |
| 1121757 | ADRB2 | 116686129 | NM_000024.4 | 206170_at | 15.57336633 |
| 1140236 | FCRL2 | 74048626 | NM_138738.2 | 221239_s_at | 15.20264513 |
| 1099140 | | 28835721 | BC047541.1 | 227052_at | 15.11929571 |
| 1099549 | | 7154210 | AW516128.1 | 227533_at | 14.92883027 |
| 1139054 | ZBED5 | 49574209 | NM_021211.2 | 218263_s_at | 14.63422275 |
| 1138818 | ILF3 | 24234752 | NM_004516.2 | 217804_s_at | 14.50621028 |
| 1109444 | | 31317247 | NM_006850.3 | 239122_at | 14.20430672 |
| 1124534 | GPATCH8 | 50962881 | NM_001002909.1 | 212485_at | 14.18537487 |
| 1098277 | PRICKLE1 | 23308518 | NM_153026.1 | 226065_at | 13.98526258 |
| 1131687 | TLK1 | 33636697 | NM_012290.3 | 202606_s_at | 13.97468703 |
| 1125112 | PLCL2 | 142369931 | NM_015184.3 | 213309_at | 13.85714318 |
| 1125397 | RABL4 | 9257237 | NM_006860.2 | 213784_at | 13.85049805 |

TABLE 2388

MCL vs. PTLD predictor genes

| UNIQID | Gene symbol | gi | GENBANK Accession | Affymetrix probe set ID | Scale Factor |
|---|---|---|---|---|---|
| 1109603 | | 14060141 | BG749488.1 | 239292_at | 19.95553782 |
| 1138222 | CD24 | 73623396 | NM_013230.2 | 216379_x_at | 15.95397369 |
| 1135138 | CD24 | 73623396 | NM_013230.2 | 209771_x_at | 15.89198725 |
| 1134230 | RASGRP2 | 149158726 | NM_001098670.1 | 208206_s_at | 15.80452978 |
| 1139411 | OSBPL10 | 23111057 | NM_017784.3 | 219073_s_at | 14.32818885 |
| 1140416 | FAIM3 | 34147517 | NM_005449.3 | 221601_s_at | 13.89685188 |
| 1132834 | SOX11 | 30581115 | NM_003108.3 | 204914_s_at | 13.78424818 |
| 1121739 | ZNFI35 | 34419632 | NM_003436.2 | 206142_at | 13.02195529 |
| 1098156 | MAP3K1 | 153945764 | NM_005921.1 | 225927_at | 12.95032505 |
| 1099270 | AFF3 | 68348715 | NM_001025108.1 | 227198_at | 12.7877735 |
| 1139012 | MAP4K4 | 46249361 | NM_004834.3 | 218181_s_at | 12.70176225 |
| 1120854 | EDG1 | 87196352 | NM_001400.3 | 204642_at | 12.25264341 |
| 1120985 | ARHGAP25 | 55770897 | NM_001007231.1 | 204882_at | 12.04626201 |
| 1115952 | ATXN1L | 21734020 | AL833385.1 | 226095_at | 11.96299478 |
| 1120825 | CHL1 | 27894375 | NM_006614.2 | 204591_at | 11.82402907 |
| 1131636 | SPOCK2 | 7662035 | NM_014767.1 | 202524_s_at | 11.80417657 |
| 1136706 | PCMTD2 | 157388996 | NM_001104925.1 | 212406_s_at | 11.74962191 |
| 1113560 | | 14589868 | NM_032966.1 | 243798_at | 11.72049882 |
| 1133851 | P4HA1 | 63252885 | NM_000917.2 | 207543_s_at | −12.59876059 |
| 1137459 | BCAT1 | 72187658 | NM_005504.4 | 214390_s_at | −14.00465411 |

TABLE 2389

MCL vs. SLL predictor genes

| UNIQID | Gene symbol | gi | GENBANK Accession | Affymetrix probe set ID | Scale Factor |
|---|---|---|---|---|---|
| 1132834 | SOX11 | 30581115 | NM_003108.3 | 204914_s_at | 23.59602107 |
| 1101987 | K1AA1909 | 148529024 | NM_052909.3 | 230441_at | 14.50254794 |

TABLE 2389-continued

MCL vs. SLL predictor genes

| UNIQID | Gene symbol | gi | GENBANK Accession | Affymetrix probe set ID | Scale Factor |
|---|---|---|---|---|---|
| 1103711 |  | 10433184 | AK021895.1 | 232478_at | 13.31375894 |
| 1096070 | DNMT3A | 28559066 | NM_022552.3 | 222640_at | 12.37453972 |
| 1130926 | C5orf13 | 4758865 | NM_004772.1 | 201310_s_at | 11.27840239 |
| 1120645 | FADS3 | 34304362 | NM_021727.3 | 204257_at | 11.14057287 |
| 1138099 | FADS3 | 34304362 | NM_021727.3 | 216080_s_at | 10.92729287 |
| 1097887 | MAST4 | 148727254 | NM_015183.1 | 225611_at | 10.37913127 |
| 1099941 |  | 15750678 | BI759100.1 | 227985_at | 10.33953409 |
| 1130373 | MAST4 | 148727254 | NM_015183.1 | 40016_g_at | 10.01524528 |
| 1110957 | SYNE2 | 118918402 | NM_015180.4 | 240777_at | 9.865436185 |
| 1130320 | MAST4 | 148727254 | NM_015183.1 | 222348_at | 9.807091644 |
| 1124373 | LPIN1 | 22027647 | NM_145693.1 | 212274_at | 9.024985551 |
| 1128813 | KREMEN2 | 27437002 | NM_024507.2 | 219692_at | 8.903791941 |
| 1131130 | MARCKS | 153070259 | NM_002356.5 | 201670_s_at | 8.688979176 |
| 1120825 | CHL1 | 27894375 | NM_006614.2 | 204591_at | 8.685132271 |
| 1119752 | BASP1 | 30795230 | NM_006317.3 | 202391_at | 8.663402838 |
| 1131854 | GCLC | 45359851 | NM_001498.2 | 202923_s_at | -8.761521136 |
| 1105801 | MAN2A1 | 51477713 | NM_002372.2 | 235103_at | -8.828675125 |
| 1097824 | MAP2 | 87578393 | NM_001039538.1 | 225540_at | -9.345688564 |

TABLE 2390

MCL vs. splenic predictor genes

| UNIQID | Gene symbol | gi | GENBANK Accession | Affymetrix probe set ID | Scale Factor |
|---|---|---|---|---|---|
| 1106855 | KIAA1909 | 148529024 | NM_052909.3 | 236255_at | 14.48278638 |
| 1121739 | ZNF135 | 34419632 | NM_003436.2 | 206142_at | 11.95918572 |
| 1111850 |  | BC047698.1 | BC047698.1 | 241808_at | 11.13464157 |
| 1098024 | RSPRY1 | 45387948 | NM_133368.1 | 225774_at | 10.10869886 |
| 1130764 | HNRNPA0 | 52426775 | NM_006805.3 | 201055_s_at | 10.06898534 |
| 1135342 | SHOX2 | 87044887 | NM_003030.3 | 210135_s_at | 9.565884385 |
| 1097218 | TCEAL8 | 55749465 | NM_001006684.1 | 224819_at | 9.187725705 |
| 1117193 | ZBTB10 | 157694498 | NM_001105539.1 | 233899_x_at | 9.12522795 |
| 1139564 | PSMD10 | 28605122 | NM_002814.2 | 219485_s_at | 9.066714773 |
| 1132834 | SOX11 | 30581115 | NM_003108.3 | 204914_s_at | 8.908574745 |
| 1131130 | MARCKS | 153070259 | NM_002356.5 | 201670_s_at | 8.732921026 |
| 1131756 | PDCD4 | 34304340 | NM_014456.3 | 202730_s_at | 8.441424593 |
| 1102187 | PKHD1L1 | 126116588 | NM_177531.4 | 220673_at | 8.391861029 |
| 1098195 | TMEM64 | 116089278 | NM_001008495.2 | 225974_at | 8.349839204 |
| 1101211 | STRBP | 21361744 | NM_018387.2 | 229513_at | 8.337208237 |
| 1136673 | GNAS | 117938757 | NM_000516.4 | 212273_x_at | 8.254076655 |
| 1139116 | USP16 | 50312663 | NM_001001992.1 | 218386_x_at | 8.179384251 |
| 1098694 | SBK1 | 67906173 | NM_001024401.2 | 226548_at | 7.935903681 |
| 1120519 | WWP2 | 40806206 | NM_007014.3 | 204022_at | -7.881202253 |
| 1114916 | CPLX3 | 75677370 | NM_001030005.2 | 222927_s_at | -8.33683119 |

With so many candidate predictor genes being utilized, it is possible to generate a predictor model that accurately predicts every element of a training set but fails to perform on an independent sample. This occurs because the model incorporates and "learns" individual characteristics of each sample in the training set. Leave-one-out cross-validation was used to verify that the prediction models generated above would work on independent samples that the models had not encountered previously. In this cross-validation method, a single sample is removed from the training set, and the predictor is developed again using the remaining data. The resulting model is then used to predict the sample that was removed. This method is repeated with each individual sample taken out. Since no sample is predicted from a model that includes that sample, this method provides an unbiased estimate of predictor accuracy.

When the predictors developed above were evaluated by leave-one-out cross-validation, all but one of the 21 MCL samples were correctly identified as MCL and none of the 489 non-MCL samples were mistakenly identified as MCL.

Example 12

Identification of Lymphoma Samples as MCL Based on Bayesian Gene Expression Data from a Lymphochip Microarray Lymphoma samples with morphology consistent with MCL were identified by pathological review. Since t(11; 14) translocation and cyclin D1 overexpression have been consistently associated with MCL, cyclin D1 mRNA levels were measured in each sample by quantitative RT-PCR. Of the 101 samples analyzed, 92 expressed cyclin D1 mRNA. These 92 samples, which were deemed the "core group" of MCLs, were divided into a training set and a validation set. Gene expression was measured in all 101 samples using a Lymphochip microarray (Alizadeh 1999). For comparison, gene expression was measure in 20 samples identified as SLL. In addition, MCL expression data was compared to expression data obtained previously for GCB (134 cases) and ABC (83 cases) (Rosenwald 2002). Several thousand genes were differentially expressed between cyclin D1-positive MCL and the other lymphoma types with high statistical significance (p<0.001). A complete listing of these genes is available at Rosenwald et al., *Cancer Cell,* 3:185-197 (2003), which is referenced therein at page 194 and which is hosted by the Lymphoma/Leukemia Molecular Profiling Project Gateways at the National Institute of Health web site.

Three different binary predictor models were developed: MCL vs. SLL, MCL vs. GCB, and MCL vs. ABC. Each of these models was designed to calculate the probability that a sample was MCL rather than the other lymphoma type in the pair. For each pair, the genes that were most differentially expressed between MCL and the other lymphoma type in the pair were identified, and the difference in expression between the lymphoma types was quantified using a Student's t-test. An LPS was then calculated for each sample using the following formula:

$$LPS(X) = \sum_{j \in G} t_j X_j,$$

where $X_j$ is the expression of gene j in sample X and $t_j$ is the t-statistic for the difference in expression of gene j between the two lymphoma types in the pair. Cyclin D1 was excluded from the calculation of LPS so that the model could be used to identify potential MCL cases that were cyclin D1 negative.

After an LPS had been formulated for each lymphoma sample, the mean and standard deviation of these LPS's was calculated for each lymphoma type. For a new sample X, Bayes' rule can be used to estimate the probability q that the sample belongs to MCL rather than the second lymphoma type in the pair using the following equation:

$$q(X \text{ is } MCL) = \frac{\phi(LPS(X); \hat{\mu}_{MCL}, \hat{\sigma}_{MCL})}{\phi(LPS(X); \hat{\mu}_{MCL}, \hat{\sigma}_{MCL}) + \phi(LPS(X); \hat{\mu}_2, \hat{\sigma}_2)}$$

where $\phi(x; \mu, \sigma)$ is the normal density function with mean $\mu$ and standard deviation $\sigma$, $\hat{\mu}_{MCL}$ and $\hat{\sigma}_{MCL}$ are the sample mean and variance of the LPS values for MCL, and $\hat{\mu}_2$ and $\hat{\sigma}_2$ are the sample mean and variance of the LPS values for the second lymphoma type of the pair. A cut-off point of 90% was selected for assigning a sample to a particular lymphoma type. Every sample in the training set were classified correctly using this model (FIG. 16). When applied to the validation set, the model correctly classified 98% of the cyclin D1-positive MCL cases as MCL (FIG. 16).

This diagnostic test was applied to nine lymphoma cases that were morphologically consistent with MCL, but negative for cyclin D1 expression. Seven of these samples were classified as MCL, one was classified as GCB, and one was not assigned to any lymphoma type because none of the pairs generated a probability of 90% or greater.

Example 13

Classification of DLBCL Samples Based on Bayesian Analysis of Gene Expression Data from the Lymphochip Microarray A statistical method to classify DLBCL samples based on Bayesian analysis was developed using gene expression data obtained using the Lymphochip cDNA microarray (Rosenwald 2002). This data is available at http://llmpp.nih.gov/DLBCL. The data was divided into two sets: a training set used to create and optimize the prediction model, and a validation set to evaluate the performance of the model. The training set consisted of 42 ABC DLBCL samples and 67 GCB DLBCL samples, while the validation set consisted of 41 ABC DLBCL samples, 67 GCB DLBCL samples, and 57 type 3 DLBCL samples (Shipp 2002).

Genes that were listed as present on >50% of the samples were identified, and the signal value for these genes on each microarray was normalized to 1,000. After normalization, all signal values under 50 were set to 50. A $\log_2$ transformation was then performed on all the signal values.

An LPS for distinguishing between two lymphoma types was calculated for each sample X in the training set using an equation:

$$LPS(X) = \sum_j t_j X_j,$$

where $X_j$ represents the expression level of gene j and $t_j$ is a scaling factor whose value depends on the difference in expression of gene j between the two lymphoma types. The scaling factor used in this example was the t-statistic generated by a t test of the difference in gene j expression between two lymphoma types. Only those genes with the largest t-statistics were included when calculating the LPS for each sample. The list of genes used to generate the LPS was narrowed further by including only those genes that were most variably expressed within the training set. Only genes in the top third with respect to variance were included. Genes that displayed a correlation with proliferation or lymph node signatures (Shaffer 2001; Rosenwald 2002) were eliminated from consideration, because these genes are often variably expressed within samples from a single lymphoma type (Rosenwald 2002).

Since the LPS is a linear combination of gene expression values, its distribution within each lymphoma type should be approximately normal, provided that it includes a sufficient number of genes and the correlation structure of those genes is not extreme. The mean and variance of these normal distributions within a lymphoma type can then be estimated from the combined LPS's of all samples within the type. The LPS distribution of two lymphoma types can be used to estimate the probability that a new sample belongs to one of the types using Bayes' rule. The probability q that a sample Y belongs to lymphoma type 1 can be determined by an equation:

$$q(Y \text{ is subtype } 1) = \frac{\phi(LPS(Y); \hat{\mu}_1, \hat{\sigma}_1)}{\phi(LPS(Y); \hat{\mu}_1, \hat{\sigma}_1) + \phi(LPS(Y); \hat{\mu}_2, \hat{\sigma}_2)}$$

where $\phi(x; \mu, \sigma)$ is the normal density function with means $\mu$ and standard deviation $\phi$, $\hat{\mu}_1$ and $\hat{\sigma}_1$ are the sample mean and variance of the LPS values for lymphoma type 1, and $\hat{\mu}_2$ and $\hat{\sigma}_2$ are the sample mean and variance of the LPS values for lymphoma type 2. This calculation was used to determine the probability that each sample in the training set belonged to GCB or ABC. A sample was classified as a particular type if it had a 90% or greater probability of belonging to that type. The number of genes in the predictor model was optimized based on the accuracy with which the predictor classified samples into the ABC or GCB subtypes defined previously by hierarchical clustering (Rosenwald 2002). The final predictor incorporated 27 genes, and correctly classified 87% of the training set samples into the subtype to which they had been assigned by hierarchical clustering (FIG. 17). The genes included in the predictor are listed in Table 2391.

TABLE 2391

| UNIQID | Unigene ID Build 167 | Gene symbol | gi | GENBANK Accession | Affymetrix probe set ID |
|---|---|---|---|---|---|
| 19375 | 235860 | FOXP1 | 60498986 | NM_001012505.1 | 224837_at |
| 19346 | 109150 | SH3BP5 | 109134343 | NM_001018009.2 | 201810_s_at |
| 19227 | 193857 | LOC96597 | 89041248 | XM_378655.2 | 233483_at |
| 16049 | 439852 | IGHM | 21757751 | AK097859.1 | |
| 32529 | 55098 | CCDC50 | 33186926 | NM_174908.2 | 226713_at |
| 24729 | 127686 | IRF4 | 4505286 | NM_002460.1 | 204562_at |
| 24899 | 81170 | PIM1 | 31543400 | NM_002648.2 | 209193_at |
| 19348 | NA | IGHM | 21757751 | AK097859.1 | |
| 27565 | 444105 | ENTPD1 | 147905699 | NM_001098175.1 | 209474_s_at |
| 17227 | 170359 | IL16 | 148833502 | NM_004513.4 | 209827_s_at |
| 26919 | 118722 | FUT8 | 30410721 | NM_004480.3 | 203988_s_at |
| 24321 | 171262 | ETV6 | 153267458 | NM_001987.4 | 217377_x_at |
| 29385 | 167746 | BLNK | 40353774 | NM_013314.2 | 207655_s_at |
| 16858 | 376071 | CCND2 | 16950656 | NM_001759.2 | 200951_s_at |
| 31801 | 386140 | BMF | 51558687 | NM_001003940.1 | 226530_at |
| 19234 | 418004 | PTPN1 | 18104977 | NM_002827.2 | 202716_at |
| 26385 | 307734 | MME | 116256328 | NM_000902.3 | 203434_s_at |
| 24361 | 388737 | | 76779240 | BC106050.1 | |
| 24570 | 446198 | SAMD12 | 156119596 | NM_001101676.1 | |
| 24904 | 18166 | KIAA0870 | 50345869 | NM_014957.2 | 212975_at |
| 24429 | 155024 | BCL6 | 21040323 | NM_001706.2 | 228758_at |
| 28224 | 387222 | NEK6 | 34147501 | NM_014397.3 | 223158_s_at |
| 27673 | 124922 | LRMP | 42789728 | NM_006152.2 | 204674_at |
| 24376 | 317970 | SERPINA11 | 110225348 | NM_001042518.1 | |
| 17496 | 300592 | MYBL1 | 122937230 | NM_001080416.1 | 213906_at |
| 17218 | 283063 | LMO2 | 6633806 | NM_005574.2 | 204249_s_at |
| 28338 | 78877 | ITPKB | 38569399 | NM_002221.2 | 203723_at |

Since the samples used to estimate the distribution of the LPS's were the same samples used to generate the model, there was a possibility of overfitting. Overfitting would result in a model that indicates a larger separation between the LPS's of two lymphoma types than would be found in independent data. To ensure that overfitting was not taking place, the model was tested on the validation set. The reproducibility of the predictor model was verified by its ability to correctly classify 88% of the samples in the validation set (FIG. 18). Interestingly, 56% of the DLBCL samples that had been placed in the type 3 subtype by hierarchical clustering were classified as either ABC or GCB using this Bayesian model.

In previous experiments, the genes that were used to distinguish GCB and ABC were deliberately selected to include those that were preferentially expressed in normal GC B cells (Alizadeh 2000; Rosenwald 2002). In the present analysis, the predictor model was not biased a priori to include such genes. The ABC and GCB lymphoma types as defined by the Bayesian model were analyzed for differential expression of GC B cell restricted genes. Thirty seven genes were found to be both more highly expressed in GC B cells than at other stages of differentiation (p<0.001) and differentially expressed between DLBCL subtypes (p<0.001) (FIG. 19A). These 37 genes are listed in Table 2392.

TABLE 2392

| UNIQID | Unigene ID Build 167 | Gene symbol |
|---|---|---|
| 28014 | 300592 | MYBL1 |
| 24376 | 317970 | SERPINA11 |
| 24429 | 155024 | BCL6 |
| 16886 | 124922 | LRMP |

TABLE 2392-continued

| UNIQID | Unigene ID Build 167 | Gene symbol |
|---|---|---|
| 27374 | 283063 | LMO2 |
| 29912 | 446198 | |
| 24510 | 266175 | PAG |
| 24854 | 439767 | TOX |
| 32171 | 307734 | MME |
| 24361 | 388737 | |
| 19365 | 171857 | Cyorf15a |
| 27292 | 272251 | KLHL5 |
| 24822 | 283794 | PCDHGC3 |
| 30923 | 446195 | |
| 24825 | 88556 | HDAC1 |
| 31696 | 91139 | SLC1A1 |
| 26976 | 434281 | PTK2 |
| 19279 | 49614 | GCET2 |
| 17866 | 1765 | LCK |
| 24386 | 437459 | MYO1E |
| 33013 | 293130 | VNN2 |
| 25126 | | |
| 30498 | 157441 | SPI1 |
| 26512 | 379414 | MFHAS1 |
| 26582 | 153260 | SH3KBP1 |
| 17840 | 132311 | MAP2K1 |
| 26000 | 25155 | NET1 |
| 24323 | 149342 | AICDA |
| 30922 | 435904 | C21orf107 |
| 30641 | 79299 | LHFPL2 |
| 19308 | 179608 | DHRS9 |
| 24455 | 405387 | |
| 30034 | 300208 | SEC23IP |
| 24977 | 169939 | HS2ST1 |
| 24449 | 206097 | RRAS2 |
| 30763 | 446198 | |
| 27987 | 73792 | CR2 |

All but two (AICDA and DHRS9) of these 37 genes were more highly expressed in GCB than in ABC. This demonstrates that the DLBCL subtypes defined by the Bayesian predictor seem to differ with respect to their cell of origin, with GCB retaining the gene expression program of normal GC B cells.

ABC, on the other hand, displayed higher expression of genes characteristic of plasma cells (FIG. 19B). Twenty four genes were found to be both more highly expressed in plasma cells than in B cells at earlier developmental stages (p<0.001) and differentially expressed between the DLBCL subtypes (p<0.001). These 24 genes are listed in Table 2393.

TABLE 2393

| UNIQID | Unigene ID Build 167 | Gene symbol |
|---|---|---|
| 16614 | 127686 | IRF4 |
| 26907 | 118722 | FUT8 |
| 31104 | 313544 | NS |
| 19219 | 355724 | CFLAR |
| 26174 | 28707 | SSR3 |
| 24566 | 169948 | KCNA3 |
| 34500 | 442808 | B4GALT2 |
| 26991 | 314828 | UPP1 |
| 30191 | 438695 | FKBP11 |
| 27402 | 259855 | EEF2K |
| 26096 | 434937 | PPIB |
| 15887 | 2128 | DUSP5 |
| 32440 | 512686 | C20orf59 |
| 34827 | 429975 | PM5 |
| 29232 | 437638 | XBP1 |
| 17763 | 76640 | RGC32 |
| 32163 | 445862 | RAB30 |
| 17814 | 5353 | CASP10 |
| 31460 | 409223 | SSR4 |
| 26693 | 83919 | GCS1 |
| 25130 | 409563 | PACAP |
| 16436 | 267819 | PPP1R2 |
| 31610 | 76901 | PDIR |
| 28961 | 212296 | ITGA6 |

The majority of these plasma cell-restricted genes were more highly expressed in ABC than in GCB. Eight of the 32 genes encode proteins that reside and function in the endoplasmic reticulum (ER) or Golgi apparatus, suggesting that ABCs have increased the intracellular machinery for protein secretion. These eight genes are denoted in the above list by the designation "ER" or "golgi" in parentheses. Another gene on this list, XBP-1 transcription factor, encodes a protein that is required for plasma cell differentiation (Reimold 2001) and is involved in the response to unfolded proteins in the ER (Calfon 2002). ABC have not undergone full plasmacytic differentiation, however, because other key plasma cell genes such as Blimp-1 were not more highly expressed in ABC.

Example 14

Classification of DLBCL Samples Based on Bayesian Analysis of Gene Expression Data from the Affymetrix HU6800 Microarray The prediction method described in Example 13 above was applied to gene expression data from 58 DLBCL samples obtained using an Affymetrix HU 6800 oligonucleotide microarray (Shipp 2002). This data is available at www-.genome.wi.mit.edu/MPR/lymphoma. The first step in analyzing this data was to exclude all microarray features with a median signal value of <200 across the samples. Multiple microarray features representing the same gene were then averaged. Of the 27 genes in the DLBCL subtype predictor developed using the Lymphochip data (above), only 14 were represented on the Affymetrix array and passed this filtering process. These 14 genes are listed in Table 2394.

TABLE 2394

| UNIQID | Unigene ID Build 167 | Gene symbol | gi | GENBANK Accession | Affymetrix probe set ID |
|---|---|---|---|---|---|
| 24729 | 127686 | IRF4 | 4505286 | NM_002460.1 | 204562_at |
| 17227 | 170359 | IL16 | 148833502 | NM_004513.4 | 209827_s_at |
| 26907 | 118722 | FUT8 | 30410721 | NM_004480.3 | 203988_s_at |
| 27565 | 444105 | ENTPD1 | 147905699 | NM_001098175.1 | 209474_s_at |
| 16858 | 376071 | CCND2 | 16950656 | NM_001759.2 | 200951_s_at |
| 24899 | 81170 | PIM1 | 31543400 | NM_002648.2 | 209193_at |
| 16947 | 418004 | PTPN1 | 18104977 | NM_002827.2 | 202716_at |
| 16049 | 439852 | IGHM | 21757751 | AK097859.1 | |
| 26385 | 307734 | MME | 116256328 | NM_000902.3 | 203434_s_at |
| 27673 | 124922 | LRMP | 42789728 | NM_006152.2 | 204674_at |
| 24429 | 155024 | BCL6 | 21040323 | NM_001706.2 | 228758_at |
| 17218 | 283063 | LMO2 | 6633806 | NM_005574.2 | 204249_s_at |
| 28338 | 78877 | ITPKB | 38569399 | NM_002221.2 | 203723_at |
| 17496 | 300592 | MYBL1 | 122937230 | NM_001080416.1 | 213906at |

These 14 genes were used to create a new DLBCL subtype predictor in which the LPS scaling coefficients were again calculated based on the DLBCL subtype distinction in the Lymphochip data set (Rosenwald 2002). To account for systematic measuring differences between the Affymetrix and Lymphochip microarrays, the expression value of each gene on the Affymetrix microarray was shifted and scaled to match the mean and variance of the corresponding expression values on the Lymphochip. The adjusted expression values for each of the 14 genes were then used to calculate LPS's for each sample. DLBCL subtype membership was again assigned on a cut-off of 90% certainty. Several observations suggested that the predictor identified ABC and GCB samples within the Affymetrix data set that were comparable to those found in the Lymphochip data set. First, the relative proportions of ABC (29%) and GCB (53%) were very similar to the corresponding proportions in the Lymphochip data set (34% and 49%, respectively). Second, 43 genes were found to be differentially expressed between the two DLBCL subtypes with high significance (p<0.001) in the Affymetrix data. This number is substantially higher than would be expected by chance, given that the Affymetrix microarray measures the expression of approximately 5,720 genes. The symbols for these 43 genes were: IGHM; TCF4; IRF4; CCND2; SLA; BATF; KIAA0171; PRKCB1; P2RX5; GOT2; SPIB; CSNK1E; PIM2; MARCKS; PIM1; TPM2; FUT8; CXCR4; SP140; BCL2; PTPN1; KIAA0084; HLA-DMB; ACP1; HLA-DQA1; RTVP1; VCL; RPL21; ITPKB; SLAM; KRT8; DCK; PLEK; SCA1; PSIP2; FAM3C; GPR18; HMG14; CSTB; SPINK2; LRMP; MYBL1; and LMO2. Third, the 43 genes differentially expressed between the types included 22 genes that were not used in the predictor but were represented on Lymphochip arrays. Fourteen of these 22 genes were differentially expressed on the Lymphochip array with high statistical significance (p<0.001). Finally, the expression of the c-rel gene was previously found to correspond to amplification of the c-rel genomic locus in DLBCL tumor cells, and oncogenic event occurring in GCB but not ABC (Rosenwald 2002). In the Affymetrix data set, c-rel was differentially expressed between the two subtypes (p=0.0025), and was highly expressed only in a subset of GCB's.

Example 15

Identification of DLBCL Samples as PMBL Based on Bayesian Analysis of Gene Expression Data from the Lymphochip Microarray 310 lymphoma biopsy samples identified as DLBCL by a panel of hematopathologists were divided into a 36 sample training set and a 274 sample validation set, with the validation set consisting of the DLBCL samples as classified previously in Example 13. All patients from whom the samples were derived had been treated with anthracycline-containing multiagent chemotherapy protocols, with some patients additionally receiving radiation therapy. The training set was profiled for gene expression using Lymphochip microarrays comprising 15,133 cDNA elements as described previously (Alizadeh 2000). The data is available at the web site companion for Rosenwald et al., *J. Exp. Med.*, 198: 851-862 (2003), which is referenced therein at page 852 and which is hosted by Lymphoma/Leukemia Molecular Profiling Project Gateway at the National Institute of Health web site. The validation set had previously been profiled using Lymphochip microarrays comprising 12,196 cDNA elements (Rosenwald 2002). This data is available at the web site companion for Rosenwald et al., *New Eng. J. Med.*, 346: 1937-1947 (2002), which is referenced therein at page 1938 and which is hosted by the Lymphoma/Leukemia Molecular Profiling Project Gateway at the National Institute of Health web site.

A hierarchical clustering algorithm (Eisen 1998) was used to organize the genes by their expression patterns across the 36 samples in the training set. A large group of genes that were more highly expressed in lymphomas with mediastinal involvement than in other DLBCLs was shown to be tightly clustered in the resulting dendrogram (FIG. 20A). This cluster of genes included two genes, MAL and FIG. 1, previously shown to be highly expressed in PMBL (Copie-Bergman 2002; Copie-Bergman 2003). Several of the lymphomas with mediastinal involvement did not express this set of putative PMBL signature genes, and it was suspected that these samples were more likely to be conventional DLBCL than PMBL. Hierarchical clustering was used to organize the samples according to their expression of the PMBL signature genes, resulting in two major clusters of cases (FIG. 20B). One cluster contained 21 samples designated "PMBL core" samples by virtue of their higher expression of PMBL signature genes. The other cluster contained some samples that had virtually no expression of these genes, and other samples that did express these genes but at lower levels than the PMBL core samples.

A gene expression-based method for distinguishing PMBL core cases from GCB and ABC DLBCL cases based on Bayesian analysis was developed using the methods described in Examples 13 and 14. A set of genes were selected that were differentially expressed between the PMBL core samples and both GCB and ABC (p<0.001). This set of genes included all of the PMBL signature genes identified by hierarchical clustering (FIG. 20A), as well as a large number of additional genes. Many of the genes in this set belonged to the lymph node gene expression signature (Alizadeh 2000; Rosenwald 2002). These genes were excluded from the final predictor because they might cause some DLBCL samples with higher expression of lymph node gene expression signature genes to be misclassified as PMBL. The list of PMBL distinction genes was refined by adding a requirement that they also be differentially expressed between the PMBL core samples and a subgroup of six DLBCL samples with higher expression of lymph node gene expression signature genes (p<0.001). The resulting set of 46 genes included 35 genes that were more highly expressed in PMBL and 11 genes that were more highly expressed in DLBCL (FIG. 21A). The 46 genes in this set were PDL2, SNFT, IL13RA1, FGFR1, FLJ10420, CCL17/TARC, TNFRSF8/CD30, E2F2, MAL, TNFSF4/OX40 ligand, IL411/Fig1, IMAGE:686580, BST2, FLJ31131, FCER2/CD23, SAMSN1, JAK2, FLJ0066, MST1R, TRAF1, SLAM, LY75, TNFRSF6/Fas, FNBP1, TLR7, TNFRSF17/BCMA, CDKN1A/p21CIP1, RGS9, IMAGE:1340506, NFKB2, KIAA0339, ITGAM, IL23A, SPINT2, MEF2A, PFDN5, ZNF141, IMAGE:4154313, IMAGE:825382, DLEU1, ITGAE, SH3BP5, BANK, TCL1A, PRKAR1B, and CARD 11. A series of linear predictor scores were generated based on the expression of this gene set. Based on the distribution of linear predictor scores within a particular lymphoma type, Bayes' rule can be used to estimate the probability that a particular sample belongs to either of the two types. An arbitrary probability cut-off of 90% or greater was used to classify a sample as a particular lymphoma type. All of the PMBL core samples were classified as PMBL using this method, as were six of the other lymphoma samples with mediastinal involvement. However, nine of the lymphoma samples with mediastinal involvement were classified as a DLBCL, as were all of the GCB and ABC samples.

In the validation set, 11 samples were identified on clinical grounds as being consistent with a diagnosis of PMBL, and the Bayesian model classified nine of these as PMBL (FIG. 21B). Interestingly, 12 of the remaining 263 DLBCL samples were classified as PMBL by the predictor. FIG. 21B shows that these cases were indistinguishable by gene expression from the nine cases diagnosed as PMBL on clinical grounds. As expected, the average expression of the PMBL predictor genes in the 249 samples classified as DLBCL was notably lower than in the 22 PMBL cases. Thus, PMBL represents a third subgroup of DLBCL than can be distinguished from ABC and GCB by gene expression profiling.

Table 2395 compares the clinical parameters of patients assigned to the PMBL, ABC, and GCB subgroups of DLBCL using this prediction method.

TABLE 2395

|  | ABC DLBCL | GCB DLBCL | PMBL Training set | PMBL Validation set | PMBL All cases | P value |
|---|---|---|---|---|---|---|
| Median age | 66 | 61 | 33 | 33 | 33 | 4.4E−16 |
| Age <35 | 5% | 10% | 52% | 56% | 53% | 7.2E−14 |
| Age 35-60 | 29% | 38% | 44% | 28% | 37% |  |
| Age >60 | 66% | 52% | 4% | 17% | 9% |  |
| Gender = male | 59% | 53% | 44% | 50% | 47% | 0.38 |
| Female <35 | 2% | 3% | 32% | 39% | 35% | 1.1E−12 |
| Male <35 | 2% | 7% | 20% | 17% | 19% |  |
| Female 35-60 | 6% | 18% | 24% | 6% | 16% |  |
| Male 35-60 | 23% | 19% | 20% | 22% | 21% |  |
| Female >60 | 33% | 25% | 0% | 6% | 2% |  |
| Male >60 | 34% | 27% | 4% | 11% | 7% |  |

PMBL patients were significantly younger than other DLBCL patients, with a median age at diagnosis of 33 years compared with a median age of 66 and 61 years for ABC and GCB patients, respectively. Although there was no significant difference in gender distribution among the DLBCL subgroups, young women (<35 years) accounted for 35% of PMBL patients, more than any other DLBCL subgroup. Young men (<35 years) were also more frequently represented in the PMBL subgroup, accounting for 19% of the patients. Correspondingly, older men and women (age>60) were significantly underrepresented in the PMBL subgroup. These clinical characteristics were observed in both the training set and the validation set of PMBL cases, demonstrating that the PMBL predictor reproducibly identified a clinically distinct subgroup of DLBCL patients.

The PMBL subgroup defined by the PMBL predictor had a relatively favorable overall survival rate after therapy (FIG. 22). PMBL patients had a five-year survival rate of 64%, superior to the 46% rate seen in DLBCL patients as a whole (p=0.0067). The survival of the PMBL subgroup was significantly better than the 30% five-year survival rate of the ABC subgroup (FIG. 22; p=5.8E-5), but only marginally better than the 59% five-year survival rate of the GCB subgroup (p=0.18).

Example 16

Classification of Lymphomas into Types Based on Bayesian Analysis of Gene Expression Data from the Lymph Dx Microarray Based on the clustering of the Lymph Dx microarray signals for the DLBCL samples, a cluster of "proliferation signature" genes and a cluster of "lymph node signature" genes were identified. The expression of these genes was averaged to form a proliferation signature and a lymph node signature. Each gene represented on the Lymph Dx microarray was placed into one of three "gene-list categories" based on its correlation with the proliferation or lymph node gene signatures. "Proliferation" genes were defined as those genes for which the correlation between their expression and the proliferation signature was greater than 0.35. Lymph node genes were defined as those genes for which the correlation between their expression and the lymph node signature was greater than 0.35. The remaining genes on the array were classified as standard genes. This classification resulted in 323 proliferation genes and 375 lymph node genes.

Two stages of lymphoma classification were performed using the gene expression data obtained for the above samples using the Lymph Dx microarray. The general procedure used to classify the samples is presented in flow chart form in FIG. 1.

For the first stage of expression analysis, the samples were divided into five types: FL, MCL, SLL, FH, and a class of aggressive lymphomas that included DLBCL and BL. Samples obtained from subjects with other diagnoses (e.g., MALT, LPC) were omitted from this analysis. Data from the Lymph Dx microarray was then used to compare gene expression in each possible lymphoma type pair (e.g., FH vs. FL, MCL vs. SLL, etc.). This resulted in the creation of ten "pair-wise models" (one for each possible lymphoma type pair) for predicting whether a sample fell into a particular lymphoma type.

For each lymphoma type pair, the difference in expression between the two types for every gene on the microarray was calculated, and a t-statistic was generated to represent this difference. Within each gene-list category (proliferation, lymph node, and standard), individual genes were ordered based on the absolute value of their t-statistic. Only those genes that displayed a statistically significant difference in expression between the two types were included in the model. Those genes with largest absolute t-statistics in each gene-list category were then used to generate a linear predictor score (LPS) for each sample. For a sample X and a set of genes G, the LPS was defined as:

$$LPS(X) = \sum_{j \in G} t_j X_j,$$

where $X_j$ is the expression of gene j in the sample and $t_j$ is the t-statistic representing the difference in expression of gene j between the two lymphoma types. This formulation of LPS, known as the compound covariate predictor, has previously been used successfully (Radmacher 2002; Rosenwald 2003; Wright 2003). Other ways to formulate an LPS include Fisher linear discriminant analysis (Dudoit 2002), weighted voting (Golub 1999), linear support vector machines (Ramaswamy 2001), and nearest shrunken centroids (Tibshirani 2002).

In order to optimize the number of genes used to generate the LPS, a series of LPS's were generated for each sample using between five and 100 genes from each gene-list category. The optimal number of genes is that number which generates a maximum t-statistic when comparing the LPS of two samples from different lymphoma types (FIG. 23). This optimization procedure was repeated for every gene-list category in every pair-wise model, meaning that 30 optimizations were performed in all.

It was recognized that for some pair-wise models, it would be useful to calculate LPS's using different combinations of gene-list categories. LPS's were calculated for each sample using four different combinations. In the first, LPS was calculated using the standard genes only. In the second, LPS's were calculated for both the standard and proliferation genes, but not the lymph node genes. In the third, LPS's were calculated for both the standard and lymph node genes, but not the proliferation genes. In the fourth, LPS's were calculated using all three gene-list categories.

Depending on the number of gene-list categories included, between one and three LPS's were calculated for each sample in the pair-wise models. Thus, each sample could be thought of as a vector in a space of between one and three dimensions. Since the LPS's were sums of individual expressions, it was reasonable to approximate the distributions as normal. Multivariate normal distributions are defined by two quantities: a mean vector, which indicates the average value of each of the models within a given lymphoma type, and a covariance matrix, which indicates the magnitude and orientation spread of points away from this center. Both of these quantities can be estimated empirically from the observed data. FIG. 24 shows the Standard and Proliferation LPS's for the FL vs. DLBCL/BL pair-wise model. The dotted lines indicate the standard deviations from the fitted multivariate normal distributions.

Once the multidimensional distributions have been estimated, Bayes' rule (Bayes 1763) can be used to estimate the probability that a given sample belongs to one lymphoma type or another. Bayesian analysis of an LPS has been successfully employed in the past to distinguish DLBCL subtypes (Rosenwald 2003, Wright 2003). For a sample X, the probability q of the sample belonging to a first lymphoma type rather than a second lymphoma type can be calculated using the formula:

$$q = \frac{\phi(LPS(X); \hat{\mu}_1, \hat{\sigma}_1)}{\phi(LPS(X); \hat{\mu}_1, \hat{\sigma}_1) + \phi(LPS(X); \hat{\mu}_2, \hat{\sigma}_2)}$$

where LPS(X) is the linear predictor score for sample X, $\phi(x; \mu, \sigma)$ is the normal density function with mean $\mu$ and standard deviation $\sigma$, $\hat{\mu}_1$ and $\hat{\sigma}_1$ are the mean and variance of the LPS's for the first lymphoma type, and $\hat{\mu}_2$ and $\hat{\sigma}_2$ are the mean and variance of the LPS's for the second lymphoma type. Using this equation, a single probability q value can be developed for each sample and for each of the four LPS combinations. This q value can then be used to classify a sample as a first lymphoma type, a second lymphoma type, or unclassified. Samples with the highest q values are classified as the first lymphoma type, while samples with the lowest q values are classified as the second lymphoma type. Samples with middle range q values are deemed unclassified. Classifying the samples in this manner requires two cut-off points: a lower cut-off point between the second lymphoma type and unclassified, and an upper cut-off point between unclassified and the first lymphoma type. To develop these cut-off points, samples were ordered by their q values, and each possible cut-off point between adjacent samples was considered. To ensure that the cut-off points were reasonable, the lower cut-off point was restricted to between 0.01 and 0.5 and the upper cut-off point was restricted to between 0.5 and 0.99.

Every cut-off point and model combination was analyzed by the following equation:

3.99*[(% of type 1 misidentified as type 2)+(% of type 2 misidentified as type 1)]+[(% of type 1 unclassified)+(% of type 2 misidentified)].

Using this equation, the cut-off point would be adjusted to allow an additional error only if this adjustment resulted in four or more unclassified samples becoming correctly classified. The final model and cut-off point for a given pair-wise analysis was that which minimized this equation. The equation utilizes percentages rather than the actual number of cases in order to account for the different number of samples in each class.

All cut-off points between a given pair of adjacent q-values will produce the same division of data. Since cut-off point optimality is defined in terms of dividing the data into subtypes, all cut-off points between a pair of borderline cases will be equally optimal. In choosing where to place the actual cut-off point values, values were chosen that would lead to a larger unclassified region. When the lower cut-off point was being defined, a value would be chosen that was ⅕ of the way from the smallest borderline case to the largest. When the upper cut-off point was being defined, a value would be chosen that was ⅘ of the way from the smallest borderline case to the largest. FIG. 25 illustrates the q-results of optimizing the cut-point for the FL versus DLBCL/BL samples. The optimal lower cut-off point for these samples was found at q=0.49, while the optimal upper cut-off point was found at q=0.84. FIG. 26 indicates how this choice of cut-off points divided the space of LPS's.

The above procedures resulted in a series of pair-wise models for comparing every lymphoma type to every other lymphoma type. If there are n types, then there will be n−1 pair-wise models for each type. Since there were five lymphoma types in the stage 1 analysis, each type was involved in 4 pair-wise models. For instance, there were four different pair-wise models for MCL: MCL vs. FH, MCL vs. FL, MCL vs. SLL, and MCL vs. DLBCL/BL. For each sample tested, each pair-wise model will produce one of three possible results: 1) the sample belongs to the first lymphoma type of the pair-wise model, 2) the sample belongs to the second lymphoma type of the pair-wise model, or 3) the sample is unclassified. If each of the n−1 models agrees that the sample belongs to a particular lymphoma type, then the sample is designated as belonging to that type. If the n−1 models do not all agree that the sample belongs to a particular lymphoma type, the sample is designated as unclassified.

To ensure that the above methods did not result in overfitting (i.e., models that fit particular idiosyncrasies of the training set but fail when applied to independent data), the models were validated by leave-one-out cross-validation fashion (Hills 1966). Each sample was removed from the data one at a time, and a predictive model was developed as described above using the remaining data. This model was then used to predict the sample that was removed. Since the model being used to predict a given sample was generated from data that did not include that sample, this method provided an unbiased estimate of the accuracy of the model.

The results of the leave-one-out predictions are set forth in Tables 2396 and 2397, below. The rows in each table correspond to different sample groups, while the columns indicate the prediction results. The standard to which the prediction results were compared in this stage was the diagnoses of a panel of eight expert hematopathologists who used histological morphology and immunohistochemistry to classify the samples. Table 2396 provides classification results for the five lymphoma types tested (DLBCL/BL, FL, FH, MCL, SLL), while Table 2397 provides more specific results for classification of subtypes within these five lymphoma types. The results set forth in Table 2396 are also summarized in FIG. 27.

As seen in Table 2396, perfect prediction of SLL, MCL, and FH samples was obtained. The success rate for predicting FL and the aggressive lymphomas (DLBCL/BL) was also very good, with only 3% of the samples being classified incorrectly. As seen in Table 2397, perfect prediction was also obtained for ABC and PMBL samples within the DLBCL samples.

Example 17

Classification of DLBCL/BL Samples into Subtypes Based on Bayesian Analysis of Gene Expression Data from the Lymph Dx Microarray Samples identified as DLBCL/BL in Example 16 were subdivided into four types: ABC, GCB, PMBL, and BL. These samples were then used to generate six pair-wise models using the same procedure described in Example 16. The results of the leave-one-out predictions using these pair-wise models are set forth in Table 2398, below. These results are also summarized in FIG. 28. The rows in the table correspond to different sample groups, while the columns indicate the prediction results. In this stage, the ability of the prediction method to identify BL was again measured against the diagnoses of hematopathologists. The ability of the prediction method to identify the various DLBCL subtypes, on the other hand, was measured against previous studies in which this distinction between subtypes was based on gene expression data from a Lymphochip microarray (Alizadeh 2000, Rosenwald 2002, Rosenwald 2003, Wright 2003).

TABLE 2396

|  | DLBCL/BL | FL | FH | MCL | SLL | Unclassified | Total | % Correct | % Unclassified | % Error |
|---|---|---|---|---|---|---|---|---|---|---|
| DLBCL/BL | 249 | 6 | 0 | 0 | 0 | 7 | 262 | 95% | 2% | 3% |
| FL | 5 | 154 | 0 | 0 | 0 | 14 | 173 | 89% | 8% | 3% |
| FH | 0 | 0 | 17 | 0 | 0 | 0 | 17 | 100% | 0% | 0% |
| MCL | 0 | 0 | 0 | 22 | 0 | 0 | 22 | 100% | 0% | 0% |
| SLL | 0 | 0 | 0 | 0 | 14 | 0 | 14 | 100% | 0% | 0% |

TABLE 2397

|  | DLBCL/BL | FL | FH | MCL | SLL | Unclassified | Total | % Correct | % Unclassified | % Error |
|---|---|---|---|---|---|---|---|---|---|---|
| ABC | 78 | 0 | 0 | 0 | 0 | 0 | 78 | 100% | 0% | 0% |
| GCB | 77 | 4 | 0 | 0 | 0 | 4 | 85 | 91% | 5% | 5% |
| PMBL | 33 | 0 | 0 | 0 | 0 | 0 | 33 | 100% | 0% | 0% |
| Unclassified DLBCL | 27 | 1 | 0 | 0 | 0 | 2 | 30 | 90% | 7% | 3% |
| DLBCL (not yet subclassed) | 14 | 0 | 0 | 0 | 0 | 1 | 15 | 93% | 7% | 0% |
| BL | 20 | 1 | 0 | 0 | 0 | 0 | 21 | 95% | 0% | 5% |
| FL grade 1 | 1 | 78 | 0 | 0 | 0 | 3 | 82 | 95% | 4% | 1% |
| FL grade 2 | 2 | 58 | 0 | 0 | 0 | 3 | 63 | 92% | 5% | 3% |
| FL grade 3A | 2 | 18 | 0 | 0 | 0 | 8 | 28 | 64% | 29% | 7% |
| Combined FL grades 1, 2, 3A | 5 | 154 | 0 | 0 | 0 | 14 | 173 | 89% | 8% | 3% |
| FL grade 3B | 2 | 1 | 0 | 0 | 0 | 4 | 7 | 14% | 57% | 29% |
| FL unknown grade | 3 | 11 | 0 | 0 | 0 | 0 | 14 | 79% | 0% | 21% |
| FH | 0 | 0 | 17 | 0 | 0 | 0 | 17 | 100% | 0% | 0% |
| MCL | 0 | 0 | 0 | 22 | 0 | 0 | 22 | 100% | 0% | 0% |
| SLL | 0 | 0 | 0 | 0 | 14 | 0 | 14 | 100% | 0% | 0% |

TABLE 2398

|  | ABC | GCB | PMBL | BL | Unclassified | Total | % Correct | % Unclassified | % Error |
|---|---|---|---|---|---|---|---|---|---|
| ABC | 76 | 0 | 0 | 0 | 2 | 78 | 97% | 3% | 0% |
| GCB | 1 | 66 | 2 | 0 | 4 | 77 | 86% | 9% | 5% |
| PMBL | 0 | 2 | 27 | 0 | 4 | 33 | 82% | 12% | 6% |
| Unclassified DLBCL | 5 | 9 | 1 | 1 | 11 | 27 | NA | 41% | 4% |
| DLBCL (not yet subclassed) | 5 | 5 | 0 | 1 | 3 | 14 | NA | 21% | 7% |
| BL | 0 | 1 | 0 | 18 | 1 | 20 | 90% | 5% | 5% |
| FL grade 1 | 0 | 1 | 0 | 0 | 0 | 1 |  |  |  |
| FL grade 2 | 0 | 1 | 0 | 0 | 1 | 2 |  |  |  |
| FL grade 3A | 0 | 2 | 0 | 0 | 0 | 2 |  |  |  |
| Combined FL grades 1, 2, 3A | 0 | 4 | 0 | 0 | 1 | 5 |  |  |  |
| FL grade 3B | 0 | 1 | 0 | 0 | 1 | 2 |  |  |  |
| FL unknown grade | 0 | 1 | 0 | 1 | 1 | 3 |  |  |  |

As seen in Table 2398, only 1 of the 20 BL lymphoma samples was classified incorrectly. The classification of DLBCL into subtypes was also quite effective. All previously identified ABC subtype samples were again assigned to the ABC subtype, while only 5% of the GCB samples and 6% of the PMBL samples were assigned to a different subtype than they were assigned to previously.

The above classification was implemented using S+ software and the S+ subtype predictor script contained in the file entitled "Subtype_Predictor.txt," located in the computer program listing appendix contained on CD number 22 of 22. This S+ script implements the lymphoma prediction algorithm. When this script is pasted into an S+ script window and run in a working directory containing the data set files discussed below, it will produce a text file entitled "PredictionResults.txt," which indicates the results of the predictive algorithm. The other files in the computer program listing appendix contain the required data sets, in their required format, for carrying out the lymphoma type identification described above. The file entitled "GeneData.txt" contains the gene expression values for each sample analyzed. This file is included in the working directory when the S+ subtype predictor script is run. The file entitled "GeneID.txt" contains information about the genes in the GeneData.txt file, and is also included in the working directory when the S+ subtype predictor script is run. This file indicates the UNIQID for each gene, as well as the extent to which the gene is associated with the lymph node and proliferation signatures ("LN.cor" and "pro.cor," respectively). The file entitled "SampleID.txt" contains information about the samples included in the "GeneData.txt" file, specifically the original classification of all the samples. This file is also included in the working directory when the S+ subtype predictor script is run. The file entitled "PredictionResults.txt" is an example of the productive output of the prediction algorithm.

After the above model was validated using leave-one-out cross-validation, the model was re-fit using all of the data to generate a final predictor that could be applied to a new set of data. Tables 2399-2414 indicate for each of the pair wise models the list of genes used, the weight given to each of those genes, the signature with which each gene was associated, the mean values and covariance matrices associated with the subtypes being compared, and the q-value cut-points of the pair-wise model.

TABLE 2399

ABC vs. BL

| Signature | Scale | UNIQID | Unigene ID Build 167 | Probe set | Gene symbol |
|---|---|---|---|---|---|
| Standard | −18.87 | 1101149 | 517226 | 229437_at | BIC |
| Standard | −17.4 | 1121452 | 227817 | 205681_at | BCL2A1 |
| Standard | −16.42 | 1123163 | 421342 | 208991_at | STAT3 |
| Standard | −16.2 | 1121629 | 41691 | 205965_at | BATF |
| Standard | −15 | 1134095 | 89555 | 208018_s_at | HCK |
| Standard | −14.75 | 1132636 | 306278 | 204490_s_at | CD44 |
| Standard | −14.33 | 1119939 | 170087 | 202820_at | AHR |
| Standard | −14.25 | 1100138 | 278391 | 228234_at | TIRP |
| Standard | −14.02 | 1128626 | 501452 | 219424_at | EB13 |
| Standard | −13.89 | 1132883 | 432453 | 205027_s_at | MAP3K8 |
| Standard | −13.88 | 1134991 | 444105 | 209474_s_at | ENTPD1 |
| Standard | −13.37 | 1109913 | 355724 | 239629_at | CFLAR |
| Standard | −13.25 | 1120389 | 75367 | 203761_at | SLA |
| Standard | −12.99 | 1131497 | 114931 | 202295_s_at | CTSH |
| Standard | −12.71 | 1115071 | 390476 | 223218_s_at | MAIL |
| Standard | −12.46 | 1136329 | 132739 | 211675_s_at | HIC |
| Standard | −12.41 | 1128195 | 115325 | 218699_at | RAB7L1 |
| Standard | −12.37 | 1124381 | 440808 | 212288_at | FNBP1 |
| Standard | −12.30 | 1100562 | 26608 | 228737_at | C20orf100 |
| Standard | −12.24 | 1101272 | 179089 | 229584_at | DKFZp434 |
| Standard | −12.18 | 1128536 | 21126 | 219279_at | DOCK10 |
| Standard | −11.64 | 1098271 | 300670 | 226056_at | CDGAP |
| Standard | −11.41 | 1119566 | 433506 | 201954_at | ARPC1B |

TABLE 2399-continued

ABC vs. BL

| | | | | | |
|---|---|---|---|---|---|
| Standard | −11.11 | 1120651 | 80205 | 204269_at | PIM2 |
| Standard | −10.89 | 1098952 | 62264 | 226841_at | KIAA0937 |
| Standard | −10.80 | 1099939 | 488173 | 227983_at | MGC7036 |
| Standard | −10.67 | 1134270 | 352119 | 208284_x_at | GGT1 |
| Standard | −10.44 | 1134145 | 4750 | 208091_s_at | DKFZP564 |
| Standard | −10.39 | 1123437 | 73090 | 209636_at | NFKB2 |
| Standard | −10.17 | 1119884 | 418004 | 202716_at | PTPM1 |
| Standard | −10.14 | 1129269 | 62919 | 220358_at | SNFT |
| Standard | −10.13 | 1126293 | 504816 | 215346_at | TNFRSF5 |
| Standard | −10.12 | 1112344 | 163242 | 242406_at | |
| Standard | −10.10 | 1135550 | 221811 | 210550_s_at | RASGRF1 |
| Standard | −10.08 | 1135165 | 170359 | 209827_s_at | IL16 |
| Standard | −10.05 | 1120808 | 127686 | 204562_at | IRF4 |
| Standard | −10.01 | 1122087 | 72927 | 206693_at | IL7 |
| Standard | −9.97 | 1132004 | 415117 | 203217_s_at | SIAT9 |
| Standard | −9.88 | 1114824 | 193370 | 222762_x_at | LIMD1 |
| Standard | −9.87 | 1132034 | 410455 | 203271_s_at | UNC119 |
| Standard | −9.87 | 1099680 | 210387 | 227677_at | JAK3 |
| Standard | −9.86 | 1132830 | 31210 | 204908_s_at | BCL3 |
| Standard | −9.79 | 1099631 | 367639 | 227624_at | FLJ20032 |
| Standard | −9.78 | 1120267 | 256278 | 203508_at | TNFRSF1B |
| Standard | −9.77 | 1124187 | 378738 | 211986_at | MGC5395 |
| Standard | −9.73 | 1108970 | 140489 | 238604_at | |
| Standard | −9.71 | 1136216 | 512152 | 211528_x_at | HLA-G |
| Standard | −9.71 | 1120993 | 327 | 204912_at | IL10RA |
| Standard | −9.68 | 1100847 | 97411 | 229070_at | C6orf105 |
| Standard | −9.64 | 1123413 | 418291 | 209575_at | IL10RB |
| Standard | −9.62 | 1115704 | 350268 | 224569_s_at | IRF2BP2 |
| Standard | −9.58 | 1108237 | 126232 | 237753_at | |
| Standard | −9.55 | 1121695 | 511759 | 206082_at | HCP5 |
| Standard | −9.48 | 1101905 | 170843 | 230345_at | |
| Standard | −9.42 | 1119243 | 440165 | 201171_at | ATP6V0E |
| Standard | −9.39 | 1140457 | 210546 | 221658_s_at | IL21R |
| Standard | −9.32 | 1098506 | 193400 | 226333_at | IL6R |
| Standard | −9.31 | 1139805 | 414362 | 220230_s_at | CYB5R2 |
| Standard | −9.30 | 1139037 | 173380 | 218223_s_at | CKIP-1 |
| Standard | −9.28 | 1130533 | 76507 | 200706_s_at | LITAF |
| Standard | −9.15 | 1098678 | 386140 | 226530_at | BMF |
| Standard | −9.04 | 1133210 | 434374 | 205842_s_at | JAK2 |
| Standard | 9.05 | 1116432 | 409362 | 229356_x_at | KIAA1259 |
| Standard | 9.17 | 1097281 | 7037 | 224892_at | PLDN |
| Standard | 9.17 | 1140018 | 438482 | 220917_s_at | PWDMP |
| Standard | 9.30 | 1119997 | 367811 | 202951_at | STK38 |
| Standard | 9.41 | 1119817 | 409194 | 202561_at | TNKS |
| Standard | 9.55 | 1139842 | 133523 | 220367_s_at | SAP130 |
| Standard | 9.64 | 1132122 | 307734 | 203434_s_at | MME |
| Standard | 9.77 | 1119258 | 88556 | 201209_at | HDAC1 |
| Standard | 9.80 | 1128248 | 234149 | 218802_at | FLJ20647 |
| Standard | 10.38 | 1101211 | 287659 | 229513_at | STRBP |
| Standard | 10.52 | 1123419 | 170195 | 209590_at | BMP7 |
| Standard | 10.71 | 1133755 | 404501 | 207318_s_at | CDC2L5 |
| Standard | 10.80 | 1128192 | 102506 | 218696_at | EIF2AK3 |
| Standard | 10.85 | 1124786 | 22370 | 212847_at | NEXN |
| Standard | 10.92 | 1130114 | 445084 | 221965_at | MPHOSPH9 |
| Standard | 11.00 | 1126081 | 309763 | 215030_at | GRSF1 |
| Standard | 11.17 | 1118736 | 96731 | 38340_at | HIP1R |
| Standard | 11.26 | 1124613 | 296720 | 212599_at | AUTS2 |
| Standard | 11.43 | 1125456 | 300592 | 213906_at | MYBL1 |
| Standard | 11.60 | 1097177 | 9691 | 224761_at | GNA13 |
| Standard | 12.11 | 1120400 | 152207 | 203787_at | SSBP2 |
| Standard | 12.12 | 1139266 | 76640 | 218723_s_at | RGC32 |
| Standard | 12.22 | 1100770 | 65578 | 228976_at | |
| Standard | 12.73 | 1131246 | 153752 | 201853_s_at | CDC25B |
| Standard | 13.48 | 1096503 | 21379 | 223522_at | C9orf45 |
| Standard | 14.50 | 1124920 | 6150 | 213039_at | ARHGEF1 |
| Standard | 15.03 | 1128360 | 445043 | 218988_at | SLC35E3 |
| Standard | 15.24 | 1099444 | 434489 | 227407_at | FLJ90013 |
| Standard | 21.03 | 1134582 | 78202 | 208794_s_at | SMARCA4 |

Standard

| | | | |
|---|---|---|---|
| Mean ABC | −4179.76 | Cut 1 | 0.20 |
| Mean BL | −1894.68 | Cut 2 | 0.80 |
| Covariance ABC | 53707.58 | | |
| Covariance BL | 194887.5 | | |

TABLE 2400

| | | | ABC vs. GCB | | |
|---|---|---|---|---|---|
| Signature | Scale | UNIQID | Unigene ID Build 167 | Probe set | Gene symbol |
| Standard | −15.31 | 1122645 | 158341 | 207641_at | TNFRSF13B |
| Standard | −14.56 | 1120651 | 80205 | 204269_at | PIM2 |
| Standard | −14.18 | 1120808 | 127686 | 204562_at | IRF4 |
| Standard | −13.84 | 1114824 | 193370 | 222762_x_at | LIMD1 |
| Standard | −13.44 | 1136687 | 59943 | 212345_s_at | CREB3L2 |
| Standard | −13.12 | 1139805 | 414362 | 220230_s_at | CYB5R2 |
| Standard | −12.23 | 1104552 | 193857 | 233483_at | LOC96597 |
| Standard | −12.19 | 1097236 | 235860 | 224837_at | FOXP1 |
| Standard | −12.06 | 1121629 | 41691 | 205965_at | BATF |
| Standard | −11.93 | 1128195 | 115325 | 218699_at | RAB7L1 |
| Standard | −11.72 | 1111503 | 502910 | 241383_at | KBRAS2 |
| Standard | −11.66 | 1134991 | 444105 | 209474_s_at | ENTPD1 |
| Standard | −11.27 | 1098678 | 386140 | 226530_at | BMF |
| Standard | −10.9 | 1131074 | 76894 | 201572_x_at | DCTD |
| Standard | −10.82 | 1135165 | 170359 | 209827_s_at | IL16 |
| Standard | −10.7 | 1132396 | 118722 | 203988_s_at | FUT8 |
| Standard | −10.54 | 1131541 | 310230 | 202369_s_at | TRAM2 |
| Standard | −10.47 | 1105759 | 171262 | 235056_at | ETV6 |
| Standard | −10.38 | 1121564 | 437783 | 205865_at | ARID3A |
| Standard | −10.16 | 1130472 | 192374 | 200599_s_at | TRA1 |
| Standard | −10.04 | 1132058 | 161999 | 203313_s_at | TGIF |
| Standard | −10.03 | 1105684 | 195155 | 234973_at | SLC38A5 |
| Standard | −9.95 | 1097735 | 26765 | 225436_at | LOC58489 |
| Standard | −9.94 | 1115071 | 390476 | 223218_s_at | MAIL |
| Standard | −9.85 | 1101149 | 517226 | 229437_at | BIC |
| Standard | −9.83 | 1119884 | 418004 | 202716_at | PTPN1 |
| Standard | −9.71 | 1134095 | 89555 | 208018_s_at | HCK |
| Standard | −9.68 | 1135550 | 221811 | 210550_s_at | RASGRF1 |
| Standard | −9.61 | 1098927 | 356216 | 226811_at | FLJ20202 |
| Standard | −9.6 | 1120389 | 75367 | 203761_at | SLA |
| Standard | −9.58 | 1133910 | 167746 | 207655_s_at | BLNK |
| Standard | 9.56 | 1118736 | 96731 | 38340_at | HIP1R |
| Standard | 9.58 | 1128860 | 323634 | 219753_at | STAG3 |
| Standard | 9.68 | 1134582 | 78202 | 208794_s_at | SMARCA4 |
| Standard | 9.7 | 1121853 | 98243 | 206310_at | SPINK2 |
| Standard | 10.14 | 1119258 | 88556 | 201209_at | HDAC1 |
| Standard | 10.19 | 1132122 | 307734 | 203434_s_at | MME |
| Standard | 10.23 | 1120400 | 152207 | 203787_at | SSBP2 |
| Standard | 10.48 | 1529344 | 317970 | Lymph_Dx_065_at | SERPINA11 |
| Standard | 10.64 | 1124613 | 296720 | 212599_at | AUTS2 |
| Standard | 10.72 | 1132159 | 147868 | 203521_s_at | ZNF318 |
| Standard | 10.98 | 1097901 | 266175 | 225626_at | PAG |
| Standard | 11.1 | 1128287 | 300063 | 218862_at | ASB13 |
| Standard | 12.26 | 1099686 | 117721 | 227684_at | |
| Standard | 12.45 | 1112674 | 310320 | 242794_at | MAML3 |
| Standard | 13.15 | 1120370 | 78877 | 203723_at | ITPKB |
| Standard | 14.23 | 1125456 | 300592 | 213906_at | MYBL1 |
| Lymph Node | 6.8 | 1097202 | 386779 | 224796_at | DDEF1 |
| Lymph Node | 6.85 | 1131755 | 241257 | 202729_s_at | LTBP1 |
| Lymph Node | 7.27 | 1136273 | 13775 | 211597_s_at | HOP |
| Lymph Node | 7.35 | 1119424 | 75485 | 201599_at | OAT |
| Lymph Node | 7.86 | 1095985 | 83883 | 222450_at | TMEPAI |
| Lymph Node | 8.02 | 1124875 | 18166 | 212975_at | KIAA0870 |
| Lymph Node | 8.32 | 1124655 | 79299 | 212658_at | LHFPL2 |
| Lymph Node | 8.62 | 1115034 | 387222 | 223158_s_at | NEK6 |
| Proliferation | −9.11 | 1120583 | 153768 | 204133_at | RNU3IP2 |
| Proliferation | −7.87 | 1135492 | 408615 | 210448_s_at | P2RX5 |
| Proliferation | −7.68 | 1127756 | 313544 | 217850_at | NS |
| Proliferation | −7.57 | 1097195 | 149931 | 224785_at | MGC29814 |
| Proliferation | −7.31 | 1127813 | 14317 | 217962_at | NOLA3 |
| Proliferation | −7.24 | 1138944 | 84753 | 218051_s_at | FLJ12442 |
| Proliferation | −6.99 | 1139226 | 266514 | 218633_x_at | FLJ11342 |
| Proliferation | −6.7 | 1137486 | 441069 | 214442_s_at | MIZ1 |
| Proliferation | −6.51 | 1133786 | 153591 | 207396_s_at | ALG3 |
| Proliferation | −6.45 | 1131150 | 75514 | 201695_s_at | NP |
| Proliferation | −6.45 | 1119076 | 268849 | 200681_at | GLO1 |
| Proliferation | −6.38 | 1115679 | 8345 | 224523_s_at | MGC4308 |
| Proliferation | −6.34 | 1110223 | 212709 | 239973_at | |
| Proliferation | −6.3 | 1529338 | 284275 | Lymph_Dx_058_s_at | PAK2 |
| Proliferation | −6.24 | 1135164 | 458360 | 209825_s_at | UMPK |
| Proliferation | −6.24 | 1128738 | 335550 | 219581_at | MGC2776 |
| Proliferation | −6.01 | 1099088 | 14355 | 226996_at | |
| Proliferation | −5.98 | 1123192 | 315177 | 209100_at | IFRD2 |

TABLE 2400-continued

ABC vs. GCB

| Signature | Scale | UNIQID | Unigene ID | Probe set | Gene Symbol |
|---|---|---|---|---|---|
| Proliferation | −5.83 | 1116073 | 146161 | 227103_s_at | MGC2408 |
| Proliferation | 5.79 | 1097388 | 278839 | 225024_at | C20orf77 |
| Proliferation | 6.13 | 1124563 | 249441 | 212533_at | WEE1 |

|  | Standard | Lymph Node | Proliferation |  |  |
|---|---|---|---|---|---|
| Mean ABC | −2226.57 | 476.67 | −1096.34 | Cut 1 | 0.50 |
| Mean GCB | −1352.02 | 547.18 | −1005.72 | Cut 2 | 0.74 |
| Covariance ABC | 33472.10 | 3418.91 | 4347.99 |  |  |
|  | 3418.91 | 1296.05 | 846.32 |  |  |
|  | 4347.99 | 846.32 | 1609.13 |  |  |
| Covariance GCB | 53751.59 | 466.34 | 751.08 |  |  |
|  | 466.34 | 777.74 | 249.29 |  |  |
|  | 751.08 | 249.29 | 1708.67 |  |  |

TABLE 2401

ABC vs. PMBL

| Signature | Scale | UNIQID | Unigene ID Build 167 | Probe set | Gene Symbol |
|---|---|---|---|---|---|
| Standard | −14.61 | 1097236 | 235860 | 224837_at | FOXP1 |
| Standard | −14.47 | 1104552 | 193857 | 233483_at | LOC96597 |
| Standard | −13.62 | 1122645 | 158341 | 207641_at | TNFRSF13B |
| Standard | −12.05 | 1135102 | 349845 | 209685_s_at | PRKCB1 |
| Standard | −11.65 | 1096499 | 293867 | 223514_at | CARD11 |
| Standard | −11.26 | 1124770 | 153261 | 212827_at | IGHM |
| Standard | −11.25 | 1125010 | 43728 | 213170_at | GPX7 |
| Standard | −11.13 | 1109545 | 63187 | 239231_at |  |
| Standard | −10.99 | 1109220 | 445977 | 238880_at | GTF3A |
| Standard | −10.87 | 1131074 | 76894 | 201572_x_at | DCTD |
| Standard | −10.68 | 1134517 | 75807 | 208690_s_at | PDLIM1 |
| Standard | −10.63 | 1098604 | 32793 | 226444_at | SLC39A10 |
| Standard | −10.56 | 1131219 | 109150 | 201810_s_at | SH3BP5 |
| Standard | −10.52 | 1120651 | 80205 | 204269_at | PIM2 |
| Standard | −10.39 | 1133910 | 167746 | 207655_s_at | BLNK |
| Standard | −10.32 | 1099396 | 435949 | 227346_at | ZNFN1A1 |
| Standard | −10.25 | 1529297 | 132335 | Lymph_Dx_015_at |  |
| Standard | −10.17 | 1107575 | 424589 | 237033_at | MGC52498 |
| Standard | −10.11 | 1117211 | 356509 | 233955_x_at | HSPC195 |
| Standard | 10.06 | 1129517 | −33 | 220712_at |  |
| Standard | 10.29 | 1139950 | 437385 | 220731_s_at | FLJ10420 |
| Standard | 10.35 | 1097553 | 197071 | 225214_at | PSMB7 |
| Standard | 10.41 | 1119516 | 6061 | 201834_at | PRKAB1 |
| Standard | 10.47 | 1122772 | 66742 | 207900_at | CCL17 |
| Standard | 10.55 | 1132762 | 80395 | 204777_s_at | MAL |
| Standard | 10.77 | 1099265 | 375762 | 227193_at |  |
| Standard | 10.81 | 1095996 | 288801 | 222482_at | SSBP3 |
| Standard | 11.14 | 1100770 | 65578 | 228976_at |  |
| Standard | 11.19 | 1133801 | 181097 | 207426_s_at | TNFSF4 |
| Standard | 11.61 | 1099154 | 97927 | 227066_at | MOBKL2C |
| Standard | 11.63 | 1120370 | 78877 | 203723_at | ITPKB |
| Standard | 11.8 | 1112674 | 310320 | 242794_at | MAML3 |
| Standard | 12.57 | 1105178 | 283961 | 234284_at | GNG8 |
| Standard | 12.63 | 1124613 | 296720 | 212599_at | AUTS2 |
| Standard | 13.28 | 1106415 | 169071 | 235774_at |  |
| Standard | 13.3 | 1121762 | 32970 | 206181_at | SLAMF1 |
| Standard | 13.6 | 1121853 | 98243 | 206310_at | SPINK2 |
| Lymph Node | 10.91 | 1105838 | 129837 | 235142_at | ZBTB8 |
| Lymph Node | 10.99 | 1136273 | 13775 | 211597_s_at | HOP |
| Lymph Node | 11.02 | 1099418 | 172792 | 227370_at | KIAA1946 |
| Lymph Node | 11.46 | 1124875 | 18166 | 212975_at | KIAA0870 |
| Lymph Node | 11.99 | 1120299 | 79334 | 203574_at | NFIL3 |
| Lymph Node | 12.49 | 1135871 | 104717 | 211031_s_at | CYLN2 |
| Lymph Node | 13.33 | 1121767 | 458324 | 206187_at | PTGIR |
| Proliferation | −13.17 | 1138944 | 84753 | 218051_s_at | FLJ12442 |
| Proliferation | −11.61 | 1116122 | 42768 | 227408_s_at | DKFZp761O0113 |
| Proliferation | −11.16 | 1110223 | 212709 | 239973_at |  |
| Proliferation | −9.93 | 1120717 | 444159 | 204394_at | SLC43A1 |
| Proliferation | −9.54 | 1110099 | 116665 | 239835_at | TA-KRP |
| Proliferation | −9.49 | 1130942 | 445977 | 201338_x_at | GTF3A |
| Proliferation | −9.28 | 1123192 | 315177 | 209100_at | IFRD2 |

TABLE 2401-continued

ABC vs. PMBL

| Proliferation | −9.14 | 1135492 | 408615 | 210448_s_at | P2RX5 |
| Proliferation | −9.03 | 1120011 | 3068 | 202983_at | SMARCA3 |
| Proliferation | −9.01 | 1096738 | 87968 | 223903_at | TLR9 |
| Proliferation | −8.91 | 1108961 | 292088 | 238593_at | FLJ22531 |

| | Standard | Lymph Node | Proliferation | | |
|---|---|---|---|---|---|
| Mean ABC | −849.47 | 531.79 | −1027.48 | Cut 1 | 0.20 |
| Mean PMBL | 27.99 | 750.84 | −872.43 | Cut 2 | 0.80 |
| Covariance ABC | 14028.46 | 3705.84 | 3118.60 | | |
| | 3705.84 | 2326.91 | 1083.37 | | |
| | 3118.60 | 1083.37 | 1589.42 | | |
| Covariance PMBL | 19425.29 | 5109.98 | 2199.28 | | |
| | 5109.98 | 2084.28 | 620.86 | | |
| | 2199.28 | 620.86 | 1028.44 | | |

TABLE 2402

BL vs. GCB

| Signature | Scale | UNIQID | Unigene ID Build 167 | Probe set | Gene Symbol |
|---|---|---|---|---|---|
| Standard | −12.78 | 1131246 | 153752 | 201853_s_at | CDC25B |
| Standard | −11.35 | 1099444 | 434489 | 227407_at | FLJ90013 |
| Standard | −10.4 | 1116432 | 409362 | 229356_x_at | KIAA1259 |
| Standard | −10.3 | 1134582 | 78202 | 208794_s_at | SMARCA4 |
| Standard | −10.01 | 1133998 | 76884 | 207826_s_at | ID3 |
| Standard | −9.3 | 1126081 | 309763 | 215030_at | GRSF1 |
| Standard | −9.19 | 1096503 | 21379 | 223522_at | C9orf45 |
| Standard | −8.95 | 1529340 | −99 | Lymph_Dx_061_at | |
| Standard | −8.88 | 1138128 | 390428 | 216199_s_at | MAP3K4 |
| Standard | −8.8 | 1099152 | 351247 | 227064_at | MGC15396 |
| Standard | −8.69 | 1133757 | 6113 | 207320_x_at | STAU |
| Standard | −8.54 | 1116593 | 422889 | 230329_s_at | NUDT6 |
| Standard | −8.4 | 1130926 | 508741 | 201310_s_at | C5orf13 |
| Standard | −8.39 | 1135685 | 371282 | 210776_x_at | TCF3 |
| Standard | −8.39 | 1140520 | 11747 | 221741_s_at | C20orf21 |
| Standard | −8.34 | 1119802 | 7370 | 202522_at | PITPNB |
| Standard | −8.31 | 1096149 | 410205 | 222824_at | NUDT5 |
| Standard | −8.23 | 1124786 | 22370 | 212847_at | NEXN |
| Standard | −8.07 | 1098012 | 355669 | 225756_at | CSNK1E |
| Standard | −7.89 | 1116317 | 526415 | 228661_s_at | |
| Standard | −7.86 | 1109195 | 416155 | 238853_at | |
| Standard | −7.71 | 1134880 | 168799 | 209265_s_at | METTL3 |
| Standard | −7.66 | 1529298 | 136707 | Lymph_Dx_016_at | |
| Standard | −7.55 | 1128660 | 413071 | 219471_at | C13orf18 |
| Standard | −7.55 | 1138973 | 11270 | 218097_s_at | C10orf66 |
| Standard | −7.46 | 1127294 | 421986 | 217028_at | CXCR4 |
| Standard | 7.47 | 1134270 | 352119 | 208284_x_at | GGT1 |
| Standard | 7.48 | 1120743 | 79197 | 204440_at | CD83 |
| Standard | 7.5 | 1098179 | 163725 | 225956_at | LOC153222 |
| Standard | 7.55 | 1121400 | 223474 | 205599_at | TRAF1 |
| Standard | 7.59 | 1114967 | 7905 | 223028_s_at | SNX9 |
| Standard | 7.6 | 1122087 | 72927 | 206693_at | IL7 |
| Standard | 7.64 | 1101905 | 170843 | 230345_at | |
| Standard | 7.77 | 1120700 | 410745 | 204362_at | SCAP2 |
| Standard | 7.8 | 1120572 | 84 | 204116_at | IL2RG |
| Standard | 7.84 | 1098271 | 300670 | 226056_at | CDGAP |
| Standard | 7.9 | 1115073 | 131315 | 223220_s_at | BAL |
| Standard | 7.9 | 1133210 | 434374 | 205842_s_at | JAK2 |
| Standard | 8 | 1129269 | 62919 | 220358_at | SNFT |
| Standard | 8.01 | 1131940 | 1103 | 203085_s_at | TGFB1 |
| Standard | 8.07 | 1098506 | 193400 | 226333_at | IL6R |
| Standard | 8.13 | 1120601 | 441129 | 204166_at | KIAA0963 |
| Standard | 8.21 | 1102540 | 434881 | 231093_at | FCRH3 |
| Standard | 8.24 | 1121695 | 511759 | 206082_at | HCP5 |
| Standard | 8.33 | 1136877 | 409934 | 212998_x_at | HLA-DQB1 |
| Standard | 8.37 | 1100138 | 278391 | 228234_at | TIRP |
| Standard | 8.46 | 1126293 | 504816 | 215346_at | TNFRSF5 |
| Standard | 8.46 | 1127805 | 380627 | 217947_at | CKLFSF6 |
| Standard | 8.59 | 1136573 | 914 | 211991_s_at | HLA-DPA1 |

TABLE 2402-continued

| | | | BL vs. GCB | | |
|---|---|---|---|---|---|
| Standard | 8.62 | 1119111 | 35052 | 200804_at | TEGT |
| Standard | 8.7 | 1136329 | 132739 | 211675_s_at | HIC |
| Standard | 8.74 | 1123690 | 111805 | 210176_at | TLR1 |
| Standard | 8.81 | 1138677 | 390440 | 217436_x_at | |
| Standard | 8.89 | 1113993 | 131811 | 244286_at | |
| Standard | 8.89 | 1132651 | 439767 | 204529_s_at | TOX |
| Standard | 8.91 | 1119566 | 433506 | 201954_at | ARPC1B |
| Standard | 9.01 | 1128626 | 501452 | 219424_at | EBI3 |
| Standard | 9.17 | 1101272 | 179089 | 229584_at | DKFZp434H2111 |
| Standard | 9.33 | 1136777 | 387679 | 212671_s_at | HLA-DQA1 |
| Standard | 9.33 | 1109756 | 530304 | 239453_at | |
| Standard | 9.4 | 1136216 | 512152 | 211528_x_at | HLA-G |
| Standard | 9.4 | 1124381 | 440808 | 212288_at | FNBP1 |
| Standard | 9.46 | 1099680 | 210387 | 227677_at | JAK3 |
| Standard | 9.49 | 1109913 | 355724 | 239629_at | CFLAR |
| Standard | 9.55 | 1132636 | 306278 | 204490_s_at | CD44 |
| Standard | 9.59 | 1119243 | 440165 | 201171_at | ATP6V0E |
| Standard | 9.72 | 1101149 | 517226 | 229437_at | BIC |
| Standard | 9.8 | 1130674 | 381008 | 200905_x_at | HLA-E |
| Standard | 10.34 | 1119939 | 170087 | 202820_at | AHR |
| Standard | 10.44 | 1132883 | 432453 | 205027_s_at | MAP3K8 |
| Standard | 10.74 | 1121452 | 227817 | 205681_at | BCL2A1 |
| Standard | 10.84 | 1137360 | 429658 | 214196_s_at | CLN2 |
| Standard | 12.08 | 1132520 | 283063 | 204249_s_at | LMO2 |
| Standard | 12.33 | 1131497 | 114931 | 202295_s_at | CTSH |
| Standard | 13.58 | 1123163 | 421342 | 208991_at | STAT3 |
| Lymph Node | −9.1 | 1138136 | 433574 | 216215_s_at | RBM9 |
| Lymph Node | 8.78 | 1130121 | 411958 | 221978_at | HLA-F |
| Lymph Node | 9.22 | 1139830 | 221851 | 220330_s_at | SAMSN1 |
| Lymph Node | 9.23 | 1131705 | 386467 | 202638_s_at | ICAM1 |
| Lymph Node | 9.62 | 1130168 | 75626 | 222061_at | CD58 |
| Lymph Node | 9.66 | 1121844 | 83077 | 206295_at | IL18 |
| Lymph Node | 9.68 | 1121000 | 519033 | 204924_at | TLR2 |
| Lymph Node | 9.83 | 1102437 | 437023 | 230966_at | IL4I1 |
| Lymph Node | 10.71 | 1119475 | 296323 | 201739_at | SGK |
| Lymph Node | 11.09 | 1131786 | 375957 | 202803_s_at | ITGB2 |
| Proliferation | −11.07 | 1133141 | 344524 | 205677_s_at | DLEU1 |
| Proliferation | −10.04 | 1138259 | 89525 | 216484_x_at | HDGF |
| Proliferation | −9.74 | 1131578 | 202453 | 202431_s_at | MYC |
| Proliferation | −9.45 | 1137449 | 223745 | 214363_s_at | MATR3 |
| Proliferation | −9.43 | 1130468 | 166463 | 200594_x_at | HNRPU |
| Proliferation | −9.21 | 1138157 | 82563 | 216251_s_at | KIAA0153 |
| Proliferation | −9.15 | 1127756 | 313544 | 217850_at | NS |
| Proliferation | −9 | 1130433 | 246112 | 200058_s_at | U5-200KD |
| Proliferation | −8.76 | 1123108 | 108112 | 208828_at | POLE3 |
| Proliferation | −8.75 | 1128738 | 335550 | 219581_at | MGC2776 |
| Proliferation | −8.74 | 1122400 | 439911 | 207199_at | TERT |
| Proliferation | −8.66 | 1097948 | 69476 | 225684_at | LOC348235 |
| Proliferation | −8.6 | 1119460 | 76122 | 201696_at | SFRS4 |
| Proliferation | −8.6 | 1136401 | 27258 | 211761_s_at | SIP |
| Proliferation | −8.58 | 1099088 | 14355 | 226996_at | |
| Proliferation | −8.51 | 1134653 | 253536 | 208901_s_at | TOP1 |
| Proliferation | −8.49 | 1140584 | 294083 | 221932_s_at | C14orf87 |
| Proliferation | −8.43 | 1121309 | 23642 | 205449_at | HSU79266 |
| Proliferation | −8.43 | 1120385 | 36708 | 203755_at | BUB1B |
| Proliferation | −8.38 | 1136710 | 75782 | 212429_s_at | GTF3C2 |
| Proliferation | −8.36 | 1136605 | 448398 | 212064_x_at | MAZ |
| Proliferation | −8.24 | 1120697 | 323462 | 204355_at | DHX30 |
| Proliferation | −8.19 | 1127833 | 382044 | 218001_at | MRPS2 |
| Proliferation | −8.11 | 1096903 | 437460 | 224185_at | FLJ10385 |
| Proliferation | −8.1 | 1120596 | 4854 | 204159_at | CDKN2C |
| Proliferation | −8.1 | 1120779 | 28853 | 204510_at | CDC7 |

| | Standard | Lymph Node | Proliferation | | |
|---|---|---|---|---|---|
| Mean BL | 1098.69 | 576.05 | −2392.12 | Cut 1 | 0.09 |
| Mean GCB | 2187.37 | 768.53 | −2129.35 | Cut 2 | 0.53 |
| Covariance BL | 75263.67 | 12684.43 | 15734.77 | | |
| | 12684.43 | 2650.81 | 2358.05 | | |
| | 15734.77 | 2358.05 | 4653.00 | | |
| Covariance GCB | 50548.22 | 9301.12 | 14182.83 | | |
| | 9301.12 | 2602.51 | 3028.21 | | |
| | 14182.83 | 3028.21 | 5983.04 | | |

TABLE 2403

BL vs. PMBL

| Signature | Scale | UNIQID | Unigene ID Build 167 | Probe set | Gene Symbol |
|---|---|---|---|---|---|
| Standard | −13.54 | 1099444 | 434489 | 227407_at | FLJ90013 |
| Standard | −13.42 | 1096503 | 21379 | 223522_at | C9orf45 |
| Standard | −13.36 | 1130114 | 445084 | 221965_at | MPHOSPH9 |
| Standard | −13.27 | 1124786 | 22370 | 212847_at | NEXN |
| Standard | −13.27 | 1134582 | 78202 | 208794_s_at | SMARCA4 |
| Standard | −12.37 | 1096149 | 410205 | 222824_at | NUDT5 |
| Standard | −11.95 | 1130855 | 77515 | 201189_s_at | ITPR3 |
| Standard | −11.66 | 1529298 | 136707 | Lymph_Dx_016_at | |
| Standard | −11.35 | 1131246 | 153752 | 201853_s_at | CDC25B |
| Standard | −11.17 | 1136925 | 436939 | 213154_s_at | BICD2 |
| Standard | −11.08 | 1124188 | 282346 | 211987_at | TOP2B |
| Standard | −11.06 | 1133998 | 76884 | 207826_s_at | ID3 |
| Standard | −10.76 | 1139266 | 76640 | 218723_s_at | RGC32 |
| Standard | −10.74 | 1134880 | 168799 | 209265_s_at | METTL3 |
| Standard | −10.69 | 1140520 | 11747 | 221741_s_at | C20orf21 |
| Standard | −10.6 | 1109545 | 63187 | 239231_at | |
| Standard | −10.55 | 1106043 | 266331 | 235372_at | FREB |
| Standard | −10.52 | 1110214 | 144519 | 239964_at | TCL6 |
| Standard | −10.49 | 1098592 | 283707 | 226431_at | ALS2CR13 |
| Standard | −10.45 | 1109220 | 445977 | 238880_at | GTF3A |
| Standard | −10.41 | 1131263 | 249955 | 201877_s_at | PPP2R5C |
| Standard | 10.54 | 1122772 | 66742 | 207900_at | CCL17 |
| Standard | 10.59 | 1109913 | 355724 | 239629_at | CFLAR |
| Standard | 10.82 | 1119884 | 418004 | 202716_at | PTPN1 |
| Standard | 10.83 | 1135189 | 137569 | 209863_s_at | TP73L |
| Standard | 10.89 | 1123437 | 73090 | 209636_at | NFKB2 |
| Standard | 11.15 | 1124381 | 440808 | 212288_at | FNBP1 |
| Standard | 11.26 | 1108237 | 126232 | 237753_at | |
| Standard | 11.34 | 1101149 | 517226 | 229437_at | BIC |
| Standard | 11.77 | 1139774 | 15827 | 220140_s_at | SNX11 |
| Standard | 11.87 | 1123163 | 421342 | 208991_at | STAT3 |
| Standard | 11.93 | 1129269 | 62919 | 220358_at | SNFT |
| Standard | 12.03 | 1132636 | 306278 | 204490_s_at | CD44 |
| Standard | 12.1 | 1138677 | 390440 | 217436_x_at | |
| Standard | 12.2 | 1139950 | 437385 | 220731_s_at | FLJ10420 |
| Standard | 12.25 | 1134270 | 352119 | 208284_x_at | GGT1 |
| Standard | 12.27 | 1136216 | 512152 | 211528_x_at | HLA-G |
| Standard | 12.79 | 1121400 | 223474 | 205599_at | TRAF1 |
| Standard | 12.82 | 1119939 | 170087 | 202820_at | AHR |
| Standard | 13.12 | 1126293 | 504816 | 215346_at | TNFRSF5 |
| Standard | 13.44 | 1100138 | 278391 | 228234_at | TIRP |
| Standard | 13.74 | 1132883 | 432453 | 205027_s_at | MAP3K8 |
| Standard | 13.94 | 1131497 | 114931 | 202295_s_at | CTSH |
| Standard | 14.15 | 1121762 | 32970 | 206181_at | SLAMF1 |
| Standard | 14.51 | 1132520 | 283063 | 204249_s_at | LMO2 |
| Standard | 14.68 | 1121452 | 227817 | 205681_at | BCL2A1 |
| Standard | 15.24 | 1105178 | 283961 | 234284_at | GNG8 |
| Lymph Node | 10.95 | 1121205 | 2488 | 205269_at | LCP2 |
| Lymph Node | 11.22 | 1140845 | 21486 | AFFX-HUMISGF3A/M97935_3_at | STAT1 |
| Lymph Node | 11.45 | 1131068 | 118400 | 201564_s_at | FSCN1 |
| Lymph Node | 11.92 | 1131705 | 386467 | 202638_s_at | ICAM1 |
| Lymph Node | 12.06 | 1131038 | 81328 | 201502_s_at | NFKBIA |
| Lymph Node | 12.49 | 1121444 | 153563 | 205668_at | LY75 |
| Lymph Node | 13.01 | 1123457 | 446304 | 209684_at | RIN2 |
| Lymph Node | 13.19 | 1140404 | 354740 | 221584_s_at | KCNMA1 |
| Lymph Node | 13.26 | 1124875 | 18166 | 212975_at | KIAA0870 |
| Lymph Node | 14.06 | 1102437 | 437023 | 230966_at | IL4I1 |
| Lymph Node | 14.11 | 1132766 | 82359 | 204781_s_at | TNFRSF6 |
| Lymph Node | 15.31 | 1121767 | 458324 | 206187_at | PTGIR |
| Lymph Node | 15.32 | 1135871 | 104717 | 211031_s_at | CYLN2 |
| Lymph Node | 15.34 | 1138652 | 444471 | 217388_s_at | KYNU |
| Lymph Node | 16.01 | 1139830 | 221851 | 220330_s_at | SAMSN1 |

| | Standard | Lymph Node | | |
|---|---|---|---|---|
| Mean BL | −66.97 | 1445.63 | Cut 1 | 0.20 |
| Mean PMBL | 1205.38 | 2041.25 | Cut 2 | 0.80 |
| Covariance BL | 35263.67 | 13424.88 | | |
| | 13424.88 | 7458.56 | | |
| Covariance PMBL | 12064.38 | 5113.74 | | |
| | 5113.74 | 3216.53 | | |

TABLE 2404

FH vs. DLBCL-BL

| Signature | Scale | UNIQID | Unigene ID Build 167 | Probe set | Gene Symbol |
|---|---|---|---|---|---|
| Standard | −12.81 | 1104910 | 458262 | 233969_at | IGL@ |
| Standard | −11.54 | 1102898 | 145519 | 231496_at | FKSG87 |
| Standard | −11.46 | 1117298 | 449586 | 234366_x_at | |
| Standard | −11.46 | 1132973 | 169294 | 205255_x_at | TCF7 |
| Standard | −11.22 | 1133099 | 88646 | 205554_s_at | DNASE1L3 |
| Standard | −10.76 | 1131531 | 153647 | 202350_s_at | MATN2 |
| Standard | −10.59 | 1124283 | 406612 | 212144_at | UNC84B |
| Standard | −10.35 | 1099847 | 36723 | 227867_at | LOC129293 |
| Standard | −10.22 | 1136430 | 102950 | 211798_x_at | IGLJ3 |
| Standard | −10.05 | 1117394 | −13 | 234792_x_at | |
| Standard | −9.95 | 1133047 | 528338 | 205434_s_at | AAK1 |
| Standard | −9.95 | 1098865 | 250905 | 226741_at | LOC51234 |
| Standard | −9.82 | 1108515 | 98132 | 238071_at | LCN6 |
| Standard | −9.8 | 1131407 | 154248 | 202125_s_at | ALS2CR3 |
| Standard | −9.77 | 1128469 | 390817 | 219173_at | FLJ22686 |
| Standard | −9.7 | 1123875 | 428 | 210607_at | FLT3LG |
| Standard | −9.69 | 1131875 | 169172 | 202965_s_at | CAPN6 |
| Standard | −9.69 | 1135173 | 3781 | 209841_s_at | LRRN3 |
| Standard | −9.48 | 1099798 | 411081 | 227811_at | FGD3 |
| Standard | −9.41 | 1119046 | 349499 | 200606_at | DSP |
| Standard | −9.36 | 1122449 | 278694 | 207277_at | CD209 |
| Standard | −9.34 | 1114017 | 133255 | 244313_at | |
| Standard | −9.34 | 1122767 | 652 | 207892_at | TNFSF5 |
| Standard | −9.24 | 1123369 | 79025 | 209481_at | SNRK |
| Standard | −9.16 | 1098954 | 128905 | 226844_at | MOBKL2B |
| Standard | −9.14 | 1135513 | 421437 | 210481_s_at | CD209L |
| Standard | −9.08 | 1100904 | 426296 | 229145_at | LOC119504 |
| Standard | −8.99 | 1122738 | 81743 | 207840_at | CD160 |
| Standard | −8.94 | 1120925 | 204891 | 204773_at | IL11RA |
| Standard | 9.09 | 1123055 | 185726 | 208691_at | TFRC |
| Standard | 9.62 | 1134858 | 405954 | 209226_s_at | TNPO1 |
| Standard | 10.19 | 1123052 | 180909 | 208680_at | PRDX1 |
| Standard | 10.81 | 1124178 | 446579 | 211969_at | HSPCA |
| Lymph Node | −10.59 | 1137597 | 3903 | 214721_x_at | CDC42EP4 |
| Lymph Node | −9.69 | 1119684 | 439586 | 202242_at | TM4SF2 |
| Lymph Node | −9.25 | 1125593 | 8910 | 214180_at | MAN1C1 |
| Lymph Node | −8.44 | 1124318 | 21858 | 212190_at | SERPINE2 |
| Lymph Node | −8.09 | 1119448 | 212296 | 201656_at | ITGA6 |
| Lymph Node | −8.07 | 1125546 | 125036 | 214081_at | PLXDC1 |
| Lymph Node | −7.7 | 1097683 | 132569 | 225373_at | PP2135 |
| Lymph Node | −7.56 | 1101305 | 112742 | 229623_at | |
| Lymph Node | 7.45 | 1135240 | 436852 | 209955_s_at | FAP |
| Proliferation | 6.97 | 1135101 | 20830 | 209680_s_at | KIFC1 |
| Proliferation | 7.03 | 1130426 | 432607 | 200039_s_at | PSMB2 |
| Proliferation | 7.04 | 1130501 | 2795 | 200650_s_at | LDHA |
| Proliferation | 7.08 | 1130744 | 158688 | 201027_s_at | EIF5B |
| Proliferation | 7.23 | 1137506 | 75258 | 214501_s_at | H2AFY |
| Proliferation | 7.32 | 1131474 | 95577 | 202246_s_at | CDK4 |
| Proliferation | 7.39 | 1130871 | 159087 | 201222_s_at | RAD23B |
| Proliferation | 7.42 | 1119375 | 381072 | 201489_at | PPIF |
| Proliferation | 7.47 | 1136595 | 404814 | 212038_s_at | VDAC1 |
| Proliferation | 7.7 | 1135858 | 90093 | 211015_s_at | HSPA4 |
| Proliferation | 7.78 | 1130527 | 184233 | 200692_s_at | HSPA9B |
| Proliferation | 7.78 | 1130820 | 151777 | 201144_s_at | EIF2S1 |
| Proliferation | 7.83 | 1115829 | 433213 | 225253_s_at | METTL2 |
| Proliferation | 7.84 | 1134699 | 439683 | 208974_x_at | KPNB1 |
| Proliferation | 7.87 | 1120274 | 31584 | 203517_at | MTX2 |
| Proliferation | 7.92 | 1136786 | 63788 | 212694_s_at | PCCB |
| Proliferation | 7.95 | 1097172 | 434886 | 224753_at | CDCA5 |
| Proliferation | 8.4 | 1138537 | −12 | 217140_s_at | |
| Proliferation | 8.53 | 1119488 | 154672 | 201761_at | MTHFD2 |
| Proliferation | 8.58 | 1130799 | 233952 | 201114_x_at | PSMA7 |
| Proliferation | 8.72 | 1135673 | 82159 | 210759_s_at | PSMA1 |
| Proliferation | 9.4 | 1114679 | 16470 | 222503_s_at | FLJ10904 |

| | Standard | Lymph Node | Proliferation | | |
|---|---|---|---|---|---|
| Mean FH | −2193.59 | −588.21 | 1571.78 | Cut 1 | 0.50 |
| Mean DLBCL-BL | −1448.27 | −441.91 | 1735.00 | Cut 2 | 0.92 |
| Covariance FH | 6729.73 | 1223.99 | 2541.22 | | |
| | 1223.99 | 405.22 | 293.72 | | |
| | 2541.22 | 293.72 | 1797.58 | | |

TABLE 2404-continued

FH vs. DLBCL-BL

| Covariance DLBCL-BL | 17675.23 | 3642.41 | 4158.43 |
|---|---|---|---|
| | 3642.41 | 1379.81 | 1066.48 |
| | 4158.43 | 1066.48 | 2858.21 |

TABLE 2405

FH vs. FL

| Signature | Scale | UNIQID | Unigene ID Build 167 | Probe set | Gene Symbol |
|---|---|---|---|---|---|
| Standard | −11.23 | 1117298 | 449586 | 234366_x_at | |
| Standard | −10.62 | 1121953 | 38365 | 206478_at | KIAA0125 |
| Standard | −10.6 | 1104910 | 458262 | 233969_at | IGL@ |
| Standard | −10.39 | 1136430 | 102950 | 211798_x_at | IGLJ3 |
| Standard | −9.96 | 1129281 | 395486 | 220377_at | C14orf110 |
| Standard | −9.73 | 1118835 | 102336 | 47069_at | ARHGAP8 |
| Standard | −9.21 | 1127807 | 7236 | 217950_at | NOSIP |
| Standard | −9.05 | 1128377 | 371003 | 219014_at | PLAC8 |
| Standard | −8.85 | 1101004 | 2969 | 229265_at | SKI |
| Standard | 9.06 | 1139411 | 368238 | 219073_s_at | OSBPL10 |
| Standard | 9.07 | 1120789 | 154729 | 204524_at | PDPK1 |
| Standard | 9.21 | 1136464 | 159428 | 211833_s_at | BAX |
| Standard | 9.29 | 1125279 | 445652 | 213575_at | TRA2A |
| Standard | 9.45 | 1529390 | 79241 | Lymph_Dx_120_at | BCL2 |
| Standard | 9.52 | 1132022 | 173911 | 203247_s_at | ZNF24 |
| Standard | 9.57 | 1139645 | 134051 | 219757_s_at | C14orf101 |
| Standard | 9.64 | 1137561 | 67397 | 214639_s_at | HOXA1 |
| Standard | 9.66 | 1114893 | 314623 | 222891_s_at | BCL11A |
| Standard | 10.38 | 1098095 | 131059 | 225852_at | ANKRD17 |
| Standard | 10.4 | 1134858 | 405954 | 209226_s_at | TNPO1 |
| Standard | 12.65 | 1101054 | 173328 | 229322_at | PPP2R5E |
| Standard | 12.79 | 1124178 | 446579 | 211969_at | HSPCA |
| Standard | 13.34 | 1135489 | 288178 | 210438_x_at | SSA2 |

| | Standard | | |
|---|---|---|---|
| MeanFH | 136.43 | Cut 1 | 0.50 |
| MeanFL | 640.38 | Cut 2 | 0.99 |
| CovarianceFH | 10719.40 | | |
| CovarianceFL | 9373.11 | | |

TABLE 2406

FH vs. MCL

| Signature | Scale | UNIQID | Unigene ID Build 167 | Probe set | Gene Symbol |
|---|---|---|---|---|---|
| Standard | 13.05 | 1100258 | 88442 | 228377_at | KIAA1384 |
| Standard | 13.43 | 1529382 | 371468 | Lymph_Dx_111_at | CCND1 |
| Standard | 13.54 | 1106855 | 455101 | 236255_at | KIAA1909 |
| Standard | 13.73 | 1529308 | 193014 | Lymph_Dx_027_x_at | |
| Standard | 14.56 | 1100873 | 445884 | 229103_at | |
| Standard | 21.12 | 1132834 | 432638 | 204914_s_at | SOX11 |
| Lymph Node | −8.44 | 1130378 | 234434 | 44783_s_at | HEY1 |
| Lymph Node | −7.92 | 1123552 | 423077 | 209879_at | SELPLG |
| Lymph Node | −7.7 | 1131218 | 76753 | 201809_s_at | ENG |
| Lymph Node | −7.4 | 1097683 | 132569 | 225373_at | PP2135 |
| Lymph Node | −7.15 | 1136273 | 13775 | 211597_s_at | HOP |
| Lymph Node | 14.16 | 1134532 | 371468 | 208711_s_at | CCND1 |

| | | Standard | Lymph Node | | |
|---|---|---|---|---|---|
| Mean | FH | 451.68 | −282.65 | Cut 1 | 0.20 |
| MeanMCFL | | 863.16 | −156.82 | Cut 2 | 0.80 |
| Covariance | FH | 1617.92 | 222.89 | | |
| | | 222.89 | 271.65 | | |
| Covariance | MCL | 3154.38 | 917.30 | | |
| | | 917.30 | 659.94 | | |

TABLE 2407

FH vs. SLL

| Signature | Scale | UNIQID | Unigene ID Build 167 | Probe set | Gene Symbol |
|---|---|---|---|---|---|
| Standard | −13.14 | 1120765 | 343329 | 204484_at | PIK3C2B |
| Standard | −12.9 | 1097897 | 266175 | 225622_at | PAG |
| Standard | 12.72 | 1133195 | 274243 | 205805_s_at | ROR1 |
| Standard | 12.74 | 1140416 | 58831 | 221601_at | TOSO |
| Standard | 13.53 | 1131687 | 369280 | 202606_s_at | TLK1 |
| Standard | 13.57 | 1107044 | 163426 | 236458_at | |
| Standard | 14.43 | 1529389 | 79241 | Lymph_Dx_119_at | BCL2 |
| Standard | 14.51 | 1129026 | 135146 | 220007_at | FLJ13984 |
| Standard | 14.77 | 1136987 | 21695 | 213370_s_at | SFMBT1 |
| Standard | 14.79 | 1137109 | 469653 | 213689_x_at | RPL5 |
| Standard | 15.37 | 1529308 | 193014 | Lymph_Dx_027_x_at | |
| Standard | 15.82 | 1120832 | 57856 | 204604_at | PFTK1 |
| Standard | 17.37 | 1135550 | 221811 | 210550_s_at | RASGRF1 |
| Standard | 18.98 | 1122864 | 434384 | 208195_at | TTN |
| Lymph Node | −12.89 | 1123038 | 119000 | 208636_at | ACTN1 |
| Lymph Node | −12.8 | 1130378 | 234434 | 44783_s_at | HEY1 |
| Lymph Node | −11.59 | 1124875 | 18166 | 212975_at | KIAA0870 |
| Lymph Node | −11.47 | 1103497 | 50115 | 232231_at | |
| Lymph Node | −10.31 | 1099358 | 93135 | 227300_at | |
| Lymph Node | −10.27 | 1121129 | 285401 | 205159_at | CSF2RB |
| Lymph Node | −10.23 | 1100249 | 388674 | 228367_at | HAK |
| Lymph Node | −10.05 | 1132345 | 109225 | 203868_s_at | VCAM1 |
| Lymph Node | −9.93 | 1123401 | 50130 | 209550_at | NDN |
| Lymph Node | −9.75 | 1120500 | 82568 | 203979_at | CYP27A1 |
| Lymph Node | −9.57 | 1124318 | 21858 | 212190_at | SERPINE2 |
| Lymph Node | −9.48 | 1120288 | 17483 | 203547_at | CD4 |
| Lymph Node | −9.45 | 1123372 | 195825 | 209487_at | RBPMS |
| Lymph Node | −9.39 | 1123376 | 37682 | 209496_at | RARRES2 |
| Lymph Node | −9.29 | 1123213 | 12956 | 209154_at | TIP-1 |
| Lymph Node | −9.23 | 1098412 | 409515 | 226225_at | MCC |
| Lymph Node | −9.23 | 1125593 | 8910 | 214180_at | MAN1C1 |
| Lymph Node | −9.17 | 1131786 | 375957 | 202803_s_at | ITGB2 |
| Lymph Node | −9.04 | 1097683 | 132569 | 225373_at | PP2135 |
| Lymph Node | −8.91 | 1097255 | 380144 | 224861_at | |
| Lymph Node | −8.76 | 1131068 | 118400 | 201564_s_at | FSCN1 |
| Lymph Node | −8.7 | 1119074 | 54457 | 200675_at | CD81 |
| Lymph Node | −8.68 | 1125130 | 35861 | 213338_at | RIS1 |
| Lymph Node | −8.59 | 1139661 | 416456 | 219806_s_at | FN5 |

| | Standard | Lymph Node | | |
|---|---|---|---|---|
| Mean FH | 1144.02 | −2223.71 | Cut 1 | 0.20 |
| MeanSLL | 1592.27 | −1798.11 | Cut 2 | 0.80 |
| Covariance FH | 902.56 | 442.69 | | |
| | 442.69 | 809.90 | | |
| CovarianceSLL | 2426.26 | 2938.58 | | |
| | 2938.58 | 9435.72 | | |

TABLE 2408

FL vs. DLBCL-BL

| Signature | Scale | UNIQID | Unigene ID Build 167 | Probe set | Gene Symbol |
|---|---|---|---|---|---|
| Standard | −23.03 | 1124833 | 356416 | 212914_at | CBX7 |
| Standard | −22.25 | 1099204 | 193784 | 227121_at | |
| Standard | −22.2 | 1119766 | 93231 | 202423_at | MYST3 |
| Standard | −22.04 | 1099798 | 411081 | 227811_at | FGD3 |
| Standard | −22.01 | 1102898 | 145519 | 231496_at | FKSG87 |
| Standard | −21.79 | 1131197 | 269902 | 201778_s_at | KIAA0494 |
| Standard | −21.69 | 1098415 | 130900 | 226230_at | KIAA1387 |
| Standard | −21.57 | 1120834 | 57907 | 204606_at | CCL21 |
| Standard | −21.39 | 1130155 | 436657 | 222043_at | CLU |
| Standard | −20.98 | 1100904 | 426296 | 229145_at | LOC119504 |
| Standard | −20.8 | 1131531 | 153647 | 202350_s_at | MATN2 |
| Standard | −20.72 | 1137582 | 433732 | 214683_s_at | CLK1 |
| Standard | −20.66 | 1119782 | 155418 | 202478_at | TRB2 |
| Standard | −20.59 | 1122767 | 652 | 207892_at | TNFSF5 |
| Standard | −20.58 | 1125001 | 16193 | 213158_at | |
| Standard | −20.56 | 1134921 | 413513 | 209341_s_at | IKBKB |
| Standard | −20.56 | 1132973 | 169294 | 205255_x_at | TCF7 |
| Standard | −20.53 | 1136984 | 498154 | 213364_s_at | SNX1 |

TABLE 2408-continued

FL vs. DLBCL-BL

| | | | | | |
|---|---|---|---|---|---|
| Standard | −20.41 | 1115888 | 35096 | 225629_s_at | ZBTB4 |
| Standard | −20.37 | 1120160 | 436976 | 203288_at | KIAA0355 |
| Standard | −20.36 | 1139054 | 25726 | 218263_s_at | LOC58486 |
| Standard | −20.31 | 1130030 | 301872 | 221834_at | LONP |
| Standard | −20.08 | 1133024 | 436987 | 205383_s_at | ZNF288 |
| Standard | −20.05 | 1124666 | 526394 | 212672_at | ATM |
| Standard | −19.3 | 1529397 | 406557 | Lymph_Dx_127_s_at | CLK4 |
| Standard | −19.16 | 1116056 | 243678 | 226913_s_at | SOX8 |
| Standard | −19.14 | 1098433 | 202577 | 226250_at | |
| Standard | −19.1 | 1123635 | 408614 | 210073_at | SIAT8A |
| Standard | −18.95 | 1138920 | 24395 | 218002_s_at | CXCL14 |
| Standard | −18.84 | 1133099 | 88646 | 205554_s_at | DNASE1L3 |
| Standard | −18.83 | 1098495 | 443668 | 226318_at | TBRG1 |
| Standard | −18.64 | 1100879 | 119983 | 229111_at | MASP2 |
| Standard | −18.59 | 1120695 | 385685 | 204352_at | TRAF5 |
| Standard | −18.55 | 1119983 | 409783 | 202920_at | ANK2 |
| Standard | −18.5 | 1101276 | 1098 | 229588_at | ERdj5 |
| Standard | −18.47 | 1099140 | 500350 | 227052_at | |
| Standard | −18.46 | 1529331 | 374126 | Lymph_Dx_051_s_at | |
| Standard | −18.45 | 1131752 | 170133 | 202724_s_at | FOXO1A |
| Standard | −18.45 | 1099265 | 375762 | 227193_at | |
| Standard | −18.32 | 1098179 | 163725 | 225956_at | LOC153222 |
| Standard | −18.29 | 1119568 | 269777 | 201957_at | PPP1R12B |
| Standard | −18.19 | 1099900 | 444508 | 227934_at | |
| Standard | −18.17 | 1119361 | 391858 | 201448_at | TIA1 |
| Standard | −18.02 | 1121650 | 421137 | 206002_at | GPR64 |
| Standard | −17.91 | 1100911 | 320147 | 229152_at | C4orf7 |
| Standard | −17.86 | 1529285 | 348929 | Lymph_Dx_002_at | KIAA1219 |
| Standard | −17.47 | 1529357 | 444651 | Lymph_Dx_081_at | |
| Standard | −17.42 | 1131863 | 2316 | 202936_s_at | SOX9 |
| Standard | −17.16 | 1129943 | 512828 | 221626_at | ZNF506 |
| Standard | −17.12 | 1121301 | 449971 | 205437_at | ZNF134 |
| Standard | −17.11 | 1131340 | 437457 | 202018_s_at | LTF |
| Standard | −17.1 | 1124606 | 444324 | 212588_at | PTPRC |
| Standard | −17.08 | 1131407 | 154248 | 202125_s_at | ALS2CR3 |
| Standard | −16.97 | 1118939 | 198161 | 60528_at | PLA2G4B |
| Standard | −16.91 | 1134738 | 75842 | 209033_s_at | DYRK1A |
| Standard | −16.9 | 1134083 | 285091 | 207996_s_at | C18orf1 |
| Standard | −16.89 | 1120925 | 204891 | 204773_at | IL11RA |
| Standard | −16.86 | 1110070 | −101 | 239803_at | |
| Standard | −16.83 | 1100042 | 351413 | 228113_at | RAB37 |
| Standard | −16.82 | 1120134 | 75545 | 203233_at | IL4R |
| Standard | −16.75 | 1124283 | 406612 | 212144_at | UNC84B |
| Standard | −16.72 | 1109603 | −100 | 239292_at | |
| Standard | −16.71 | 1120509 | 155090 | 204000_at | GNB5 |
| Standard | −16.65 | 1133538 | 1416 | 206760_s_at | FCER2 |
| Standard | −16.64 | 1130735 | 179526 | 201009_s_at | TXNIP |
| Standard | −16.59 | 1100150 | 9343 | 228248_at | MGC39830 |
| Standard | −16.54 | 1124237 | 258855 | 212080_at | MLL |
| Standard | −16.51 | 1124416 | 283604 | 212331_at | RBL2 |
| Standard | −16.48 | 1133091 | 73792 | 205544_s_at | CR2 |
| Standard | −16.46 | 1131263 | 249955 | 201877_s_at | PPP2R5C |
| Standard | −16.44 | 1118347 | 528404 | 243366_s_at | ITGA4 |
| Standard | −16.43 | 1529343 | 521948 | Lymph_Dx_064_at | |
| Standard | −16.43 | 1099549 | 446665 | 227533_at | |
| Standard | 17.05 | 1529453 | 372679 | Lymph_Dx_085_at | FCGR3A |
| Standard | 17.41 | 1097540 | 388087 | 225195_at | |
| Standard | 18.47 | 1140473 | 17377 | 221676_s_at | CORO1C |
| Standard | 18.55 | 1121100 | 301921 | 205098_at | CCR1 |
| Standard | 20.07 | 1124254 | 301743 | 212110_at | SLC39A14 |
| Standard | 20.2 | 1130771 | 61153 | 201068_s_at | PSMC2 |
| Standard | 21.46 | 1137583 | 273415 | 214687_x_at | ALDOA |
| Standard | 21.55 | 1098168 | 22151 | 225943_at | NLN |
| Standard | 24.07 | 1123055 | 185726 | 208691_at | TFRC |
| Standard | 24.09 | 1123052 | 180909 | 208680_at | PRDX1 |
| Lymph Node | −20.5 | 1137597 | 3903 | 214721_x_at | CDC42EP4 |
| Lymph Node | −18.52 | 1124318 | 21858 | 212190_at | SERPINE2 |
| Lymph Node | −18.5 | 1136762 | 380138 | 212624_s_at | CHN1 |
| Lymph Node | −18.07 | 1101305 | 112742 | 229623_at | |
| Lymph Node | −17.75 | 1100249 | 388674 | 228367_at | HAK |
| Lymph Node | −16.1 | 1098412 | 409515 | 226225_at | MCC |
| Lymph Node | −15.51 | 1140464 | 111676 | 221667_s_at | HSPB8 |
| Lymph Node | −15.43 | 1136832 | 434959 | 212842_x_at | RANBP2L1 |
| Lymph Node | −15.37 | 1119684 | 439586 | 202242_at | TM4SF2 |
| Lymph Node | −15.02 | 1097448 | 250607 | 225093_at | UTRN |
| Lymph Node | −14.83 | 1136844 | 16007 | 212875_s_at | C21orf25 |
| Lymph Node | −14.73 | 1135056 | 169946 | 209604_s_at | GATA3 |

TABLE 2408-continued

FL vs. DLBCL-BL

| | | | | | |
|---|---|---|---|---|---|
| Lymph Node | −14.48 | 1097202 | 386779 | 224796_at | DDEF1 |
| Lymph Node | −14.44 | 1121278 | 21355 | 205399_at | DCAMKL1 |
| Lymph Node | −14.22 | 1125009 | 27621 | 213169_at | |
| Lymph Node | −13.97 | 1100288 | 26981 | 228411_at | ALS2CR19 |
| Lymph Node | −13.51 | 1132462 | 14845 | 204131_s_at | FOXO3A |
| Lymph Node | −13.37 | 1135322 | 450230 | 210095_s_at | IGFBP3 |
| Lymph Node | −13.35 | 1097280 | 423523 | 224891_at | |
| Lymph Node | −12.86 | 1137097 | 20107 | 213656_s_at | KNS2 |
| Lymph Node | −12.85 | 1098809 | 359394 | 226682_at | |
| Lymph Node | −12.28 | 1124875 | 18166 | 212975_at | KIAA0870 |
| Lymph Node | −12.18 | 1132345 | 109225 | 203868_s_at | VCAM1 |
| Lymph Node | −12 | 1097561 | 19221 | 225224_at | DKFZP566G1424 |
| Lymph Node | −11.71 | 1123401 | 50130 | 209550_at | NDN |
| Lymph Node | −11.04 | 1136996 | 283749 | 213397_x_at | RNASE4 |
| Lymph Node | −10.77 | 1136788 | 355455 | 212698_s_at | 36778 |
| Lymph Node | −10.71 | 1098822 | 443452 | 226695_at | PRRX1 |
| Lymph Node | −10.63 | 1134200 | 90786 | 208161_s_at | ABCC3 |
| Lymph Node | −10.47 | 1136427 | 276506 | 211795_s_at | FYB |
| Lymph Node | −10.46 | 1121186 | 100431 | 205242_at | CXCL13 |
| Lymph Node | −10.39 | 1099332 | 32433 | 227272_at | |
| Lymph Node | −10.39 | 1098978 | 124863 | 226869_at | |
| Lymph Node | −10.22 | 1103303 | 49605 | 232000_at | C9orf52 |
| Lymph Node | −10.16 | 1131325 | 13313 | 201990_s_at | CREBL2 |
| Lymph Node | −10.16 | 1098174 | 274401 | 225949_at | LOC340371 |
| Lymph Node | −9.93 | 1124733 | 66762 | 212771_at | LOC221061 |
| Lymph Node | −9.42 | 1123372 | 195825 | 209487_at | RBPMS |
| Lymph Node | −9.36 | 1132220 | 448805 | 203632_s_at | GPRC5B |
| Lymph Node | −9.29 | 1120703 | 83974 | 204368_at | SLCO2A1 |
| Lymph Node | −9.26 | 1132013 | 434961 | 203232_s_at | SCA1 |
| Lymph Node | −9.25 | 1097307 | 379754 | 224929_at | LOC340061 |
| Lymph Node | −9.18 | 1119251 | 433941 | 201194_at | SEPW1 |
| Lymph Node | −9.08 | 1097609 | 6093 | 225283_at | ARRDC4 |
| Lymph Node | −9.07 | 1136459 | 252550 | 211828_s_at | KIAA0551 |
| Lymph Node | −8.86 | 1132775 | 1027 | 204803_s_at | RRAD |
| Lymph Node | −8.78 | 1098946 | 135121 | 226834_at | ASAM |
| Lymph Node | −8.68 | 1140589 | 433488 | 221942_s_at | GUCY1A3 |
| Lymph Node | −8.44 | 1116966 | 301124 | 232744_x_at | |
| Lymph Node | −8.39 | 1100130 | 76494 | 228224_at | PRELP |
| Lymph Node | −8.36 | 1110019 | −94 | 239744_at | |
| Lymph Node | −8.3 | 1134647 | 298654 | 208892_s_at | DUSP6 |
| Lymph Node | −8.28 | 1125593 | 8910 | 214180_at | MAN1C1 |
| Lymph Node | 7.97 | 1134370 | 1422 | 208438_s_at | FGR |
| Lymph Node | 8.05 | 1123566 | 155935 | 209906_at | C3AR1 |
| Lymph Node | 8.09 | 1131119 | 349656 | 201647_s_at | SCARB2 |
| Lymph Node | 8.11 | 1123586 | 93841 | 209948_at | KCNMB1 |
| Lymph Node | 8.13 | 1128615 | 104800 | 219410_at | FLJ10134 |
| Lymph Node | 8.21 | 1097297 | 166254 | 224917_at | VMP1 |
| Lymph Node | 8.23 | 1120299 | 79334 | 203574_at | NFIL3 |
| Lymph Node | 8.37 | 1128157 | 23918 | 218631_at | VIP32 |
| Lymph Node | 8.4 | 1130054 | 82547 | 221872_at | RARRES1 |
| Lymph Node | 8.41 | 1098152 | 377588 | 225922_at | KIAA1450 |
| Lymph Node | 8.53 | 1101566 | 98558 | 229947_at | |
| Lymph Node | 8.59 | 1135251 | 21486 | 209969_s_at | STAT1 |
| Lymph Node | 8.84 | 1099167 | 381105 | 227080_at | MGC45731 |
| Lymph Node | 9.01 | 1132920 | 753 | 205119_s_at | FPR1 |
| Lymph Node | 9.26 | 1097253 | 77873 | 224859_at | B7H3 |
| Lymph Node | 9.29 | 1120500 | 82568 | 203979_at | CYP27A1 |
| Lymph Node | 9.36 | 1131507 | 172928 | 202311_s_at | COL1A1 |
| Lymph Node | 9.38 | 1096456 | 82407 | 223454_at | CXCL16 |
| Lymph Node | 9.49 | 1136172 | 38084 | 211470_s_at | SULT1C1 |
| Lymph Node | 10.03 | 1138244 | 418138 | 216442_x_at | FN1 |
| Lymph Node | 10.34 | 1134424 | −17 | 208540_x_at | S100A14 |
| Lymph Node | 10.48 | 1136152 | 458436 | 211434_s_at | CCRL2 |
| Lymph Node | 10.51 | 1118708 | 7835 | 37408_at | MRC2 |
| Lymph Node | 10.6 | 1136540 | 179657 | 211924_s_at | PLAUR |
| Lymph Node | 10.63 | 1098278 | 166017 | 226066_at | MITF |
| Lymph Node | 10.76 | 1119477 | 163867 | 201743_at | CD14 |
| Lymph Node | 10.81 | 1096429 | 64896 | 223405_at | NPL |
| Lymph Node | 11.58 | 1123672 | 67846 | 210152_at | LILRB4 |
| Lymph Node | 12 | 1096364 | 29444 | 223276_at | NID67 |
| Lymph Node | 12.16 | 1119070 | 445570 | 200663_at | CD63 |
| Lymph Node | 12.3 | 1133065 | 77274 | 205479_s_at | PLAU |
| Lymph Node | 12.5 | 1135240 | 436852 | 209955_s_at | FAP |
| Lymph Node | 13.09 | 1116826 | 26204 | 231823_s_at | KIAA1295 |
| Lymph Node | 13.32 | 1119068 | 417004 | 200660_at | S100A11 |
| Lymph Node | 13.45 | 1120266 | 246381 | 203507_at | CD68 |
| Lymph Node | 13.63 | 1133216 | 502577 | 205872_x_at | PDE4DIP |

TABLE 2408-continued

FL vs. DLBCL-BL

| | | | | | |
|---|---|---|---|---|---|
| Lymph Node | 13.67 | 1131815 | 386678 | 202856_s_at | SLC16A3 |
| Lymph Node | 14.38 | 1132132 | 279910 | 203454_s_at | ATOX1 |
| Lymph Node | 15.25 | 1134682 | 411701 | 208949_s_at | LGALS3 |
| Lymph Node | 15.46 | 1119237 | 389964 | 201141_at | GPNMB |
| Lymph Node | 15.89 | 1137698 | 442669 | 215001_s_at | GLUL |
| Lymph Node | 17.8 | 1137782 | 384944 | 215223_s_at | SOD2 |
| Lymph Node | 20.11 | 1130629 | 135226 | 200839_s_at | CTSB |
| Proliferation | 21.02 | 1119375 | 381072 | 201489_at | PPIF |
| Proliferation | 21.24 | 1119488 | 154672 | 201761_at | MTHFD2 |
| Proliferation | 21.31 | 1119467 | 21635 | 201714_at | TUBG1 |
| Proliferation | 21.68 | 1130820 | 151777 | 201144_s_at | EIF2S1 |
| Proliferation | 21.69 | 1131474 | 95577 | 202246_s_at | CDK4 |
| Proliferation | 22.2 | 1125249 | 244723 | 213523_at | CCNE1 |
| Proliferation | 22.97 | 1130501 | 2795 | 200650_s_at | LDHA |
| Proliferation | 23.12 | 1136913 | 99962 | 213113_s_at | SLC43A3 |
| Proliferation | 24.05 | 1130426 | 432607 | 200039_s_at | PSMB2 |

| | | Standard | Lymph Node | Proliferation | | |
|---|---|---|---|---|---|---|
| Mean | FL | −11121.51 | −1603.39 | 1890.60 | Cut 1 | 0.34 |
| MeanDLBCL-BL | | −8760.65 | −460.71 | 2101.10 | Cut 2 | 0.94 |
| Covariance | FL | 246359.77 | 111505.42 | 28908.20 | | |
| | | 111505.42 | 67036.17 | 13130.59 | | |
| | | 28908.20 | 13130.59 | 4617.24 | | |
| CovarianceDLBCL-BL | | 413069.12 | 178811.32 | 30151.89 | | |
| | | 178811.32 | 106324.53 | 10877.26 | | |
| | | 30151.89 | 10877.26 | 5180.68 | | |

TABLE 2409

FL vs. MCL

| Signature | Scale | UNIQID | Unigene ID Build 167 | Probe set | Gene Symbol |
|---|---|---|---|---|---|
| Standard | −24.56 | 1123731 | 17165 | 210258_at | RGS13 |
| Standard | −22.56 | 1133192 | 24024 | 205801_s_at | RASGRP3 |
| Standard | −21.12 | 1114543 | 156189 | 244887_at | |
| Standard | −18.49 | 1120090 | 155024 | 203140_at | BCL6 |
| Standard | −18.07 | 1124646 | 436432 | 212646_at | RAFTLIN |
| Standard | −17.24 | 1132122 | 307734 | 203434_s_at | MME |
| Standard | −16.63 | 1105986 | 49614 | 235310_at | GCET2 |
| Standard | −15.09 | 1120134 | 75545 | 203233_at | IL4R |
| Standard | −14.05 | 1132651 | 439767 | 204529_s_at | TOX |
| Standard | 13.8 | 1098277 | 6786 | 226065_at | PRICKLE1 |
| Standard | 13.85 | 1109560 | 207428 | 239246_at | FARP1 |
| Standard | 13.86 | 1103504 | 142517 | 232239_at | |
| Standard | 13.88 | 1132734 | 126248 | 204724_s_at | COL9A3 |
| Standard | 13.91 | 1115905 | 301478 | 225757_s_at | CLMN |
| Standard | 14.89 | 1098840 | 55098 | 226713_at | C3orf6 |
| Standard | 14.97 | 1100873 | 445884 | 229103_at | |
| Standard | 14.99 | 1139393 | 170129 | 219032_x_at | OPN3 |
| Standard | 16.13 | 1124864 | 411317 | 212960_at | KIAA0882 |
| Standard | 16.36 | 1106855 | 455101 | 236255_at | KIAA1909 |
| Standard | 16.43 | 1120858 | 410683 | 204647_at | HOMER3 |
| Standard | 17.38 | 1130926 | 508741 | 201310_s_at | C5orf13 |
| Standard | 18.3 | 1103711 | 288718 | 232478_at | |
| Standard | 18.62 | 1109505 | 8162 | 239186_at | MGC39372 |
| Standard | 20.31 | 1132834 | 432638 | 204914_s_at | SOX11 |
| Standard | 22.61 | 1096070 | 241565 | 222640_at | DNMT3A |
| Standard | 28.66 | 1529382 | 371468 | Lymph_Dx_111_at | CCND1 |
| Lymph Node | −10.77 | 1097202 | 386779 | 224796_at | DDEF1 |
| Lymph Node | −10.22 | 1119546 | 433898 | 201921_at | GNG10 |
| Lymph Node | −9.89 | 1132766 | 82359 | 204781_s_at | TNFRSF6 |
| Lymph Node | −9.4 | 1138867 | 10706 | 217892_s_at | EPLIN |
| Lymph Node | 9.65 | 1125025 | 301094 | 213196_at | |
| Lymph Node | 10.44 | 1134797 | 433394 | 209118_s_at | TUBA3 |
| Lymph Node | 22.6 | 1529456 | 371468 | Lymph_Dx_113_at | CCND1 |
| Proliferation | −7.36 | 1097948 | 69476 | 225684_at | LOC348235 |
| Proliferation | −7.31 | 1130747 | 234489 | 201030_x_at | LDHB |
| Proliferation | −6.95 | 1130923 | 459987 | 201306_s_at | ANP32B |
| Proliferation | −6.87 | 1120205 | 5198 | 203405_at | DSCR2 |
| Proliferation | −6.64 | 1132468 | 79353 | 204147_s_at | TFDP1 |
| Proliferation | −6.1 | 1119916 | 177584 | 202780_at | OXCT |
| Proliferation | −6.08 | 1119873 | 446393 | 202697_at | CPSF5 |

TABLE 2409-continued

FL vs. MCL

| | | | | | |
|---|---|---|---|---|---|
| Proliferation | −6.08 | 1119488 | 154672 | 201761_at | MTHFD2 |
| Proliferation | −6.04 | 1130658 | 447492 | 200886_s_at | PGAM1 |
| Proliferation | −5.82 | 1132825 | 512813 | 204900_x_at | SAP30 |
| Proliferation | −5.53 | 1115607 | 435733 | 224428_s_at | CDCA7 |
| Proliferation | −5.44 | 1120316 | 63335 | 203611_at | TERF2 |
| Proliferation | −5.34 | 1114970 | 279529 | 223032_x_at | PX19 |
| Proliferation | −5.32 | 1140843 | 169476 | AFFX-HUMGAPDH/M33197_5_at | GAPD |
| Proliferation | −5.28 | 1131081 | 180610 | 201586_s_at | SFPQ |
| Proliferation | −5.15 | 1121062 | 408658 | 205034_at | CCNE2 |
| Proliferation | 5.15 | 1120986 | 172052 | 204886_at | PLK4 |
| Proliferation | 5.16 | 1097195 | 149931 | 224785_at | MGC29814 |
| Proliferation | 5.2 | 1120011 | 3068 | 202983_at | SMARCA3 |
| Proliferation | 5.47 | 1100183 | 180582 | 228286_at | FLJ40869 |
| Proliferation | 5.67 | 1121012 | 96055 | 204947_at | E2F1 |
| Proliferation | 5.84 | 1115679 | 8345 | 224523_s_at | MGC4308 |
| Proliferation | 5.88 | 1135285 | 449501 | 210024_s_at | UBE2E3 |
| Proliferation | 5.92 | 1120520 | 35120 | 204023_at | RFC4 |
| Proliferation | 6.16 | 1529361 | 388681 | Lymph_Dx_086_s_at | HDAC3 |
| Proliferation | 6.45 | 1096054 | 21331 | 222606_at | FLJ10036 |
| Proliferation | 6.45 | 1096738 | 87968 | 223903_at | TLR9 |
| Proliferation | 6.51 | 1136781 | 120197 | 212680_x_at | PPP1R14B |
| Proliferation | 6.63 | 1119466 | 179718 | 201710_at | MYBL2 |
| Proliferation | 6.65 | 1136285 | 182490 | 211615_s_at | LRPPRC |
| Proliferation | 6.67 | 1136853 | 66170 | 212922_s_at | SMYD2 |
| Proliferation | 7.45 | 1119390 | 77254 | 201518_at | CBX1 |
| Proliferation | 8.87 | 1116122 | 42768 | 227408_s_at | DKFZp761O0113 |
| Proliferation | 10.12 | 1119515 | 3352 | 201833_at | HDAC2 |

| | Standard | Lymph Node | Proliferation | | |
|---|---|---|---|---|---|
| Mean FL | −18.82 | −33.90 | 23.53 | Cut 1 | 0.14 |
| MeanMCL | 1558.10 | 113.95 | 165.48 | Cut 2 | 0.58 |
| Covariance FL | 21302.14 | 1098.24 | 678.04 | | |
| | 1098.24 | 226.29 | 75.99 | | |
| | 678.04 | 75.99 | 315.67 | | |
| CovarianceMCL | 81008.29 | 5261.37 | 9185.20 | | |
| | 5261.37 | 2047.34 | 875.56 | | |
| | 9185.20 | 875.56 | 1447.43 | | |

TABLE 2410

FL vs. SLL

| Signature | Scale | UNIQID | Unigene ID Build 167 | Probe set | Gene Symbol |
|---|---|---|---|---|---|
| Standard | −21.04 | 1123731 | 17165 | 210258_at | RGS13 |
| Standard | −20.91 | 1124646 | 436432 | 212646_at | RAFTLIN |
| Standard | −18.82 | 1099651 | 120785 | 227646_at | EBF |
| Standard | −18.12 | 1114543 | 156189 | 244887_at | |
| Standard | −17.85 | 1105986 | 49614 | 235310_at | GCET2 |
| Standard | −16.73 | 1100911 | 320147 | 229152_at | C4orf7 |
| Standard | −15.77 | 1132122 | 307734 | 203434_s_at | MME |
| Standard | −15.12 | 1120090 | 155024 | 203140_at | BCL6 |
| Standard | −14.89 | 1097897 | 266175 | 225622_at | PAG |
| Standard | −14.36 | 1529343 | 521948 | Lymph_Dx_064_at | |
| Standard | −14.32 | 1529318 | 291954 | Lymph_Dx_038_at | |
| Standard | −14.06 | 1128694 | 171466 | 219517_at | ELL3 |
| Standard | −13.61 | 1101586 | 187884 | 229971_at | GPR114 |
| Standard | −13.57 | 1119752 | 511745 | 202391_at | BASP1 |
| Standard | −13.13 | 1137561 | 67397 | 214639_s_at | HOXA1 |
| Standard | −12.85 | 1097247 | 388761 | 224851_at | CDK6 |
| Standard | −12.43 | 1529344 | 317970 | Lymph_Dx_065_at | SERPINA11 |
| Standard | −12.4 | 1120765 | 343329 | 204484_at | PIK3C2B |
| Standard | −12.33 | 1130155 | 436657 | 222043_at | CLU |
| Standard | −12.07 | 1529292 | −92 | Lymph_Dx_010_at | |
| Standard | −12.01 | 1119939 | 170087 | 202820_at | AHR |
| Standard | −11.82 | 1119919 | 199263 | 202786_at | STK39 |
| Standard | −11.77 | 1099686 | 117721 | 227684_at | |
| Standard | −11.63 | 1119782 | 155418 | 202478_at | TRB2 |
| Standard | 10.97 | 1529309 | 512797 | Lymph_Dx_028_at | HSH2 |
| Standard | 10.97 | 1139393 | 170129 | 219032_x_at | OPN3 |
| Standard | 11.04 | 1131246 | 153752 | 201853_s_at | CDC25B |

TABLE 2410-continued

FL vs. SLL

| Signature | Scale | UNIQID | Unigene ID Build 167 | Probe set | Gene Symbol |
|---|---|---|---|---|---|
| Standard | 11.07 | 1140391 | 44865 | 221558_s_at | LEF1 |
| Standard | 11.16 | 1140416 | 58831 | 221601_s_at | TOSO |
| Standard | 11.35 | 1127807 | 7236 | 217950_at | NOSIP |
| Standard | 11.67 | 1529317 | −98 | Lymph_Dx_037_at | |
| Standard | 11.81 | 1117343 | 306812 | 234643_x_at | BUCS1 |
| Standard | 11.82 | 1102081 | 506977 | 230551_at | |
| Standard | 11.82 | 1135042 | 79015 | 209582_s_at | MOX2 |
| Standard | 11.96 | 1132734 | 126248 | 204724_s_at | COL9A3 |
| Standard | 12.09 | 1137109 | 469653 | 213689_x_at | RPL5 |
| Standard | 12.14 | 1099939 | 488173 | 227983_at | MGC7036 |
| Standard | 12.19 | 1129103 | 99430 | 220118_at | TZFP |
| Standard | 12.47 | 1135592 | 758 | 210621_s_at | RASA1 |
| Standard | 12.78 | 1108970 | 140489 | 238604_at | |
| Standard | 12.92 | 1097143 | 74335 | 224716_at | HSPCB |
| Standard | 13.18 | 1136865 | 412128 | 212959_s_at | MGC4170 |
| Standard | 13.96 | 1098220 | 80720 | 226002_at | GAB1 |
| Standard | 14.06 | 1100847 | 97411 | 229070_at | C6orf105 |
| Standard | 14.39 | 1098865 | 250905 | 226741_at | LOC51234 |
| Standard | 15.57 | 1136687 | 59943 | 212345_s_at | CREB3L2 |
| Standard | 15.75 | 1107044 | 163426 | 236458_at | |
| Standard | 16.52 | 1123622 | 8578 | 210051_at | EPAC |
| Standard | 17.74 | 1136987 | 21695 | 213370_s_at | SFMBT1 |
| Standard | 19.15 | 1129026 | 135146 | 220007_at | FLJ13984 |
| Standard | 19.65 | 1131854 | 414985 | 202923_s_at | GCLC |
| Lymph Node | −14.99 | 1124875 | 18166 | 212975_at | KIAA0870 |
| Lymph Node | −14.33 | 1099358 | 93135 | 227300_at | |
| Lymph Node | −13.26 | 1121129 | 285401 | 205159_at | CSF2RB |
| Lymph Node | −12.61 | 1119074 | 54457 | 200675_at | CD81 |
| Lymph Node | −12.52 | 1121029 | 412999 | 204971_at | CSTA |
| Lymph Node | −11.48 | 1137247 | 234734 | 213975_s_at | LYZ |
| Lymph Node | −10.97 | 1128781 | 79741 | 219648_at | FLJ10116 |
| Lymph Node | 11.79 | 1119880 | 442844 | 202709_at | FMOD |
| Lymph Node | 14.4 | 1134370 | 1422 | 208438_s_at | FGR |

|  | Standard | Lymph Node |  |  |
|---|---|---|---|---|
| Mean FL | −663.95 | −730.08 | Cut 1 | 0.20 |
| MeanSLL | 1332.84 | −484.93 | Cut 2 | 0.80 |
| Covariance FL | 37097.15 | 1710.73 | | |
|  | 1710.73 | 663.78 | | |
| CovarianceSLL | 85989.25 | 17661.52 | | |
|  | 17661.52 | 4555.06 | | |

TABLE 2411

GCB vs. PMBL

| Signature | Scale | UNIQID | Unigene ID Build 167 | Probe set | Gene Symbol |
|---|---|---|---|---|---|
| Standard | −8.39 | 1096440 | 231320 | 223423_at | GPR160 |
| Standard | −8.13 | 1096108 | 292871 | 222731_at | ZDHHC2 |
| Standard | −8.12 | 1125231 | 446375 | 213489_at | MAPRE2 |
| Standard | −8.02 | 1136759 | 188882 | 212605_s_at | |
| Standard | −7.91 | 1096499 | 293867 | 223514_at | CARD11 |
| Standard | −7.8 | 1099388 | 124024 | 227336_at | DTX1 |
| Standard | −7.71 | 1139623 | 193736 | 219667_s_at | BANK1 |
| Standard | −7.68 | 1098592 | 283707 | 226431_at | ALS2CR13 |
| Standard | −7.67 | 1107575 | 424589 | 237033_at | MGC52498 |
| Standard | −7.63 | 1116829 | 115467 | 231840_x_at | LOC90624 |
| Standard | −7.42 | 1130114 | 445084 | 221965_at | MPHOSPH9 |
| Standard | −7.27 | 1098909 | 446408 | 226789_at | |
| Standard | 7.34 | 1138759 | 396404 | 217707_x_at | SMARCA2 |
| Standard | 7.37 | 1120355 | 80420 | 203687_at | CX3CL1 |
| Standard | 7.4 | 1134270 | 352119 | 208284_x_at | GGT1 |
| Standard | 7.44 | 1115441 | 5470 | 224156_x_at | IL17RB |
| Standard | 7.78 | 1103054 | 341531 | 231690_at | |
| Standard | 7.91 | 1119765 | 81234 | 202421_at | IGSF3 |
| Standard | 7.92 | 1119438 | 118110 | 201641_at | BST2 |
| Standard | 8.09 | 1135645 | 31439 | 210715_s_at | SPINT2 |
| Standard | 8.15 | 1106015 | 96885 | 235343_at | FLJ12505 |
| Standard | 8.18 | 1121400 | 223474 | 205599_at | TRAF1 |
| Standard | 8.38 | 1139950 | 437385 | 220731_s_at | FLJ10420 |
| Standard | 8.73 | 1122112 | 1314 | 206729_at | TNFRSF8 |
| Standard | 8.77 | 1122772 | 66742 | 207900_at | CCL17 |

TABLE 2411-continued

GCB vs. PMBL

| Standard | 8.84 | 1132762 | 80395 | 204777_s_at | MAL |
|---|---|---|---|---|---|
| Standard | 9.64 | 1139774 | 15827 | 220140_s_at | SNX11 |
| Standard | 10.53 | 1133801 | 181097 | 207426_s_at | TNFSF4 |
| Standard | 11.52 | 1106415 | 169071 | 235774_at | |
| Standard | 12.09 | 1129269 | 62919 | 220358_at | SNFT |

| | | Standard | | |
|---|---|---|---|---|
| Mean | GCB | 292.76 | Cut 1 | 0.16 |
| Mean | PMBL | 725.28 | Cut 2 | 0.50 |
| Covariance | GCB | 8538.86 | | |
| Covariance | PMBL | 11405.23 | | |

TABLE 2412

MCL vs. DLBCL-BL

| Signature | Scale | UNIQID | Unigene ID Build 167 | Probe set | Gene Symbol |
|---|---|---|---|---|---|
| Standard | −26.11 | 1529382 | 371468 | Lymph_Dx_111_at | CCND1 |
| Standard | −18.35 | 1103711 | 288718 | 232478_at | |
| Standard | −17.03 | 1106855 | 455101 | 236255_at | KIAA1909 |
| Standard | −16.49 | 1098840 | 55098 | 226713_at | C3orf6 |
| Standard | −15.41 | 1109505 | 8162 | 239186_at | MGC39372 |
| Standard | −15.11 | 1098954 | 128905 | 226844_at | MOBKL2B |
| Standard | −14.96 | 1103504 | 142517 | 232239_at | |
| Standard | −14.74 | 1096070 | 241565 | 222640_at | DNMT3A |
| Standard | −13.81 | 1137663 | 247362 | 214909_s_at | DDAH2 |
| Standard | −13.8 | 1124864 | 411317 | 212960_at | KIAA0882 |
| Standard | −13.62 | 1140127 | 125300 | 221044_s_at | TRIM34 |
| Standard | −13.62 | 1119361 | 391858 | 201448_at | TIA1 |
| Standard | −13.37 | 1127849 | 76691 | 218032_at | SNN |
| Standard | 13.72 | 1133192 | 24024 | 205801_s_at | RASGRP3 |
| Standard | 13.85 | 1137583 | 273415 | 214687_x_at | ALDOA |
| Standard | 15.02 | 1123052 | 180909 | 208680_at | PRDX1 |
| Standard | 16.21 | 1097611 | 438993 | 225285_at | BCAT1 |
| Lymph Node | −19.18 | 1529456 | 371468 | Lymph_Dx_113_at | CCND1 |
| Lymph Node | −10.71 | 1098978 | 124863 | 226869_at | |
| Lymph Node | −9.17 | 1097448 | 250607 | 225093_at | UTRN |
| Lymph Node | 8.84 | 1135240 | 436852 | 209955_s_at | FAP |
| Lymph Node | 9.11 | 1119475 | 296323 | 201739_at | SGK |
| Lymph Node | 9.22 | 1119237 | 389964 | 201141_at | GPNMB |
| Lymph Node | 9.46 | 1130629 | 135226 | 200839_s_at | CTSB |
| Lymph Node | 10.1 | 1130054 | 82547 | 221872_at | RARRES1 |

| | | Standard | Lymph Node | | |
|---|---|---|---|---|---|
| Mean | MCL | −1417.55 | −25.58 | Cut 1 | 0.50 |
| Mean | DLBCL-BL | −756.07 | 202.29 | Cut 2 | 0.88 |
| Covariance | MCL | 15347.98 | 3525.48 | | |
| | | 3525.48 | 5420.31 | | |
| Covariance | DLBCL-BL | 5132.06 | 1007.64 | | |
| | | 1007.64 | 991.38 | | |

TABLE 2413

MCL vs. SLL

| Signature | Scale | UNIQID | Unigene ID Build 167 | Probe set | Gene Symbol |
|---|---|---|---|---|---|
| Standard | −20.18 | 1132834 | 432638 | 204914_s_at | SOX11 |
| Standard | −15.17 | 1130926 | 508741 | 201310_s_at | C5orf13 |
| Standard | 13.44 | 1116150 | 16229 | 227606_s_at | AMSH-LP |
| Standard | 14.44 | 1120134 | 75545 | 203233_at | IL4R |
| Standard | 15.18 | 1529437 | 445162 | Lymph_Dx_175_at | BTLA |
| Standard | 15.19 | 1529317 | −98 | Lymph_Dx_037_at | |
| Standard | 16.2 | 1135042 | 79015 | 209582_s_at | MOX2 |

| | | Standard | | |
|---|---|---|---|---|
| Mean | MCL | 181.38 | Cut 1 | 0.20 |
| Mean | SLL | 564.92 | Cut 2 | 0.80 |

TABLE 2413-continued

| MCL vs. SLL | |
|---|---|
| CovarianceMCL | 1734.42 |
| Covariance SLL | 910.75 |

TABLE 2414

SLL vs. DLBCL-BL

| Signature | Scale | UNIQID | Unigene ID Build 167 | Probe set | Gene Symbol |
|---|---|---|---|---|---|
| Standard | −16.014498 | 1123622 | 8578 | 210051_at | EPAC |
| Standard | −15.26356533 | 1102081 | 506977 | 230551_at | |
| Standard | −14.82150028 | 1107044 | 163426 | 236458_at | |
| Standard | −14.17813266 | 1098865 | 250905 | 226741_at | LOC51234 |
| Standard | −12.92844719 | 1110740 | 416810 | 240538_at | |
| Standard | −12.86520757 | 1129026 | 135146 | 220007_at | FLJ13984 |
| Standard | −12.2702748 | 1135592 | 758 | 210621_s_at | RASA1 |
| Standard | −11.87309449 | 1117343 | 306812 | 234643_x_at | BUCS1 |
| Standard | −11.81789137 | 1136987 | 21695 | 213370_s_at | SFMBT1 |
| Standard | −11.78631706 | 1124830 | 9059 | 212911_at | KIAA0962 |
| Standard | −11.39454435 | 1133538 | 1416 | 206760_s_at | FCER2 |
| Standard | −11.39050362 | 1135802 | 439343 | 210944_s_at | CAPN3 |
| Standard | 11.72928644 | 1120770 | 300825 | 204493_at | BID |
| Lymph Node | −12.21593247 | 1119880 | 442844 | 202709_at | FMOD |
| Lymph Node | 9.514704847 | 1135240 | 436852 | 209955_s_at | FAP |
| Lymph Node | 9.739298877 | 1096429 | 64896 | 223405_at | NPL |
| Lymph Node | 10.05087645 | 1119475 | 296323 | 201739_at | SGK |
| Lymph Node | 13.11985922 | 1119237 | 389964 | 201141_at | GPNMB |
| Proliferation | 10.47525875 | 1128106 | 14559 | 218542_at | C10orf3 |
| Proliferation | 10.53295782 | 1132825 | 512813 | 204900_x_at | SAP30 |
| Proliferation | 11.93918891 | 1130501 | 2795 | 200650_s_at | LDHA |
| Proliferation | 11.98738778 | 1123439 | 287472 | 209642_at | BUB1 |
| Proliferation | 11.99741644 | 1115607 | 435733 | 224428_s_at | CDCA7 |

| | | Standard | Lymph Node | Proliferation | | |
|---|---|---|---|---|---|---|
| Mean | SLL | −1383.640809 | 177.4452398 | 467.2463569 | Cut 1 | 0.201266305 |
| MeanDLBCL-BL | | −926.7275468 | 329.6795845 | 582.9070266 | Cut 2 | 0.799816116 |
| Covariance | SLL | 3591.384775 | 1789.7516 | 856.0703202 | | |
| | | 1789.7516 | 1421.869535 | 663.4782048 | | |
| | | 856.0703202 | 663.4782048 | 965.6470151 | | |
| CovarianceDLBCL-BL | | 2922.643347 | 473.543487 | 634.3258773 | | |
| | | 473.543487 | 931.9845277 | −53.85584619 | | |
| | | 634.3258773 | −53.85584619 | 767.3545404 | | |

The following List of Materials submitted by Compact Disc is provided in accordance with 37 C.F.R. § 1.52(e)(5). Any reference to a table or file in the foregoing specification should be considered an incorporation by reference of the contents of the table and/or file at that particular place in the specification.

List of Materials Submitted by Compact Disc

| Table No. | File Name | File size (bytes) | Date Created |
|---|---|---|---|
| | Disc 1 of 22 | | |
| 2 | Table_0002_LymphDx_Probe_List.txt | 91,364 | Aug. 31, 2004 |
| 3 | Table_0003_ABC_304_A.txt | 12,168,568 | Aug. 10, 2004 |
| 4 | Table_0004_ABC_304_B.txt | 11,943,114 | Aug. 10, 2004 |
| 5 | Table_0005_ABC_305_A.txt | 12,213,467 | Aug. 10, 2004 |
| 6 | Table_0006_ABC_305_B.txt | 12,154,905 | Aug. 10, 2004 |
| 7 | Table_0007_ABC_309_A.txt | 12,141,759 | Aug. 10, 2004 |
| 8 | Table_0008_ABC_309_B.txt | 11,973,212 | Aug. 10, 2004 |
| 9 | Table_0009_ABC_413_A.txt | 12,301,325 | Aug. 10, 2004 |
| 10 | Table_0010_ABC_413_B.txt | 12,109,937 | Aug. 10, 2004 |
| 11 | Table_0011_ABC_428_A.txt | 12,329,882 | Aug. 10, 2004 |
| 12 | Table_0012_ABC_428_B.txt | 12,126,615 | Aug. 10, 2004 |

-continued

| | | | | |
|---|---|---|---|---|
| 13 | Table_0013_ABC_432_A.txt | | 12,316,197 | Aug. 10, 2004 |
| 14 | Table_0014_ABC_432_B.txt | | 12,017,441 | Aug. 10, 2004 |
| 15 | Table_0015_ABC_446_A.txt | | 12,285,490 | Aug. 10, 2004 |
| 16 | Table_0016_ABC_446_B.txt | | 12,041,763 | Aug. 10, 2004 |
| 17 | Table_0017_ABC_462_A.txt | | 12,274,795 | Aug. 10, 2004 |
| 18 | Table_0018_ABC_452_B.txt | | 12,056,215 | Aug. 10, 2004 |
| 19 | Table_0019_ABC_477_A.txt | | 12,182,261 | Aug. 10, 2004 |
| 20 | Table_0020_ABC_477_B.txt | | 12,091,353 | Aug. 10, 2004 |
| 21 | Table_0021_ABC_481_A.txt | | 12,311,932 | Aug. 10, 2004 |
| 22 | Table_0022_ABC_481_B.txt | | 12,143,332 | Aug. 10, 2004 |
| 23 | Table_0023_ABC_482_A.txt | | 12,259,053 | Aug. 10, 2004 |
| 24 | Table_0024_ABC_482_B.txt | | 12,126,711 | Aug. 10, 2004 |
| 25 | Table_0025_ABC_538_A.txt | | 12,269,821 | Aug. 10, 2004 |
| 26 | Table_0026_ABC_538_B.txt | | 12,135,241 | Aug. 10, 2004 |
| 27 | Table_0027_ABC_541_A.txt | | 12,159,265 | Aug. 11, 2004 |
| 28 | Table_0028_ABC_541_B.txt | | 11,960,425 | Aug. 11, 2004 |
| 29 | Table_0029_ABC_544_A.txt | | 12,199,335 | Aug. 11, 2004 |
| 30 | Table_0030_ABC_544_B.txt | | 11,995,098 | Aug. 11, 2004 |
| 31 | Table_0031_ABC_547_A.txt | | 12,174,490 | Aug. 11, 2004 |
| 32 | Table_0032_ABC_547_B.txt | | 11,948,698 | Aug. 11, 2004 |
| 33 | Table_0033_ABC_577_A.txt | | 12,015,593 | Aug. 11, 2004 |
| 34 | Table_0034_ABC_577_B.txt | | 11,850,326 | Aug. 11, 2004 |
| 35 | Table_0035_ABC_616_A.txt | | 12,151,453 | Aug. 11, 2904 |
| 36 | Table_0036_ABC_616_B.txt | | 11,877,346 | Aug. 11, 2004 |
| 37 | Table_0037_ABC_626_A.txt | | 12,319,773 | Aug. 11, 2004 |
| 38 | Table_0038_ABC_626_B.txt | | 12,099,972 | Aug. 11, 2004 |
| 39 | Table_0039_ABC_633_A.txt | | 12,144,330 | Aug. 11, 2004 |
| 40 | Table_0040_ABC_633_B.txt | | 12,051,373 | Aug. 11, 2004 |
| 41 | Table_0041_ABC_642_A.txt | | 12,062,720 | Aug. 11, 2004 |
| 42 | Table_0042_ABC_642_B.txt | | 11,924,314 | Aug. 11, 2004 |
| 43 | Table_0043_ABC_644_A.txt | | 12,095,292 | Aug. 11, 2004 |
| 44 | Table_0044_ABC_644_B.txt | | 12,026,946 | Aug. 11, 2004 |
| 45 | Table_0045_ABC_645_A.txt | | 12,142,419 | Aug. 11, 2004 |
| 46 | Table_0046_ABC_645_B.txt | | 11,922,646 | Aug. 11, 2004 |
| 47 | Table_0047_ABC_646_A.txt | | 12,170,447 | Aug. 11, 2004 |
| 48 | Table_0048_ABC_646_B.txt | | 12,005,366 | Aug. 11, 2004 |
| 49 | Table_0049_ABC_651_A.txt | | 12,045,047 | Aug. 11, 2004 |
| 50 | Table_0050_ABC_651_B.txt | | 11,922,418 | Aug. 11, 2004 |
| 51 | Table_0051_ABC_652_A.txt | | 12,103,596 | Aug. 11, 2004 |
| 52 | Table_0052_ABC_652_B.txt | | 11,970,072 | Aug. 11, 2004 |
| 53 | Table_0053_ABC_660_A.txt | | 12,149,615 | Aug. 11, 2004 |
| 54 | Table_0054_ABC_660_B.txt | | 12,035,417 | Aug. 11, 2004 |
| 55 | Table_0055_ABC_663_A.txt | | 12,295,719 | Aug. 11, 2004 |
| 56 | Table_0056_ABC_663_B.txt | | 12,153,562 | Aug. 11, 2004 |
| | | Disc 2 of 22 | | |
| 57 | Table_0057_ABC_668_A.txt | | 12,254,586 | Aug. 11, 2004 |
| 58 | Table_0058_ABC_668_B.txt | | 12,077,180 | Aug. 11, 2004 |
| 59 | Table_0059_ABC_676_A.txt | | 12,042,636 | Aug. 11, 2004 |
| 60 | Table_0060_ABC_676_B.txt | | 11,923,373 | Aug. 11, 2004 |
| 61 | Table_0061_ABC_678_A.txt | | 12,051,214 | Aug. 11, 2004 |
| 62 | Table_0002_ABC_678_B.txt | | 11,885,465 | Aug. 11, 2004 |
| 63 | Table_0063_ABC_687_A.txt | | 12,288,163 | Aug. 11, 2004 |
| 64 | Table_0064_ABC_687_B.txt | | 12,114,176 | Aug. 11, 2004 |
| 65 | Table_0065_ABC_689_A.txt | | 12,239,706 | Aug. 11, 2004 |
| 66 | Table_0066_ABC_689_B.txt | | 11,999,699 | Aug. 11, 2004 |
| 67 | Table_0067_ABC_692_A.txt | | 12,193,147 | Aug. 11, 2004 |
| 68 | Table_0068_ABC_692_B.txt | | 11,876,485 | Aug. 11, 2004 |
| 69 | Table_0069_ABC_694_A.txt | | 12,256,974 | Aug. 11, 2004 |
| 70 | Table_0070_ABC_694_B.txt | | 12,011,057 | Aug. 11, 2004 |
| 71 | Table_0071_ABC_700_A.txt | | 12,085,982 | Aug. 11, 2004 |
| 72 | Table_0072_ABC_700_B.txt | | 11,917,957 | Aug. 11, 2004 |
| 73 | Table_0073_ABC_702_A.txt | | 12,121,512 | Aug. 11, 2004 |
| 74 | Table_0074_ABC_702_B.txt | | 11,939,438 | Aug. 11, 2004 |
| 75 | Table_0075_ABC_704_A.txt | | 12,287,602 | Aug. 11, 2004 |
| 76 | Table_0076_ABC_704_B.txt | | 12,103,199 | Aug. 11, 2004 |
| 77 | Table_0077_ABC_709_A.txt | | 12,212,735 | Aug. 11, 2004 |
| 78 | Table_0078_ABC_709_B.txt | | 11,967,460 | Aug. 11, 2004 |
| 79 | Table_0079_ABC_712_A.txt | | 12,253,447 | Aug. 11, 2004 |
| 80 | Table_0080_ABC_712_B.txt | | 12,070,582 | Aug. 11, 2004 |
| 81 | Table_0081_ABC_714_A.txt | | 12,144,498 | Aug. 11, 2004 |
| 82 | Table_0082_ABC_714_B.txt | | 11,920,284 | Aug. 11, 2004 |
| 83 | Table_0083_ABC_717_A.txt | | 12,142,496 | Aug. 11, 2004 |
| 84 | Table_0084_ABC_717_B.txt | | 11,954,244 | Aug. 11, 2004 |
| 85 | Table_0085_ABC_725_A.txt | | 12,080,186 | Aug. 11, 2004 |
| 86 | Table_0086_ABC_725_B.txt | | 11,751,528 | Aug. 11, 2004 |
| 87 | Table_0087_ABC_726_A.txt | | 11,989,772 | Aug. 11, 2004 |
| 88 | Table_0088_ABC_726_B.txt | | 11,763,881 | Aug. 11, 2004 |
| 89 | Table_0089_ABC_730_A.txt | | 12,080,456 | Aug. 11, 2004 |

-continued

| | | | | |
|---|---|---|---|---|
| 90 | Table_0090_ABC_730_B.txt | | 11,902,874 | Aug. 11, 2004 |
| 91 | Table_0091_ABC_753_A.txt | | 12,200,060 | Aug. 11, 2004 |
| 92 | Table_0092_ABC_753_B.txt | | 11,936,481 | Aug. 11, 2004 |
| 93 | Table_0093_ABC_756_A.txt | | 12,280,005 | Aug. 11, 2004 |
| 94 | Table_0094_ABC_756_B.txt | | 11,983,560 | Aug. 11, 2004 |
| 95 | Table_0095_ABC_771_A.txt | | 12,137,758 | Aug. 11, 2004 |
| 96 | Table_0096_ABC_771_B.txt | | 11,975,832 | Aug. 11, 2004 |
| 97 | Table_0097_ABC_779_A.txt | | 12,297,481 | Aug. 11, 2004 |
| 98 | Table_0098_ABC_779_B.txt | | 12,002,334 | Aug. 11, 2004 |
| 99 | Table_0099_ABC_789_A.txt | | 12,206,349 | Aug. 11, 2004 |
| 100 | Table_0100_ABC_789_B.txt | | 12,016,648 | Aug. 11, 2004 |
| 101 | Table_0101_ABC_800_A.txt | | 12,003,215 | Aug. 11, 2004 |
| 102 | Table_0102_ABC_800_B.txt | | 11,934,562 | Aug. 11, 2004 |
| 103 | Table_0103_ABC_807_A.txt | | 12,103,858 | Aug. 11, 2004 |
| 104 | Table_0104_ABC_807_B.txt | | 11,887,326 | Aug. 11, 2004 |
| 105 | Table_0105_ABC_809_A.txt | | 12,058,952 | Aug. 11, 2004 |
| 106 | Table_0106_ABC_809_B.txt | | 11,797,773 | Aug. 11, 2004 |
| 107 | Table_0107_ABC_816_A.txt | | 11,979,780 | Aug. 11, 2004 |
| 108 | Table_0108_ABC_816_B.txt | | 11,874,102 | Aug. 11, 2004 |
| 109 | Table_0109_ABC_820_A.txt | | 12,073,993 | Aug. 11, 2004 |
| 110 | Table_0110_ABC_820_B.txt | | 11,837,974 | Aug. 11, 2004 |
| | | Disc 3 of 22 | | |
| 111 | Table_0111_ABC_823_A.txt | | 12,082,433 | Aug. 11, 2004 |
| 112 | Table_0112_ABC_823_B.txt | | 11,864,483 | Aug. 11, 2004 |
| 113 | Table_0113_ABC_835_A.txt | | 12,235,272 | Aug. 11, 2004 |
| 114 | Table_0114_ABC_835_B.txt | | 12,002,461 | Aug. 11, 2004 |
| 115 | Table_0115_ABC_839_A.txt | | 12,203,437 | Aug. 11, 2004 |
| 116 | Table_0116_ABC_839_B.txt | | 11,920,023 | Aug. 11, 2004 |
| 117 | Table_0117_ABC_841_A.txt | | 12,331,151 | Aug. 11, 2004 |
| 118 | Table_0118_ABC_841_B.txt | | 12,078,461 | Aug. 11; 2004 |
| 119 | Table_0119_ABC_858_A.txt | | 12,207,153 | Aug. 11, 2004 |
| 120 | Table_0120_ABC_858_B.txt | | 12,040,055 | Aug. 11, 2004 |
| 121 | Table_0121_ABC_872_A.txt | | 12,160,913 | Aug. 11, 2004 |
| 122 | Table_0122_ABC_872_B.txt | | 11,972,706 | Aug. 11, 2004 |
| 123 | Table_0123_ABC_875_A.txt | | 12,062,435 | Aug. 11, 2Q04 |
| 124 | Table_0124_ABC_875_B.txt | | 11,868,039 | Aug. 11, 2004 |
| 125 | Table_0125_ABC_912_A.txt | | 12,203,349 | Aug. 11, 2004 |
| 126 | Table_0126_ABC_912_B.txt | | 12,056,482 | Aug. 11, 2004 |
| 127 | Table_0127_ABC_996_A.txt | | 12,145,520 | Aug. 11, 2004 |
| 128 | Table_0128_ABC_996_B.txt | | 11,926,049 | Aug. 11, 2004 |
| 129 | Table_0129_ABC_1000_A.txt | | 12,172,512 | Aug. 10, 2004 |
| 130 | Table_0130_ABC_1000_B.txt | | 11,960,378 | Aug. 10, 2004 |
| 131 | Table_0131_ABC_1002_A.txt | | 12,136,443 | Aug. 10, 2004 |
| 132 | Table_0132_ABC_1002_B.txt | | 11,912,994 | Aug. 10, 2004 |
| 133 | Table_0133_ABC_1023_A.txt | | 12,043,351 | Aug. 10, 2004 |
| 134 | Table_0134_ABC_1023_B.txt | | 12,005,776 | Aug. 10, 2004 |
| 135 | Table_0135_ABC_1027_A.txt | | 12,225,822 | Aug. 10, 2004 |
| 136 | Table_0136_ABC_1027_B.txt | | 12,090,475 | Aug. 10, 2004 |
| 137 | Table_0137_ABC_1031_A.txt | | 12,144,420 | Aug. 10, 2004 |
| 138 | Table_0138_ABC_1031_B.txt | | 12,031,947 | Aug. 10, 2004 |
| 139 | Table_0139_ABC_1034_A.txt | | 12,086,509 | Aug. 10, 2004 |
| 140 | Table_0140_ABC_1034_B.txt | | 12,009,740 | Aug. 10, 2004 |
| 141 | Table_0141_ABC_1038_A.txt | | 12,141,976 | Aug. 10, 2004 |
| 142 | Table_0142_ABC_1038_B.txt | | 12,000,420 | Aug. 10, 2004 |
| 143 | Table_0143_ABC_1043_A.txt | | 12,139,378 | Aug. 10, 2004 |
| 144 | Table_0144_ABC_1043_B.txt | | 11,983,541 | Aug. 10, 2004 |
| 145 | Table_0145_ABC_1045_A.txt | | 11,979,407 | Aug. 10, 2004 |
| 144 | Table_0146_ABC_1045_B.txt | | 11,901,031 | Aug. 10, 2004 |
| 147 | Table_0147_ABC_1055_A.txt | | 12,018,874 | Aug. 10, 2004 |
| 148 | Table_0148_ABC_1055_B.txt | | 11,954,387 | Aug. 10, 2004 |
| 149 | Table_0149_ABC_1057_A.txt | | 12,062,420 | Aug. 10, 2004 |
| 150 | Table_0150_ABC_1057_B.txt | | 11,923,795 | Aug. 10, 2004 |
| 151 | Table_0151_ABC_1059_A.txt | | 12,037,304 | Aug. 10, 2004 |
| 152 | Table_0152_ABC_1059_B.txt | | 11,846,923 | Aug. 10, 2004 |
| 153 | Table_0153_ABC_1061_A.txt | | 12,162,153 | Aug. 10, 2004 |
| 154 | Table_0154_ABC_1061_B.txt | | 11,957,326 | Aug. 10, 2004 |
| 155 | Table_0155_ABC_1994_A.txt | | 12,063,327 | Aug. 10, 2004 |
| 156 | Table_0156_ABC_1994_B.txt | | 11,792,424 | Aug. 10, 2004 |
| 157 | Table_0157_ABC_2001_A.txt | | 12,144,366 | Aug. 10, 2004 |
| 158 | Table_0158_ABC_2001_B.txt | | 11,966,468 | Aug. 10, 2004 |
| 159 | Table_0159_BL_2032_A.txt | | 12,259,980 | Aug. 12, 2004 |
| 160 | Table_0160_BL_2032_B.txt | | 11,940,823 | Aug. 12, 2004 |
| 161 | Table_0161_BL_2033_A.txt | | 12,118,946 | Aug. 13, 2004 |
| 162 | Table_0462_BL_2033_B.txt | | 11,844,470 | Aug. 13, 2004 |
| 163 | Table_0163_BL_2035_A.txt | | 12,122,606 | Aug. 13, 2004 |
| 164 | Table_0164_BL_2035_B.txt | | 11,910,764 | Aug. 13, 2004 |

-continued

Disc 4 of 22

| 165 | Table_0165_BL_2036_A.txt | 12,079,985 | Aug. 13, 2004 |
| --- | --- | --- | --- |
| 166 | Table_0166_BL_2036_B.txt | 11,804,136 | Aug. 13, 2004 |
| 167 | Table_0167_BL_2037_A.txt | 12,236,363 | Aug. 13, 2004 |
| 168 | Table_0168_BL_2037_B.txt | 12,114,941 | Aug. 13, 2004 |
| 169 | Table_0169_BL_2038_A.txt | 12,044,025 | Aug. 13, 2004 |
| 170 | Table_0170_BL_2038_B.txt | 11,887,911 | Aug. 13, 2004 |
| 171 | Table_0171_BL_2082_A.txt | 11,857,967 | Aug. 13, 2004 |
| 172 | Table_0172_BL_2082_B.txt | 11,730,035 | Aug. 13, 2004 |
| 173 | Table_0173_BL_2083_A.txt | 11,963,716 | Aug. 13, 2004 |
| 174 | Table_0174_BL_2083_B.txt | 11,796,670 | Aug. 13 2004 |
| 175 | Table_0175_BL_2086_A.txt | 12,104,019 | Aug. 13, 2004 |
| 176 | Table_0176_BL_2086_B.txt | 11,965,947 | Aug. 13, 2004 |
| 177 | Table_0177_BL_2088_A.txt | 11,933,503 | Aug. 13, 2004 |
| 178 | Table_0178_BL_2088_B.txt | 11,706,861 | Aug. 13, 2004 |
| 179 | Table_0179_BL_2090_A.txt | 12,174,470 | Aug. 13, 2004 |
| 180 | Table_0180_BL_2090_B.txt | 12,102,048 | Aug. 13, 2004 |
| 181 | Table_0181_BL_2091_A.txt | 12,053,564 | Aug. 13, 2004 |
| 182 | Table_0182_BL_2091_B.txt | 12,003,445 | Aug. 13, 2004 |
| 183 | Table_0183_BL_2097_A.txt | 12,060,060 | Aug. 13, 2004 |
| 184 | Table_0184_BL_2097_B.txt | 11,779,676 | Aug. 13, 2004 |
| 185 | Table_0185_BL_2099_A.txt | 12,082,566 | Aug. 13, 2004 |
| 186 | Table_0186_BL_2099_B.txt | 11,894,123 | Aug. 13, 2004 |
| 187 | Table_0187_BL_2100_A.txt | 12,090,939 | Aug. 13, 2004 |
| 188 | Table_0188_BL_2100_B.txt | 11,854,774 | Aug. 13, 2004 |
| 189 | Table_0189_BL_2101_A.txt | 12,077,697 | Aug. 13, 2004 |
| 190 | Table_0190_BL_2101_B.txt | 11,863,914 | Aug. 13, 2004 |
| 191 | Table_0191_BL_2103_A.txt | 12,181,215 | Aug. 13, 2004 |
| 192 | Table_0192_BL_2103_B.txt | 11,983,322 | Aug. 13, 2004 |
| 193 | Table_0193_BL_2125_A.txt | 12,171,375 | Aug. 13, 2004 |
| 194 | Table_0194_BL_2125_B.txt | 12,007,032 | Aug. 13, 2004 |
| 195 | Table_0195_BL_2126_A.txt | 12,175,436 | Aug. 13, 2004 |
| 196 | Table_0196_BL_2126_B.txt | 12,022,582 | Aug. 13, 2004 |
| 197 | Table_0197_BL_2127_A.txt | 12,154,107 | Aug. 13, 2004 |
| 198 | Table_0198_BL_2127_B.txt | 12,008,547 | Aug. 13, 2004 |
| 199 | Table_0199_BL_2128_A.txt | 12,052,741 | Aug. 13, 2004 |
| 200 | Table_0200_BL_2128_B.txt | 11,936,004 | Aug. 13, 2004 |
| 201 | Table_0201_BL_2129_A.txt | 12,103,006 | Aug. 13, 2004 |
| 202 | Table_0202_BL_2129_B.txt | 12,004,781 | Aug. 13, 2004 |
| 203 | Table_0203_BL_2267_A.txt | 12,233,969 | Aug. 13, 2004 |
| 204 | Table_0204_BL_2267_B.txt | 12,000,442 | Aug. 13, 2004 |
| 205 | Table_0205_BL_2268_A.txt | 12,235,002 | Aug. 13, 2004 |
| 206 | Table_0206_BL_2268_B.txt | 12,040,217 | Aug. 13, 2004 |
| 207 | Table_0207_BL_2269_A.txt | 12,293,134 | Aug. 13, 2004 |
| 208 | Table_0208_BL_2269_B.txt | 12,083,796 | Aug. 13, 2004 |
| 209 | Table_0209_BL_2271_A.txt | 12,251,188 | Aug. 13, 2004 |
| 210 | Table_0210_BL_2271_B.txt | 12,033,626 | Aug. 13, 2004 |
| 211 | Table_0211_CD1negMCL_1013_A.txt | 12,069,354 | Aug. 12, 2004 |
| 212 | Table_0212_CD1negMCL_1013_B.txt | 11,916,758 | Aug. 12, 2004 |
| 213 | Table_0213_CD1negMCL_1161_A.txt | 12,063,571 | Aug. 12, 2004 |
| 214 | Table_0214_CD1negMCL_1116_B.txt | 11,602,903 | Aug. 12, 2004 |
| 215 | Table_0215_CD1negMCL_1125_A.txt | 11,980,433 | Aug. 12, 2004 |
| 216 | Table_0216_CD1negMCL_1125_B.txt | 11,802,606 | Aug. 12, 2004 |
| 217 | Table_0217_CD1negMCL_1265_A.txt | 12,073,913 | Aug. 12, 2004 |
| 218 | Table_0218_CD1negMCL_1265_B.txt | 11,806,792 | Aug. 12, 2004 |
| 219 | Table_0219_CD1negMCL_2198_A.txt | 12,205,777 | Aug. 12, 2004 |
| 220 | Table_0220_CD1negMCL_2198_B.txt | 11,953,251 | Aug. 12, 2004 |

Disc 5 of 22

| 221 | Table_0221_CD1negMCL_2272_A.txt | 12,140,519 | Aug. 12, 2004 |
| --- | --- | --- | --- |
| 222 | Table_0222_CD1negMCL_2272_B.txt | 11,903,198 | Aug. 12, 2004 |
| 223 | Table_0223_CD1negMCL_930_A.txt | 12,085,551 | Aug. 12, 2004 |
| 224 | Table_0224_CD1negMCL_930_B.txt | 12,029,054 | Aug. 12, 2004 |
| 225 | Table_0225_CD1negMCL_950_A.txt | 12,048,303 | Aug. 12, 2004 |
| 226 | Table_0226_CD1negMCL_950_B.txt | 11,966,572 | Aug. 12, 2004 |
| 227 | Table_0227_CD1negMCL_985_A.txt | 12,152,037 | Aug. 12, 2004 |
| 228 | Table_0228_CD1negMCL_985_B.txt | 11,987,764 | Aug. 12, 2004 |
| 229 | Table_0229_CD1negMCL_991_A.txt | 11,970,755 | Aug. 12, 2004 |
| 230 | Table_0230_CD1negMCL_991_B.txt | 11,906,922 | Aug. 12, 2004 |
| 231 | Table_0231_FH_2043_A.txt | 12,107,383 | Aug. 13, 2004 |
| 232 | Table_0232_FH_2043_B.txt | 11,759,404 | Aug. 13, 2004 |
| 233 | Table_0233_FH_2045_A.txt | 12,018,780 | Aug. 13, 2004 |
| 234 | Table_0234_FH_2045_B.txt | 11,760,937 | Aug. 13, 2004 |
| 235 | Table_0235_FH_2047_A.txt | 12,196,386 | Aug. 13, 2004 |
| 236 | Table_0236_FH_2047_B.txt | 12,038,844 | Aug. 13, 2004 |
| 237 | Table_0237_FH_2120_A.txt | 12,057,634 | Aug. 13, 2004 |
| 238 | Table_0238_FH_2120_B.txt | 11,899,644 | Aug. 13, 2004 |
| 239 | Table_0239_FH_2123_A.txt | 12,102,087 | Aug. 13, 2004 |

-continued

| | | | | |
|---|---|---|---|---|
| 240 | Table_0240_FH_2123_B.txt | | 11,974,939 | Aug. 13, 2004 |
| 241 | Table_0241_FH_2124_A.txt | | 11,981,409 | Aug. 13, 2004 |
| 242 | Table_0242_FH_2124_B.txt | | 11,728,703 | Aug. 13, 2004 |
| 243 | Table_0243_FH_2138_A.txt | | 12,246,913 | Aug. 13, 2004 |
| 244 | Table_0244_FH_2138_B.txt | | 12,113,245 | Aug. 13, 2004 |
| 245 | Table_0245_FH_2139_A.txt | | 12,131,403 | Aug. 13, 2004 |
| 248 | Table_0246_FH_2139_B.txt | | 12,113,768 | Aug. 13, 2004 |
| 247 | Table_0247_FH_2140_A.txt | | 12,195,197 | Aug. 13, 2004 |
| 248 | Table_0248_FH_2140_B.txt | | 12,119,738 | Aug. 13, 2004 |
| 249 | Table_0249_FH_2141_A.txt | | 12,208,402 | Aug. 13, 2004 |
| 250 | Table_0250_FH_2141_B.txt | | 12,147,002 | Aug. 13, 2004 |
| 251 | Table_0251_FH_2142_A.txt | | 12,219,828 | Aug. 13, 2004 |
| 252 | Table_0252_FH_2142_B.txt | | 12,085,775 | Aug. 13, 2004 |
| 253 | Table_0253_FH_2143_A.txt | | 12,006,329 | Aug. 13, 2004 |
| 254 | Table_0254_FH_2143_B.txt | | 11,935,243 | Aug. 13, 2004 |
| 255 | Table_0255_FH_2159_A.txt | | 12,188,960 | Aug. 13, 2004 |
| 256 | Table_0256_FH_2159_B.txt | | 11,879,679 | Aug. 12, 2004 |
| 257 | Table_0257_FH_2160_A.txt | | 12,192,094 | Aug. 13, 2004 |
| 258 | Table_0258_FH_2160_B.txt | | 11,931,687 | Aug. 13, 2004 |
| 259 | Table_0259_FH_2161_A.txt | | 12,253,214 | Aug. 13, 2004 |
| 260 | Table_0260_FH_2161_B.txt | | 12,051,739 | Aug. 16, 2004 |
| 261 | Table_0261_FH_2162_A.txt | | 12,191,210 | Aug. 16, 2004 |
| 262 | Table_0262_FH_2162_B.txt | | 11,952,602 | Aug. 13, 2004 |
| 263 | Table_0263_FH_2164_A.txt | | 12,272,173 | Aug. 13, 2004 |
| 264 | Table_0264_FH_2164_B.txt | | 12,019,060 | Aug. 13, 2004 |
| 265 | Table_0265_FH_2167_A.txt | | 12,337,573 | Aug. 13, 2004 |
| 266 | Table_0266_FH_2167_B.txt | | 12,107,528 | Aug. 16, 2004 |
| 267 | Table_0267_FL_1073_A.txt | | 12,249,411 | Aug. 13, 2004 |
| 268 | Table_0268_FL_1073_B.txt | | 12,008,104 | Aug. 16, 2004 |
| 269 | Table_0269_FL_1074_A.txt | | 12,197,601 | Aug. 13, 2004 |
| 270 | Table_0270_FL_1074_B.txt | | 11,933,006 | Aug. 16, 2004 |
| 271 | Table_0271_FL_1075_A.txt | | 12,222,781 | Aug. 16, 2004 |
| 272 | Table_0272_FL_1075_B.txt | | 12,070,708 | Aug. 13, 2004 |
| 273 | Table_0273_FL_1076_A.txt | | 12,270,162 | Aug. 16, 2004 |
| 274 | Table_0274_FL_1076_B.txt | | 12,076,340 | Aug. 16, 2004 |
| 275 | Table_0275_FL_1077_A.txt | | 12,180,432 | Aug. 16, 2004 |
| 276 | Table_0276_FL_1077_B.txt | | 11,836,673 | Aug. 13, 2004 |
| | | Disc 6 of 22 | | |
| 277 | Table_0277_FL_1078_A.txt | | 12,240,701 | Aug. 13, 2004 |
| 278 | Table_0278_FL_1078_B.txt | | 11,975,063 | Aug. 13, 2004 |
| 279 | Table_0279_FL_1080_A.txt | | 12,227,672 | Aug. 13, 2004 |
| 280 | Table_0280_FL_1080_B.txt | | 12,004,087 | Aug. 16, 2004 |
| 281 | Table_0281_FL_1081_A.txt | | 12,081,406 | Aug. 13, 2004 |
| 282 | Table_0282_FL_1081_B.txt | | 11,942,019 | Aug. 16, 2004 |
| 283 | Table_0283_FL_1083_A.txt | | 12,197,692 | Aug. 13, 2004 |
| 284 | Table_0284_FL_1083_B.txt | | 12,000,356 | Aug. 13, 2004 |
| 285 | Table_0285_FL_1085_A.txt | | 12,198,722 | Aug. 13, 2004 |
| 286 | Table_0286_FL_1085_B.txt | | 11,966,361 | Aug. 16, 2004 |
| 287 | Table_0287_FL_1086_A.txt | | 12,202,810 | Aug. 16, 2004 |
| 288 | Table_0288_FL_1086_B.txt | | 12,059,339 | Aug. 16, 2004 |
| 289 | Table_0289_FL_735_A.txt | | 12,093,811 | Aug. 15, 2004 |
| 290 | Table_0290_FL_735_B.txt | | 11,986,038 | Aug. 13, 2004 |
| 291 | Table_0291_FL_738_A.txt | | 12,150,187 | Aug. 16, 2004 |
| 292 | Table_0292_FL_738_B.txt | | 11,937,614 | Aug. 13, 2004 |
| 293 | Table_0293_FL_739_A.txt | | 12,166,069 | Aug. 16, 2004 |
| 294 | Table_0294_FL_739_B.txt | | 11,924,390 | Aug. 13, 2004 |
| 295 | Table_0295_FL_878_A.txt | | 12,199,551 | Aug. 16, 2004 |
| 296 | Table_0296_FL_878_B.txt | | 11,965,688 | Aug. 16, 2004 |
| 297 | Table_0297_FL_879_A.txt | | 12,153,527 | Aug. 16, 2004 |
| 298 | Table_0298_FL_879_B.txt | | 11,953,408 | Aug. 13, 2004 |
| 299 | Table_0299_FL_886_A.txt | | 12,167,246 | Aug. 16, 2004 |
| 300 | Table_0300_FL_886_B.txt | | 11,837,538 | Aug. 16, 2004 |
| 301 | Table_0301_FL_888_A.txt | | 12,069,433 | Aug. 16, 2004 |
| 302 | Table_0302_FL_888_B.txt | | 1,768,475 | Aug. 16, 2004 |
| 303 | Table_0303_FL_1087_A.txt | | 12,234,602 | Aug. 16, 2004 |
| 304 | Table_0304_FL_1087_B.txt | | 12,029,081 | Aug. 16, 2004 |
| 305 | Table_0305_FL_1088_A.txt | | 12,176,960 | Aug. 12, 2004 |
| 306 | Table_0306_FL_1088_B.txt | | 11,929,385 | Aug. 13, 2004 |
| 307 | Table_0307_FL_1089_A.txt | | 12,235,001 | Aug. 16, 2004 |
| 308 | Table_0308_FL_1089_B.txt | | 12,002,707 | Aug. 16, 2004 |
| 309 | Table_0309_FL_1090_A.txt | | 12,187,091 | Aug. 13, 2004 |
| 310 | Table_0310_FL_1090_B.txt | | 11,930,228 | Aug. 13, 2004 |
| 311 | Table_0311_FL_1097_A.txt | | 12,035,807 | Aug. 12, 2004 |
| 312 | Table_0312_FL_1097_B.txt | | 11,998,469 | Aug. 12, 2004 |
| 313 | Table_0313_FL_1098_A.txt | | 12,163,535 | Aug. 13, 2004 |
| 314 | Table_0314_FL_1098_B.txt | | 11,910,993 | Aug. 12, 2004 |
| 315 | Table_0315_FL_1099_A.txt | | 12,140,701 | Aug. 16, 2004 |
| 316 | Table_0316_FL_1099_B.txt | | 11,963,778 | Aug. 12, 2004 |

-continued

| | | | | |
|---|---|---|---|---|
| 317 | Table_0317_FL_1102_A.txt | | 12,041,808 | Aug. 13, 2004 |
| 318 | Table_0318_FL_1102_B.txt | | 11,873,396 | Aug. 13, 2004 |
| 319 | Table_0319_FL_1104_A.txt | | 12,147,511 | Aug. 16, 2004 |
| 320 | Table_0320_FL_1104_B.txt | | 11,972,622 | Aug. 13, 2004 |
| 321 | Table_0321_FL_1106_A.txt | | 12,074,579 | Aug. 13, 2004 |
| 322 | Table_0322_FL_1106_B.txt | | 11,991,893 | Aug. 16, 2004 |
| 323 | Table_0323_FL_1107_A.txt | | 12,022,734 | Aug. 13, 2004 |
| 324 | Table_0324_FL_1107_B.txt | | 11,887,794 | Aug. 16, 2004 |
| 325 | Table_0325_FL_1183_A.txt | | 12,062,144 | Aug. 16, 2004 |
| 326 | Table_0326_FL_1183_B.txt | | 11,831,515 | Aug. 16, 2004 |
| 327 | Table_0327_FL_1184_A.txt | | 12,095,457 | Aug. 13, 2004 |
| 328 | Table_0328_FL_1184_B.txt | | 11,978,023 | Aug. 16, 2004 |
| 329 | Table_0329_FL_1185_A.txt | | 11,929,326 | Aug. 13, 2004 |
| 330 | Table_0330_FL_1185_B.txt | | 11,784,070 | Aug. 12, 2004 |
| 331 | Table_0331_FL_1186_A.txt | | 11,962,956 | Aug. 16, 2004 |
| 332 | Table_0332_FL_1186_B.txt | | 11,896,127 | Aug. 12, 2004 |
| | | Disc 7 of 22 | | |
| 333 | Table_0333_FL_1416_A.txt | | 12,185,087 | Aug. 16, 2004 |
| 334 | Table_0334_FL_1416_B.txt | | 12,073,389 | Aug. 12, 2004 |
| 335 | Table_0335_FL_1417_A.txt | | 12,131,418 | Aug. 13, 2004 |
| 336 | Table_0336_FL_1417_B.txt | | 12,019,667 | Aug. 13, 2004 |
| 337 | Table_0337_FL_1418_A.txt | | 12,063,921 | Aug. 13, 2004 |
| 338 | Table_0338_FL_1418_B.txt | | 11,790,370 | Aug. 16, 2004 |
| 339 | Table_0339_FL_1419_A.txt | | 12,182,797 | Aug. 16, 2004 |
| 340 | Table_0340_FL_1419_B.txt | | 12,070,844 | Aug. 16, 2004 |
| 341 | Table_0341_FL_1422_A.txt | | 12,008,099 | Aug. 13, 2004 |
| 342 | Table_0342_FL_1422_B.txt | | 11,933,820 | Aug. 13, 2004 |
| 343 | Table_0343_FL_1425_A.txt | | 12,144,306 | Aug. 16, 2004 |
| 344 | Table_0344_FL_1425_B.txt | | 12,018,656 | Aug. 16, 2004 |
| 345 | Table_0345_FL_1426_A.txt | | 12,156,576 | Aug. 12, 2004 |
| 346 | Table_0346_FL_1426_B.txt | | 12,009,428 | Aug. 16, 2004 |
| 347 | Table_0347_FL_1427_A.txt | | 11,984,418 | Aug. 13, 2004 |
| 348 | Table_0348_FL_1427_B.txt | | 11,739,570 | Aug. 16, 2004 |
| 349 | Table_0349_FL_1428_A.txt | | 12,158,088 | Aug. 16, 2004 |
| 350 | Table_0350_FL_1428_B;txt | | 11,971,322 | Aug. 13, 2004 |
| 351 | Table_0351_FL_1429_A.txt | | 11,886,842 | Aug. 13, 2004 |
| 352 | Table_0352_FL_1429_B.txt | | 11,785,560 | Aug. 13, 2004 |
| 353 | Table_0353_FL_1432_A.txt | | 11,936,050 | Aug. 13, 2004 |
| 354 | Table_0354_FL_1432_B.txt | | 11,718,155 | Aug. 16, 2004 |
| 355 | Table_0355_FL_1436_A.txt | | 12,095,379 | Aug. 13, 2004 |
| 356 | Table_0356_FL_1436_B.txt | | 11,970,436 | Aug. 13, 2004 |
| 357 | Table_0357_FL_1440_A.txt | | 12,133,947 | Aug. 16, 2004 |
| 358 | Table_0358_FL_1440_B.txt | | 11,797,142 | Aug. 16, 2004 |
| 359 | Table_0359_FL_1445_A.txt | | 12,110,202 | Aug. 16, 2004 |
| 360 | Table_0360_FL_1445_B.txt | | 11,848,178 | Aug. 16, 2004 |
| 361 | Table_0361_FL_1450_A.txt | | 12,106,422 | Aug. 16, 2004 |
| 362 | Table_0362_FL_1450_B.txt | | 11,943,968 | Aug. 12, 2004 |
| 363 | Table_0363_FL_1472_A.txt | | 12,212,076 | Aug. 13, 2004 |
| 364 | Table_0364_FL_1472_B.txt | | 12,036,719 | Aug. 16, 2004 |
| 365 | Table_0365_FL_1473_A.txt | | 12,221,319 | Aug. 13, 2004 |
| 366 | Table_0366_FL_1473_B.txt | | 12,071,897 | Aug. 13, 2004 |
| 367 | Table_0367_FL_1474_A.txt | | 12,150,017 | Aug. 12, 2004 |
| 368 | Table_0368_FL_1474_B.txt | | 11,998,046 | Aug. 16, 2004 |
| 369 | Table_0369_FL_1476_A.txt | | 12,125,076 | Aug. 16, 2004 |
| 370 | Table_0370_FL_1476_B.txt | | 11,895,072 | Aug. 13, 2004 |
| 371 | Table_0371_FL_1477_A.txt | | 12,017,848 | Aug. 16, 2004 |
| 372 | Table_0372_FL_1477_B.txt | | 11,864,262 | Aug. 16, 2004 |
| 373 | Table_0373_FL_1478_A.txt | | 11,952,576 | Aug. 13, 2004 |
| 374 | Table_0374_FL_1478_B.txt | | 11,803,675 | Aug. 16, 2004 |
| 375 | Table_0375_FL_1479_A.txt | | 12,010,188 | Aug. 13, 2004 |
| 376 | Table_0376_FL_1479_B.txt | | 11,818,187 | Aug. 16, 2004 |
| 377 | Table_0377_FL_1480_A.txt | | 11,988,630 | Aug. 13, 2004 |
| 378 | Table_0378_FL_1480_B.txt | | 11,730,265 | Aug. 13, 2004 |
| 379 | Table_0379_FL_1579_A.txt | | 12,081,097 | Aug. 13, 2004 |
| 380 | Table_0380_FL_1579_B.txt | | 11,905,139 | Aug. 13, 2004 |
| 381 | Table_0381_FL_1580_A.txt | | 12,135,862 | Aug. 12, 2004 |
| 382 | Table_0382_FL_1580_B.txt | | 11,949,530 | Aug. 16, 2004 |
| 383 | Table_0383_FL_1581_A.txt | | 12,108,683 | Aug. 13, 2004 |
| 384 | Table_0384_FL_1581_B.txt | | 1,883,016 | Aug. 13, 2004 |
| 385 | Table_0385_FL_1582_A.txt | | 12,176,104 | Aug. 13, 2004 |
| 386 | Table_0386_FL_1582_B.txt | | 11,970,276 | Aug. 16, 2004 |
| 387 | Table_0387_FL_1583_A.txt | | 12,078,610 | Aug. 16, 2004 |
| 388 | Table_0388_FL_1583_B.txt | | 11,871,179 | Aug. 13, 2004 |
| | | Disc 8 of 22 | | |
| 389 | Table_0389_FL_1584_A.txt | | 12,169,682 | Aug. 13, 2004 |
| 390 | Table_0390_FL_1584_B.txt | | 12,035,358 | Aug. 16, 2004 |
| 391 | Table_0391_FL_1585_A.txt | | 12,228,755 | Aug. 13, 2004 |

-continued

| | | | | |
|---|---|---|---|---|
| 392 | Table_0392_FL_1585_B.txt | | 11,995,646 | Aug. 13, 2004 |
| 393 | Table_0393_FL_1586_A.txt | | 12,133,764 | Aug. 16, 2004 |
| 394 | Table_0394_FL_1586_B.txt | | 11,897,600 | Aug. 16, 2004 |
| 395 | Table_0395_FL_1588_A.txt | | 11,934,635 | Aug. 12, 2004 |
| 396 | Table_0396_FL_1588_B.txt | | 11,772,260 | Aug. 13, 2004 |
| 397 | Table_0397_FL_1589_A.txt | | 12,139,333 | Aug. 13, 2004 |
| 398 | Table_0398_FL_1589_B.txt | | 12,016,431 | Aug. 13, 2004 |
| 399 | Table_0399_FL_1591_A.txt | | 12,007,646 | Aug. 13, 2004 |
| 400 | Table_0400_FL_1591_B.txt | | 12,031,102 | Aug. 13, 2004 |
| 401 | Table_0401_FL_1594_A.txt | | 11,931,355 | Aug. 16, 2004 |
| 402 | Table_0402_FL_1594_B.txt | | 12,009,670 | Aug. 13, 2004 |
| 403 | Table_0403_FL_1595_A.txt | | 11,824,656 | Aug. 16, 2004 |
| 404 | Table_0404_FL_1595_B.txt | | 11,867,729 | Aug. 13, 2004 |
| 405 | Table_0405_FL_1598_A.txt | | 12,136,878 | Aug. 13, 2004 |
| 406 | Table_0406_FL_1598_B.txt | | 12,067,658 | Aug. 16, 2004 |
| 407 | Table_0407_FL_1599_A.txt | | 12,029,574 | Aug. 16, 2004 |
| 408 | Table_0408_FL_1599_B.txt | | 11,820,074 | Aug. 16, 2004 |
| 409 | Table_0409_FL_1603_A.txt | | 12,091,394 | Aug. 13, 2004 |
| 410 | Table_0410_FL_1603_B.txt | | 11,869,687 | Aug. 12, 2004 |
| 411 | Table_0411_FL_1604_A.txt | | 12,027,557 | Aug. 16, 2004 |
| 412 | Table_0412_FL_1604_B.txt | | 11,817,875 | Aug. 13, 2004 |
| 413 | Table_0413_FL_1606_A.txt | | 12,068,506 | Aug. 13, 2004 |
| 414 | Table_0414_FL_1606_B.txt | | 11,902,253 | Aug. 13, 2004 |
| 415 | Table_0415_FL_1607_A.txt | | 12,088,022 | Aug. 13, 2004 |
| 416 | Table_0416_FL_1607_B.txt | | 11,942,795 | Aug. 16, 2004 |
| 417 | Table_0417_FL_1608_A.txt | | 12,051,428 | Aug. 16, 2004 |
| 418 | Table_0418_FL_1608_B.txt | | 11,758,034 | Aug. 16, 2004 |
| 419 | Table_0419_FL_1610_A.txt | | 12,164,325 | Aug. 13, 2004 |
| 420 | Table_0420_FL_1610_B.txt | | 11,884,041 | Aug. 16, 2004 |
| 421 | Table_0421_FL_1611_A.txt | | 12,052,511 | Aug. 16, 2004 |
| 422 | Table_0422_FL_1611_B.txt | | 11,821,581 | Aug. 13, 2004 |
| 423 | Table_0423_FL_1616_A.txt | | 12,183,189 | Aug. 16, 2004 |
| 424 | Table_0424_FL_1616_B.txt | | 11,967,672 | Aug. 13, 2004 |
| 425 | Table_0425_FL_1617_A.txt | | 12,059,647 | Aug. 13, 2004 |
| 426 | Table_0426_FL_1617_B.txt | | 11,857,787 | Aug. 13, 2004 |
| 427 | Table_0427_FL_1619_A.txt | | 12,145,748 | Aug. 13, 2004 |
| 428 | Table_0428_FL_1619_B.txt | | 12,010,810 | Aug. 16, 2004 |
| 429 | Table_0429_FL_1620_A.txt | | 12,151,309 | Aug. 16, 2004 |
| 430 | Table_0430_FL_1620_B.txt | | 11,970,646 | Aug. 13, 2004 |
| 431 | Table_0431_FL_1622_A.txt | | 12,153,195 | Aug. 13, 2004 |
| 432 | Table_0432_FL_1622_B.txt | | 12,003,231 | Aug. 13, 2004 |
| 433 | Table_0433_FL_1623_A.txt | | 12,252,791 | Aug. 16, 2004 |
| 434 | Table_0434_FL_1623_B.txt | | 12,120,904 | Aug. 16, 2004 |
| 435 | Table_0435_FL_1624_A.txt | | 12,175,743 | Aug. 13, 2004 |
| 436 | Table_0436_FL_1624_B.txt | | 12,146,244 | Aug. 13, 2004 |
| 437 | Table_0437_FL_1625_A.txt | | 12,212,124 | Aug. 13, 2004 |
| 438 | Table_0438_FL_1625_B.txt | | 12,042,056 | Aug. 13, 2004 |
| 439 | Table_0439_FL_1626_A.txt | | 12,180,263 | Aug. 13, 2004 |
| 440 | Table_0440_FL_1626_B.txt | | 12,013,477 | Aug. 16, 2004 |
| 441 | Table_0441_FL_1627_A.txt | | 12,168,379 | Aug. 13, 2004 |
| 442 | Table_0442_FL_1627_B.txt | | 12,025,929 | Aug. 13, 2004 |
| 443 | Table_0443_FL_1628_A.txt | | 12,164,556 | Aug. 13, 2004 |
| 444 | Table_0444_FL_1628_B.txt | | 11,605,629 | Aug. 13, 2004 |
| | | Disc 9 of 22 | | |
| 445 | Table_0445_FL_1637_A.txt | | 12,059,851 | Aug. 13, 2004 |
| 446 | Table_0446_FL_1637_B.txt | | 11,851,760 | Aug. 16, 2004 |
| 447 | Table_0447_FL_1638_A.txt | | 12,155,584 | Aug. 12, 2004 |
| 448 | Table_0448_FL_1638_B.txt | | 11,953,771 | Aug. 13, 2004 |
| 449 | Table_0449_FL_1639_A.txt | | 12,104,432 | Aug. 13, 2004 |
| 450 | Table_0450_FL_1639_B.txt | | 11,885,752 | Aug. 16, 2004 |
| 451 | Table_0451_FL_1643_A.txt | | 12,113,590 | Aug. 16, 2004 |
| 452 | Table_0452_FL_1643_B.txt | | 11,976,289 | Aug. 16, 2004 |
| 453 | Table_0453_FL_1644_A.txt | | 12,135,052 | Aug. 16, 2004 |
| 454 | Table_0454_FL_1644_B.txt | | 11,864,285 | Aug. 13, 2004 |
| 455 | Table_0455_FL_1645_A.txt | | 12,082,408 | Aug. 13, 2004 |
| 456 | Table_0456_FL_1645_B.txt | | 11,794,548 | Aug. 16, 2004 |
| 457 | Table_0457_FL_1646_A.txt | | 12,205,460 | Aug. 16, 2004 |
| 458 | Table_0458_FL_1646_B.txt | | 12,063,381 | Aug. 13, 2004 |
| 459 | Table_0459_FL_1647_A.txt | | 12,014,730 | Aug. 16, 2004 |
| 460 | Table_0460_FL_1647_B.txt | | 11,815,426 | Aug. 13, 2004 |
| 461 | Table_0461_FL_1648_A.txt | | 12,129,890 | Aug. 13, 2004 |
| 462 | Table_0462_FL_1648_B.txt | | 11,970,207 | Aug. 13, 2004 |
| 463 | Table_0463_FL_1652_A.txt | | 12,094,102 | Aug. 16, 2004 |
| 464 | Table_0464_FL_1652_B.txt | | 11,858,393 | Aug. 12, 2004 |
| 465 | Table_0465_FL_1654_A.txt | | 12,054,434 | Aug. 16, 2004 |
| 466 | Table_0466_FL_1654_B.txt | | 11,835,533 | Aug. 13, 2004 |
| 467 | Table_0467_FL_1655_A.txt | | 12,011,007 | Aug. 12, 2004 |
| 468 | Table_0468_FL_1655_B.txt | | 11,839,935 | Aug. 12, 2004 |

-continued

| | | | | |
|---|---|---|---|---|
| 469 | Table_0469_FL_1656_A.txt | | 11,998,067 | Aug. 16, 2004 |
| 470 | Table_0470_FL_1656_B.txt | | 11,783,615 | Aug. 13, 2004 |
| 471 | Table_0471_FL_1657_A.txt | | 12,095,831 | Aug. 13, 2004 |
| 472 | Table_0472_FL_1657_B.txt | | 11,872,675 | Aug. 12, 2004 |
| 473 | Table_0473_FL_1660_A.txt | | 11,984,440 | Aug. 13, 2004 |
| 474 | Table_0474_FL_1660_B.txt | | 11,793,957 | Aug. 16, 2004 |
| 475 | Table_0475_FL_1661_A.txt | | 12,115,368 | Aug. 13, 2004 |
| 476 | Table_0476_FL_1661_B.txt | | 11,907,640 | Aug. 16, 2004 |
| 477 | Table_0477_FL_1662_A.txt | | 11,935,841 | Aug. 13, 2004 |
| 478 | Table_0478_FL_1662_B.txt | | 11,655,368 | Aug. 16, 2004 |
| 479 | Table_0479_FL_1664_A.txt | | 12,057,315 | Aug. 13, 2004 |
| 480 | Table_0480_FL_1664_B.txt | | 11,881,016 | Aug. 13, 2004 |
| 481 | Table_0481_FL_1669_A.txt | | 12,067,483 | Aug. 16, 2004 |
| 482 | Table_0482_FL_1669_B.txt | | 11,942,861 | Aug. 13, 2004 |
| 483 | Table_0483_FL_1670_A.txt | | 12,037,021 | Aug. 16, 2004 |
| 484 | Table_0484_FL_1670_B.txt | | 11,862,504 | Aug. 13, 2004 |
| 485 | Table_0485_FL_1675_A.txt | | 12,062,632 | Aug. 16, 2004 |
| 486 | Table_0486_FL_1675_B.txt | | 11,823,358 | Aug. 13, 2004 |
| 487 | Table_0487_FL_1681_A.txt | | 11,978,013 | Aug. 13, 2004 |
| 488 | Table_0488_FL_1681_B.txt | | 11,745,731 | Aug. 16, 2004 |
| 489 | Table_0489_FL_1883_A.txt | | 11,919,352 | Aug. 12, 2004 |
| 490 | Table_0490_FL_1683_B.txt | | 11,780,543 | Aug. 12, 2004 |
| 491 | Table_0491_FL_1684_A.txt | | 12,186,541 | Aug. 13, 2004 |
| 492 | Table_0492_FL_1684_B.txt | | 12,056,872 | Aug. 13, 2004 |
| 493 | Table_0493_FL_1716_A.txt | | 12,160,373 | Aug. 16, 2004 |
| 494 | Table_0494_FL_1716_B.txt | | 11,995,492 | Aug. 13, 2004 |
| 495 | Table_0495_FL_1717_A.txt | | 11,938,675 | Aug. 13, 2004 |
| 496 | Table_0496_FL_1717_B.txt | | 11,950,078 | Aug. 12, 2004 |
| 497 | Table_0497_FL_1718_A.txt | | 12,102,928 | Aug. 12, 2004 |
| 498 | Table_0498_FL_1718_B.txt | | 1,946,324 | Aug. 12, 2004 |
| 499 | Table_0499_FL_1719_A.txt | | 11,980,431 | Aug. 16, 2004 |
| 500 | Table_0500_FL_1719_B.txt | | 11,941,393 | Aug. 13, 2004 |
| 501 | Table_0501_FL_1720_A.txt | | 11,957,606 | Aug. 31, 2004 |
| 502 | Table_0502_FL_1720_B.txt | | 11,790,878 | Aug. 31, 2004 |
| 503 | Table_0503_FL_1729_A.txt | | 12,015,501 | Aug. 31, 2004 |
| 504 | Table_0504_FL_1729_B.txt | Disc 10 of 22 | 12,003,112 | Aug. 31, 2004 |
| 505 | Table_0505_FL_1732_A.txt | | 12,019,768 | Aug. 31, 2004 |
| 506 | Table_0506_FL_1732_B.txt | | 11,937,384 | Aug. 31, 2004 |
| 507 | Table_0507_FL_1735_A.txt | | 12,229,281 | Aug. 31, 2004 |
| 508 | Table_0508_FL_1735_B.txt | | 12,010,813 | Aug. 31, 2004 |
| 509 | Table_0509_FL_1761_A.txt | | 12,013,113 | Aug. 31, 2004 |
| 510 | Table_0510_FL_1761_B.txt | | 11,84S,381 | Aug. 31, 2004 |
| 511 | Table_0511_FL_1764_A.txt | | 12,072,874 | Aug. 31, 2004 |
| 512 | Table_0512_FL_1764_B.txt | | 12,067,878 | Aug. 31, 2004 |
| 513 | Table_0513_FL_1768_A.txt | | 12,164,392 | Aug. 31, 2004 |
| 514 | Table_0514_FL_1768_B.txt | | 12,159,717 | Aug. 31, 2004 |
| 515 | Table_0515_FL_1771_A.txt | | 12,171,432 | Aug. 31, 2004 |
| 516 | Table_0516_FL_1771_B.txt | | 11,981,937 | Aug. 31, 2004 |
| 517 | Table_0517_FL_1772_A.txt | | 12,099,592 | Aug. 31, 2004 |
| 518 | Table_0518_FL_1772_B.txt | | 12,044,119 | Aug. 31, 2004 |
| 519 | Table_0519_FL_1788_A.txt | | 12,057,485 | Aug. 31, 2004 |
| 520 | Table_0520_FL_1788_B.txt | | 12,000,622 | Aug. 31, 2004 |
| 521 | Table_0521_FL_1790_A.txt | | 11,866,178 | Aug. 13, 2004 |
| 522 | Table_0522_FL_1790_B.txt | | 11,879,605 | Aug. 16, 2004 |
| 523 | Table_0523_FL_1792_A.txt | | 12,107,831 | Aug. 12, 2004 |
| 524 | Table_0524_FL_1792_B.txt | | 11,981,731 | Aug. 16, 2004 |
| 525 | Table_0525_FL_1795_A.txt | | 12,147,382 | Aug. 13, 2004 |
| 526 | Table_0526_FL_1795_B.txt | | 12,027,851 | Aug. 13, 2004 |
| 527 | Table_0527_FL_1797_A.txt | | 12,007,290 | Aug. 16, 2004 |
| 528 | Table_0528_FL_1797_B.txt | | 11,977,859 | Aug. 13, 2004 |
| 529 | Table_0529_FL_1799_A.txt | | 12,136,510 | Aug. 13, 2004 |
| 530 | Table_0530_FL_1799_B.txt | | 12,019,206 | Aug. 16, 2004 |
| 531 | Table_0531_FL_1810_A.txt | | 12,086,662 | Aug. 13, 2004 |
| 532 | Table_0532_FL_1810_B.txt | | 11,977,958 | Aug. 16, 2004 |
| 533 | Table_0533_FL_1811_A.txt | | 12,122,670 | Aug. 16, 2004 |
| 534 | Table_0534_FL_1811_B.txt | | 11,929,935 | Aug. 13, 2004 |
| 535 | Table_0535_FL_1825_A.txt | | 11,967,784 | Aug. 13, 2004 |
| 536 | Table_0536_FL_1825_B.txt | | 11,932,434 | Aug. 12, 2004 |
| 537 | Table_0537_FL_1827_A.txt | | 11,955,058 | Aug. 13, 2004 |
| 538 | Table_0538_FL_1827_B.txt | | 11,969,116 | Aug. 13, 2004 |
| 539 | Table_0539_FL_1828_A.txt | | 12,029,099 | Aug. 12, 2004 |
| 540 | Table_0540_FL_1828_B.txt | | 11,877,005 | Aug. 13, 2004 |
| 541 | Table_0541_FL_1829_A.txt | | 12,014,127 | Aug. 13, 2004 |
| 542 | Table_0542_FL_1829_B.txt | | 11,885,190 | Aug. 12, 2004 |
| 543 | Table_0543_FL_1830_A.txt | | 12,089,030 | Aug. 13, 2004 |
| 544 | Table_0544_FL_1830_B.txt | | 11,935,691 | Aug. 13, 2004 |
| 545 | Table_0545_FL_1833_A.txt | | 12,162,920 | Aug. 16, 2004 |

-continued

| | | | | |
|---|---|---|---|---|
| 546 | Table_0546_FL_1833_B.txt | | 11,990,591 | Aug. 13, 2004 |
| 547 | Table_0547_FL_1834_A.txt | | 11,952,185 | Aug. 13, 2004 |
| 548 | Table_0548_FL_1834_B.txt | | 11,906,810 | Aug. 12, 2004 |
| 549 | Table_0549_FL_1835_A.txt | | 12,122,553 | Aug. 13, 2004 |
| 559 | Table_0550_FL_1835_B.txt | | 12,017,691 | Aug. 12, 2004 |
| 551 | Table_0551_FL_1836_A.txt | | 12,187,532 | Aug. 13, 2004 |
| 552 | Table_0552_FL_1836_B.txt | | 12,063,526 | Aug. 16, 2004 |
| 553 | Table_0553_FL_1837_A.txt | | 12,044,450 | Aug. 16, 2004 |
| 554 | Table_0554_FL_1837_B.txt | | 1,945,547 | Aug. 16, 2004 |
| 555 | Table_0555_FL_1038_A.txt | | 12,024,726 | Aug. 13, 2004 |
| 556 | Table_0556_FL_1838_B.txt | | 11,908,269 | Aug. 16, 2004 |
| 557 | Table_0557_FL_1839_A.txt | | 12,063,812 | Aug. 16, 2004 |
| 558 | Table_0558_FL_1839_B.txt | | 11,957,591 | Aug. 13, 2004 |
| 559 | Table_0559_FL_1841_A.txt | | 12,137,503 | Aug. 13, 2004 |
| 560 | Table_0560_FL_1841_B.txt | | 11,977,376 | Aug. 13, 2004 |
| | | Disc 11 of 22 | | |
| 561 | Table_0561_FL_1842_A.txt | | 11,838,323 | Aug. 13, 2004 |
| 562 | Table_0562_FL_1042_B.txt | | 11,777,270 | Aug. 13, 2004 |
| 563 | Table_0563_FL_1844_A.txt | | 12,101,060 | Aug. 13, 2004 |
| 564 | Table_0564_FL_1844_B.txt | | 11,948,925 | Aug. 12, 2004 |
| 565 | Table_0565_FL_1845_A.txt | | 12,080,776 | Aug. 13, 2004 |
| 566 | Table_0566_FL_1845_B.txt | | 11,896,386 | Aug. 12, 2004 |
| 567 | Table_0567_FL_1846_A.txt | | 12,068,884 | Aug. 13, 2004 |
| 568 | Table_0568_FL_1846_B.txt | | 11,927,246 | Aug. 16, 2004 |
| 569 | Table_0569_FL_1848_A.txt | | 12,203,436 | Aug. 13, 2004 |
| 570 | Table_0570_FL_1848_B.txt | | 12,066,922 | Aug. 16, 2004 |
| 571 | Table_0571_FL_1850_A.txt | | 12,150,601 | Aug. 16, 2004 |
| 572 | Table_0572_FL_1850_B.txt | | 12,041,327 | Aug. 16, 2004 |
| 573 | Table_0573_FL_1851_A.txt | | 12,182,233 | Aug. 12, 2004 |
| 574 | Table_0574_FL_1851_B.txt | | 12,075,493 | Aug. 16, 2004 |
| 575 | Table_0575_FL_1853_A.txt | | 12,087,688 | Aug. 13, 2004 |
| 576 | Table_0576_FL_1853_B.txt | | 11,933,285 | Aug. 16, 2004 |
| 577 | Table_0577_FL_1854_A.txt | | 12,155,291 | Aug. 12, 2004 |
| 578 | Table_0578_FL_1854_B.txt | | 11,959,793 | Aug. 16, 2004 |
| 579 | Table_0579_FL_1855_A.txt | | 12,238,359 | Aug. 16, 2004 |
| 580 | Table_0580_FL_1855_B.txt | | 12,034,894 | Aug. 12, 2004 |
| 581 | Table_0581_FL_1857_A.txt | | 12,205,129 | Aug. 16, 2004 |
| 582 | Table_0582_FL_1857_B.txt | | 12,076,155 | Aug. 16, 2004 |
| 583 | Table_0583_FL_1861_A.txt | | 12,040,917 | Aug. 16, 2004 |
| 584 | Table_0584_FL_1861_B.txt | | 11,858,142 | Aug. 13, 2004 |
| 585 | Table_0585_FL_1862_A.txt | | 12,041,052 | Aug. 13, 2004 |
| 585 | Table_0586_FL_1862_B.txt | | 11,924,463 | Aug. 13, 2004 |
| 587 | Table_0587_FL_1863_A.txt | | 12,058,282 | Aug. 13, 2004 |
| 588 | Table_0588_FL_1863_B.txt | | 11,905,465 | Aug. 12, 2004 |
| 589 | Table_0589_FL_1864_A.txt | | 12,114,627 | Aug. 16, 2004 |
| 590 | Table_0590_FL_1864_B.txt | | 11,910,825 | Aug. 13, 2004 |
| 591 | Table_0591_FL_1866_A.txt | | 12,192,098 | Aug. 12, 2004 |
| 592 | Table_0592_FL_1866_B.txt | | 12,052,374 | Aug. 13, 2004 |
| 593 | Table_0593_FL_1870_A.txt | | 12,017,057 | Aug. 13, 2004 |
| 594 | Table_0594_FL_1870_B.txt | | 11,959,328 | Aug. 16, 2004 |
| 595 | Table_0595_FL_1873_A.txt | | 11,193,964 | Aug. 12, 2004 |
| 596 | Table_0596_FL_1873_B.txt | | 12,071,638 | Aug. 13, 2004 |
| 597 | Table_0597_FL_1874_A.txt | | 12,096,385 | Aug. 13, 2004 |
| 598 | Table_0598_FL_1874_B.txt | | 12,004,410 | Aug. 16, 2004 |
| 599 | Table_0599_FL_1876_A.txt | | 12,130,466 | Aug. 13, 2004 |
| 600 | Table_0600_FL_1876_B.txt | | 11,894,443 | Aug. 13, 2004 |
| 601 | Table_0601_FL_1879_A.txt | | 12,047,598 | Aug. 16, 2004 |
| 602 | Table_0602_FL_1879_B.txt | | 11,816,302 | Aug. 16, 2004 |
| 603 | Table_0603_FL_1880_A.txt | | 11,925,145 | Aug. 16, 2004 |
| 604 | Table_0604_FL_1880_B.txt | | 11,872,612 | Aug. 12, 2004 |
| 605 | Table_0605_FL_1882_A.txt | | 12,006,192 | Aug. 13, 2004 |
| 696 | Table_0606_FL_1882_B.txt | | 11,755,896 | Aug. 13, 2004 |
| 607 | Table_0607_FL_1884_A.txt | | 11,983,446 | Aug. 13, 2004 |
| 608 | Table_0608_FL_1884_B.txt | | 11,850,008 | Aug. 12, 2004 |
| 609 | Table_0609_FL_1885_A.txt | | 12,000,301 | Aug. 13, 2004 |
| 610 | Table_0610_FL_1885_B.txt | | 11,802,742 | Aug. 16, 2004 |
| 611 | Table_0611_FL_1887_A.txt | | 12,008,565 | Aug. 13, 2004 |
| 612 | Table_0612_FL_1887_B.txt | | 11,916,475 | Aug. 16, 2004 |
| 613 | Table_0613_FL_1888_A.txt | | 12,027,927 | Aug. 13, 2004 |
| 614 | Table_0614_FL_1888_B.txt | | 11,850,399 | Aug. 13, 2004 |
| 615 | Table_0615_FL_1890_A.txt | | 11,991,887 | Aug. 13, 2004 |
| 616 | Table_0616_FL_1890_B.txt | | 11,723,176 | Aug. 16, 2004 |
| 617 | Table_0617_FL_1894_A.txt | | 11,970,378 | Aug. 12, 2004 |
| 618 | Table_0618_FL_1894_B.txt | | 11,814,812 | Aug. 16, 2004 |
| 619 | Table_0619_FL_1896_A.txt | | 11,986,044 | Aug. 13, 2004 |
| 620 | Table_0620_FL_1896_B.txt | | 11,846,067 | Aug. 16, 2004 |
| 621 | Table_0621_FL_1897_A.txt | | 11,936,008 | Aug. 13, 2004 |

-continued

Disc 12 of 22

| | | | | |
|---|---|---|---|---|
| 622 | Table_0622_FL_1897_B.txt | | 11,766,595 | Aug. 16, 2004 |
| 623 | Table_0623_FL_1898_A.txt | | 12,044,053 | Aug. 16, 2004 |
| 624 | Table_0624_FL_1898_B.txt | | 11,886,226 | Aug. 13, 2004 |
| 625 | Table_0625_FL_1900_A.txt | | 11,950,630 | Aug. 13, 2004 |
| 626 | Table_0626_FL_1900_B.txt | | 11,714,418 | Aug. 13, 2004 |
| 627 | Table_0627_FL_1903_A.txt | | 12,114,153 | Aug. 13, 2004 |
| 628 | Table_0628_FL_1903_B.txt | | 11,971,160 | Aug. 13, 2004 |
| 629 | Table_0629_FL_1904_A.txt | | 12,005,503 | Aug. 12, 2004 |
| 630 | Table_0630_FL_1904_B.txt | | 11,844,302 | Aug. 13, 2004 |
| 631 | Table_0631_FL_1905_A.txt | | 12,001,380 | Aug. 13, 2004 |
| 632 | Table_0632_FL_1905_B.txt | | 11,761,255 | Aug. 16, 2004 |
| 633 | Table_0633_FL_1906_A.txt | | 11,942,117 | Aug. 13, 2904 |
| 634 | Table_0634_FL_1906_B.txt | | 11,733,601 | Aug. 13, 2004 |
| 635 | Table_0635_FL_1907_A.txt | | 11,966,185 | Aug. 16, 2004 |
| 636 | Table_0636_FL_1907_B.txt | | 11,824,403 | Aug. 16, 2004 |
| 637 | Table_0637_FL_1910_A.txt | | 12,086,740 | Aug. 16, 2004 |
| 638 | Table_0638_FL_1910_B.txt | | 11,975,275 | Aug. 13, 2004 |
| 639 | Table_0639_FL_1912_A.txt | | 12,103,924 | Aug. 13, 2004 |
| 640 | Table_0640_FL_1912_B.txt | | 11,961,340 | Aug. 13, 2004 |
| 641 | Table_0641_FL_1913_A.txt | | 12,113,471 | Aug. 12, 2004 |
| 642 | Table_0642_FL_1913_B.txt | | 11,876,693 | Aug. 13, Z004 |
| 643 | Table_0643_FL_1916_A.txt | | 12,083,419 | Aug. 12, 2004 |
| 644 | Table_0644_FL_1916_B.txt | | 11,867,823 | Aug. 16, 2004 |
| 645 | Table_0645_FL_1918_A.txt | | 12,100,679 | Aug. 13, 2004 |
| 646 | Table_0646_FL_1918_B.txt | | 11,752,183 | Aug. 16, 2004 |
| 647 | Table_0647_FL_1919_A.txt | | 11,911,303 | Aug. 13, 2004 |
| 648 | Table_0648_FL_1919_B.txt | | 11,746,064 | Aug. 16, 2004 |
| 649 | Table_0649_GCB_412_A.txt | | 12,159,887 | Aug. 16, 2004 |
| 650 | Table_0650_GCB_412_B.txt | | 11,936,122 | Aug. 16, 2004 |
| 651 | Table_0651_GCB_415_A.txt | | 12,127,395 | Aug. 13, 2004 |
| 652 | Table_0652_GCB_415_B.txt | | 11,974,456 | Aug. 13, 2004 |
| 663 | Table_0653_GCB_421_A.txt | | 12,089,656 | Aug. 12, 2004 |
| 654 | Table_0654_GCB_421_B.txt | | 11,977,458 | Aug. 13, 2004 |
| 655 | Table_0655_GCB_424_A.txt | | 12,234,103 | Aug. 12, 2004 |
| 656 | Table_0656_GCB_424_B.txt | | 11,982,465 | Aug. 12, 2004 |
| 657 | Table_0657_GCB_433_A.txt | | 12,281,184 | Aug. 16, 2004 |
| 658 | Table_0658_GCB_433_B.txt | | 12,083,431 | Aug. 13, 2004 |
| 659 | Table_0659_GCB_434_A.txt | | 12,293,242 | Aug. 13, 2004 |
| 660 | Table_0660_GCB_434_B.txt | | 12,107,279 | Aug. 16, 2004 |
| 661 | Table_0661_GCB_438_A.txt | | 12,221,161 | Aug. 16, 2004 |
| 662 | Table_0662_GCB_438_B.txt | | 12,019,388 | Aug. 13, 2004 |
| 663 | Table_0663_GCB_439_A.txt | | 11,992,537 | Aug. 13, 2004 |
| 664 | Table_0664_GCB_439_B.txt | | 11,899,300 | Aug. 16, 2004 |
| 665 | Table_0665_GCB_459_A.txt | | 12,290,334 | Aug. 16, 2004 |
| 666 | Table_0666_GCB_459_B.txt | | 12,042,592 | Aug. 12, 2004 |
| 667 | Table_0667_GCB_470_A.txt | | 12,105,369 | Aug. 13, 2004 |
| 668 | Table_0668_GCB_470_B.txt | | 11,860,994 | Aug. 16, 2004 |
| 669 | Table_0669_GCB_479_A.txt | | 11,959,122 | Aug. 16, 2004 |
| 670 | Table_0870_GCB_479_B.txt | | 11,939,440 | Aug. 13, 2004 |
| 671 | Table_0671_GCB_492_A.txt | | 12,215,479 | Aug. 16, 2004 |
| 672 | Table_0672_GCB_492_B.txt | | 11,973,889 | Aug. 13, 2004 |
| 673 | Table_0673_GCB_517_A.txt | | 12,123,982 | Aug. 16, 2004 |
| 674 | Table_0674_GCB_517_B.txt | | 11,944,186 | Aug. 13, 2004 |
| 675 | Table_0675_GCB_523_A.txt | | 12,154,045 | Aug. 16, 2004 |
| 676 | Table_0676_GCB_523_B.txt | | 12,048,726 | Aug. 13, 2004 |
| 677 | Table_0677_GCB_524_A.txt | | 12,128,784 | Aug. 16, 2004 |
| 678 | Table_0678_GCB_524_B.txt | | 12,079,921 | Aug. 16, 2004 |
| 679 | Table_0679_GCB_529_A.txt | | 12,295,640 | Aug. 12, 2004 |
| 680 | Table_0680_GCB_529_B.txt | | 12,053,344 | Aug. 13, 2004 |
| 681 | Table_0681_GCB_533_A.txt | | 12,048,079 | Aug. 12, 2004 |
| 682 | Table_0682_GCB_533_B.txt | | 11,849,351 | Aug. 16, 2004 |
| | | Disc 13 of 22 | | |
| 683 | Table_0683_GCB_537_A.txt | | 12,151,426 | Aug. 16, 2004 |
| 684 | Table_0684_GCB_537_B.txt | | 12,017,692 | Aug. 16, 2004 |
| 685 | Table_0685_GCB_543_A.txt | | 12,163,497 | Aug. 13, 2004 |
| 686 | Table_0686_GCB_543_B.txt | | 11,981,555 | Aug. 13, 2004 |
| 687 | Table_0687_GCB_545_A.txt | | 12,102,161 | Aug. 12, 2004 |
| 688 | Table_0688_GCB_545_B.txt | | 11,881,457 | Aug. 13, 2004 |
| 689 | Table_0689_GCB_549_A.txt | | 12,161,840 | Aug. 13, 2004 |
| 690 | Table_0690_GCB_549_B.txt | | 12,020,632 | Aug. 13, 2004 |
| 691 | Table_0691_GCB_550_A.txt | | 12,171,880 | Aug. 12, 2004 |
| 692 | Table_0692_GCB_550_B.txt | | 11,944,012 | Aug. 13, 2004 |
| 693 | Table_0693_GCB_553_A.txt | | 12,111,245 | Aug. 16, 2004 |
| 694 | Table_0694_GCB_553_B.txt | | 11,864,058 | Aug. 13, 2004 |
| 695 | Table_0695_GCB_565_A.txt | | 12,063,661 | Aug. 13, 2004 |
| 696 | Table_0696_GCB_565_B.txt | | 11,965,851 | Aug. 13, 2004 |

| | | | | |
|---|---|---|---|---|
| 697 | Table_0697_GCB_572_A.txt | | 12,108,923 | Aug. 16, 2004 |
| 698 | Table_0698_GCB_572_B.txt | | 11,888,114 | Aug. 16, 2004 |
| 699 | Table_0699_GCB_617_A.txt | | 12,130,626 | Aug. 13, 2004 |
| 700 | Table_0700_GCB_617_B.txt | | 11,901,308 | Aug. 13, 2004 |
| 701 | Table_0701_GCB_618_A.txt | | 12,190,874 | Aug. 12, 2004 |
| 702 | Table_0702_GCB_618_B.txt | | 11,980,754 | Aug. 16, 2004 |
| 703 | Table_0703_GCB_619_A.txt | | 12,140,602 | Aug. 13, 2004 |
| 704 | Table_0704_GCB_619_B.txt | | 11,905,019 | Aug. 16, 2004 |
| 705 | Table_0705_GCB_623_A.txt | | 12,265,682 | Aug. 13, 2004 |
| 706 | Table_0706_GCB_623_B.txt | | 12,090,817 | Aug. 13, 2004 |
| 707 | Table_0707_GCB_627_A.txt | | 12,173,309 | Aug. 16, 2004 |
| 708 | Table_0708_GCB_627_B.txt | | 11,958,281 | Aug. 16, 2004 |
| 709 | Table_0709_GCB_654_A.txt | | 12,127,035 | Aug. 13, 2004 |
| 710 | Table_0710_GCB_654_B.txt | | 11,929,393 | Aug. 16, 2004 |
| 711 | Table_0711_GCB_661_A.txt | | 12,192,238 | Aug. 12, 2004 |
| 712 | Table_0712_GCB_661_B.txt | | 12,030,163 | Aug. 13, 2004 |
| 713 | Table_0713_GCB_669_A.txt | | 12,273,029 | Aug. 16, 2004 |
| 714 | Table_0714_GCB_669_B.txt | | 12,103,510 | Aug. 12, 2004 |
| 715 | Table_0715_GCB_672_A.txt | | 12,146,779 | Aug. 13, 2004 |
| 716 | Table_0716_GCB_672_B.txt | | 11,942,479 | Aug. 13, 2004 |
| 717 | Table_0717_GCB_674_A.txt | | 12,096,808 | Aug. 13, 2004 |
| 718 | Table_0718_GCB_674_B.txt | | 11,907,095 | Aug. 13, 2004 |
| 719 | Table_0719_GCB_675_A.txt | | 12,026,251 | Aug. 16, 2004 |
| 720 | Table_0720_GCB_675_B.txt | | 11,875,031 | Aug. 13, 2004 |
| 721 | Table_0721_GCB_681_A.txt | | 12,218,121 | Aug. 16, 2004 |
| 722 | Table_0722_GCB_681_B.txt | | 12,001,615 | Aug. 13, 2004 |
| 723 | Table_0723_GCB_688_A.txt | | 12,228,824 | Aug. 16, 2004 |
| 724 | Table_0724_GCB_688_B.txt | | 11,984,738 | Aug. 13, 2004 |
| 725 | Table_0725_GCB_695_A.txt | | 12,239,383 | Aug. 13, 2004 |
| 726 | Table_0726_GCB_695_B.txt | | 12,064,067 | Aug. 13, 2004 |
| 727 | Table_0727_GCB_698_A.txt | | 12,041,776 | Aug. 13, 2004 |
| 728 | Table_0728_GCB_698_B.txt | | 11,913,341 | Aug. 13, 2004 |
| 729 | Table_0729_GCB_701_A.txt | | 12,052,305 | Aug. 13, 2004 |
| 730 | Table_0730_GCB_701_B.txt | | 11,822,784 | Aug. 12, 2004 |
| 731 | Table_0731_GCB_710_A.txt | | 12,150,765 | Aug. 13, 2004 |
| 732 | Table_0732_GCB_710_B.txt | | 11,950,813 | Aug. 12, 2004 |
| 733 | Table_0733_GCB_711_A.txt | | 12,132,273 | Aug. 12, 2004 |
| 734 | Table_0734_GCB_711_B.txt | | 11,858,885 | Aug. 13, 2004 |
| 735 | Table_0735_GCB_722_A.txt | | 12,154,845 | Aug. 13, 2004 |
| 736 | Table_0736_GCB_722_B.txt | | 11,985,108 | Aug. 13, 2004 |
| 737 | Table_0737_GCB_724_A.txt | | 12,146,329 | Aug. 12, 2004 |
| 738 | Table_0738_GCB_724_B.txt | | 11,887,755 | Aug. 13, 2004 |
| | | Disc 14 of 22 | | |
| 739 | Table_0739_GCB_731_A.txt | | 12,126,039 | Aug. 13, 2004 |
| 740 | Table_0740_GCB_731_B.txt | | 11,973,046 | Aug. 13, 2004 |
| 741 | Table_0741_GCB_742_A.txt | | 12,278,477 | Aug. 12, 2004 |
| 742 | Table_0742_GCB_742_B.txt | | 12,060,190 | Aug. 12, 2004 |
| 743 | Table_0743_GCB_744_A.txt | | 12,204,260 | Aug. 13, 2004 |
| 744 | Table_0744_GCB_744_B.txt | | 12,068,199 | Aug. 13, 2004 |
| 745 | Table_0745_GCB_745_A.txt | | 12,051,759 | Aug. 12, 2004 |
| 746 | Table_0746_GCB_745_B.txt | | 11,873,505 | Aug. 13, 2004 |
| 747 | Table_0747_GCB_747_A.txt | | 12,216,121 | Aug. 12, 2004 |
| 748 | Table_0748_GCB_747_B.txt | | 12,053,883 | Aug. 12, 2004 |
| 749 | Table_0749_GCB_749_A.txt | | 12,177,049 | Aug. 13, 2004 |
| 750 | Table_0750_GCB_749_B.txt | | 11,994,174 | Aug. 12, 2004 |
| 751 | Table_0751_GCB_758_A.txt | | 12,068,828 | Aug. 12, 2004 |
| 752 | Table_0752_GCB_758_B.txt | | 11,949,711 | Aug. 12, 2004 |
| 753 | Table_0753_GCB_772_A.txt | | 12,075,532 | Aug. 12, 2004 |
| 754 | Table_0754_GCB_772_B.txt | | 11,838,179 | Aug. 12, 2004 |
| 755 | Table_0755_GCB_777_A.txt | | 12,103,965 | Aug. 13, 2004 |
| 756 | Table_0756_GCB_777_B.txt | | 11,960,816 | Aug. 13, 2004 |
| 757 | Table_0757_GCB_792_A.txt | | 12,219,173 | Aug. 12, 2004 |
| 758 | Table_0758_GCB_792_B.txt | | 11,971,063 | Aug. 12, 2004 |
| 759 | Table_0759_GCB_795_A.txt | | 12,060,906 | Aug. 13, 2004 |
| 760 | Table_0760_GCB_795_B.txt | | 11,854,024 | Aug. 12, 2004 |
| 761 | Table_0761_GCB_797_A.txt | | 12,139,552 | Aug. 12, 2004 |
| 762 | Table_0762_GCB_797_B.txt | | 11,876,726 | Aug. 13, 2004 |
| 763 | Table_0763_GCB_803_A.txt | | 12,082,131 | Aug. 13, 2004 |
| 764 | Table_0764_GCB_803_B.txt | | 11,884,112 | Aug. 12, 2004 |
| 765 | Table_0765_GCB_810_A.txt | | 12,105,907 | Aug. 12, 2004 |
| 766 | Table_0766_GCB_810_B.txt | | 11,939,716 | Aug. 12, 2004 |
| 767 | Table_0767_GCB_817_A.txt | | 12,130,570 | Aug. 12, 2004 |
| 768 | Table_0768_GCB_817_B.txt | | 11,987,031 | Aug. 12, 2004 |
| 769 | Table_0769_GCB_818_A.txt | | 12,106,200 | Aug. 12, 2004 |
| 770 | Table_0770_GCB_818_B.txt | | 11,871,105 | Aug. 13, 2004 |
| 771 | Table_0771_GCB_819_A.txt | | 12,086,504 | Aug. 13, 2004 |
| 772 | Table_0772_GCB_819_B.txt | | 11,897,319 | Aug. 12, 2004 |
| 773 | Table_0773_GCB_821_A.txt | | 12,064,950 | Aug. 13, 2004 |

| | | | | |
|---|---|---|---|---|
| 774 | Table_0774_GCB_821_B.txt | | 11,958,861 | Aug. 12, 2004 |
| 775 | Table_0775_GCB_832_A.txt | | 12,068,809 | Aug. 12, 2004 |
| 776 | Table_0776_GCB_832_B.txt | | 11,964,104 | Aug. 13, 2004 |
| 777 | Table_0777_GCB_836_A.txt | | 12,171,469 | Aug. 13, 2004 |
| 778 | Table_0778_GCB_836_B.txt | | 11,996,845 | Aug. 13, 2004 |
| 779 | Table_0779_GCB_840_A.txt | | 12,038,865 | Aug. 12, 2004 |
| 780 | Table_0780_GCB_840_B.txt | | 11,799,648 | Aug. 12, 2004 |
| 781 | Table_0781_GCB_847_A.txt | | 12,084,291 | Aug. 13, 2004 |
| 782 | Table_0782_GCB_847_B.txt | | 11,950,648 | Aug. 13, 2004 |
| 783 | Table_0783_GCB_1005_A.txt | | 12,100,992 | Aug. 13, 2004 |
| 784 | Table_0784_GCB_1005_B.txt | | 11,961,124 | Aug. 12, 2004 |
| 785 | Table_0785_GCB_1008_A.txt | | 12,084,812 | Aug. 13, 2004 |
| 786 | Table_0786_GCB_1008_B.txt | | 11,995,015 | Aug. 13, 2004 |
| 787 | Table_0787_GCB_1009_A.txt | | 11,943,142 | Aug. 13, 2004 |
| 788 | Table_0788_GCB_1009_B.txt | | 11,924,190 | Aug. 13, 2004 |
| 789 | Table_0789_GCB_1021_A.txt | | 12,113,951 | Aug. 13, 2004 |
| 790 | Table_0790_GCB_1021_B.txt | | 11,934,678 | Aug. 13, 2004 |
| 791 | Table_0791_GCB_1025_A.txt | | 12,101,376 | Aug. 12, 2004 |
| 792 | Table_0792_GCB_1025_B.txt | | 12,034,295 | Aug. 12, 2004 |
| 793 | Table_0793_GCB_1026_A.txt | | 11,998,844 | Aug. 12, 2004 |
| 794 | Table_0794_GCB_1026_B.txt | | 11,924,830 | Aug. 13, 2004 |
| 795 | Table_0795_GCB_1037_A.txt | | 12,102,751 | Aug. 13, 2004 |
| 796 | Table_0796_GCB_1037_B.txt | | 12,033,344 | Aug. 12, 2004 |
| 797 | Table_0797_GCB_1039_A.txt | | 12,138,545 | Aug. 13, 2004 |
| 798 | Table_0798_GCB_1039_B.txt | | 11,995,022 | Aug. 13, 2004 |
| 799 | Table_0799_GCB_1049_A.txt | | 11,910,885 | Aug. 13, 2004 |
| | | Disc 15 of 22 | | |
| 800 | Table_0800_GCB_1049_B.txt | | 11,900,529 | Aug. 12, 2004 |
| 801 | Table_0801_GCB_1051_A.txt | | 12,096,658 | Aug. 12, 2004 |
| 802 | Table_0802_GCB_1051_B.txt | | 11,899,594 | Aug. 12, 2004 |
| 803 | Table_0803_GCB_1058_A.txt | | 12,014,086 | Aug. 12, 2004 |
| 804 | Table_0804_GCB_1058_B.txt | | 11,833,626 | Aug. 13, 2004 |
| 805 | Table_0805_GCB_1060_A.txt | | 12,148,321 | Aug. 13, 2004 |
| 806 | Table_0806_GCB_1060_B.txt | | 11,922,074 | Aug. 12, 2004 |
| 807 | Table_0807_GCB_1990_A.txt | | 12,081,238 | Aug. 12, 2004 |
| 808 | Table_0808_GCB_1990_B.txt | | 11,844,167 | Aug. 13, 2004 |
| 809 | Table_0809_GCB_1991_A.txt | | 12,099,680 | Aug. 12, 2004 |
| 810 | Table_0810_GCB_1991_B.txt | | 11,928,351 | Aug. 12, 2004 |
| 811 | Table_0811_GCB_2017_A.txt | | 12,118,675 | Aug. 13, 2004 |
| 812 | Table_0812_GCB_2017_B.txt | | 11,975,326 | Aug. 13, 2004 |
| 813 | Table_0813_GCB_2018_A.txt | | 11,925,112 | Aug. 12, 2004 |
| 814 | Table_0814_GCB_2018_B.txt | | 11,835,888 | Aug. 13, 2004 |
| 815 | Table_0815_GCB_2095_A.txt | | 11,853,266 | Aug. 12, 2004 |
| 816 | Table_0816_GCB_2095_B.txt | | 11,623,773 | Aug. 12, 2004 |
| 817 | Table_0817_GCB_880_A.txt | | 12,152,952 | Aug. 13, 2004 |
| 818 | Table_0818_GCB_860_B.txt | | 12,010,773 | Aug. 13, 2004 |
| 819 | Table_0819_GCB_871_A.txt | | 12,244,981 | Aug. 13, 2004 |
| 820 | Table_0820_GCB_871_B.txt | | 12,006,799 | Aug. 12, 2004 |
| 821 | Table_0821_GCB_874_A.txt | | 12,105,710 | Aug. 13, 2004 |
| 822 | Table_0822_GCB_874_B.txt | | 11,844,703 | Aug. 13, 2004 |
| 823 | Table_0823_GCB_995_A.txt | | 12,155,927 | Aug. 12, 2004 |
| 824 | Table_0824_GCB_995_B.txt | | 11,924,018 | Aug. 13, 2004 |
| 825 | Table_0825_LPC_2224_A.txt | | 12,213,302 | Aug. 12, 2004 |
| 826 | Table_0826_LPC_2224_B.txt | | 12,044,437 | Aug. 13, 2004 |
| 827 | Table_0827_LPC_2232_A.txt | | 12,166,888 | Aug. 12, 2004 |
| 828 | Table_0828_LPC_2232_B.txt | | 12,125,903 | Aug. 12, 2004 |
| 829 | Table_0829_LPC_2261_A.txt | | 12,228,399 | Aug. 13, 2004 |
| 830 | Table_0830_LPC_2261_B.txt | | 12,102,498 | Aug. 12, 2604 |
| 831 | Table_0831_LPC_2262_A.txt | | 12,312,435 | Aug. 13, 2004 |
| 832 | Table_0832_LPC_2262_B.txt | | 12,152,420 | Aug. 12, 2004 |
| 833 | Table_0833_LPC_2263_A.txt | | 12,224,752 | Aug. 12, 2004 |
| 834 | Table_0834_LPC_2263_B.txt | | 12,026,718 | Aug. 12, 2004 |
| 835 | Table_0835_LPC_2265_A.txt | | 12,285,962 | Aug. 12, 2004 |
| 836 | Table_0836_LPC_2265_B.txt | | 12,154,010 | Aug. 12, 2004 |
| 837 | Table_0837_Lymbl_2185_A.txt | | 12,108,958 | Aug. 12, 2004 |
| 838 | Table_0838_Lymbl_2185_B.txt | | 11,820,956 | Aug. 12, 2004 |
| 839 | Table_0839_Lymbl_2186_A.txt | | 12,308,145 | Aug. 12, 2004 |
| 840 | Table_0840_Lymbl_2186_B.txt | | 11,977,289 | Aug. 12, 2004 |
| 841 | Table_0841_Lymbl_2249_A.txt | | 12,199,046 | Aug. 12, 2004 |
| 842 | Table_0842_Lymbl_2249_B.txt | | 12,100,855 | Aug. 12, 2004 |
| 843 | Table_0843_MALT_gastric_2021_A.txt | | 12,069,340 | Aug. 12, 2004 |
| 844 | Table_0844_MALT_gastric_2021_B.txt | | 11,713,090 | Aug. 12, 2004 |
| 845 | Table_0845_MALT_gastric_2041_A.txt | | 12,022,811 | Aug. 12, 2004 |
| 846 | Table_0846_MALT_gastric_2041_B.txt | | 11,764,218 | Aug. 12, 2004 |
| 847 | Table_0847_MALT_gastric_2065_A.txt | | 12,078,944 | Aug. 12, 2004 |
| 848 | Table_0848_MALT_gastric_2065_B.txt | | 11,791,876 | Aug. 12, 2004 |
| 849 | Table_0849_MALT_gastric_2067_A.txt | | 12,202,669 | Aug. 12, 2004 |
| 850 | Table_0850_MALT_gastric_2067_B.txt | | 11,926,251 | Aug. 12, 2004 |

-continued

| | | | |
|---|---|---|---|
| 851 | Table_0851_MALT_gastric_2070_A.txt | 11,759,597 | Aug. 12, 2004 |
| 852 | Table_0852_MALT_gastric_2070_B.txt | 11,923,213 | Aug. 12, 2004 |
| 853 | Table_0853_MALT_gastric_2110_A.txt | 11,989,061 | Aug. 12, 2004 |
| 854 | Table_0854_MALT_gastric_2110_B.txt | 11,861,974 | Aug. 12, 2004 |
| 855 | Table_0855_MALT_gastric_2111_A.txt | 11,875,847 | Aug. 12, 2004 |
| 856 | Table_0856_MALT_gastric_2111_B.txt | 11,771,686 | Aug. 12, 2004 |
| 857 | Table_0857_MALT_gastric_2112_A.txt | 11,987,235 | Aug. 12, 2004 |
| 858 | Table_0858_MALT_gastric_2112_B.txt | 11,789,775 | Aug. 12, 2004 |
| 859 | Table_0859_MALT_gastric_2270_A.txt | 12,163,208 | Aug. 12, 2004 |
| 860 | Table_0860_MALT_gastric_2270_B.txt | 11,933,606 | Aug. 12, 2004 |
| | Disc 16 of 22 | | |
| 861 | Table_0861_MALT_lung_2202_A.txt | 12,272,098 | Aug. 12, 2004 |
| 862 | Table_0862_MALT_lung_2202_B.txt | 12,060,494 | Aug. 12, 2004 |
| 863 | Table_0863_MALT_salivary_2243_A.txt | 12,192,735 | Aug. 12, 2004 |
| 864 | Table_0864_MALT_salivary_2243_B.txt | 11,939,205 | Aug. 12, 2004 |
| 865 | Table_0865_MALT_tonsil_2211_A.txt | 12,292,687 | Aug. 12, 2004 |
| 866 | Table_0866_MALT_tonsil_2211_B.txt | 12,028,847 | Aug. 12, 2004 |
| 867 | Table_0867_MALT_unk_2178_A.txt | 12,272,896 | Aug. 12, 2004 |
| 868 | Table_0868_MALT_unk_2178_B.txt | 11,942,813 | Aug. 12, 2004 |
| 869 | Table_0869_MALT_unk_2182_A.txt | 12,152,087 | Aug. 12, 2004 |
| 870 | Table_0870_MALT_unk_2182_B.txt | 11,862,788 | Aug. 12, 2004 |
| 871 | Table_0871_MALT_unk_2183_A.txt | 12,240,465 | Aug. 12, 2004 |
| 872 | Table_0872_MALT_unk_2183_B.txt | 11,910,769 | Aug. 12, 2004 |
| 873 | Taable_0873_MALT_unk_2184_A.txt | 12,131,543 | Aug. 12, 2004 |
| 874 | Table_0874_MALT_unk_2184_A.txt | 11,790,493 | Aug. 12, 2004 |
| 875 | Table_0875_MCL_1012_A.txt | 12,095,014 | Aug. 12, 2004 |
| 876 | Table_0876_MCL_1012_B.txt | 12,009,170 | Aug. 12, 2004 |
| 877 | Table_0877_MCL_885_A.txt | 12,252,079 | Aug. 13, 2004 |
| 878 | Table_0878_MCL_885_B.txt | 12,003,985 | Aug. 12, 2004 |
| 879 | Table_0879_MCL_918_A.txt | 12,067,434 | Aug. 12, 2004 |
| 880 | Table_0880_MCL_918_B.txt | 11,913,221 | Aug. 13, 2004 |
| 881 | Table_0881_MCL_924_A.txt | 12,132,102 | Aug. 12, 2004 |
| 882 | Table_0882_MCL_924_B.txt | 11,963,278 | Aug. 12, 2004 |
| 883 | Table_0883_MCL_925_A.txt | 12,192,477 | Aug. 13, 2004 |
| 884 | Table_0884_MCL_925_B.txt | 11,969,040 | Aug. 13, 2004 |
| 885 | Table_0885_MCL_926_A.txt | 12,235,529 | Aug. 13, 2004 |
| 886 | Table_0886_MCL_926_B.txt | 12,047,299 | Aug. 13, 2004 |
| 887 | Table_0887_MCL_936_A.txt | 12,241,467 | Aug. 13, 2004 |
| 888 | Table_0888_MCL_936_B.txt | 12,045,327 | Aug. 13, 2004 |
| 889 | Table_0889_MCL_939_A.txt | 12,202,107 | Aug. 13, 2004 |
| 890 | Table_0890_MCL_939_B.txt | 11,958,874 | Aug. 12, 2004 |
| 891 | Table_0891_MCL_953_A.txt | 11,892,010 | Aug. 12, 2004 |
| 892 | Table_0892_MCL_953_B.txt | 11,760,154 | Aug. 13, 2004 |
| 893 | Table_0893_MCL_956_A.txt | 12,251,157 | Aug. 13, 2004 |
| 894 | Tabte_0894_MCL_956_B.txt | 12,111,836 | Aug. 12, 2004 |
| 895 | Table_0895_MCL_964_A.txt | 12,275,186 | Aug. 13, 2004 |
| 898 | Table_0896_MCL_964_B.txt | 12,133,152 | Aug. 12, 2004 |
| 897 | Table_0897_MCL_966_A.txt | 12,259,135 | Aug. 12, 2004 |
| 898 | Table_0898_MCL_966_B.txt | 12,024,326 | Aug. 12, 2004 |
| 899 | Table_0899_MCL_968_A.txt | 12,155,882 | Aug. 13, 2004 |
| 900 | Table_0900_MCL_968_B.txt | 11,994,843 | Aug. 13, 2004 |
| 901 | Table_0901_MCL_970_A.txt | 12,088,529 | Aug. 13, 2004 |
| 902 | Table_0902_MCL_970_B.txt | 11,954,394 | Aug. 13, 2004 |
| 903 | Table_0903_MCL_1091_A.txt | 12,094,827 | Aug. 13, 2004 |
| 904 | Table_0904_MCL_1091_B.txt | 11,874,993 | Aug. 13, 2004 |
| 905 | Table_0905_MCL_1114_A.txt | 12,245,076 | Aug. 13, 2004 |
| 906 | Table_0906_MCL_1114_B.txt | 12,198,851 | Aug. 13, 2004 |
| 907 | Table_0907_MCL_1128_A.txt | 12,001,197 | Aug. 13, 2004 |
| 908 | Table_0908_MCL_1128_B.txt | 11,988,339 | Aug. 12, 2004 |
| 909 | Table_0909_MCL_1150_A.txt | 12,152,268 | Aug. 13, 2004 |
| 910 | Table_0910_MCL_1150_B.txt | 11,985,382 | Aug. 13, 2004 |
| 911 | Table_0911_MCL_1162_A.txt | 12,052,700 | Aug. 13, 2004 |
| 912 | Table_0912_MCL_1162_B.txt | 11,813,424 | Aug. 13, 2004 |
| 913 | Table_0913_MCL_1166_A.txt | 12,154,210 | Aug. 12, 2004 |
| 914 | Table_0914_MCL_1166_B.txt | 11,978,362 | Aug. 12, 2004 |
| 915 | Table_1915_MCL_1194_A.txt | 12,219,860 | Aug. 12, 2004 |
| 916 | Table_0916_MCL_1194_B.txt | 11,956,615 | Aug. 12, 2004 |
| 917 | Table_0917_Mult_Myeloma_H1112_100001_A.txt | 11,811,143 | Aug. 12, 2004 |
| 918 | Table_0918_Mult_Myeloma_H1112_100001_B.txt | 1,607,110 | Aug. 12, 2004 |
| 919 | Table_0919_Mult_Myeloma_HDLM2_100002_A.txt | 12,201,407 | Aug. 12, 2004 |
| 920 | Table_0920_Mult_Myeloma_HDLM2_100002_B.txt | 12,064,162 | Aug. 12, 2004 |
| 921 | Table_0921_Mult_Myeloma_JIM3_100003_A.txt | 12,018,803 | Aug. 12, 2004 |
| | Disc 17 of 22 | | |
| 922 | Table_0922_Mult_Myeloma_JJM3_100003_B.txt | 11,829,274 | Aug. 12, 2004 |
| 923 | Table_0923_Mult_Myeloma_JJN3_100004_A.txt | 11,938,479 | Aug. 12, 2004 |
| 924 | Table_0924_Mult_Myeloma_JJN3_100004_B.txt | 11,783,677 | Aug. 12, 2004 |
| 925 | Table_0925_Mult_Myeloma_KMS11_100005_A.txt | 12,049,424 | Aug. 12, 2004 |

-continued

| | | | | |
|---|---|---|---|---|
| 926 | Table_0926_Mult_Myeloma_KMS11_100005_B.txt | | 11,830,659 | Aug. 12, 2004 |
| 927 | Table_0927_Mult_Myeloma_KMS12_100008_A.txt | | 11,987,299 | Aug. 12, 2004 |
| 928 | Table_0928_Mult_Myeloma_KMS12_100006_B.txt | | 11,843,592 | Aug. 12, 2004 |
| 929 | Table_0929_Mult_Myeloma_LB84_100007_A.txt | | 12,013,517 | Aug. 12, 2004 |
| 930 | Table_0930_Mult_Myeloma_LB84_100007_B.txt | | 11,779,980 | Aug. 12, 2004 |
| 931 | Table_0931_Mult_Myeloma_LP1_100008_A.txt | | 11,881,584 | Aug. 12, 2004 |
| 932 | Table_0932_Mult_Myeloma_LP1_100008_B.txt | | 11,697,789 | Aug. 12, 2004 |
| 933 | Table_0933_Mult_Myeloma_U266_100009_A.txt | | 11,911,589 | Aug. 12, 2004 |
| 934 | Table_0934_Mult_Myeloma_U266_100009_B.txt | | 11,746,068 | Aug. 12, 2004 |
| 935 | Table_0935_NMZ_2231_A.txt | | 12,102,948 | Aug. 12, 2004 |
| 936 | Table_0936_NMZ_2231_B.txt | | 11,924,657 | Aug. 13, 2004 |
| 937 | Table_0937_NMZ_2242_A.txt | | 12,155,728 | Aug. 13, 2004 |
| 938 | Table_0938_NMZ_2242_B.txt | | 11,868,614 | Aug. 12, 2004 |
| 939 | Table_0939_NMZ_2254_A.txt | | 12,192,220 | Aug. 12, 2004 |
| 940 | Table_0940_NMZ_2254_B.txt | | 11,993,870 | Aug. 13, 2004 |
| 941 | Table_0941_PMBL_484_A.txt | | 12,082,526 | Aug. 12, 2004 |
| 942 | Table_0942_PMBL_484_B.txt | | 11,815,878 | Aug. 12, 2004 |
| 943 | Table_0943_PMBL_546_A.txt | | 12,246,074 | Aug. 12, 2004 |
| 944 | Table_0944_PMBL_546_B.txt | | 12,018,016 | Aug. 13, 2004 |
| 945 | Table_0945_PMBL_570_A.txt | | 12,022,732 | Aug. 13, 2004 |
| 946 | Table_0946_PMBL_570_B.txt | | 11,987,920 | Aug. 12, 2004 |
| 947 | Table_0947_PMBL_621_A.txt | | 12,274,976 | Aug. 13, 2004 |
| 948 | Table_0948_PMBL_621_B.txt | | 11,990,316 | Aug. 12, 2004 |
| 949 | Table_0949_PMBL_638_A.txt | | 12,127,006 | Aug. 12, 2004 |
| 950 | Table_0950_PMBL_638_B.txt | | 11,914,175 | Aug. 13, 2004 |
| 951 | Table_0951_PMBL_691_A.txt | | 12,212,873 | Aug. 13, 2004 |
| 952 | Table_0952_PMBL_691_B.txt | | 11,914,318 | Aug. 12, 2004 |
| 953 | Table_0953_PMBL_791_A.txt | | 12,097,450 | Aug. 13, 2004 |
| 954 | Table_0954_PMBL_791_B.txt | | 11,992,010 | Aug. 13, 2004 |
| 955 | Table_0955_PMBL_824_A.txt | | 12,088,222 | Aug. 12, 2004 |
| 956 | Table_0956_PMBL_824_B.txt | | 11,955,158 | Aug. 12, 2004 |
| 957 | Table_0957_PMBL_906_A.txt | | 12,132,964 | Aug. 13, 2004 |
| 958 | Table_0958_PMBL_906_B.txt | | 11,995,056 | Aug. 12, 2004 |
| 959 | Table_0959_PMBL_994_A.txt | | 12,174,956 | Aug. 13, 2004 |
| 960 | Table_0960_PMBL_994_B.txt | | 11,819,415 | Aug. 12, 2004 |
| 961 | Table_0961_PMBL_998_A.txt | | 12,084,009 | Aug. 13, 2004 |
| 962 | Table_0962_PMBL_998_B.txt | | 11,893,733 | Aug. 12, 2004 |
| 963 | Table_0963_PMBL_1006_A.txt | | 12,028,424 | Aug. 10, 2004 |
| 964 | Table_0964_PMBL_1006_B.txt | | 11,935,369 | Aug. 10, 2004 |
| 965 | Table_0965_PMBL_1024_A.txt | | 11,957,270 | Aug. 10, 2004 |
| 966 | Table_0966_PMBL_1024_B.txt | | 11,764,809 | Aug. 10, 2004 |
| 967 | Table_0967_PMBL_1048_A.txt | | 11,897,468 | Aug. 10, 2004 |
| 968 | Table_0968_PMBL_1048_B.txt | | 11,883,251 | Aug. 10, 2004 |
| 969 | Table_0969_PMBL_1053_A.txt | | 11,875,959 | Aug. 10, 2004 |
| 970 | Table_0970_PMBL_1053_B.txt | | 11,710,774 | Aug. 10, 2004 |
| 971 | Table_0971_PMBL_1920_A.txt | | 12,226,172 | Aug. 10, 2004 |
| 972 | Table_0972_PMBL_1920_B.txt | | 12,193,948 | Aug. 10, 2004 |
| 973 | Table_0973_PMBL_1921_A.txt | | 12,143,375 | Aug. 10, 2004 |
| 974 | Table_0974_PMBL_1921_B.txt | | 11,908,102 | Aug. 10, 2004 |
| 975 | Table_0975_PMBL_1923_A.txt | | 12,198,159 | Aug. 10, 2004 |
| 976 | Table_0976_PMBL_1923_B.txt | | 11,946,971 | Aug. 10, 2004 |
| 977 | Table_0977_PMBL_1924_A.txt | | 12,122,855 | Aug. 10, 2004 |
| 978 | Table_0978_PMBL_1924_B.txt | | 11,890,275 | Aug. 10, 2004 |
| 979 | Table_0979_PMBL_1935_A.txt | | 12,068,019 | Aug. 10, 2004 |
| 980 | Table_0980_PMBL_1935_B.txt | | 11,985,509 | Aug. 10, 2004 |
| 981 | Table_0981_PMBL_1941_A.txt | | 12,119,223 | Aug. 10, 2004 |
| 982 | Table_0982_PMBL_1941_B.txt | | 11,930,039 | Aug. 10, 2004 |
| | | Disc 18 of 22 | | |
| 983 | Table_0983_PMBL_1942_A.txt | | 12,067,442 | Aug. 10, 2004 |
| 984 | Table_0984_PMBL_1942_B.txt | | 11,920,274 | Aug. 10, 2004 |
| 985 | Table_0985_PMBL_1943_A.txt | | 12,071,233 | Aug. 10, 2004 |
| 986 | Table_0986_PMBL_1943_B.txt | | 11,873,515 | Aug. 10, 2004 |
| 987 | Table_0987_PMBL_1945_A.txt | | 12,127,286 | Aug. 10, 2004 |
| 988 | Table_0988_PMBL_1945_B.txt | | 11,893,206 | Aug. 10, 2004 |
| 989 | Table_0989_PMBL_1948_A.txt | | 12,166,081 | Aug. 10, 2004 |
| 990 | Table_0990_PMBL_1948_B.txt | | 11,844,013 | Aug. 10, 2004 |
| 991 | Table_0991_PMBL_1949_A.txt | | 12,127,499 | Aug. 10, 2004 |
| 992 | Table_0992_PMBL_1949_B.txt | | 12,009,898 | Aug. 10, 2004 |
| 993 | Table_0993_PMBL_1989_A.txt | | 11,979,711 | Aug. 10, 2004 |
| 994 | Table_0994_PMBL_1989_B.txt | | 11,831,156 | Aug. 10, 2004 |
| 995 | Table_0995_PMBL_1992_A.txt | | 11,982,288 | Aug. 10, 2004 |
| 996 | Table_0996_PMBL_1992_B.txt | | 11,805,053 | Aug. 10, 2004 |
| 997 | Table_0997_PMBL_1993_A.txt | | 11,965,853 | Aug. 10, 2004 |
| 998 | Table_0998_PMBL_1993_B.txt | | 11,781,282 | Aug. 10, 2004 |
| 999 | Table_0999_PMBL_2002_A.txt | | 12,145,467 | Aug. 10, 2004 |
| 1000 | Table_1000_PMBL_2002_B.txt | | 11,908,468 | Aug. 10, 2004 |
| 1001 | Table_1001_PMBL_2019_A.txt | | 12,060,714 | Aug. 10, 2004 |
| 1002 | Table_1002_PMBL_2019_B.txt | | 11,835,919 | Aug. 10, 2004 |

-continued

| | | | | |
|---|---|---|---|---|
| 1003 | Table_1003_PMBL_2020_A.txt | | 11,923,777 | Aug. 10, 2004 |
| 1004 | Table_1004_PMBL_2020_B.txt | | 11,763,296 | Aug. 10, 2004 |
| 1005 | Table_1005_PMBL_2092_A.txt | | 11,790,019 | Aug. 10, 2004 |
| 1006 | Table_1006_PMBL_2092_B.txt | | 11,681,328 | Aug. 10, 2004 |
| 1007 | Table_1007_PTLD_1817_A.txt | | 11,963,639 | Aug. 10, 2004 |
| 1008 | Table_1008_PTLD_1817_B.txt | | 11,841,407 | Aug. 10, 2004 |
| 1009 | Table_1009_PTLD_1824_A.txt | | 11,948,464 | Aug. 10, 2004 |
| 1010 | Table_1010_PTLD_1824_B.txt | | 11,908,800 | Aug. 10, 2004 |
| 1011 | Table_1011_PTLD_1981_A.txt | | 12,117,957 | Aug. 10, 2004 |
| 1012 | Table_1012_PTLD_1981_B.txt | | 11,889,503 | Aug. 10, 2004 |
| 1013 | Table_1013_PTLD_1986_A.txt | | 12,190,747 | Aug. 10, 2004 |
| 1014 | Table_1014_PTLD_1986_B.txt | | 11,999,062 | Aug. 10, 2004 |
| 1015 | Table_1015_SLL_1151_A.txt | | 12,137,203 | Aug. 10, 2004 |
| 1016 | Table_1016_SLL_1151_B.txt | | 12,068,815 | Aug. 10, 2004 |
| 1017 | Table_1017_SLL_1153_A.txt | | 12,167,324 | Aug. 10, 2004 |
| 1018 | Table_1018_SLL_1153_B.txt | | 11,973,110 | Aug. 10, 2004 |
| 1019 | Table_1019_SLL_1155_A.txt | | 12,014,085 | Aug. 10, 2004 |
| 1020 | Table_1020_SLL_1155_B.txt | | 11,972,994 | Aug. 10, 2004 |
| 1021 | Table_1021_SLL_1156_A.txt | | 12,049,347 | Aug. 10, 2004 |
| 1022 | Table_1022_SLL_1156_B.txt | | 12,067,063 | Aug. 10, 2004 |
| 1023 | Table_1023_SLL_1158_A.txt | | 12,133,241 | Aug. 13, 2004 |
| 1024 | Table_1024_SLL_1158_B.txt | | 11,956,872 | Aug. 13, 2004 |
| 1025 | Table_1025_SLL_1213_A.txt | | 12,143,857 | Aug. 13, 2004 |
| 1026 | Table_1026_SLL_1213_B.txt | | 12,011,763 | Aug. 13, 2004 |
| 1027 | Table_1027_SLL_1214_A.txt | | 12,045,032 | Aug. 13, 2004 |
| 1028 | Table_1028_SLL_1214_B.txt | | 12,031,831 | Aug. 13, 2004 |
| 1029 | Table_1029_SLL_1216_A.txt | | 11,833,813 | Aug. 13, 2004 |
| 1030 | Table_1030_SLL_1216_B.txt | | 11,772,139 | Aug. 13, 2004 |
| 1031 | Table_1031_SLL_1217_A.txt | | 12,094,981 | Aug. 12, 2004 |
| 1032 | Table_1032_SLL_1217_B.txt | | 11,937,188 | Aug. 12, 2004 |
| 1033 | Table_1033_SLL_1218_A.txt | | 11,940,236 | Aug. 13, 2004 |
| 1034 | Table_1034_SLL_1218_B.txt | | 11,959,292 | Aug. 13, 2004 |
| 1035 | Table_1035_SLL_1220_A.txt | | 12,120,053 | Aug. 13, 2004 |
| 1036 | Table_1036_SLL_1220_B.txt | | 12,048,618 | Aug. 13, 2004 |
| 1037 | Table_1037_SLL_1229_A.txt | | 12,163,710 | Aug. 13, 2004 |
| | | Disc 19 of 22 | | |
| 1038 | Table_1038_SLL_1229_B.txt | | 12,055,954 | Aug. 13, 2004 |
| 1039 | Table_1039_SLL_1231_A.txt | | 12,991,514 | Aug. 12, 2004 |
| 1040 | Table_1040_SLL_1231_B.txt | | 12,005,235 | Aug. 13, 2004 |
| 1041 | Table_1041_SLL_1235_A.txt | | 12,080,267 | Aug. 13, 2904 |
| 1042 | Table_1042_SLL_1235_B.txt | | 11,994,892 | Aug. 12, 2004 |
| 1043 | Table_1043_SLL_1236_A.txt | | 12,084,789 | Aug. 13, 2004 |
| 1044 | Table_1044_SLL_1236_B.txt | | 12,026,667 | Aug. 13, 2004 |
| 1045 | Table_1045_SLL_1238_A.txt | | 12,082,819 | Aug. 12, 2004 |
| 1046 | Table_1046_SLL_1238_B.txt | | 11,974,701 | Aug. 13, 2004 |
| 1047 | Table_1047_SLL_1240_A.txt | | 12,107,426 | Aug. 13, 2004 |
| 1048 | Table_1048_SLL_1240_B.txt | | 12,007,704 | Aug. 12, 2004 |
| 1049 | Table_1049_SPLENIC_2061_A.txt | | 12,008,092 | Aug. 12, 2004 |
| 1050 | Table_1050_SPLENIC_2061_B.txt | | 11,899,642 | Aug. 12, 2004 |
| 1051 | Table_1051_SPLENIC_2074_A.txt | | 11,955,622 | Aug. 12, 2004 |
| 1052 | Table_1052_SPLENIC_2074_B.txt | | 11,890,462 | Aug. 12, 2004 |
| 1053 | Table_1053_SPLENIC_2075_A.txt | | 11,810,049 | Aug. 12, 2004 |
| 1954 | Table_1054_SPLENIC_2075_B.txt | | 11,772,595 | Aug. 12, 2004 |
| 1055 | Table_1055_SPLENIC_2077_A.txt | | 12,051,083 | Aug. 12, 2004 |
| 1056 | Table_1056_SPLENIC_2077_B.txt | | 11,816,491 | Aug. 12, 2004 |
| 1057 | Table_1057_SPLENIC_2079_A.txt | | 12,028,337 | Aug. 13, 2004 |
| 1058 | Table_1058_SPLENIC_2079_B.txt | | 11,666,448 | Aug. 12, 2004 |
| 1059 | Table_1059_SPLENIC_2104_A.txt | | 11,964,762 | Aug. 12, 2004 |
| 1060 | Table_1060_SPLENIC_2104_B.txt | | 11,883,377 | Aug. 12, 2004 |
| 1061 | Table_1061_SPLENIC_2105_A.txt | | 12,027,922 | Aug. 13, 2004 |
| 1062 | Table_1062_SPLENIC_2105_B.txt | | 11,816,300 | Aug. 12, 2004 |
| 1063 | Table_1063_SPLENIC_2106_A.txt | | 11,927,458 | Aug. 12, 2004 |
| 1064 | Table_1064_SPLENIC_2106_B.txt | | 11,707,237 | Aug. 13, 2004 |
| 1065 | Table_1065_SPLENIC_2256_A.txt | | 12,134,849 | Aug. 12, 2004 |
| 1066 | Table_1066_SPLENIC_2256_B.txt | | 12,000,432 | Aug. 12 2004 |
| 1067 | Table_1067_SPLENIC_2257_A.txt | | 12,095,918 | Aug. 12, 2004 |
| 1068 | Table_1088_SPLENIC_2257_B.txt | | 11,860,498 | Aug. 12, 2004 |
| 1069 | Table_1069_SPLENIC_2258_A.txt | | 12,173,033 | Aug. 12, 2004 |
| 1070 | Table_1070_SPLENIC_2258_B.txt | | 12,097,740 | Aug. 13, 2004 |
| 1071 | Table_1071_SPLENIC_2259_A.txt | | 12,070,761 | Aug. 12, 2004 |
| 1072 | Table_1072_SPLENIC_2259_B.txt | | 11,905,682 | Aug. 12, 2004 |
| 1073 | Table_1073_SPLENIC_2260_A.txt | | 12,218,038 | Aug. 12, 2004 |
| 1074 | Table_1074_SPLENIC_2260_B.txt | | 11,987,269 | Aug. 13, 2004 |
| 1075 | Table_1075_UC_DLBCL_306_A.txt | | 12,197,523 | Aug. 13, 2004 |
| 1076 | Table_1076_UC_DLBCL_306_B.txt | | 12,022,523 | Aug. 13, 2004 |
| 1077 | Table_1077_UC_DLBCL_310_A.txt | | 12,200,397 | Aug. 12, 2004 |
| 1078 | Table_1078_UC_DLBCL_310_B.txt | | 12,031,998 | Aug. 12, 2004 |
| 1079 | Table_1079_UC_DLBCL_449_A.txt | | 12,190,478 | Aug. 12, 2004 |

-continued

| | | | | |
|---|---|---|---|---|
| 1080 | Table_1080_UC_DLBCL_449_B.txt | | 11,975,216 | Aug. 12, 2004 |
| 1081 | Table_1081_UC_DLBCL_452_A.txt | | 12,131,303 | Aug. 12, 2004 |
| 1082 | Table_1082_UC_DLBCL_452_B.txt | | 11,894,8Z0 | Aug. 13, 2004 |
| 1083 | Table_1083_UC_DLBCL_1001_A.txt | | 12,196,485 | Aug. 13, 2004 |
| 1084 | Table_1084_UC_DLBCL_1001_B.txt | | 11,918,908 | Aug. 13, 2004 |
| 1085 | Table_1085_UC_DLBCL_1004_A.txt | | 12,085,125 | Aug. 12, 2004 |
| 1086 | Table_1086_UC_DLBCL_1004_B.txt | | 11,976,628 | Aug. 13, 2004 |
| 1087 | Table_1087_UC_DLBCL_1007_A.txt | | 12,008,629 | Aug. 13, 2004 |
| 1088 | Table_1088_UC_DLBCL_1007_B.txt | | 11,894,817 | Aug. 12, 2004 |
| 1089 | Table_1089_UC_DLBCL_1018_A.txt | | 11,978,212 | Aug. 12, 2004 |
| 1090 | Table_1090_UC_DLBCL_1018_B.txt | | 11,779,082 | Aug. 12, 2004 |
| 1091 | Table_1091_UC_DLBCL_1041_A.txt | | 12,075,817 | Aug. 12, 2004 |
| 1092 | Table_1092_UC_DLBCL_1041_B.txt | | 11,954,441 | Aug. 13, 2004 |
| 1093 | Table_1093_UC_DLBCL_1054_A.txt | | 12,072,956 | Aug. 13, 2004 |
| 1094 | Table_1094_UC_DLBCL_1054_B.txt | | 11,888,591 | Aug. 12, 2004 |
| 1095 | Table_1095_UC_DLBCL_1946_A.txt | | 12,146,234 | Aug. 12, 2004 |
| 1096 | Table_1096_UC_DLBCL_1946_B.txt | | 11,972,987 | Aug. 13, 2004 |
| 1097 | Table_1097_UC_DLBCL_458_A.txt | | 12,259,814 | Aug. 12, 2004 |
| 1098 | Table_1098_UC_DLBCL_458_B.txt | | 12,079,665 | Aug. 12, 2004 |
| | | Disc 20 of 22 | | |
| 1099 | Table_1099_UC_DLBCL_460_A.txt | | 12,291,473 | Aug. 12, 2004 |
| 1100 | Table_1100_UC_DLBCL_460_B.txt | | 12,152,157 | Aug. 12, 2004 |
| 1101 | Table_1101_UC_DLBCL_491_A.txt | | 12,1Z7,657 | Aug. 12, 2004 |
| 1102 | Table_1102_UC_DLBCL_491_B.txt | | 11,939,054 | Aug. 12, 2004 |
| 1103 | Table_1103_UC_DLCBL_528_A.txt | | 12,222,657 | Aug. 12, 2004 |
| 1104 | Table_1104_UC_DLCBL_528_B.txt | | 12,030,161 | Aug. 12, 2004 |
| 1105 | Table_1105_UC_DLCBL_615_A.txt | | 12,093,006 | Aug. 12, 2004 |
| 1106 | Table_l106_UC_DLCBL_615_B.txt | | 11,905,401 | Aug. 12, 2004 |
| 1107 | Table_1107_UC_DLCBL_625_A.txt | | 12,182,746 | Aug. 12, 2004 |
| 1108 | Table_1108_UC_DLCBL_625_B.txt | | 11,978,584 | Aug. 12, 2004 |
| 1109 | Table_1109_UC_DLCBL_664_A.txt | | 12,147,340 | Aug. 12, 2004 |
| 1110 | Table_1110_UC_DLCBL_664_B.txt | | 11,921,611 | Aug. 12, 2004 |
| 1111 | Table_1111_UC_DLCBL_671_A.txt | | 12,235,865 | Aug. 12, 2004 |
| 1112 | Table_1112_UC_DLCBL_671_B.txt | | 12,025,944 | Aug. 12, 2004 |
| 1113 | Table_1113_UC_DLCBL_682_A.txt | | 12,139,932 | Aug. 12, 2004 |
| 1114 | Table_1114_UC_DLCBL_682_B.txt | | 11,999,845 | Aug. 12, 2004 |
| 1115 | Table_1115_UC_DLCBL_683_A.txt | | 12,159,705 | Aug. 12, 2004 |
| 1116 | Table_1116_UC_DLCBL_683_B.txt | | 11,904,634 | Aug. 12, 2004 |
| 1117 | Table_1117_UC_DLCBL_684_A.txt | | 12,172,978 | Aug. 12, 2004 |
| 1118 | Table_1118_UC_DLCBL_684_B.txt | | 11,926,785 | Aug. 12, 2004 |
| 1119 | Table_1119_UC_DLCBL_748_A.txt | | 12,035,936 | Aug. 12, 2004 |
| 1120 | Table_1120_UC_DLCBL_748_B.txt | | 11,907,789 | Aug. 12, 2004 |
| 1121 | Table_1707_UC_DLCBL_751_A.txt | | 12,044,311 | Aug. 12, 2004 |
| 1122 | Table_1708_UC_DLCBL_751_B.txt | | 11,684,690 | Aug. 12, 2004 |
| 1123 | Table_1709_UC_DLCBL_808_A.txt | | 12,173,769 | Aug. 12, 2004 |
| 1124 | Table_1710_UC_DLCBL_808_B.txt | | 11,894,695 | Aug. 12, 2004 |
| 1125 | Table_1711_UC_DLCBL_831_A.txt | | 12,093,914 | Aug. 12, 2004 |
| 1126 | Table_1712_UC_DLCBL_831_B.txt | | 11,864,674 | Aug. 12, 2004 |
| 1127 | Table_1713_UC_DLCBL_834_A.txt | | 12,104,086 | Aug. 12, 2004 |
| 1128 | Table_1714_UC_DLCBL_834_B.txt | | 11,923,742 | Aug. 12, 2004 |
| 1129 | Table_1715_UC_DLCBL_838_A.txt | | 12,098,316 | Aug. 12, 2004 |
| 1130 | Table_1716_UC_DLCBL_838_B.txt | | 11,966,988 | Aug. 12, 2004 |
| 1131 | Table_1717_UC_DLCBL_851_A.txt | | 12,228,013 | Aug. 12, 2004 |
| 1132 | Table_1718_UC_DLCBL_851_B.txt | | 12,052,993 | Aug. 12, 2004 |
| 1133 | Table_1719_UC_DLCBL_854_A.txt | | 12,265,143 | Aug. 12, 2004 |
| 1134 | Table_1720_UC_DLCBL_854_B.txt | | 12,132,832 | Aug. 12, 2004 |
| 1135 | Table_1721_UC_DLCBL_855_A.txt | | 12,008,306 | Aug. 12, 2004 |
| 1136 | Table_1722_UC_DLCBL_855_B.txt | | 11,859,284 | Aug. 12, 2004 |
| 1137 | Table_1723_UC_DLCBL_856_A.txt | | 12,049,127 | Aug. 12, 2004 |
| 1138 | Table_1138_UC_DLCBL_856_B.txt | | 11,827,365 | Aug. 12, 2004 |
| 1139 | Table_1139_ABC_1000_log_signal.txt | | 719,801 | Aug. 5, 2004 |
| 1140 | Table_1140_ABC_1002_log_signal.txt | | 719,835 | Aug. 5, 2004 |
| 1141 | Table_1141_ABC_1023_log_signal.txt | | 719,881 | Aug. 5, 2004 |
| 1142 | Table_1142_ABC_1027_log_signal.txt | | 719,747 | Aug. 5, 2004 |
| 1143 | Table_1143_ABC_1031_log_signal.txt | | 719,600 | Aug. 5, 2004 |
| 1144 | Table_1144_ABC_1034_log_signal.txt | | 719,676 | Aug. 5, 2004 |
| 1145 | Table_1145_ABC_1038_log_signal.txt | | 719,775 | Aug. 5, 2004 |
| 1146 | Table_1146_ABC_1043_log_signal.txt | | 719,870 | Aug. 5, 2004 |
| 1147 | Table_1147_ABC_1045_log_signal.txt | | 719,737 | Aug. 5, 2004 |
| 1148 | Table_1148_ABC_1055_log_signal.txt | | 719,776 | Aug. 5, 2004 |
| 1149 | Table_1149_ABC_1057_log_signal.txt | | 719,889 | Aug. 5, 2004 |
| 1150 | Table_1150_ABC_1059_log_signal.txt | | 719,667 | Aug. 5, 2004 |
| 1151 | Table_1151_ABC_1061_log_signal.txt | | 719,846 | Aug. 5, 2004 |
| 1152 | Table_1152_ABC_1946_log_signal.txt | | 719,287 | Aug. 5, 2004 |
| 1153 | Table_1153_ABC_1994_log_signal.txt | | 719,569 | Aug. 5, 2004 |
| 1154 | Table_1154_ABC_2001_log_signal.txt | | 719,782 | Aug. 5, 2004 |
| 1155 | Table_1155_ABC_304_log_signal.txt | | 719,749 | Aug. 5, 2004 |
| 1156 | Table_1156_ABC_305_log_signal.txt | | 719,882 | Aug. 5, 2004 |

-continued

| | | | |
|---|---|---|---|
| 1157 | Table_1157_ABC_309_log_signal.txt | 719,614 | Aug. 5, 2004 |
| 1158 | Table_1158_ABC_413_log_signal.txt | 719,850 | Aug. 5, 2004 |
| 1159 | Table_1159_ABC_428_log_signal.txt | 719,605 | Aug. 5, 2004 |
| 1160 | Table_1160_ABC_432_log_signal.txt | 719,814 | Aug. 5, 2004 |
| 1161 | Table_1161_ABC_446_log_signal.txt | 719,655 | Aug. 5, 2004 |
| 1162 | Table_1162_ABC_462_log_signal.txt | 719,759 | Aug. 5, 2004 |
| 1163 | Table_1163_ABC_477_log_signal.txt | 719,684 | Aug. 5, 2004 |
| 1164 | Table_1164_ABC_481_log_signal.txt | 719,824 | Aug. 5, 2004 |
| 1165 | Table_1165_ABC_482_log_signal.txt | 719,812 | Aug. 5, 2004 |
| 1166 | Table_1166_ABC_538_log_signal.txt | 719,582 | Aug. 5, 2004 |
| 1167 | Table_1167_ABC_539_log_signal.txt | 719,812 | Aug. 5, 2004 |
| 1168 | Table_1168_ABC_544_log_signal.txt | 719,917 | Aug. 5, 2004 |
| 1169 | Table_1169_ABC_547_log_signal.txt | 719,719 | Aug. 5, 2004 |
| 1170 | Table_1170_ABC_577_log_signal.txt | 719,622 | Aug. 5, 2004 |
| 1171 | Table_1171_ABC_616_log_signal.txt | 719,564 | Aug. 5, 2004 |
| 1172 | Table_1172_ABC_626_log_signal.txt | 719,672 | Aug. 5, 2004 |
| 1173 | Table_1173_ABC_633_log_signal.txt | 719,756 | Aug. 5, 2004 |
| 1174 | Table_1174_ABC_642_log_signal.txt | 719,791 | Aug. 5, 2004 |
| 1175 | Table_1175_ABC_644_log_signal.txt | 719,998 | Aug. 5, 2004 |
| 1176 | Table_1176_ABC_645_log_signal.txt | 719,824 | Aug. 5, 2004 |
| 1177 | Table_1177_ABC_646_log_signal.txt | 719,780 | Aug. 5, 2004 |
| 1178 | Table_1178_ABC_651_log_signal.txt | 719,979 | Aug. 5, 2004 |
| 1179 | Table_1179_ABC_652_log_signal.txt | 719,932 | Aug. 5, 2004 |
| 1180 | Table_1180_ABC_660_log_signal.txt | 719,428 | Aug. 5, 2004 |
| 1181 | Table_1181_ABC_663_log_signal.txt | 719,951 | Aug. 5, 2004 |
| 1182 | Table_1182_ABC_668_log_signal.txt | 719,742 | Aug. 5, 2004 |
| 1183 | Table_1183_ABC_676_log_signal.txt | 719,842 | Aug. 5, 2004 |
| 1184 | Table_1184_ABC_678_log_signal.txt | 719,668 | Aug. 5, 2004 |
| 1185 | Table_1185_ABC_687_log_signal.txt | 719,947 | Aug. 5, 2004 |
| 1186 | Table_1186_ABC_689_log_signal.txt | 719,928 | Aug. 5, 2004 |
| 1187 | Table_1187_ABC_692_log_signal.txt | 719,778 | Aug. 5, 2004 |
| 1188 | Table_1188_ABC_694_log_signal.txt | 719,758 | Aug. 5, 2004 |
| 1189 | Table_1189_ABC_700_log_signal.txt | 719,746 | Aug. 5, 2004 |
| 1190 | Table_1190_ABC_702_log_signal.txt | 719,782 | Aug. 5, 2004 |
| 1191 | Table_1191_ABC_704_log_signal.txt | 719,787 | Aug. 5, 2004 |
| 1192 | Table_1192_ABC_709_log_signal.txt | 719,756 | Aug. 5, 2004 |
| 1193 | Table_1193_ABC_712_log_signal.txt | 719,071 | Aug. 5, 2004 |
| 1194 | Table_1194_ABC_714_log_signal.txt | 719,901 | Aug. 5, 2004 |
| 1195 | Table_1195_ABC_717_log_signal.txt | 719,580 | Aug. 5, 2004 |
| 1196 | Table_1196_ABC_725_log_signal.txt | 719,602 | Aug. 5, 2004 |
| 1197 | Table_1197_ABC_726_log_signal.txt | 719,595 | Aug. 5, 2004 |
| 1198 | Table_1198_ABC_730_log_signal.txt | 719,857 | Aug. 5, 2004 |
| 1199 | Table_1199_ABC_753_log_signal.txt | 719,754 | Aug. 5, 2004 |
| 1200 | Table_1200_ABC_756_log_signal.txt | 719,818 | Aug. 5, 2004 |
| 1201 | Table_1201_ABC_771_log_signal.txt | 719,890 | Aug. 5, 2004 |
| 1202 | Table_1202_ABC_779_log_signal.txt | 719,647 | Aug. 5, 2004 |
| 1203 | Table_1203_ABC_789_log_signal.txt | 719,947 | Aug. 5, 2004 |
| 1204 | Table_1204_ABC_800_log_signal.txt | 719,536 | Aug. 5, 2004 |
| 1205 | Table_1205_ABC_807_log_signal.txt | 719,798 | Aug. 5, 2004 |
| 1206 | Table_1206_ABC_809_log_signal.txt | 719,863 | Aug. 5, 2004 |
| 1207 | Table_1207_ABC_816_log_signal.txt | 719,339 | Aug. 5, 2004 |
| 1208 | Table_1208_ABC_820_log_signal.txt | 719,562 | Aug. 5, 2004 |
| 1209 | Table_1209_ABC_823_log_signal.txt | 719,555 | Aug. 5, 2004 |
| 1210 | Table_1210_ABC_835_log_signal.txt | 719,584 | Aug. 5, 2004 |
| 1211 | Table_1211_ABC_839_log_signal.txt | 719,866 | Aug. 5, 2004 |
| 1212 | Table_1212_ABC_841_log_signal.txt | 719,900 | Aug. 5, 2004 |
| 1213 | Table_1213_ABC_858_log_signal.txt | 719,601 | Aug. 5, 2004 |
| 1214 | Table_1214_ABC_872_log_signal.txt | 719,762 | Aug. 5, 2004 |
| 1215 | Table_1215_ABC_875_log_signal.txt | 719,888 | Aug. 5, 2004 |
| 1216 | Table_1216_ABC_912_log_signal.txt | 719,587 | Aug. 5, 2004 |
| 1217 | Table_1217_ABC_996_log_signal.txt | 719,844 | Aug. 5, 2004 |
| 1218 | Table_1218_BL_2032_log_signal.txt | 719,439 | Aug. 5, 2004 |
| 1219 | Table_1219_BL_2033_log_signal.txt | 719,466 | Aug. 5, 2004 |
| 1220 | Table_1220_BL_2035_log_signal.txt | 719,468 | Aug. 5, 2004 |
| 1221 | Table_1221_BL_2036_log_signal.txt | 719,517 | Aug. 5, 2004 |
| 1222 | Table_1222_BL_2037_log_signal.txt | 720,059 | Aug. 5, 2004 |
| 1223 | Table_1223_BL_2038_log_signal.txt | 719,518 | Aug. 5, 2004 |
| 1224 | Table_1224_BL_2082_log_signal.txt | 719,809 | Aug. 5, 2004 |
| 1225 | Table_1225_BL_2083_log_signal.txt | 719,328 | Aug. 5, 2004 |
| 1226 | Table_1226_BL_2086_log_signal.txt | 719,338 | Aug. 5, 2004 |
| 1227 | Table_1227_BL_2088_log_signal.txt | 719,656 | Aug. 5, 2004 |
| 1228 | Table_1228_BL_2090_log_signal.txt | 719,526 | Aug. 5, 2004 |
| 1229 | Table_1229_BL_2091_log_signal.txt | 719,721 | Aug. 5, 2004 |
| 1230 | Table_1230_BL_2097_log_signal.txt | 719,754 | Aug. 5, 2004 |
| 1231 | Table_1231_BL_2099_log_signal.txt | 719,574 | Aug. 5, 2004 |
| 1232 | Table_1232_BL_2100_log_signal.txt | 719,808 | Aug. 5, 2004 |
| 1233 | Table_1233_BL_2101_log_signal.txt | 719,733 | Aug. 5, 2004 |
| 1234 | Table_1234_BL_2103_log_signal.txt | 719,692 | Aug. 5, 2004 |
| 1235 | Table_1235_BL_2125_log_signal.txt | 719,778 | Aug. 5, 2004 |

| | | | |
|---|---|---|---|
| 1236 | Table_1236_BL_2126_log_signal.txt | 719,298 | Aug. 5, 2004 |
| 1237 | Table_1237_BL_2127_log_signal.txt | 719,313 | Aug. 5, 2004 |
| 1238 | Table_1238_BL_2128_log_signal.txt | 719,339 | Aug. 5, 2004 |
| 1239 | Table_1239_BL_2129_log_signal.txt | 719,494 | Aug. 5, 2004 |
| 1240 | Table_1240_BL_2267_log_signal.txt | 719,913 | Aug. 5, 2004 |
| 1241 | Table_1241_BL_2268_log_signal.txt | 719,897 | Aug. 5, 2004 |
| 1242 | Table_1242_BL_2269_log_signal.txt | 719,982 | Aug. 5, 2004 |
| 1243 | Table_1243_BL_2271_log_signal.txt | 719,810 | Aug. 5, 2004 |
| 1244 | Table_1244_CDnegMCL_1013_log_signal.txt | 719,496 | Aug. 5, 2004 |
| 1245 | Table_1245_CDnegMCL_1116_log_signal.txt | 719,808 | Aug. 5, 2004 |
| 1246 | Table_1246_CDnegMCL_1125_log_signal.txt | 719,557 | Aug. 5, 2004 |
| 1247 | Table_1247_CDnegMCL_1265_log_signal.txt | 719,740 | Aug. 5, 2004 |
| 1248 | Table_1248_CDnegMCL_2198_log_signal.txt | 720,028 | Aug. 5, 2004 |
| 1249 | Table_1249_CDnegMCL_2272_log_signal.txt | 719,923 | Aug. 5, 2004 |
| 1250 | Table_1250_CDnegMCL_930_log_signal.txt | 719,949 | Aug. 5, 2004 |
| 1251 | Table_1251_CDnegMCL_950_log_signal.txt | 719,891 | Aug. 5, 2004 |
| 1252 | Table_1252_CDnegMCL_985_log_signal.txt | 719,797 | Aug. 5, 2004 |
| 1253 | Table_1253_CDnegMCL_991_log_signal.txt | 719,686 | Aug. 5, 2004 |
| 1254 | Table_1254_FH_2043_log_signal.txt | 719,919 | Aug. 5, 2004 |
| 1255 | Table_1255_FH_2045_log_signal.txt | 719,763 | Aug. 5, 2004 |
| 1256 | Table_1256_FH_2047_log_signal.txt | 719,878 | Aug. 5, 2004 |
| 1257 | Table_1257_FH_2120_log_signal.txt | 719,940 | Aug. 5, 2004 |
| 1258 | Table_1258_FH_2123_log_signal.txt | 719,708 | Aug. 5, 2004 |
| 1259 | Table_1259_FH_2124_log_signal.txt | 719,815 | Aug. 5, 2004 |
| 1260 | Table_1260_FH_2138_log_signal.txt | 719,598 | Aug. 5, 2004 |
| 1261 | Table_1261_FH_2139_log_signal.txt | 719,714 | Aug. 5, 2004 |
| 1262 | Table_1262_FH_2140_log_signal.txt | 719,841 | Aug. 5, 2004 |
| 1263 | Table_1263_FH_2141_log_signal.txt | 719,943 | Aug. 5, 2004 |
| 1264 | Table_1264_FH_2142_log_signal.txt | 720,060 | Aug. 5, 2004 |
| 1265 | Table_1265_FH_2143_log_signal.txt | 719,848 | Aug. 5, 2004 |
| 1266 | Table_1266_FH_2159_log_signal.txt | 719,736 | Aug. 5, 2004 |
| 1267 | Table_1267_FH_2160_log_signal.txt | 719,593 | Aug. 5, 2004 |
| 1268 | Table_1268_FH_2161_log_signal.txt | 719,835 | Aug. 5, 2004 |
| 1269 | Table_1269_FH_2162_log_signal.txt | 719,992 | Aug. 5, 2004 |
| 1270 | Table_1270_FH_2164_log_signal.txt | 719,854 | Aug. 5, 2004 |
| 1271 | Table_1271_FH_2167_log_signal.txt | 719,840 | Aug. 5, 2004 |
| 1272 | Table_1272_FL_1073_log_signal.txt | 720,209 | Aug. 5, 2004 |
| 1273 | Table_1273_FL_1074_log_signal.txt | 719,873 | Aug. 5, 2004 |
| 1274 | Table_1274_FL_1075_log_signal.txt | 719,955 | Aug. 5, 2004 |
| 1275 | Table_1275_FL_1076_log_signal.txt | 719,619 | Aug. 5, 2004 |
| 1276 | Table_1276_FL_1077_log_signal.txt | 720,121 | Aug. 5, 2004 |
| 1277 | Table_1277_FL_1078_log_signal.txt | 719,889 | Aug. 5, 2004 |
| 1278 | Table_1278_FL_1080_log_signal.txt | 719,874 | Aug. 5, 2004 |
| 1279 | Table_1279_FL_1081_log_signal.txt | 720,141 | Aug. 5, 2004 |
| 1280 | Table_1280_FL_1083_log_signal.txt | 719,878 | Aug. 5, 2004 |
| 1281 | Table_1281_FL_1085_log_signal.txt | 719,880 | Aug. 5, 2004 |
| 1282 | Table_1282_FL_1086_log_signal.txt | 720,121 | Aug. 5, 2004 |
| 1283 | Table_1283_FL_1087_log_signal.txt | 719,871 | Aug. 5, 2004 |
| 1284 | Table_1284_FL_1088_log_signal.txt | 720,091 | Aug. 5, 2004 |
| 1285 | Table_1285_FL_1089_log_signal.txt | 719,828 | Aug. 5, 2004 |
| 1286 | Table_1286_FL_1090_log_signal.txt | 719,732 | Aug. 5, 2004 |
| 1287 | Table_1287_FL_1097_log_signal.txt | 720,055 | Aug. 5, 2004 |
| 1288 | Table_1288_FL_1098_log_signal.txt | 719,840 | Aug. 5, 2004 |
| 1289 | Table_1289_FL_1099_log_signal.txt | 719,977 | Aug. 5, 2004 |
| 1290 | Table_1290_FL_1102_log_signal.txt | 719,965 | Aug. 5, 2004 |
| 1291 | Table_1291_FL_1104_log_signal.txt | 719,937 | Aug. 5, 2004 |
| 1292 | Table_1292_FL_1106_log_signal.txt | 720,129 | Aug. 5, 2004 |
| 1293 | Table_1293_FL_1107_log_signal.txt | 719,953 | Aug. 5, 2004 |
| 1294 | Table_1294_FL_1183_log_signal.txt | 719,964 | Aug. 5, 2004 |
| 1295 | Table_1295_FL_1184_log_signal.txt | 720,112 | Aug. 5, 2004 |
| 1296 | Table_1296_FL_1185_log_signal.txt | 719,953 | Aug. 5, 2004 |
| 1297 | Table_1297_FL_1186_log_signal.txt | 720,207 | Aug. 5, 2004 |
| 1298 | Table_1298_FL_1416_log_signal.txt | 720,101 | Aug. 5, 2004 |
| 1299 | Table_1299_FL_1417_log_signal.txt | 719,952 | Aug. 5, 2004 |
| 1300 | Table_1300_FL_1418_log_signal.txt | 719,997 | Aug. 5, 2004 |
| 1301 | Table_1301_FL_1419_log_signal.txt | 720,048 | Aug. 5, 2004 |
| 1302 | Table_1302_FL_1422_log_signal.txt | 720,019 | Aug. 5, 2004 |
| 1303 | Table_1303_FL_1425_log_signal.txt | 719,916 | Aug. 5, 2004 |
| 1304 | Table_1304_FL_1426_log_signal.txt | 719,932 | Aug. 5, 2004 |
| 1305 | Table_1305_FL_1427_log_signal.txt | 719,845 | Aug. 5, 2004 |
| 1306 | Table_1306_FL_1428_log_signal.txt | 720,012 | Aug. 5, 2004 |
| 1307 | Table_1307_FL_1429_log_signal.txt | 719,987 | Aug. 5, 2004 |
| 1308 | Table_1308_FL_1432_log_signal.txt | 719,795 | Aug. 5, 2004 |
| 1309 | Table_1309_FL_1436_log_signal.txt | 720,028 | Aug. 5, 2004 |
| 1310 | Table_1310_FL_1440_log_signal.txt | 720,006 | Aug. 5, 2004 |
| 1311 | Table_1311_FL_1445_log_signal.txt | 719,751 | Aug. 5, 2004 |
| 1312 | Table_1312_FL_1450_log_signal.txt | 719,861 | Aug. 5, 2004 |
| 1313 | Table_1313_FL_1472_log_signal.txt | 719,814 | Aug. 5, 2004 |
| 1314 | Table_1314_FL_1473_log_signal.txt | 720,151 | Aug. 5, 2004 |

| | | | |
|---|---|---|---|
| 1315 | Table_1315_FL_1474_log_signal.txt | 720,027 | Aug. 5, 2004 |
| 1316 | Table_1316_FL_1476_log_signal.txt | 720,008 | Aug. 5, 2004 |
| 1317 | Table_1317_FL_1477_log_signal.txt | 719,820 | Aug. 5, 2004 |
| 1318 | Table_1318_FL_1478_log_signal.txt | 719,706 | Aug. 5, 2004 |
| 1319 | Table_1319_FL_1479_log_signal.txt | 719,857 | Aug. 5, 2004 |
| 1320 | Table_1320_FL_1480_log_signal.txt | 719,713 | Aug. 5, 2004 |
| 1321 | Table_1321_FL_1579_log_signal.txt | 719,886 | Aug. 5, 2004 |
| 1322 | Table_1322_FL_1580_log_signal.txt | 720,037 | Aug. 5, 2004 |
| 1323 | Table_1323_FL_1581_log_signal.txt | 719,898 | Aug. 5, 2004 |
| 1324 | Table_1324_FL_1582_log_signal.txt | 720,070 | Aug. 5, 2004 |
| 1325 | Table_1325_FL_1583_log_signal.txt | 719,968 | Aug. 5, 2004 |
| 1325 | Table_1326_FL_1584_log_signal.txt | 719,970 | Aug. 5, 2004 |
| 1327 | Table_1327_FL_1585_log_signal.txt | 720,077 | Aug. 5, 2004 |
| 1328 | Table_1328_FL_1586_log_signal.txt | 719,908 | Aug. 5, 2004 |
| 1329 | Table_1329_FL_1588_log_signal.txt | 719,859 | Aug. 5, 2004 |
| 1330 | Table_1330_FL_1589_log_signal.txt | 720,122 | Aug. 5, 2004 |
| 1331 | Table_1331_FL_1591_log_signal.txt | 719,928 | Aug. 5, 2004 |
| 1332 | Table_1332_FL_1594_log_signal.txt | 719,773 | Aug. 5, 2004 |
| 1333 | Table_1333_FL_1595_log_signal.txt | 720,045 | Aug. 5, 2004 |
| 1334 | Table_1334_FL_1598_log_signal.txt | 720,003 | Aug. 5, 2004 |
| 1335 | Table_1335_FL_1599_log_signal.txt | 720,156 | Aug. 5, 2004 |
| 1336 | Table_1336_FL_1603_log_signal.txt | 720,165 | Aug. 5, 2004 |
| 1337 | Table_1337_FL_1604_log_signal.txt | 719,845 | Aug. 5, 2004 |
| 1338 | Table_1338_FL_1606_log_signal.txt | 720,024 | Aug. 5, 2004 |
| 1339 | Table_1339_FL_1607_log_signal.txt | 719,923 | Aug. 5, 2004 |
| 1340 | Table_1340_FL_1608_log_signal.txt | 719,907 | Aug. 5, 2004 |
| 1341 | Table_1341_FL_1610_log_signal.txt | 719,954 | Aug. 5, 2004 |
| 1342 | Table_1342_FL_1611_log_signal.txt | 719,961 | Aug. 5, 2004 |
| 1343 | Table_1343_FL_1616_log_signal.txt | 719,081 | Aug. 5, 2004 |
| 1344 | Table_1344_FL_1617_log_signal.txt | 719,893 | Aug. 5, 2004 |
| 1345 | Table_1345_FL_1619_log_signal.txt | 719,886 | Aug. 5, 2004 |
| 1346 | Table_1346_FL_1620_log_signal.txt | 719,913 | Aug. 5, 2004 |
| 1347 | Table_1347_FL_1622_log_signal.txt | 719,925 | Aug. 5, 2004 |
| 1348 | Table_1348_FL_1623_log_signal.txt | 720,149 | Aug. 5, 2004 |
| 1349 | Table_1349_FL_1624_log_signal.txt | 719,971 | Aug. 5, 2004 |
| 1350 | Table_1350_FL_1625_log_signal.txt | 719,688 | Aug. 5, 2004 |
| 1351 | Table_1351_FL_1626_log_signal.txt | 719,891 | Aug. 5, 2004 |
| 1352 | Table_1352_FL_1627_log_signal.txt | 719,949 | Aug. 5, 2004 |
| 1353 | Table_1353_FL_1628_log_signal.txt | 719,751 | Aug. 5, 2004 |
| 1354 | Table_1354_FL_1637_log_signal.txt | 719,870 | Aug. 5, 2004 |
| 1355 | Table_1355_FL_1638_log_signal.txt | 720,010 | Aug. 5, 2004 |
| 1356 | Table_1356_FL_1639_log_signal.txt | 719,825 | Aug. 5, 2004 |
| 1357 | Table_1357_FL_1643_log_signal.txt | 719,945 | Aug. 5, 2004 |
| 1358 | Table_1358_FL_1644_log_signal.txt | 719,707 | Aug. 5, 2004 |
| 1359 | Table_1359_FL_1645_log_signal.txt | 719,953 | Aug. 5, 2004 |
| 1360 | Table_1360_FL_1646_log_signal.txt | 719,942 | Aug. 5, 2004 |
| 1361 | Table_1361_FL_1647_log_signal.txt | 719,782 | Aug. 5, 2004 |
| 1362 | Table_1362_FL_1648_log_signal.txt | 719,810 | Aug. 5, 2004 |
| 1363 | Table_1363_FL_1652_log_signal.txt | 719,812 | Aug. 5, 2004 |
| 1364 | Table_1364_FL_1654_log_signal.txt | 719,608 | Aug. 5, 2004 |
| 1365 | Table_1365_FL_1655_log_signal.txt | 719,993 | Aug. 5, 2004 |
| 1366 | Table_1366_FL_1656_log_signal.txt | 710,658 | Aug. 5, 2004 |
| 1367 | Table_1367_FL_1657_log_signal.txt | 719,908 | Aug. 5, 2004 |
| 1368 | Table_1368_FL_1660_log_signal.txt | 720,041 | Aug. 5, 2004 |
| 1369 | Table_1369_FL_1661_log_signal.txt | 720,024 | Aug. 5, 2004 |
| 1370 | Table_1370_FL_1662_log_signal.txt | 719,835 | Aug. 5, 2004 |
| 1371 | Table_1371_FL_1664_log_signal.txt | 719,887 | Aug. 5, 2004 |
| 1372 | Table_1372_FL_1669_log_signal.txt | 719,806 | Aug. 5, 2004 |
| 1373 | Table_1373_FL_1670_log_signal.txt | 719,796 | Aug. 5, 2004 |
| 1374 | Table_1374_FL_1675_log_signal.txt | 719,960 | Aug. 5, 2004 |
| 1375 | Table_1375_FL_1681_log_signal.txt | 720,066 | Aug. 5, 2004 |
| 1376 | Table_1376_FL_1683_log_signal.txt | 719,956 | Aug. 5, 2004 |
| 1377 | Table_1377_FL_1684_log_signal.txt | 719,691 | Aug. 5, 2004 |
| 1378 | Table_1378_FL_1716_log_signal.txt | 719,855 | Aug. 5, 2004 |
| 1379 | Table_1379_FL_1717_log_signal.txt | 719,963 | Aug. 5, 2004 |
| 1380 | Table_1380_FL_1718_log_signal.txt | 720,047 | Aug. 5, 2004 |
| 1381 | Table_1381_FL_1719_log_signal.txt | 719,885 | Aug. 5, 2004 |
| 1382 | Table_1382_FL_1720_log_signal.txt | 719,792 | Aug. 5, 2004 |
| 1383 | Table_1383_FL_1729_log_signal.txt | 720,000 | Aug. 5, 2004 |
| 1384 | Table_1384_FL_1732_log_signal.txt | 719,633 | Aug. 5, 2004 |
| 1385 | Table_1385_FL_l73S_log_signal.txt | 719,887 | Aug. 5, 2004 |
| 1386 | Table_1386_FL_1761_log_signal.txt | 719,866 | Aug. 5, 2004 |
| 1387 | Table_1387_FL_1764_log_signal.txt | 720,078 | Aug. 5, 2004 |
| 1388 | Table_1388_FL_1768_log_signal.txt | 720,029 | Aug. 5, 2004 |
| 1389 | Table_1389_FL_1771_log_signal.txt | 719,929 | Aug. 5, 2004 |
| 1390 | Table_1390_FL_1772_log_signal.txt | 719,921 | Aug. 5, 2004 |
| 1391 | Table_1391_FL_1788_log_signal.txt | 719,801 | Aug. 5, 2004 |
| 1392 | Table_1392_FL_1790_log_signal.txt | 720,131 | Aug. 5, 2004 |
| 1393 | Table_1393_FL_1792_log_signal.txt | 720,113 | Aug. 5, 2004 |

-continued

| | | | |
|---|---|---|---|
| 1394 | Table__1394__FL__1795__log__signal.txt | 720,070 | Aug. 5, 2004 |
| 1395 | Table__1395__FL__1797__log__signal.txt | 719,894 | Aug. 5, 2004 |
| 1396 | Table__1396__FL__1799__log__signal.txt | 719,604 | Aug. 5, 2004 |
| 1397 | Table__1397__FL__1810__log__signal.txt | 719,706 | Aug. 5, 2004 |
| 1398 | Table__1398__FL__1811__log__signal.txt | 719,977 | Aug. 5, 2004 |
| 1399 | Table__1399__FL__1825__log__signal.txt | 719,804 | Aug. 5, 2004 |
| 1400 | Table__1400__FL__1827__log__signal.txt | 720,030 | Aug. 5, 2004 |
| 1401 | Table__1401__FL__1828__log__signal.txt | 719,848 | Aug. 5, 2004 |
| 1402 | Table__1402__FL__1829__log__signal.txt | 720,004 | Aug. 5, 2004 |
| 1403 | Table__1403__FL__1830__log__signal.txt | 719,927 | Aug. 5, 2004 |
| 1404 | Table__1404__FL__1833__log__signal.txt | 719,917 | Aug. 5, 2004 |
| 1405 | Table__1405__FL__1834__log__signal.txt | 719,704 | Aug. 5, 2004 |
| 1406 | Table__1406__FL__1835__log__signal.txt | 720,043 | Aug. 5, 2004 |
| 1407 | Table__1407__FL__1836__log__signal.txt | 719,753 | Aug. 5, 2004 |
| 1408 | Table__1408__FL__1837__log__signal.txt | 719,848 | Aug. 5, 2004 |
| 1409 | Table__1409__FL__1838__log__signal.txt | 719,787 | Aug. 5, 2004 |
| 1410 | Table__1410__FL__1839__log__signal.txt | 719,992 | Aug. 5, 2004 |
| 1411 | Table__1411__FL__1841__log__signal.txt | 719,730 | Aug. 5, 2004 |
| 1412 | Table__1412__FL__1842__log__signal.txt | 719,710 | Aug. 5, 2004 |
| 1413 | Table__1413__FL__1844__log__signal.txt | 719,997 | Aug. 5, 2004 |
| 1414 | Table__1414__FL__1845__log__signal.txt | 720,016 | Aug. 5, 2004 |
| 1415 | Table__1415__FL__1846__log__signal.txt | 719,892 | Aug. 5, 2004 |
| 1416 | Table__1416__FL__1848__log__signal.txt | 719,625 | Aug. 5, 2004 |
| 1417 | Table__1417__FL__1850__log__signal.txt | 720,047 | Aug. 5, 2004 |
| 1418 | Table__1418__FL__1851__log__signal.txt | 719,908 | Aug. 5, 2004 |
| 1419 | Table__1419__FL__1853__log__signal.txt | 719,968 | Aug. 5, 2004 |
| 1420 | Table__1420__FL__1854__log__signal.txt | 720,215 | Aug. 5, 2004 |
| 1421 | Table__1421__FL__1855__log__signal.txt | 719,792 | Aug. 5, 2004 |
| 1422 | Table__1422__FL__1857__log__signal.txt | 719,977 | Aug. 5, 2004 |
| 1423 | Table__1423__FL__1861__log__signal.txt | 719,995 | Aug. 5, 2004 |
| 1424 | Table__1424__FL__1862__log__signal.txt | 719,838 | Aug. 5, 2004 |
| 1425 | Table__1425__FL__1863__log__signal.txt | 719,960 | Aug. 5, 2004 |
| 1426 | Table__1426__FL__1864__log__signal.txt | 720,101 | Aug. 5, 2004 |
| 1427 | Talee__1427__FL__1866__log__signal.txt | 719,826 | Aug. 5, 2004 |
| 1428 | Table__1428__FL__1870__log__signal.txt | 719,906 | Aug. 5, 2004 |
| 1429 | Table__1429__FL__1873__log__signal.txt | 719,826 | Aug. 5, 2004 |
| 1430 | Table__1430__FL__1874__log__signal.txt | 719,987 | Aug. 5, 2004 |
| 1431 | Table__1431__FL__1876__log__signal.txt | 719,955 | Aug. 5, 2004 |
| 1432 | Table__1432__FL__1879__log__signal.txt | 720,033 | Aug. 5, 2004 |
| 1433 | Table__1433__FL__1880__log__signal.txt | 719,838 | Aug. 5, 2004 |
| 1434 | Table__1434__FL__1382__log__signal.txt | 719,856 | Aug. 5, 2004 |
| 1435 | Table__1435__FL__1884__log__signal.txt | 720,054 | Aug. 5, 2004 |
| 1436 | Table__1436__FL__1885__log__signal.txt | 720,091 | Aug. 5, 2004 |
| 1437 | Table__1437__FL__1887__log__signal.txt | 719,999 | Aug. 5, 2004 |
| 1438 | Table__1438__FL__1888__log__signal.txt | 719,870 | Aug. 5, 2004 |
| 1439 | Table__1439__FL__1890__log__signal.txt | 719,775 | Aug. 5, 2004 |
| 1440 | Table__1440__FL__1894__log__signal.txt | 719,951 | Aug. 5, 2004 |
| 1441 | Table__1441__FL__1896__log__signal.txt | 719,806 | Aug. 5, 2004 |
| 1442 | Table__1442__FL__1897__log__signal.txt | 719,814 | Aug. 5, 2004 |
| 1443 | Table__1443__FL__1898__log__signal.txt | 719,896 | Aug. 5, 2004 |
| 1444 | Table__1444__FL__1900__log__signal.txt | 719,881 | Aug. 5, 2004 |
| 1445 | Table__1445__FL__1903__log__signal.txt | 719,743 | Aug. 5, 2004 |
| 1446 | Table__1446__FL__1904__log__signal.txt | 719,937 | Aug. 5, 2004 |
| 1447 | Table__1447__FL__1905__log__signal.txt | 720,014 | Aug. 5, 2004 |
| 1448 | Table__1448__FL__1906__log__signal.txt | 719,525 | Aug. 5, 2004 |
| 1449 | Table__1449__FL__1907__log__signal.txt | 719,495 | Aug. 5, 2004 |
| 1450 | Table__1450__FL__1910__log__signal.txt | 719,730 | Aug. 5, 2004 |
| 1451 | Table__1451__FL__1912__log__signal.txt | 720,188 | Aug. 5, 2004 |
| 1452 | Table__1452__FL__1913__log__signal.txt | 719,864 | Aug. 5, 2004 |
| 1453 | Table__1453__FL__1916__log__signal.txt | 719,705 | Aug. 5, 2004 |
| 1454 | Table__1454__FL__1918__log__signal.txt | 719,919 | Aug. 5, 2004 |
| 1455 | Table__1455__FL__1919__log__signal.txt | 719,819 | Aug. 5, 2004 |
| 1456 | Table__1456__FL__735__log__signal.txt | 719,892 | Aug. 5, 2004 |
| 1457 | Table__1457__FL__738__log__signal.txt | 719,735 | Aug. 5, 2004 |
| 1458 | Table__1458__FL__739__log__signal.txt | 719,983 | Aug. 5, 2004 |
| 1459 | Table__1459__FL__878__log__signal.txt | 719,976 | Aug. 5, 2004 |
| 1460 | Table__1460__FL__879__log__signal.txt | 719,738 | Aug. 5, 2004 |
| 1461 | Table__1461__FL__886__log__signal.txt | 719,991 | Aug. 5, 2004 |
| 1462 | Table__1462__FL__888__log__signal.txt | 719,876 | Aug. 5, 2004 |
| 1463 | Table__1463__GCB__1005__log__signal.txt | 719,924 | Aug. 5, 2004 |
| 1464 | Table__1464__GCB__1008__log__signal.txt | 719,529 | Aug. 5, 2004 |
| 1465 | Table__1465__GCB__1009__log__signal.txt | 719,942 | Aug. 5, 2004 |
| 1466 | Table__1466__GCB__1021__log__signal.txt | 719,714 | Aug. 5, 2004 |
| 1467 | Table__1467__GCB__1025__log__signal.txt | 719,756 | Aug. 5, 2004 |
| 1468 | Table__1468__GCB__1026__log__signal.txt | 719,819 | Aug. 5, 2004 |
| 1469 | Table__1469__GCB__1037__log__signal.txt | 719,756 | Aug. 5, 2004 |
| 1470 | Table__1470__GCB__1039__log__signal.txt | 719,940 | Aug. 5, 2004 |
| 1471 | Table__1471__GCB__1049__log__signal.txt | 719,794 | Aug. 5, 2004 |
| 1472 | Table__1472__GCB__1051__log__signal.txt | 719,894 | Aug. 5, 2004 |

-continued

| | | | |
|---|---|---|---|
| 1473 | Table_1473_GCB_1058_log_signal.txt | 719,709 | Aug. 5, 2004 |
| 1474 | Table_1474_GCB_1060_log_signal.txt | 719,801 | Aug. 5, 2004 |
| 1475 | Table_1475_GCB_1990_log_signal.txt | 719,399 | Aug. 5, 2004 |
| 1476 | Table_1476_GCB_1991_log_signal.txt | 719,470 | Aug. 5, 2004 |
| 1477 | Table_1477_GCB_2017_log_signal.txt | 719,443 | Aug. 5, 2004 |
| 1478 | Table_1478_GCB_2018_log_signal.txt | 719,412 | Aug. 5, 2004 |
| 1479 | Table_1479_GCB_2095_log_signal.txt | 720,035 | Aug. 5, 2004 |
| 1480 | Table_1480_GCB_412_log_signal.txt | 719,843 | Aug. 5, 2004 |

<u>Disc 21 of 22</u>

| | | | |
|---|---|---|---|
| 1481 | Table_1481_GCB_415_log_signal.txt | 719,852 | Aug. 5, 2004 |
| 1482 | Table_1482_GCB_421_log_signal.txt | 719,661 | Aug. 5, 2004 |
| 1483 | Table_1483_GCB_424_log_signal.txt | 719,871 | Aug. 5, 2004 |
| 1484 | Table_1484_GCB_433_log_signal.txt | 719,698 | Aug. 5, 2004 |
| 1485 | Table_1485_GCB_434_log_signal.txt | 719,894 | Aug. 5, 2004 |
| 1486 | Table_1486_GCB_438_log_signal.txt | 719,648 | Aug. 5, 2004 |
| 1487 | Table_1487_GCB_439_log_signal.txt | 719,722 | Aug. 5, 2004 |
| 1488 | Table_1488_GCB_459_log_signal.txt | 719,742 | Aug. 5, 2004 |
| 1489 | Table_1489_GCB_470_log_signal.txt | 719,565 | Aug. 5, 2004 |
| 1490 | Table_1490_GCB_479_log_signal.txt | 719,713 | Aug. 5, 2004 |
| 1491 | Table_1491_GCB_492_log_signal.txt | 719,491 | Aug. 5, 2004 |
| 1492 | Tabl8_1492_GCB_517_log_signal.txt | 719,595 | Aug. 5, 2004 |
| 1493 | Table_1493_GCB_523_log_signal.txt | 719,784 | Aug. 5, 2004 |
| 1494 | Table_1494_GCB_524_log_signal.txt | 719,991 | Aug. 5, 2004 |
| 1495 | Table_1495_GCB_529_log_signal.txt | 719,591 | Aug. 5, 2004 |
| 1498 | Table_1496_GCB_533_log_signal.txt | 719,489 | Aug. 5, 2004 |
| 1497 | Table_1497_GCB_537_log_signal.txt | 719,866 | Aug. 5, 2004 |
| 1498 | Table_1498_GCB_543_log_signal.txt | 719,868 | Aug. 5, 2004 |
| 1499 | Table_1499_GCB_545_log_signal.txt | 719,723 | Aug. 5, 2004 |
| 1500 | Table_1500_GCB_549_log_signal.txt | 719,961 | Aug. 5, 2004 |
| 1501 | Table_1501_GCB_550_log_signal.txt | 719,631 | Aug. 5, 2004 |
| 1502 | Table_1502_GCB_553_log_signal.txt | 719,658 | Aug. 5, 2004 |
| 1503 | Table_1503_GCB_565_log_signal.txt | 719,779 | Aug. 5, 2004 |
| 1504 | Table_1504_GCB_572_log_signal.txt | 719,880 | Aug. 5, 2004 |
| 1505 | Table_1505_GCB_817_log_signal.txt | 719,961 | Aug. 5, 2004 |
| 1506 | Table_1506_GCB_818_log_signal.txt | 719,784 | Aug. 5, 2004 |
| 1507 | Table_1507_GCB_619_log_signal.txt | 719,917 | Aug. 5, 2004 |
| 1508 | Table_1508_GCB_623_log_signal.txt | 719,983 | Aug. 5, 2004 |
| 1509 | Table_1509_GCB_627_log_signal.txt | 719,791 | Aug. 5, 2004 |
| 1510 | Table_1510_GCB_654_log_signal.txt | 719,680 | Aug. 5, 2004 |
| 1511 | Table_1511_GCB_661_log_signal.txt | 719,750 | Aug. 5, 2004 |
| 1512 | Table_1512_GCB_689_log_signal.txt | 719,804 | Aug. 5, 2004 |
| 1513 | Table_1513_GCB_672_log_signal.txt | 719,690 | Aug. 5, 2004 |
| 1514 | Table_1514_GCB_674_log_signal.txt | 719,705 | Aug. 5, 2004 |
| 1515 | Table_1515_GCB_675_log_signal.txt | 719,403 | Aug. 5, 2004 |
| 1516 | Table_1516_GCB_681_log_signal.txt | 719,662 | Aug. 5, 2004 |
| 1517 | Table_1517_GCB_688_log_signal.txt | 719,901 | Aug. 5, 2004 |
| 1518 | Table_1518_GCB_695_log_signal.txt | 719,669 | Aug. 5, 2004 |
| 1519 | Table_1519_GCB_698_log_signal.txt | 719,863 | Aug. 5, 2004 |
| 1520 | Table_1520_GCB_701_log_signal.txt | 719,936 | Aug. 5, 2004 |
| 1521 | Table_1521_GCB_710_log_signal.txt | 719,846 | Aug. 5, 2004 |
| 1522 | Table_1522_GCB_711_log_signal.txt | 719,611 | Aug. 5, 2004 |
| 1523 | Table_1523_GCB_722_log_signal.txt | 719,778 | Aug. 5, 2004 |
| 1524 | Table_1524_GCB_724_log_signal.txt | 719,711 | Aug. 5, 2004 |
| 1525 | Table_1525_GCB_731_log_signal.txt | 719,984 | Aug. 5, 2004 |
| 1526 | Table_1526_GCB_742_log_signal.txt | 719,996 | Aug. 5, 2004 |
| 1527 | Table_1527_GCB_744_log_signal.txt | 719,908 | Aug. 5, 2004 |
| 1528 | Table_1528_GCB_745_log_signal.txt | 719,873 | Aug. 5, 2004 |
| 1529 | Table_1529_GCB_747_log_signal.txt | 719,969 | Aug. 5, 2004 |
| 1530 | Table_1530_GCB_749_log_signal.txt | 719,685 | Aug. 5, 2004 |
| 1531 | Table_1531_GCB_758_log_signal.txt | 719,776 | Aug. 5, 2004 |
| 1532 | Table_1532_GCB_772_log_signal.txt | 720,003 | Aug. 5, 2004 |
| 1533 | Table_1533_GCB_777_log_signal.txt | 719,908 | Aug. 5, 2004 |
| 1534 | Table_1534_GCB_792_log_signal.txt | 719,971 | Aug. 5, 2004 |
| 1535 | Table_1535_GCB_795_log_signal.txt | 719,759 | Aug. 5, 2004 |
| 1536 | Table_1536_GCB_797_log_signal.txt | 719,760 | Aug. 6, 2004 |
| 1537 | Table_1537_GCB_803_log_signal.txt | 719,974 | Aug. 6, 2004 |
| 1538 | Table_1538_GCB_810_log_signal.txt | 719,852 | Aug. 5, 2004 |
| 1539 | Table_1539_GCB_817_log_signal.txt | 719,764 | Aug. 5, 2004 |
| 1540 | Table_1540_GCB_818_log_signal.txt | 719,583 | Aug. 5, 2004 |
| 1541 | Table_1541_GCB_819_log_signal.txt | 719,786 | Aug. 5, 2004 |
| 1542 | Table_1542_GCB_821_log_signal.txt | 719,744 | Aug. 5, 2004 |
| 1543 | Table_1543_GCB_832_log_signal.txt | 719,702 | Aug. 5, 2004 |
| 1544 | Table_1544_GCB_836_log_signal.txt | 719,639 | Aug. 5, 2004 |
| 1545 | Table_1545_GCB_840_log_signal.txt | 720,192 | Aug. 5, 2004 |
| 1546 | Table_1546_GCB_847_log_signal.txt | 719,894 | Aug. 5, 2004 |
| 1547 | Table_1547_GCB_860_log_signal.txt | 719,781 | Aug. 5, 2004 |
| 1548 | Table_1548_GCB_871_log_signal.txt | 719,867 | Aug. 5, 2004 |
| 1549 | Table_1549_GCB_874_log_signal.txt | 719,863 | Aug. 5, 2004 |

-continued

| | | | |
|---|---|---|---|
| 1550 | Table_1550_GCB_995_log_signal.txt | 719,901 | Aug. 5, 2004 |
| 1551 | Table_1551_LPC_2224_log_signal.txt | 719,928 | Aug. 5, 2004 |
| 1552 | Table_1552_LPC_2232_log_signal.txt | 720,084 | Aug. 5, 2004 |
| 1553 | Table_1553_LPC_2261_log_signal.txt | 719,850 | Aug. 5, 2004 |
| 1554 | Table_1554_LPC_2262_log_signal.txt | 720,236 | Aug. 5, 2004 |
| 1555 | Table_1555_LPC_2263_log_signal.txt | 720,029 | Aug. 5, 2004 |
| 1556 | Table_1556_LPC_2265_log_signal.txt | 719,906 | Aug. 5, 2004 |
| 1557 | Table_1557_Lymbl_2185_log_signal.txt | 719,715 | Aug. 5, 2004 |
| 1558 | Table_1558_Lymbl_2186_log_signal.txt | 719,629 | Aug. 5, 2004 |
| 1559 | Table_1559_Lymbl_2249_log_signal.txt | 720,127 | Aug. 5, 2004 |
| 1560 | Table_1560_MALT_Gastric_2021_log_signal.txt | 719,609 | Aug. 5, 2004 |
| 1561 | Table_1561_MALT_Gastric_2041_log_signal.txt | 719,769 | Aug. 5, 2004 |
| 1562 | Table_1562_MALT_Gastric_2065_log_signal.txt | 719,679 | Aug. 5, 2004 |
| 1563 | Table_1563_MALT_Gastric_2067_log_signal.txt | 719,927 | Aug. 5, 2004 |
| 1564 | Table_1564_MALT_Gastric_2070_log_signal.txt | 719,871 | Aug. 5, 2004 |
| 1565 | Table_1565_MALT_Gastric_2110_log_signal.txt | 719,932 | Aug. 5, 2004 |
| 1566 | Table_1566_MALT_Gastric_2111_log_signal.txt | 719,305 | Aug. 5, 2004 |
| 1567 | Table_1567_MALT_Gastric_2112_log_signal.txt | 719,897 | Aug. 5, 2004 |
| 1568 | Table_1568_MALT_Gastric_2270_log_signal.txt | 719,916 | Aug. 5, 2004 |
| 1569 | Table_1569_MALT_lung_2202_log_signal.txt | 720,174 | Aug. 5, 2004 |
| 1570 | Table_1570_MALT_salivary_2243_log_signal.txt | 720,111 | Aug. 5, 2004 |
| 1571 | Table_1571_MALT_tonsil_2211_log_signal.txt | 720,102 | Aug. 5, 2004 |
| 1572 | Table_1572_MALT_unk_2178_log_signal.txt | 719,940 | Aug. 5, 2004 |
| 1573 | Table_1573_MALT_unk_2182_log_signal.txt | 719,681 | Aug. 5, 2004 |
| 1574 | Table_1574_MALT_unk_2183_log_signal.txt | 720,031 | Aug. 5, 2004 |
| 1575 | Table_1575_MALT_unk_2184_log_signal.txt | 720,023 | Aug. 5, 2004 |
| 1576 | Table_1576_MCL_1012_log_signal.txt | 719,967 | Aug. 5, 2004 |
| 1577 | Table_1577_MCL_1091_log_signal.txt | 719,861 | Aug. 5, 2004 |
| 1578 | Table_1578_MCL_1114_log_signal.txt | 720,107 | Aug. 5, 2004 |
| 1579 | Table_1579_MCL_1128_log_sighal.txt | 719,887 | Aug. 5, 2004 |
| 1580 | Table_1580_MCL_1150_log_signal.txt | 719,990 | Aug. 5, 2004 |
| 1581 | Table_1581_MCL_1162_log_signal.txt | 719,887 | Aug. 5, 2004 |
| 1582 | Table_1582_MCL_1166_log_signal.txt | 719,942 | Aug. 5, 2004 |
| 1583 | Table_1583_MCL_1194_log_signal.txt | 719,765 | Aug. 5, 2004 |
| 1584 | Table_1584_MCL_885_log_signal.txt | 719,947 | Aug. 5, 2004 |
| 1585 | Table_1585_MCL_918_log_signal.txt | 719,871 | Aug. 5, 2004 |
| 1586 | Table_1586_MCL_924_log_signal.txt | 729,318 | Aug. 5, 2004 |
| 1587 | Table_1587_MCL_925_log_signal.txt | 719,991 | Aug. 5, 2004 |
| 1588 | Table_1588_MCL_926_log_signal.txt | 720,109 | Aug. 5, 2004 |
| 1589 | Table_1589_MCL_936_log_signal.txt | 720,025 | Aug. 5, 2004 |
| 1590 | Table_1590_MCL_939_log_signal.txt | 720,025 | Aug. 5, 2004 |
| 1591 | Table_1591_MCL_953_log_signal.txt | 719,562 | Aug. 5, 2004 |
| 1592 | Table_1592_MCL_956_log_signal.txt | 719,923 | Aug. 5, 2004 |
| 1593 | Table_1593_MCL_964_log_signal.txt | 719,968 | Aug. 5, 2004 |
| 1594 | Table_1594_MCL_966_log_signal.txt | 719,679 | Aug. 5, 2004 |
| 1595 | Table_1595_MCL_968_log_signal.txt | 719,778 | Aug. 5, 2004 |
| 1596 | Table_1596_MCL_970_log_signal.txt | 719,737 | Aug. 5, 2004 |
| 1597 | Table_1597_Mult_Myeloma_H1112_100001_log_signal.txt | 719,421 | Aug. 5, 2004 |
| 1598 | Table_1598_Mult_Myeloma_HDLM2_100002_log_signal.txt | 719,052 | Aug. 5, 2004 |
| 1599 | Table_1599_Mult_Myeloma_JIM3_100003_log_signal.txt | 719,345 | Aug. 5, 2004 |
| 1600 | Table_1600_Mult_Myeloma_JJN3_100004_log_signal.txt | 719,543 | Aug. 5, 2004 |
| 1601 | Table_1601_Mult_Myeloma_KMS11_100005_log_signal.txt | 719,485 | Aug. 5, 2004 |
| 1602 | Table_1602_Mult_Myeloma_KMS12_100006_log_signal.txt | 719,226 | Aug. 5, 2004 |
| 1603 | Table_1603_Mult_Myeloma_LB84_1_100007_log_signal.txt | 719,446 | Aug. 5, 2004 |
| 1604 | Table_1604_Mult_Myeloma_LP1_100008_log_signal.txt | 719,215 | Aug. 5, 2004 |
| 1605 | Table_1505_Mult_Myeloma_U266_100009_log_signal.txt | 719,709 | Aug. 5, 2004 |
| 1606 | Table_1606_NMZ_2231_log_signal.txt | 720,065 | Aug. 5, 2004 |
| 1607 | Table_1607_NMZ_2242_log_signal.txt | 719,936 | Aug. 5, 2004 |
| 1608 | Table_1608_NMZ_2254_log_signal.txt | 719,889 | Aug. 5, 2004 |
| 1609 | Table_1609_PMBL_1006_log_signal.txt | 719,569 | Aug. 5, 2004 |
| 1610 | Table_1610_PMBL_1024_log_signal.txt | 719,689 | Aug. 5, 2004 |
| 1611 | Table_1611_PMBL_1048_log_signal.txt | 719,535 | Aug. 5, 2004 |
| 1612 | Table_1612_PMBL_1053_log_signal.txt | 719,833 | Aug. 5, 2004 |
| 1613 | Table_1613_PMBL_1920_log_signal.txt | 719,681 | Aug. 5, 2004 |
| 1614 | Table_1614_PMBL_1921_log_signal.txt | 719,749 | Aug. 5, 2004 |
| 1615 | Table_1615_PMBL_1923_log_signal.txt | 719,681 | Aug. 5, 2004 |
| 1616 | Table_1616_PMBL_1924_log_signal.txt | 719,659 | Aug. 5, 2004 |
| 1617 | Table_1617_PMBL_1935_log_signal.txt | 719,716 | Aug. 5, 2004 |
| 1618 | Table_1618_PMBL_1941_log_signal.txt | 719,793 | Aug. 5, 2004 |
| 1619 | Table_1619_PMBL_1942_log_signal.txt | 719,857 | Aug. 5, 2004 |
| 1620 | Table_1620_PMBL_1943_log_signal.txt | 719,523 | Aug. 5, 2004 |
| 1621 | Table_1621_PMBL_1945_log_signal.txt | 719,389 | Aug. 5, 2004 |
| 1622 | Table_1622_PMBL_1948_log_signal.txt | 719,581 | Aug. 5, 2004 |
| 1623 | Table_1623_PMBL_1949_log_signal.txt | 719,805 | Aug. 5, 2004 |
| 1624 | Table_1624_PMBL_1989_log_signal.txt | 719,642 | Aug. 5, 2004 |
| 1625 | Table_1625_PMBL_1992_log_signal.txt | 719,564 | Aug. 5, 2004 |
| 1626 | Table_1626_PMBL_1993_log_signal.txt | 719,621 | Aug. 5, 2004 |
| 1627 | Table_1627_PMBL_2002_log_signal.txt | 719,718 | Aug. 5, 2004 |
| 1628 | Table_1628_PMBL_2019_log_signal.txt | 719,547 | Aug. 5, 2004 |

-continued

| | | | |
|---|---|---|---|
| 1629 | Table_1629_PMBL_2020_log_signal.txt | 719,620 | Aug. 5, 2004 |
| 1630 | Table_1630_PMBL_2092_log_signal.txt | 719,844 | Aug. 5, 2004 |
| 1631 | Table_1631_PMBL_484_log_signal.txt | 719,920 | Aug. 5, 2004 |
| 1632 | Table_1632_PMBL_546_log_signal.txt | 720,204 | Aug. 5, 2004 |
| 1683 | Table_1633_PMBL_570_log_signal.txt | 719,670 | Aug. 5, 2004 |
| 1634 | Table_1634_PMBL_621_log_signal.txt | 719,915 | Aug. 5, 2004 |
| 1635 | Table_1635_PMBL_638_log_signal.txt | 719,798 | Aug. 5, 2004 |
| 1636 | Table_1636_PMBL_691_log_signal.txt | 719,763 | Aug. 5, 2004 |
| 1637 | Table_1637_PMBL_791_log_signal.txt | 719,762 | Aug. 5, 2004 |
| 1638 | Table_1638_PMBL_824_log_signal.txt | 719,876 | Aug. 5, 2004 |
| 1639 | Table_1639_PMBL_906_log_signal.txt | 719,758 | Aug. 5, 2004 |
| 1640 | Table_1640_PMBL_994_log_signal.txt | 719,755 | Aug. 5, 2004 |
| 1641 | Table_1641_PMBL_998_log_signal.txt | 719,786 | Aug. 5, 2004 |
| 1642 | Table_1642_PTLD_1817_log_signal.txt | 719,584 | Aug. 5, 2004 |
| 1643 | Tabl8_1643_PTLD_1824_log_signal.txt | 719,6Z6 | Aug. 5, 2004 |
| 1644 | Table_1644_PTLD_1981_log_signal.txt | 719,522 | Aug. 5, 2004 |
| 1645 | Table_1645_PTLD_1986_log_signal.txt | 719,870 | Aug. 5, 2004 |
| 1646 | Table_1646_SLL_1151_log_signal.txt | 719,912 | Aug. 5, 2004 |
| 1647 | Table_1647_SLL_1153_log_signal.txt | 720,059 | Aug. 5, 2004 |
| 1648 | Table_1648_SLL_1155_log_signal.txt | 720,031 | Aug. 5, 2004 |
| 1649 | Table_1649_SLL_1156_log_signal.txt | 720,140 | Aug. 5, 2004 |
| 1650 | Table_1650_SLL_1158_log_signal.txt | 720,029 | Aug. 5, 2004 |
| 1651 | Table_1651_SLL_1213_log_signal.txt | 720,069 | Aug. 5, 2004 |
| 1652 | Table_1652_SLL_1214_log_signal.txt | 719,849 | Aug. 5, 2004 |
| 1653 | Table_1653_SLL_1216_log_signal.txt | 719,817 | Aug. 5, 2004 |
| 1654 | Table_1654_SLL_1217_log_signal.txt | 719,829 | Aug. 5, 2004 |
| 1655 | Table_1655_SLL_1218_log_signal.txt | 719,694 | Aug. 5, 2004 |
| 1656 | Table_1656_SLL_1220_log_signal.txt | 719,763 | Aug. 5, 2004 |
| 1657 | Table_1657_SLL_1229_log_signal.txt | 719,434 | Aug. 5, 2004 |
| 1658 | Table_1658_SLL_1231_log_signal.txt | 719,688 | Aug. 5, 2004 |
| 1659 | Table_1659_SLL_1235_log_signal.txt | 719,578 | Aug. 5, 2004 |
| 1660 | Table_1660_SLL_1236_log_signal.txt | 719,791 | Aug. 5, 2004 |
| 1661 | Table_1661_SLL_1238_log_signal.txt | 719,633 | Aug. 5, 2004 |
| 1662 | Table_1662_SLL_1240_log_signal.txt | 719,788 | Aug. 5, 2004 |
| 1663 | Table_1663_Splenic_2061_log_signal.txt | 719,871 | Aug. 5, 2004 |
| 1664 | Table_1664_Splenic_2074_log_signal.txt | 720,044 | Aug. 5, 2004 |
| 1665 | Table_1665_Splenic_2075_log_signal.txt | 719,895 | Aug. 5, 2004 |
| 1666 | Table_1666_Splenic_2077_log_signal.txt | 720,030 | Aug. 5, 2004 |
| 1667 | Table_1667_Splenic_2079_log_signal.txt | 719,789 | Aug. 5, 2004 |
| 1668 | Table_1668_Splenic_2104_log_signal.txt | 719,813 | Aug. 5, 2004 |
| 1669 | Table_1669_Splenic_2105_log_signal.txt | 720,016 | Aug. 5, 2004 |
| 1670 | Table_1670_Splenic_2106_log_signal.txt | 719,757 | Aug. 5, 2004 |
| 1671 | Table_1671_Splenic_2256_log_signal.txt | 720,008 | Aug. 5, 2004 |
| 1672 | Table_1672_Splenic_2257_log_signal.txt | 719,730 | Aug. 5, 2004 |
| 1673 | Table_1673_Splenic_2258_log_signal.txt | 719,797 | Aug. 5, 2004 |
| 1674 | Table_1674_Splenic_2259_log_signal.txt | 719,978 | Aug. 5, 2004 |
| 1675 | Table_1675_Splenic_2260_log_signal.txt | 719,700 | Aug. 5, 2004 |
| 1676 | Table_1676_UC_DLBCL_1001_log_signal.txt | 719,781 | Aug. 5, 2004 |
| 1677 | Table_1677_UC_DLBCL_1004_log_signal.txt | 719,748 | Aug. 5, 2004 |
| 1678 | Table_1678_UC_DLBCL_1007_log_signal.txt | 719,736 | Aug. 5, 2004 |
| 1679 | Table_1679_UC_DLBCL_1018_log_signal.txt | 719,605 | Aug. 5, 2004 |
| 1680 | Table_1680_UC_DLBCL_1041_log_signal.txt | 719,657 | Aug. 5, 2004 |
| 1681 | Table_1681_UC_DLBCL_1054_log_signal.txt | 719,834 | Aug. 5, 2004 |
| 1682 | Table_1682_UC_DLBCL_306_log_signal.txt | 719,532 | Aug. 5, 2004 |
| 1683 | Table_1683_UC_DLBCL_310_log_signal.txt | 719,704 | Aug. 5, 2004 |
| 1684 | Table_1684_UC_DLBCL_449_log_signal.txt | 719,556 | Aug. 5, 2004 |
| 1685 | Table_1685_UC_DLBCL_452_log_signal.txt | 720,038 | Aug. 5, 2004 |
| 1686 | Table_1686_UC_DLBCL_458_log_signal.txt | 720,003 | Aug. 5, 2004 |
| 1687 | Table_1687_UC_DLBCL_460_log_signal.txt | 719,789 | Aug. 5, 2004 |
| 1688 | Table_1688_UC_DLBCL_491_log_signal.txt | 719,734 | Aug. 5, 2004 |
| 1689 | Table_1689_UC_DLBCL_528_log_signal.txt | 719,715 | Aug. 5, 2004 |
| 1690 | Table_1690_UC_DLBCL_615_log_signal.txt | 719,713 | Aug. 5, 2004 |
| 1691 | Table_1691_UC_DLBCL_625_log_signal.txt | 719,795 | Aug. 5, 2004 |
| 1692 | Table_1692_UC_DLBCL_664_log_signal.txt | 719,885 | Aug. 5, 2004 |
| 1693 | Table_1693_UC_DLBCL_671_log_signal.txt | 719,709 | Aug. 5, 2004 |
| 1694 | Table_1694_UC_DLBCL_682_log_signal.txt | 719,847 | Aug. 5, 2004 |
| 1695 | Table_1695_UC_DLBCL_683_log_signal.txt | 719,809 | Aug. 5, 2004 |
| 1696 | Table_1696_UC_DLBCL_684_log_signal.txt | 719,647 | Aug. 5, 2004 |
| 1697 | Table_1697_UC_DLBCL_748_log_signal.txt | 719,827 | Aug. 5, 2004 |
| 1698 | Table_1698_UC_DLBCL_751_log_signal.txt | 719,759 | Aug. 5, 2004 |
| 1699 | Table_1699_UC_DLBCL_808_log_signal.txt | 719,655 | Aug. 5, 2004 |
| 1700 | Table_1700_UC_DLBCL_831_log_signal.txt | 719,881 | Aug. 5, 2004 |
| 1701 | Table_1701_UC_DLBCL_834_log_signal.txt | 719,550 | Aug. 5, 2004 |
| 1702 | Table_1702_UC_DLBCL_838_log_signal.txt | 719,865 | Aug. 5, 2004 |
| 1703 | Table_1703_UC_DLBCL_851_log_signal.txt | 719,904 | Aug. 5, 2004 |
| 1704 | Table_1704_UC_DLBCL_854_log_signal.txt | 719,912 | Aug. 5, 2004 |
| 1705 | Table_1705_UC_DLBCL_855_log_signal.txt | 719,903 | Aug. 5, 2004 |
| 1706 | Table_1706_UC_DLBCL_856_log_signal.txt | 719,736 | Aug. 5, 2004 |
| 1707 | Table_1707_ABC_Stats.txt | 19,458666 | Aug. 22, 2004 |

-continued

| | | | |
|---|---|---|---|
| 1708 | Table_1708_BL_Stats.txt | 20,646,028 | Aug. 22, 2004 |
| 1709 | Table_1709_FH_Stats.txt | 20,631,528 | Aug. 22, 2004 |
| 1710 | Table_1710_FL_Stats.txt | 21,832,450 | Aug. 22, 2004 |
| 1711 | Table_1711_Gastric_MALT_Stats.txt | 19,429,850 | Aug. 22, 2004 |
| 1712 | Table_1712_GCB_Stats.txt | 19,460,177 | Aug. 22, 2004 |
| 1713 | Table_1713_LPC_Stats.txt | 20,569,572 | Aug. 22, 2004 |
| 1714 | Table_1714_LymbI_Stats.txt | 20,624,886 | Aug. 22, 2004 |
| 1715 | Table_1715_MCL_Stats.txt | 21,816,811 | Aug. 22, 2004 |
| 1716 | Table_1716_Mult_Myeloma_Stats.txt | 20,655,192 | Aug. 22, 2004 |
| 1717 | Table_1717_NMZ_Stats.txt | 20,633,800 | Aug. 22, 2004 |
| 1718 | Table_1718_PMBL_Stats.txt | 19,448,976 | Aug. 22, 2004 |
| 1719 | Table_1719_PTLD_Stats.txt | 20,634,040 | Aug. 22, 2004 |
| 1720 | Table_1720_SLL_Stats.txt | 20,625,386 | Aug. 22, 2004 |
| 1721 | Table_1721_Splenic_Stats.txt | 20,608,286 | Aug. 22, 2004 |
| 1722 | Table_1722_All_MALT_Stats.txt | 19,401341 | Aug. 22, 2004 |
| 1723 | Table_1723_DLBCL_Stats.txt | 18,266589 | Aug. 22, 2004 |
| 1725 | Table_1725_BL_2032_52748.txt | 182,232 | Aug. 21, 2004 |
| 1726 | Table_1726_BL_2033_52749.txt | 182,411 | Aug. 21, 2004 |
| 1727 | Table_1727_BL_2035_52750.txt | 182,439 | Aug. 21, 2004 |
| 1728 | Table_1728_BL_2036_52751.txt | 182,419 | Aug. 21, 2004 |
| 1729 | Table_1729_BL_2037_53294.txt | 182,586 | Aug. 21, 2004 |
| 1730 | Table_1730_BL_2038_52752.txt | 182,526 | Aug. 21, 2004 |
| 1731 | Table_1731_BL_2082_53031.txt | 182,367 | Aug. 23, 2004 |
| 1732 | Table_1732_BL_2083_53293.txt | 182,432 | Aug. 23, 2004 |
| 1733 | Table_1733_BL_2086_52754.txt | 182,376 | Aug. 23, 2004 |
| 1734 | Table_1734_BL_2088_52755.txt | 182,485 | Aug. 23, 2004 |
| 1735 | Table_1735_BL_2090_52758.txt | 182,594 | Aug. 23, 2004 |
| 1736 | Table_1736_BL_2091_52759.txt | 182,553 | Aug. 23, 2004 |
| 1737 | Table_1737_BL_2097_52760.txt | 182,456 | Aug. 23, 2004 |
| 1738 | Table_1738_BL_2099_52761.txt | 182,398 | Aug. 23, 2004 |
| 1739 | Table_1739_BL_2100_52762.txt | 182,615 | Aug. 23, 2004 |
| 1740 | Table_1740_BL_2101_52763.txt | 132,545 | Aug. 23, 2004 |
| 1741 | Table_1741_BL_2103_52764.txt | 182,403 | Aug. 23, 2004 |
| 1742 | Table_1742_BL_2125_52765.txt | 182,445 | Aug. 23, 2004 |
| 1743 | Table_1743_BL_2126_52766.txt | 182,313 | Aug. 23, 2004 |
| 1744 | Table_1744_BL_2127_52767.txt | 182,284 | Aug. 23, 2004 |
| 1745 | Table_1745_BL_2128_52768.txt | 182,178 | Aug. 23, 2004 |
| 1746 | Table_1746_BL_2129_52769.txt | 182,403 | Aug. 23, 2004 |
| 1747 | Table_1747_BL_2267_52770.txt | 182,514 | Aug. 23, 2004 |
| 1748 | Table_1748_BL_2268_52771.txt | 182,535 | Aug. 23, 2004 |
| 1749 | Table_1749_BL_2269_52772.txt | 182,371 | Aug. 23, 2004 |
| 1750 | Table_1750_BL_2271_52773.txt | 182,496 | Aug. 23, 2004 |
| 1751 | Table_1751_BL_2386_53355.txt | 182,265 | Aug. 23, 2004 |
| 1752 | Table_1752_BL_2387_53356.txt | 182,708 | Aug. 24, 2004 |
| 1753 | Table_1753_BL_2388_53357.txt | 182,539 | Aug. 24, 2004 |
| 1754 | Table_1754_BL_2389_53358.txt | 182,360 | Aug. 24, 2004 |
| 1755 | Table_1755_BL_2390_53359.txt | 182,449 | Aug. 25, 2004 |
| 1756 | Table_1756_BL_2391_53360.txt | 182,528 | Aug. 25, 2004 |
| 1757 | Table_1757_BL_2392_53361.txt | 182,519 | Aug. 25, 2004 |
| 1758 | Thbie_1758_BL_2393_53362.txt | 182,354 | Aug. 25, 2004 |
| 1759 | Table_1759_BL_2394_53363.txt | 182,321 | Aug. 25, 2004 |
| 1760 | Table_1760_BL_2395_53364.txt | 182,615 | Aug. 25, 2004 |
| 1761 | Table_1761_BL_2896_53365.txt | 182,395 | Aug. 25, 2004 |
| 1762 | Table_1762_BL_2400_53366.txt | 182,611 | Aug. 25, 2004 |
| 1763 | Table_1763_BL_2402_53367.txt | 182,344 | Aug. 25, 2004 |
| 1764 | Table_1764_BL_2405_53368.txt | 182,461 | Aug. 25, 2004 |
| 1765 | Table_1765_BL_2406_53369.txt | 182,368 | Aug. 25, 2004 |
| 1766 | Table_1766_BL_2409_53370.txt | 182,484 | Aug. 25, 2004 |
| 1767 | Table_1767_BL_2417_53377.txt | 182,524 | Aug. 25, 2004 |
| 1768 | Table_1768_BL_2418_53378.txt | 182,353 | Aug. 25, 2004 |
| 1769 | Table_1769_BL_2419_53379.txt | 182,524 | Aug. 25, 2004 |
| 1770 | Table_1770_BL_2420_53380.txt | 182,384 | Aug. 25, 2004 |
| 1771 | Table_1771_BL_2421_53381.txt | 182,445 | Aug. 26, 2004 |
| 1772 | Table_1772_BL_2422_53382.txt | 182,464 | Aug. 26, 2004 |
| 1923 | Table_1923_DLBCL_669_52074.txt | 182,457 | Aug. 23, 2004 |
| 1924 | Table_1924_DLBCL_671_52075.txt | 182,374 | Aug. 23, 2004 |
| 1925 | Table_1925_DLBCL_672_52076.txt | 182,417 | Aug. 23, 2004 |
| 1926 | Table_1926_DLBCL_674_52004.txt | 182,482 | Aug. 23, 2004 |
| 1927 | Table_1927_DLBCL_675_52095.txt | 182,127 | Aug. 23, 2004 |
| 1928 | Table_1928_DLBCL_676_52977.txt | 182,312 | Aug. 23, 2004 |
| 1929 | Table_1929_DLBCL_678_51829.txt | 182,308 | Aug. 23, 2004 |
| 1930 | Table_1938_DLBCL_681_52152.txt | 182,395 | Aug. 23, 2004 |
| 1931 | Table_1931_DLBCL_882_52154.txt | 182,477 | Aug. 23, 2004 |
| 1932 | Table_1932_DLBCL_683_52153.txt | 182,390 | Aug. 23, 2004 |
| 1933 | Table_1933_DLBCL_684_52155.txt | 182,346 | Aug. 23, 2004 |
| 1934 | Table_1934_DLBCL_687_52077.txt | 182,331 | Aug. 23, 2004 |
| 1935 | Table_1935_DLBCL_688_52078.txt | 182,333 | Aug. 23, 2004 |
| 1936 | Table_1936_DLBCL_689_52079.txt | 182,362 | Aug. 23, 2004 |
| 1937 | Table_1937_DLBCL_692_51825.txt | 182,320 | Aug. 23, 2004 |

-continued

| | | | |
|---|---|---|---|
| 1938 | Table_1938_DLBCL_694_52080.txt | 182,236 | Aug. 23, 2004 |
| 1939 | Table_1939_DLBCL_695_52081.txt | 182,341 | Aug. 23, 2004 |
| 1940 | Table_1940_DLBCL_698_51828.txt | 182,428 | Aug. 23, 2004 |
| 1941 | Table_1941_DLBCL_700_51835.txt | 182,292 | Aug. 23, 2004 |
| 1942 | Table_1942_DLBCL_701_52244.txt | 182,408 | Aug. 23, 2004 |
| 1943 | Table_1943_DLBCL_702_51834.txt | 182,320 | Aug. 23, 2004 |
| 1944 | Table_1944_DLBCL_704_52082.txt | 182,198 | Aug. 23, 2004 |
| 1945 | Table_1945_DLBCL_709_52123.txt | 182,355 | Aug. 23, 2004 |
| 1946 | Table_1946_DLBCL_710_52122.txt | 182,360 | Aug. 23, 2004 |
| 1947 | Table_1947_DLBCL_711_52083.txt | 182,453 | Aug. 23, 2004 |
| 1948 | Table_1948_DLBCL_712_52084.txt | 182,345 | Aug. 23, 2004 |
| 1949 | Table_1949_DLBCL_714_52125.txt | 182,513 | Aug. 23, 2004 |
| 1950 | Table_1950_DLBCL_717_52124.txt | 182,376 | Aug. 23, 2004 |
| 1951 | Table_1951_DLBCL_722_52181.txt | 182,411 | Aug. 23, 2004 |
| 1952 | Table_1952_DLBCL_724_52978.txt | 182,354 | Aug. 23, 2004 |
| 1953 | Table_1953_DLBCL_725_52979.txt | 182,349 | Aug. 23, 2004 |
| 1954 | Table_1954_DLBCL_726_52980.txt | 182,382 | Aug. 23, 2004 |
| 1955 | Table_1955_DLBCL_730_51833.txt | 182,186 | Aug. 23, 2004 |
| 1956 | Table_1956_DLBCL_731_51832.txt | 182,453 | Aug. 23, 2004 |
| 1957 | Table_1957_DLBCL_742_52085.txt | 182,445 | Aug. 23, 2004 |
| 1958 | Table_1958_DLBCL_744_52086.txt | 182,315 | Aug. 23, 2004 |
| 1959 | Table_1959_DLBCL_745_52096.txt | 182,461 | Aug. 23, 2004 |
| 1960 | Table_1960_DLBCL_747_52097.txt | 182,405 | Aug. 23, 2004 |
| 1961 | Table_1961_DLBCL_748_52245.txt | 182,432 | Aug. 23, 2004 |
| 1962 | Table_1962_DLBCL_749_51826.txt | 182,374 | Aug. 23, 2004 |
| 1963 | Table_1963_DLBCL_751_52278.txt | 182,393 | Aug. 23, 2004 |
| 1964 | Table_1964_DL8CL_753_51824.txt | 182,281 | Aug. 23, 2004 |
| 1965 | Table_1965_DLBCL_756_52098.txt | 182,335 | Aug. 23, 2004 |
| 1966 | Table_1966_DLBCL_758_51831.txt | 182,344 | Aug. 23, 2004 |
| 1967 | Table_1967_DLBCL_771_52983.txt | 182,405 | Aug. 23, 2004 |
| 1968 | Table_1968_DLBCL_772_52984.txt | 182,523 | Aug. 23, 2004 |
| 1969 | Table_1969_DLBCL_777_51827.txt | 182,369 | Aug. 23, 2004 |
| 1970 | Table_1970_DLBCL_779_51822.txt | 182,217 | Aug. 23, 2004 |
| 1971 | Table_1971_DLBCL_789_51821.txt | 182,375 | Aug. 23, 2004 |
| 1972 | Table_1972_DLBCL_792_51820.txt | 182,462 | Aug. 23, 2004 |
| 1773 | Table_1773_BL_2425_53383.txt | 182,690 | Aug. 25, 2004 |
| 1774 | Table_1774_BL_2426_53384.txt | 182,593 | Aug. 25, 2004 |
| 1775 | Table_1775_BL_2427_53385.txt | 182,514 | Aug. 25, 2004 |
| 1776 | Table_1776_BL_2428_53386.txt | 182,479 | Aug. 25, 2004 |
| 1777 | Table_1777_BL_2430_53387.txt | 182,369 | Aug. 25, 2004 |
| 1778 | Table_1778_BL_2431_53388.txt | 182,235 | Aug. 25, 2004 |
| 1779 | Table_1779_BL_2432_53389.txt | 182,564 | Aug. 25, 2004 |
| 1780 | Table_1780_BL_2433_53390.txt | 182,477 | Aug. 25, 2004 |
| 1781 | Table_1781_BL_2434_53391.txt | 182,590 | Aug. 25, 2004 |
| 1782 | Table_1782_BL_2435_53392.txt | 182,553 | Aug. 25, 2004 |
| 1783 | Table_1783_BL_2437_53393.txt | 182,354 | Aug. 26, 2004 |
| 1784 | Table_1784_BL_2438_53394.txt | 182,345 | Aug. 26, 2004 |
| 1785 | Table_1785_CD1N_1013_52338.txt | 182,526 | Aug. 25, 2004 |
| 1786 | Table_1756_CD1N_1116_52359.txt | 182,611 | Aug. 26, 2004 |
| 1787 | Table_1787_CD1N_1125_52360.txt | 182,605 | Aug. 26, 2004 |
| 1788 | Table_1788_CD1N_1265_52792.txt | 182,740 | Aug. 26, 2004 |
| 1789 | Table_1789_CD1N_2198_52794.txt | 182,606 | Aug. 26, 2004 |
| 1790 | Table_1790_CD1N_2272_52793.txt | 182,532 | Aug. 26, 2004 |
| 1791 | Table_1791_CD1N_930_52332.txt | 182,670 | Aug. 26, 2004 |
| 1792 | Table_1792_CD1N_950_52333.txt | 182,682 | Aug. 26, 2004 |
| 1793 | Table_1793_CD1N_985_52334.txt | 182,692 | Aug. 26, 2004 |
| 1794 | Table_1794_CD1N_991_52335.txt | 182,668 | Aug. 26, 2004 |
| 1795 | Table_1795_CLL_1275_52361.txt | 182,084 | Aug. 26, 2004 |
| 1796 | Table_1796_CLL_1277_52363.txt | 182,150 | Aug. 26, 2004 |
| 1797 | Table_1797_CLL_1278_52364.txt | 182,109 | Aug. 26, 2004 |
| 1798 | Table_1798_CLL_1279_52365.txt | 182,039 | Aug. 26, 2004 |
| 1799 | Table_1799_CLL_1283_52366.txt | 182,198 | Aug. 26, 2004 |
| 1800 | Table_1800_CLL_1292_52367.txt | 182,099 | Aug. 26, 2004 |
| 1801 | Table_1801_CLL_1293_52368.txt | 182,150 | Aug. 26, 2004 |
| 1802 | Table_1802_CLL_1294_52369.txt | 182,208 | Aug. 26, 2004 |
| 1803 | Table_1803_CLL_1297_52370.txt | 182,142 | Aug. 26, 2004 |
| 1804 | Table_1804_CLL_1298_52371.txt | 182,102 | Aug. 26, 2004 |
| 1805 | Table_1805_CLL_1302_52372.txt | 182,118 | Aug. 26, 2004 |
| 1806 | Table_1806_CLL_1311_52373.txt | 182,138 | Aug. 26, 2004 |
| 1807 | Table_1807_CLL_1344_51718.txt | 182,161 | Aug. 26, 2004 |
| 1808 | Table_1808_CLL_1379_51719.txt | 182,375 | Aug. 26, 2004 |
| 1809 | Table_1809_CLL_1381_51720.txt | 182,238 | Aug. 26, 2004 |
| 1810 | Table_1810_CLL_1394_51721.txt | 182,185 | Aug. 26, 2004 |
| 1811 | Table_1811_DLBCL_1000_51981.txt | 182,443 | Aug. 26, 2004 |
| 1812 | Table_1812_DLBCL_1001_52158.txt | 182,528 | Aug. 26, 2004 |
| 1813 | Table_1813_DLBCL_1002_51697.txt | 182,578 | Aug. 27, 2004 |
| 1814 | Table_1814_DLBCL_1004_52159.txt | 182,456 | Aug. 27, 2004 |
| 1815 | Table_1815_DLBCL_1005_52160.txt | 182,642 | Aug. 26, 2004 |
| 1816 | Table_1816_DLBCL_1006_52161.txt | 182,480 | Aug. 26, 2004 |

-continued

| | | | |
|---|---|---|---|
| 1817 | Table_1817_DLBCL_1007_52162.txt | 182,521 | Aug. 26, 2004 |
| 1818 | Table_1818_DLBCL_1008_5a163.txt | 182,559 | Aug. 26, 2004 |
| 1819 | Table_1819_DLBCL_1009_52971.txt | 182,393 | Aug. 26, 2004 |
| 1820 | Table_1820_DLBCL_1018_52165.txt | 182,598 | Aug. 27, 2004 |
| 1821 | Table_1821_DLBCL_1021_52166.txt | 182,432 | Aug. 27, 2004 |
| 1822 | Table_1822_DLBCL_1023_52167.txt | 182,504 | Aug. 27, 2004 |
| 1823 | Table_1823_DLBCL_1024_52168.txt | 182,695 | Aug. 27, 2004 |
| 1824 | Table_1824_DLBCL_1025_52169.txt | 182,615 | Aug. 27, 2004 |
| 1825 | Table_1825_DLBCL_1026_52170.txt | 182,575 | Aug. 27, 2004 |
| 1826 | Table_1826_DLBCL_1027_52171.txt | 182,667 | Aug. 27, 2004 |
| 1827 | Table_1827_DLBCL_1031_52172.txt | 182,494 | Aug. 27, 2004 |
| 1828 | Table_1828_DLBCL_1034_52231.txt | 182,455 | Aug. 27, 2004 |
| 1829 | Table_1829_DLBCL_1037_52200.txt | 182,455 | Aug. 30, 2004 |
| 1830 | Table_1830_DLBCL_1038_52232.txt | 182,577 | Aug. 30, 2004 |
| 1831 | Table_1831_DLBCL_1039_52233.txt | 182,501 | Aug. 30, 2004 |
| 1832 | Table_1832_DLBCL_1041_52201.txt | 182,599 | Aug. 30, 2004 |
| 1833 | Table_1833_DLBCL_1043_52202.txt | 182,598 | Aug. 30, 2004 |
| 1834 | Table_1834_DLBCL_1045_52203.txt | 182,555 | Aug. 30, 2004 |
| 1835 | Table_1835_DLBCL_1049_52204.txt | 182,569 | Aug. 30, 2004 |
| 1836 | Table_1836_DLBCL_1051_52173.txt | 182,324 | Aug. 30, 2004 |
| 1837 | Table_1837_DLBCL_1054_52174.txt | 182,590 | Aug. 30, 2004 |
| 1838 | Table_1838_DLBCL_1055_52175.txt | 182,433 | Aug. 30, 2004 |
| 1839 | Table_1838_DLBCL_1057_52176.txt | 182,524 | Aug. 30, 2004 |
| 1840 | Table_1840_DLBCL_1058_52177.txt | 182,386 | Aug. 30, 2004 |
| 1841 | Table_1841_DLBCL_1059_52178.txt | 182,651 | Aug. 30, 2004 |
| 1842 | Table_1842_DLBCL_1060_52179.txt | 182,633 | Aug. 30, 2004 |
| 1843 | Table_1843_DLBCL_1061_52180.txt | 182,530 | Aug. 30, 2004 |
| 1844 | Table_1844_DLBCL_1990_52108.txt | 182,550 | Aug. 30, 2004 |
| 1845 | Table_1845_DLBCL_1991_52109.txt | 182,503 | Aug. 30, 2004 |
| 1846 | Table_1846_DLBCL_1994_52110.txt | 182,422 | Aug. 30, 2004 |
| 1847 | Table_1847_DLBCL_2001_52111.txt | 182,439 | Aug. 30, 2004 |
| 1848 | Table_1848_DLBCL_2017_52112.txt | 182,354 | Aug. 31, 2004 |
| 1849 | Table_1849_DLBCL_2018_52113.txt | 182,479 | Aug. 31, 2004 |
| 1850 | Table_1850_DLBCL_2095_52258.txt | 182,492 | Aug. 31, 2004 |
| 1851 | Table_1851_DLBCL_304_52190.txt | 182,498 | Aug. 31, 2004 |
| 1852 | Table_1852_DLBCL_305_52191.txt | 182,502 | Aug. 31, 2004 |
| 1853 | Table_1853_DLBCL_306_52192.txt | 182,549 | Aug. 31, 2004 |
| 1854 | Table_1854_DLBCL_309_52973.txt | 182,434 | Aug. 31, 2004 |
| 1855 | Table_1855_DLBCL_310_52194.txt | 182,489 | Aug. 30, 2004 |
| 1856 | Table_1856_DLBCL_412_52009.txt | 182,344 | Aug. 30, 2004 |
| 1857 | Table_1857_DLBCL_413_52974.txt | 182,340 | Aug. 30, 2004 |
| 1858 | Table_1858_DLBCL_415_51696.txt | 182,507 | Aug. 30, 2004 |
| 1859 | Table_1859_DLBCL_421_52975.txt | 182,519 | Aug. 30, 2004 |
| 1860 | Table_1860_DLBCL_424_51989.txt | 182,537 | Aug. 30, 2004 |
| 1861 | Table_1861_DLBCL_428_51985.txt | 182,415 | Aug. 30, 2004 |
| 1862 | Table_1862_DLBCL_432_52011.txt | 182,400 | Aug. 30, 2004 |
| 1863 | Table_1863_DLBCL_433_52010.txt | 182,501 | Aug. 30, 2004 |
| 1864 | Table_1864_DLBCL_434_51693.txt | 182,610 | Aug. 30, 2004 |
| 1865 | Table_1865_DLBCL_438_51998.txt | 182,437 | Aug. 30, 2004 |
| 1866 | Table_1866_DLBCL_439_52252.txt | 182,417 | Aug. 30, 2004 |
| 1867 | Table_1867_DLBCL_446_52004.txt | 182,554 | Aug. 31, 2004 |
| 1868 | Table_1868_DLBCL_449_51995.txt | 182,556 | Aug. 31, 2004 |
| 1869 | Table_1869_DLBCL_452_52114.txt | 182,501 | Aug. 31, 2004 |
| 1870 | Table_1870_DLBCL_458_51990.txt | 182,494 | Aug. 31, 2004 |
| 1871 | Table_1871_DLBCL_459_51695.txt | 182,583 | Aug. 31, 2004 |
| 1872 | Table_1872_DLBCL_460_51986.txt | 182,618 | Aug. 31, 2004 |
| 1873 | Table_1873_DLBCL_462_51999.txt | 182,431 | Aug. 31, 2004 |
| 1874 | Table_1874_DLBCL_470_52188.txt | 182,400 | Aug. 31, 2004 |
| 1875 | Table_1875_DLBCL_477_52724.txt | 182,482 | Aug. 31, 2004 |
| 1876 | Table_1876_DLBCL_479_52017.txt | 182,484 | Aug. 31, 2004 |
| 1877 | Table_1877_DLBCL_481_51992.txt | 182,632 | Aug. 31, 2004 |
| 1878 | Table_1878_DLBCL_482_52013.txt | 182,394 | Aug. 31, 2004 |
| 1879 | Table_1879_DLBCL_491_51982.txt | 182,481 | Aug. 31, 2004 |
| 1880 | Table_1880_DLBCL_492_51694.txt | 182,573 | Aug. 31, 2004 |
| 1881 | Table_1881_DLBCL_517_52018.txt | 182,479 | Aug. 31, 2004 |
| 1882 | Table_1882_DLBCL_523_52056.txt | 182,366 | Aug. 31, 2004 |
| 1883 | Table_1883_DLBCL_524_51993.txt | 182,690 | Aug. 31, 2004 |
| 1884 | Table_1884_DLBCL_528_52001.txt | 182,438 | Aug. 31, 2004 |
| 1885 | Table_1885_DLBCL_529_52002.txt | 182,388 | Aug. 31, 2004 |
| 1886 | Table_1886_DLBCL_533_52099.txt | 182,603 | Aug. 31, 2004 |
| 1887 | Table_1887_DLBCL_537_52003.txt | 182,396 | Aug. 31, 2004 |
| 1888 | Table_1888_DLBCL_538_51698.txt | 182,531 | Aug. 31, 2004 |
| 1889 | Table_1889_DLBCL_541_52100.txt | 182,500 | Aug. 31, 2004 |
| 1890 | Table_1890_DLBCL_543_52101.txt | 182,754 | Aug. 31, 2004 |
| 1891 | Table_1891_DLBCL_544_52115.txt | 182,571 | Aug. 31, 2004 |
| 1892 | Table_1892_DLBCL_545_52117.txt | 182,644 | Aug. 31, 2004 |
| 1893 | Table_1893_DLBCL_547_52089.txt | 182,539 | Aug. 31, 2004 |
| 1894 | Table_1894_DLBCL_549_52090.txt | 182,569 | Aug. 31, 2004 |
| 1895 | Table_1895_DLBCL_550_51836.txt | 182,321 | Aug. 23, 2004 |

-continued

| | | | |
|---|---|---|---|
| 1896 | Table_1896_DLBCL_553_52091.txt | 182,456 | Aug. 23, 2004 |
| 1897 | Table_1897_DLBCL_565_52092.txt | 182,388 | Aug. 23, 2004 |
| 1898 | Table_1898_DLBCL_572_52093.txt | 182,395 | Aug. 23, 2004 |
| 1899 | Table_1899_DLBCL_577_52102.txt | 182,336 | Aug. 23, 2004 |
| 1900 | Table_1900_DLBCL_615_52014.txt | 182,286 | Aug. 23, 2004 |
| 1901 | Table_1901_DLBCL_616_52015.txt | 182,089 | Aug. 23, 2004 |
| 1902 | Table_1902_DLBCL_617_52189.txt | 182,485 | Aug. 23, 2004 |
| 1903 | Table_1903_DLBCL_618_52012.txt | 182,239 | Aug. 23, 2004 |
| 1904 | Table_1904_DLBCL_619_52005.txt | 182,336 | Aug. 23, 2004 |
| 1905 | Table_1905_DLBCL_623_51984.txt | 182,212 | Aug. 23, 2004 |
| 1906 | Table_1906_DLBCL_625_52253.txt | 182,476 | Aug. 23, 2004 |
| 1907 | Table_1907_DLBCL_626_52007.txt | 182,302 | Aug. 23, 2004 |
| 1908 | Table_1908_DLBCL_627_52006.txt | 182,273 | Aug. 2$, 2004 |
| 1909 | Table_1909_DLBCL_633_52150.txt | 182,449 | Aug. 23, 2004 |
| 1910 | Table_1910_DLBCL_638_52151.txt | 182,493 | Aug. 23, 2004 |
| 1911 | Table_1911_DLBCL_642_52254.txt | 182,293 | Aug. 23, 2004 |
| 1912 | Table_1912_DLBCL_644_52116.txt | 182,430 | Aug. 23, 2004 |
| 1913 | Table_1913_DLBCL_645_52118.txt | 182,332 | Aug. 23, 2004 |
| 1914 | Table_1914_DLBCL_646_52119.txt | 182,252 | Aug. 23, 2004 |
| 1915 | Table_1915_DLBCL_651_52121.txt | 182,380 | Aug. 23, 2004 |
| 1916 | Table_1916_DLBCL_652_52120.txt | 182,395 | Aug. 23, 2004 |
| 1917 | Table_1917_DLBCL_654_52016.txt | 182,268 | Aug. 23, 2004 |
| 1918 | Table_1918_DLBCL_660_52057.txt | 182,197 | Aug. 23, 2004 |
| 1919 | Table_1919_DLBCL_661_52058.txt | 182,346 | Aug. 23, 2004 |
| 1920 | Table_1920_DLBCL_663_52071.txt | 182,356 | Aug. 23, 2004 |
| 1921 | Table_1921_DLBCL_664_52072.txt | 182,385 | Aug. 23, 2004 |
| 1922 | Table_1922_DLBCL_668_52073.txt | 182,322 | Aug. 23, 2004 |
| 1973 | Table_1973_DLBCL_795_52156.txt | 182,448 | Aug. 23, 2004 |
| 1974 | Table_1974_DLBCL_797_52103.txt | 182,220 | Aug. 23, 2004 |
| 1975 | Table_1975_DLBCL_800_52337.txt | 182,289 | Aug. 23, 2004 |
| 1976 | Table_1976_DLBCL_803_52163.txt | 182,306 | Aug. 23, 2004 |
| 1977 | Table_1977_DLBCL_807_52104.txt | 182,252 | Aug. 23, 2004 |
| 1978 | Table_1978_DLBCL_808_52126.txt | 182,358 | Aug. 23, 2004 |
| 1979 | Table_1979_DLBCL_809_52105.txt | 182,334 | Aug. 23, 2004 |
| 1980 | Table_1980_DLBCL_810_52106.txt | 182,272 | Aug. 23, 2004 |
| 1981 | Table_1981_DLBCL_816_52985.txt | 182,117 | Aug. 23, 2004 |
| 1982 | Table_1982_DLBCL_817_52986.txt | 182,236 | Aug. 23, 2004 |
| 1983 | Table_1983_DLBCL_818_52184.txt | 182,423 | Aug. 23, 2004 |
| 1984 | Table_1984_DLBCL_819_52987.txt | 182,345 | Aug. 23, 2004 |
| 1985 | Table_1985_DLBCL_820_52988.txt | 182,366 | Aug. 23, 2004 |
| 1986 | Table_1986_DLBCL_821_52339.txt | 182,490 | Aug. 23, 2004 |
| 1987 | Table_1987_DLBCL_823_52989.txt | 182,102 | Aug. 23, 2004 |
| 1988 | Table_1988_DLBCL_831_51996.txt | 182,390 | Aug. 23, 2004 |
| 1989 | Table_1989_DLBCL_832_51997.txt | 182,459 | Aug. 23, 2004 |
| 1990 | Table_1990_DLBCL_834_52186.txt | 182,214 | Aug. 23, 2004 |
| 1991 | Table_1991_DLBCL_835_51988.txt | 182,362 | Aug. 23, 2004 |
| 1992 | Table_1992_DLBCL_836_52000.txt | 182,322 | Aug. 23, 2004 |
| 1993 | Table_1993_DLBCL_838_51987.txt | 182,402 | Aug. 23, 2004 |
| 1994 | Table_1994_DLBCL_839_51991.txt | 182,377 | Aug. 23, 2004 |
| 1995 | Table_1995_DLBCL_840_52990.txt | 182,527 | Aug. 23, 2004 |
| 1996 | Table_1996_DLBCL_841_52087.txt | 182,353 | Aug. 23, 2004 |
| 1997 | Table_1997_DLBCL_847_52187.txt | 182,422 | Aug. 23, 2004 |
| 1998 | Table_1998_DLBCL_851_52991.txt | 182,280 | Aug. 23, 2004 |
| 1999 | Table_1999_DLBCL_854_52088.txt | 182,372 | Aug. 23, 2004 |
| 2000 | Table_2000_DLBCL_855_51837.txt | 182,472 | Aug. 23, 2004 |
| 2001 | Table_2001_DLBCL_856_52992.txt | 182,213 | Aug. 23, 2004 |
| 2002 | Table_2002_DLBCL_858_52993.txt | 182,472 | Aug. 23, 2004 |
| 2003 | Table_2003_DLBCL_860_52195.txt | 182,229 | Aug. 23, 2004 |
| 2004 | Table_2004_DLBCL_871_52196.txt | 182,241 | Aug. 23, 2004 |
| 2005 | Table_2005_DLBCL_872_51700.txt | 182,279 | Aug. 23, 2004 |
| 2006 | Table_2005_DLBCL_874_52107.txt | 182,412 | Aug. 23, 2004 |
| 2007 | Table_2007_ULBOL_875_52246.txt | 182,286 | Aug. 23, 2004 |
| 2008 | Table_2008_DLBCL_912_52197.txt | 182,328 | Aug. 23, 2004 |
| 2009 | Table_2009_DLBCL_995_52198.txt | 182,356 | Aug. 23, 2004 |
| 2010 | Table_2010_DLBCL_996_52199.txt | 182,251 | Aug. 23, 2004 |
| 2011 | Table_2011_DLBCL_998_52157.txt | 182,354 | Aug. 23, 2004 |
| 2012 | Table_2012_FH_2043_52774.txt | 182,536 | Aug. 23, 2004 |
| 2013 | Table_2013_FH_2045_52775.txt | 182,609 | Aug. 23, 2004 |
| 2014 | Table_2014_FH_2047_52776.txt | 182,602 | Aug. 23, 2004 |
| 2015 | Table_2015_FH_2120_52777.txt | 182,548 | Aug. 23, 2004 |
| 2016 | Table_2016_FH_2123_52778.txt | 182,516 | Aug. 23, 2004 |
| 2017 | Table_2017_FH_2124_52779.txt | 182,535 | Aug. 23, 2004 |
| 2018 | Table_2018_FH_2138_52780.txt | 182,370 | Aug. 23, 2004 |
| 2019 | Table_2019_FH_2139_52781.txt | 182,510 | Aug. 23, 2004 |
| 2020 | Table_2020_FH_2140_52782.txt | 182,561 | Aug. 23, 2004 |
| 2021 | Table_2021_FH_2141_52783.txt | 182,575 | Aug. 23, 2004 |
| 2022 | Table_2022_FH_2142_52784.txt | 182,552 | Aug. 23, 2004 |
| 2023 | Table_2023_FH_2143_52785.txt | 182,502 | Aug. 23, 2004 |
| 2024 | Table_2024_FH_2159_52786.txt | 182,442 | Aug. 23, 2004 |

| | | | |
|---|---|---|---|
| 2025 | Table_2025_FH_2160_52787.txt | 182,430 | Aug. 23, 2004 |
| 2026 | Table_2026_FH_2161_52788.txt | 182,442 | Aug. 23, 2004 |
| 2027 | Table_2027_FH_2162_52789.txt | 182,507 | Aug. 23, 2004 |
| 2028 | Table_2028_FH_2164_52790.txt | 182,524 | Aug. 23, 2004 |
| 2029 | Table_2029_FH_2167_52791.txt | 182,593 | Aug. 23, 2004 |
| 2036 | Table_2030_FL_1073_52458.txt | 182,551 | Aug. 23, 2004 |
| 2031 | Table_2031_FL_1074_52459.txt | 182,424 | Aug. 23, 2004 |
| 2032 | Table_2032_FL_1075_52460.txt | 182,490 | Aug. 23, 2004 |
| 2033 | Table_2033_FL_1076_52461.txt | 182,391 | Aug. 23, 2004 |
| 2034 | Table_2034_FL_1077_52463.txt | 182,504 | Aug. 23, 2004 |
| 2035 | Table_2035_FL_1078_52464.txt | 182,477 | Aug. 23, 2004 |
| 2036 | Table_2036_FL_1080_52465.txt | 182,534 | Aug. 23, 2004 |
| 2037 | Table_2037_FL_1081_52660.txt | 182,448 | Aug. 23, 2004 |
| 2038 | Table_2038_FL_1083_52466.txt | 182,566 | Aug. 23, 2004 |
| 2039 | Table_2039_FL_1085_52467.txt | 182,520 | Aug. 23, 2004 |
| 2040 | Table_2040_FL_1086_52468.txt | 182,529 | Aug. 23, 2004 |
| 2041 | Table_2041_FL_1087_52469.txt | 182,476 | Aug. 23, 2004 |
| 2042 | Table_2042_FL_1088_52470.txt | 182,466 | Aug. 23, 2004 |
| 2043 | Table_2043_FL_1089_52471.txt | 182,361 | Aug. 23, 2004 |
| 2044 | Table_2044_FL_1090_52472.txt | 182,477 | Aug. 23, 2004 |
| 2045 | Table_2045_FL_1097_52473.txt | 182,532 | Aug. 23, 2004 |
| 2046 | Table_2046_FL_1098_52474.txt | 182,589 | Aug. 23, 2004 |
| 2047 | Table_2047_FL_1099_52475.txt | 182,513 | Aug. 23, 2004 |
| 2048 | Table_2048_FL_1102_52648.txt | 182,505 | Aug. 23, 2004 |
| 2049 | Table_2049_FL_1104_52649.txt | 182,423 | Aug. 23, 2004 |
| 2050 | Table_2050_FL_1106_52476.txt | 182,475 | Aug. 23, 2004 |
| 2051 | Table_2051_FL_1107_52650.txt | 182,528 | Aug. 23, 2004 |
| 2052 | Table_2052_FL_1183_52651.txt | 182,441 | Aug. 23, 2004 |
| 2053 | Table_2053_FL_1184_52652.txt | 182,560 | Aug. 23, 2004 |
| 2054 | Table_2054_FL_1185_52653.txt | 182,459 | Aug. 23, 2004 |
| 2055 | Table_2055_FL_1186_52654.txt | 182,532 | Aug. 23, 2004 |
| 2056 | Table_2056_FL_1416_52655.txt | 182,489 | Aug. 23, 2004 |
| 2057 | Table_2057_FL_1417_52656.txt | 182,381 | Aug. 23, 2004 |
| 2058 | Table_2058_FL_1418_52657.txt | 182,418 | Aug. 23, 2004 |
| 2059 | Table_2059_FL_1419_52658.txt | 182,527 | Aug. 23, 2004 |
| 2060 | Table_2060_FL_1422_52659.txt | 182,462 | Aug. 23, 2004 |
| 2061 | Table_2061_FL_1425_51703.txt | 182,392 | Aug. 23, 2004 |
| 2062 | Table_2062_FL_1426_51702.txt | 182,416 | Aug. 23, 2004 |
| 2063 | Table_2063_FL_1427_52997.txt | 182,307 | Aug. 23, 2004 |
| 2064 | Table_2064_FL_1428_51705.txt | 182,460 | Aug. 23, 2004 |
| 2065 | Table_2065_FL_1429_52661.txt | 182,411 | Aug. 23, 2004 |
| 2066 | Table_2066_FL_1432_52999.txt | 182,463 | Aug. 23, 2004 |
| 2067 | Table_2067_FL_1434_52662.txt | 182,762 | Aug. 23, 2004 |
| 2068 | Table_2068_FL_1436_52663.txt | 182,426 | Aug. 23, 2004 |
| 2069 | Table_2069_FL_1440_52664.txt | 182,383 | Aug. 23, 2004 |
| 2070 | Table_2070_FL_1445_52665.txt | 182,413 | Aug. 23, 2004 |
| 2071 | Table_2071_FL_1450_52666.txt | 182,480 | Aug. 23, 2004 |
| 2072 | Table_2072_FL_1472_52667.txt | 182,367 | Aug. 23, 2004 |
| 2073 | Table_2073_FL_1473_53000.txt | 182,558 | Aug. 23, 2004 |
| 2074 | Table_2074_FL_1474_53001.txt | 182,648 | Aug. 23, 2004 |
| 2075 | Table_2075_FL_1476_52668.txt | 182,438 | Aug. 23, 2004 |
| 2076 | Table_2076_FL_1477_52669.txt | 182,425 | Aug. 23, 2004 |
| 2077 | Table_2077_FL_1478_52670.txt | 182,377 | Aug. 23, 2004 |
| 2078 | Table_2078_FL_1479_52671.txt | 182,411 | Aug. 23, 2004 |
| 2079 | Table_2079_FL_1480_52672.txt | 182,428 | Aug. 23, 2004 |
| 2080 | Table_2080_FL_1579_52673.txt | 182,439 | Aug. 23, 2004 |
| 2081 | Tabl8_2081_FL_1580_52674.txt | 182,552 | Aug. 23, 2004 |
| 2082 | Table_2082_FL_1581_52675.txt | 182,497 | Aug. 23, 2004 |
| 2083 | Table_2083_FL_1552_52676.txt | 182,370 | Aug. 23, 2004 |
| 2084 | Table_2084_FL_1583_52677.txt | 182,535 | Aug. 23, 2004 |
| 2085 | Table_2085_FL_1584_52678.txt | 182,524 | Aug. 23, 2004 |
| 2086 | Table_2086_FL_1585_52726.txt | 182,443 | Aug. 23, 2004 |
| 2087 | Table_2087_FL_1586_52679.txt | 182,465 | Aug. 23, 2004 |
| 2088 | Table_2088_FL_1588_52680.txt | 182,490 | Aug. 23, 2004 |
| 2089 | Table_2089_FL_1589_52681.txt | 182,477 | Aug. 23, 2004 |
| 2090 | Table_2090_FL_1591_52682.txt | 182,513 | Aug. 23, 2004 |
| 2091 | Table_2091_FL_1594_52683.txt | 182,498 | Aug. 23, 2004 |
| 2092 | Table_2092_FL_1595_52684.txt | 182,547 | Aug. 23, 2004 |
| 2093 | Table_2093_FL_1598_52685.txt | 182,415 | Aug. 23, 2004 |
| 2094 | Table_2004_FL_1599_52686.txt | 182,531 | Aug. 23, 2004 |
| 2095 | Table_2095_FL_1603_52687.txt | 182,544 | Aug. 23, 2004 |
| 2090 | Table_2096_FL_1604_52688.txt | 182,394 | Aug. 23, 2004 |
| 2097 | Table_2097_FL_1606_52689.txt | 182,440 | Aug. 23, 2004 |
| 2098 | Table_2098_FL_1607_52690.txt | 182,527 | Aug. 23, 2004 |
| 2099 | Table_2099_FL_1608_52691.txt | 182,440 | Aug. 23, 2004 |
| 2100 | Table_2100_FL_1610_52692.txt | 182,452 | Aug. 23, 2004 |
| 2101 | Table_2101_FL_1611_52693.txt | 182,488 | Aug. 23, 2004 |
| 2102 | Table_2102_FL_1616_52694.txt | 182,438 | Aug. 23, 2004 |
| 2103 | Table_2103_FL_1617_52695.txt | 182,496 | Aug. 23, 2004 |

-continued

| | | | | |
|---|---|---|---|---|
| 2104 | Table_2104_FL_1619_52696.txt | | 182,544 | Aug. 23, 2004 |
| 2105 | Table_2105_FL_1622_52388.txt | | 182,452 | Aug. 23, 2004 |
| 2106 | Table_2106_FL_1623_52389.txt | | 182,521 | Aug. 23, 2004 |
| 2107 | Table_2107_FL_1624_52390.txt | | 182,474 | Aug. 23, 2004 |
| 2108 | Table_2108_FL_1625_52391.txt | | 182,364 | Aug. 23, 2004 |
| 2109 | Table_2109_FL_1626_52392.txt | | 182,350 | Aug. 23, 2004 |
| 2110 | Table_2110_FL_1627_52393.txt | | 182,558 | Aug. 23, 2004 |
| 2111 | Table_2111_FL_1628_52394.txt | | 182,561 | Aug. 23, 2004 |
| 2112 | Table_2112_FL_1637_52395.txt | | 182,562 | Aug. 23, 2004 |
| 2113 | Table_2113_FL_1638_53003.txt | | 182,388 | Aug. 23, 2004 |
| 2114 | Table_2114_FL_1639_52396.txt | | 182,466 | Aug. 23, 2004 |
| 2115 | Table_2115_FL_1643_52397.txt | | 182,502 | Aug. 23, 2004 |
| 2116 | Table_2116_FL_1644_52398.txt | | 182,453 | Aug. 23, 2004 |
| 2117 | Table_2117_FL_1645_52399.txt | | 182,430 | Aug. 23, 2004 |
| 2118 | Table_2118_FL_1646_52400.txt | | 182,457 | Aug. 23, 2004 |
| 2119 | Table_2119_FL_1647_52401.txt | | 182,386 | Aug. 23, 2004 |
| 2120 | Table_2120_FL_1648_52402.txt | | 182,358 | Aug. 23, 2004 |
| 2121 | Table_2121_FL_1652_52403.txt | | 182,506 | Aug. 23, 2004 |
| 2122 | Table_2122_FL_1654_53004.txt | | 182,392 | Aug. 23, 2004 |
| 2123 | Table_2123_FL_1655_52404.txt | | 182,479 | Aug. 23, 2004 |
| 2124 | Table_2124_FL_1656_52405.txt | | 182,364 | Aug. 23, 2004 |
| 2125 | Table_2125_FL_1657_52406.txt | | 182,439 | Aug. 23, 2004 |
| 2126 | Table_2126_FL_1660_52407.txt | | 182,458 | Aug. 23, 2004 |
| 2127 | Table_2127_FL_1661_52408.txt | | 182,602 | Aug. 23, 2004 |
| 2128 | Table_2128_FL_1662_52409.txt | | 182,469 | Aug. 23, 2004 |
| 2129 | Table_2129_FL_1664_52410.txt | | 182,507 | Aug. 23, 2004 |
| 2130 | Table_2130_FL_1669_52411.txt | | 182,451 | Aug. 23, 2004 |
| 2131 | Table_2131_FL_1670_52412.txt | | 182,471 | Aug. 23, 2004 |
| 2132 | Table_2132_FL_1675_52413.txt | | 182,442 | Aug. 23, 2004 |
| 2133 | Table_2133_FL_1681_52421.txt | | 182,476 | Aug. 23, 2004 |
| 2134 | Table_2134_FL_1683_52422.txt | | 182,531 | Aug. 23, 2004 |
| 2135 | Table_2135_FL_1684_52423.txt | | 182,455 | Aug. 23, 2004 |
| 2136 | Table_2136_FL_1716_52414.txt | | 182,416 | Aug. 23, 2004 |
| 2137 | Table_2137_FL_1717_52415.txt | | 182,526 | Aug. 23, 2004 |
| 2138 | Table_2138_FL_1718_53006.txt | | 182,411 | Aug. 23, 2004 |
| 2139 | Table_2139_FL_1719_52416.txt | | 182,449 | Aug. 23, 2004 |
| 2140 | Table_2140_FL_1720_53025.txt | | 182,424 | Aug. 23, 2004 |
| 2141 | Table_2141_FL_1729_52417.txt | | 182,495 | Aug. 23, 2004 |
| 2142 | Table_2142_FL_1732_52418.txt | | 182,340 | Aug. 23, 2004 |
| 2143 | Table_2143_FL_1735_52419.txt | | 182,212 | Aug. 23, 2004 |
| 2144 | Table_2144_FL_1761_52424.txt | | 182,512 | Aug. 23, 2004 |
| 2145 | Table_2145_FL_1764_52425.txt | | 182,533 | Aug. 23, 2004 |
| 2146 | Table_2146_FL_1768_52426.txt | | 182,520 | Aug. 23, 2004 |
| 2147 | Table_2147_FL_1771_52427.txt | | 182,487 | Aug. 23, 2004 |
| 2148 | Table_2148_FL_1772_52428.txt | | 182,547 | Aug. 23, 2004 |
| 2149 | Table_2149_FL_1788_52429.txt | | 182,481 | Aug. 23, 2004 |
| 2150 | Table_2150_FL_1790_53008.txt | | 182,535 | Aug. 23, 2004 |
| 2151 | Table_2151_FL_1792_52431.txt | | 182,458 | Aug. 23, 2004 |
| 2152 | Table_2152_FL_1795_52432.txt | | 182,548 | Aug. 23, 2004 |
| 2153 | Table_2153_FL_1797_52433.txt | | 182,519 | Aug. 23, 2004 |
| 2154 | Table_2154_FL_1799_52434.txt | | 182,430 | Aug. 23, 2004 |
| 2155 | Table_2155_FL_1810_52435.txt | | 182,362 | Aug. 23, 2004 |
| 2456 | Table_2156_FL_1811_52436.txt | | 182,501 | Aug. 23, 2004 |
| 2157 | Table_2157_FL_1825_52437.txt | | 182,460 | Aug. 23, 2004 |
| 2158 | Table_2158_FL_1827_52438.txt | | 182,528 | Aug. 23, 2004 |
| 2159 | Table_2159_FL_1828_52439.txt | | 182,506 | Aug. 23, 2004 |
| 2160 | Table_2160_FL_1829_52440.txt | | 182,533 | Aug. 23, 2004 |
| 2161 | Table_2161_FL_1830_52441.txt | | 182,448 | Aug. 23, 2004 |
| 2162 | Table_2162_FL_1833_52442.txt | | 182,523 | Aug. 23, 2004 |
| 2163 | Table_2163_FL_1834_52443.txt | | 182,477 | Aug. 23, 2004 |
| 2164 | Table_2164_FL_1835_52444.txt | | 182,469 | Aug. 23, 2004 |
| 2165 | Table_2165_FL_1836_52445.txt | | 182,504 | Aug. 23, 2004 |
| 2166 | Table_2166_FL_1837_52446.txt | | 182,453 | Aug. 23, 2004 |
| 2167 | Table_2167_FL_1838_52447.txt | | 182,465 | Aug. 23, 2004 |
| 2168 | Table_2168_FL_1839_52448.txt | | 182,343 | Aug. 23, 2004 |
| 2169 | Table_2169_FL_1841_52449.txt | | 182,524 | Aug. 23, 2004 |
| 2170 | Table_2170_FL_1842_52450.txt | | 182,510 | Aug. 23, 2004 |
| 2171 | Table_2171_FL_1844_52451.txt | | 182,456 | Aug. 23, 2004 |
| 2172 | Table_2172_FL_1845_52452.txt | | 182,582 | Aug. 23, 2004 |
| 2173 | Table_2173_FL_1846_52477.txt | | 182,514 | Aug. 23, 2004 |
| 2174 | Table_2174_FL_1848_52478.txt | | 182,510 | Aug. 23, 2004 |
| 2175 | Table_2175_FL_1850_52479.txt | | 182,504 | Aug. 23, 2004 |
| 2176 | Table_2176_FL_1851_52480.txt | | 182,536 | Aug. 23, 2004 |
| 2177 | Table_2177_FL_1853_52481.txt | | 182,501 | Aug. 23, 2004 |
| 2178 | Table_2178_FL_1854_52482.txt | | 182,554 | Aug. 23, 2004 |
| 2179 | Table_2179_FL_1855_52483.txt | | 182,515 | Aug. 23, 2004 |
| 2180 | Table_2180_FL_1857_52484.txt | | 182,644 | Aug. 23, 2004 |
| 2181 | Table_2181_FL_1861_52453.txt | | 182,539 | Aug. 23, 2004 |
| 2182 | Table_2182_FL_1862_52454.txt | | 182,489 | Aug. 23, 2004 |

-continued

| | | | |
|---|---|---|---|
| 2183 | Table_2183_FL_1863_52455.txt | 182,508 | Aug. 23, 2004 |
| 2184 | Table_2184_FL_1864_52456.txt | 182,617 | Aug. 23, 2004 |
| 2185 | Table_2185_FL_1866_52457.txt | 182,516 | Aug. 23, 2004 |
| 2186 | Table_2186_FL_1870_52697.txt | 182,562 | Aug. 23, 2004 |
| 2187 | Table_2187_FL_1873_52698.txt | 182,436 | Aug. 23, 2004 |
| 2188 | Table_2188_FL_1874_52699.txt | 182,463 | Aug. 23, 2004 |
| 2189 | Table_2189_FL_1876_52700.txt | 182,466 | Aug. 23, 2004 |
| 2190 | Table_2190_FL_1879_52701.txt | 182,465 | Aug. 23, 2004 |
| 2191 | Table_2191_FL_1880_52702.txt | 182,458 | Aug. 23, 2004 |
| 2192 | Table_2192_FL_1882_52704.txt | 182,512 | Aug. 23, 2004 |
| 2193 | Table_2193_FL_1884_52705.txt | 182,489 | Aug. 23, 2004 |
| 2194 | Table_2194_FL_1885_52706.txt | 182,507 | Aug. 23, 2004 |
| 2195 | Table_2195_FL_1887_52707.txt | 182,481 | Aug. 23, 2004 |
| 2196 | Table_2196_FL_1888_52708.txt | 182,550 | Aug. 23, 2004 |
| 2197 | Table_2197_FL_1890_52709.txt | 182,428 | Aug. 23, 2004 |
| 2198 | Table_2198_FL_1894_52710.txt | 182,442 | Aug. 23, 2004 |
| 2199 | Table_2199_FL_1896_52711.txt | 182,482 | Aug. 23, 2004 |
| 2200 | Table_2200_FL_1897_52756.txt | 182,367 | Aug. 23, 2004 |
| 2201 | Table_2201_FL_1898_52757.txt | 182,315 | Aug. 23, 2004 |
| 2202 | Table_2202_FL_1900_52712.txt | 182,352 | Aug. 23, 2004 |
| 2203 | Table_2203_FL_1903_52713.txt | 182,354 | Aug. 23, 2004 |
| 2204 | Table_2204_FL_1904_52714.txt | 182,421 | Aug. 23, 2004 |
| 2205 | Table_2205_FL_1905_52715.txt | 182,450 | Aug. 23, 2004 |
| 2206 | Table_2206_FL_1906_53010.txt | 182,295 | Aug. 23, 2004 |
| 2207 | Table_2207_FL_1907_52717.txt | 182,268 | Aug. 23, 2004 |
| 2208 | Table_2208_FL_1910_52718.txt | 182,425 | Aug. 23, 2004 |
| 2209 | Table_2209_FL_1912_52719.txt | 182,519 | Aug. 23, 2004 |
| 2210 | Table_2210_FL_1913_52720.txt | 182,464 | Aug. 23, 2004 |
| 2211 | Table_2211_FL_1916_52721.txt | 182,418 | Aug. 23, 2004 |
| 2212 | Table_2212_FL_1918_52722.txt | 182,529 | Aug. 23, 2004 |
| 2213 | Table_2213_FL_1919_52723.txt | 182,388 | Aug. 23, 2004 |
| 2214 | Table_2214_FL_735_52462.txt | 182,452 | Aug. 23, 2004 |
| 2215 | Table_2215_FL_738_52642.txt | 182,363 | Aug. 23, 2004 |
| 2216 | Table_2216_FL_739_52643.txt | 182,462 | Aug. 23, 2004 |
| 2217 | Table_2217_FL_878_52644.txt | 182,344 | Aug. 23, 2004 |
| 2218 | Table_2218_FL_879_52645.txt | 182,472 | Aug. 23, 2004 |
| 2219 | Table_2219_FL_886_52646.txt | 182,483 | Aug. 23, 2004 |
| 2220 | Table_2220_FL_888_52647.txt | 182,373 | Aug. 23, 2004 |
| 2221 | Table_2221_GMALT_2021_52795.txt | 182,498 | Aug. 23, 2004 |
| 2222 | Table_2222_GMALT_2041_52796.txt | 182,517 | Aug. 23, 2004 |
| 2223 | Table_2223_GMALT_2065_52797.txt | 182,535 | Aug. 23, 2004 |
| 2224 | Table_2224_GMALT_2067_52798.txt | 182,459 | Aug. 23, 2004 |
| 2225 | Table_2225_GMALT_2070_52799.txt | 182,458 | Aug. 23, 2004 |
| 2226 | Table_2226_GMALT_2110_52800.txt | 182,534 | Aug. 23, 2004 |
| 2227 | Table_2227_GMALT_2111_52801.txt | 182,432 | Aug. 23, 2004 |
| 2228 | Table_2228_GMALT_2112_52802.txt | 182,478 | Aug. 23, 2004 |
| 2229 | Table_2229_GMALT_2270_52803.txt | 182,595 | Aug. 23, 2004 |
| 2230 | Table_2230_LBL_2185_53023.txt | 182,457 | Aug. 23, 2004 |
| 2231 | Table_2231_LBL_2186_52823.txt | 182,329 | Aug. 23, 2004 |
| 2232 | Table_2232_LBL_2249_52824.txt | 182,381 | Aug. 23, 2004 |
| 2233 | Table_2233_LPC_2224_52842.txt | 182,646 | Aug. 23, 2004 |
| 2234 | Table_2234_LPC_2232_52843.txt | 182,608 | Aug. 23, 2004 |
| 2235 | Table_2235_LPC_2261_52821.txt | 182,504 | Aug. 23, 2004 |
| 2236 | Table_2236_LPC_2262_53542.txt | 182,616 | Aug. 23, 2004 |
| 2237 | Table_2237_LPC_2263_52844.txt | 182,430 | Aug. 23, 2004 |
| 2238 | Table_2238_LPC_2265_52845.txt | 182,451 | Aug. 23, 2004 |
| 2239 | Table_2239_LPC_2410_53371.txt | 182,412 | Aug. 23, 2004 |
| 2240 | Table_2240_LPC_2411_53372.txt | 182,521 | Aug. 23, 2004 |
| 2241 | Table_2241_LPC_2412_53373.txt | 182,573 | Aug. 23, 2004 |
| 2242 | Table_2242_LPC_2413_53374.txt | 182,501 | Aug. 23, 2004 |
| 2243 | Table_2243_LPC_2414_53375.txt | 182,489 | Aug. 23, 2004 |
| 2244 | Table_2244_MALT_2178_52827.txt | 182,515 | Aug. 23, 2004 |
| 2245 | Table_2245_MALT_2181_52828.txt | 182,440 | Aug. 23, 2004 |
| 2246 | Table_2246_MALT_2182_52829.txt | 182,507 | Aug. 23, 2004 |
| 2247 | Table_2247_MALT_2183_52830.txt | 182,467 | Aug. 23, 2004 |
| 2248 | Table_2248_MALT_2184_52831.txt | 182,543 | Aug. 23, 2004 |
| 2249 | Table_2249_MALT_2202_52833.txt | 182,668 | Aug. 23, 2004 |
| 2250 | Table_2250_MALT_2211_52836.txt | 182,623 | Aug. 23, 2004 |
| 2251 | Table_2251_MALT_2243_52832.txt | 182,505 | Aug. 23, 2004 |
| 2252 | Table_2252_MCL_1012_51716.txt | 182,396 | Aug. 23, 2004 |
| 2253 | Table_2253_MCL_1091_52328.txt | 182,428 | Aug. 23, 2004 |
| 2254 | Table_2254_MCL_1114_52329.txt | 182,400 | Aug. 23, 2004 |
| 2255 | Table_2255_MCL_1128_51717.txt | 182,335 | Aug. 23, 2004 |
| 2256 | Table_2256_MCL_1150_51714.txt | 182,428 | Aug. 23, 2004 |
| 2257 | Table_2257_MCL_1162_51715.txt | 182,412 | Aug. 23, 2004 |
| 2258 | Table_2258_MCL_1166_52330.txt | 182,469 | Aug. 23, 2004 |
| 2259 | Table_2259_MCL_1194_52331.txt | 181,991 | Aug. 23, 2004 |
| 2260 | Table_2260_MCL_885_53011.txt | 182,459 | Aug. 23, 2004 |
| 2261 | Table_2261_MCL_918_52316.txt | 182,550 | Aug. 23, 2004 |

-continued

| | | | |
|---|---|---|---|
| 2262 | Table_2262_MCL_924_52318.txt | 182,557 | Aug. 23, 2004 |
| 2263 | Table_2263_MCL_925_52317.txt | 182,463 | Aug. 23, 2004 |
| 2264 | Table_2264_MCL_926_52319.txt | 182,485 | Aug. 23, 2004 |
| 2265 | Table_2265_MCL_936_52320.txt | 182,582 | Aug. 23, 2004 |
| 2266 | Table_2266_MCL_939_52321.txt | 182,610 | Aug. 23, 2004 |
| 2267 | Table_2267_MCL_953_52322.txt | 182,492 | Aug. 23, 2004 |
| 2268 | Table_2268_MCL_956_52323.txt | 182,482 | Aug. 23, 2004 |
| 2269 | Table_2269_MCL_964_52324.txt | 182,429 | Aug. 23, 2004 |
| 2270 | Table_2270_MCL_966_52325.txt | 182,395 | Aug. 23, 2004 |
| 2271 | Table_2271_MCL_968_52326.txt | 182,403 | Aug. 23, 2004 |
| 2272 | Table_2272_MCL_970_52327.txt | 182,434 | Aug. 23, 2004 |
| 2273 | Table_2273_NMZ_2231_52834.txt | 182,506 | Aug. 23, 2004 |
| 2274 | Table_2274_NMZ_2242_52835.txt | 182,434 | Aug. 23, 2004 |
| 2275 | Table_2275_NMZ_2254_52846.txt | 182,612 | Aug. 23, 2004 |
| 2276 | Table_2276_NMZ_2416_53376.txt | 182,442 | Aug. 23, 2004 |
| 2277 | Table_2277_PMBL_1048_52288.txt | 182,443 | Aug. 23, 2004 |
| 2278 | Table_2278_PMBL_1053_52289.txt | 182,385 | Aug. 23, 2004 |
| 2279 | Table_2279_PMBL_1920_53016.txt | 182,435 | Aug. 23, 2004 |
| 2280 | Table_2280_PMBL_1921_51713.txt | 182,362 | Aug. 23, 2004 |
| 2281 | Table_2281_PMBL_1923_51712.txt | 182,440 | Aug. 23, 2004 |
| 2282 | Table_2282_PMBL_1924_51711.txt | 182,419 | Aug. 23, 2004 |
| 2283 | Table_2283_PMBL_1935_52290.txt | 182,426 | Aug. 23, 2004 |
| 2284 | Table_2284_PMBL_1941_52291.txt | 182,477 | Aug. 23, 2004 |
| 2285 | Table_2285_PMBL_1942_52292.txt | 182,441 | Aug. 23, 2004 |
| 2286 | Table_2286_PMBL_1943_52293.txt | 182,492 | Aug. 23, 2004 |
| 2287 | Table_2287_PMBL_1945_52825.txt | 182,346 | Aug. 23, 2004 |
| 2288 | Table_2288_PMBL_1946_52826.txt | 182,211 | Aug. 23, 2004 |
| 2289 | Table_2289_PMBL_1948_52294.txt | 182,305 | Aug. 23, 2004 |
| 2290 | Table_2290_PMBL_1949_52297.txt | 182,453 | Aug. 23, 2004 |
| 2291 | Table_2291_PMBL_1989_52298.txt | 182,376 | Aug. 23, 2004 |
| 2292 | Table_2292_PMBL_1992_52299.txt | 182,469 | Aug. 23, 2004 |
| 2293 | Table_2293_PMBL_1993_52300.txt | 182,356 | Aug. 23, 2004 |
| 2204 | Table_2294_PMBL_2002_52301.txt | 182,424 | Aug. 23, 2004 |
| 2295 | Table_2295_PMBL_2019_52302.txt | 182,358 | Aug. 23, 2004 |
| 2296 | Table_2296_PMBL_2020_52303.txt | 182,617 | Aug. 30, 2004 |
| 2297 | Table_2297_PMBL_2092_52304.txt | 182,611 | Aug. 30, 2004 |
| 2298 | Table_2298_PMBL_484_52279.txt | 182,564 | Aug. 30, 2004 |
| 2299 | Table_2299_PMBL_546_53018.txt | 182,646 | Aug. 28, 2004 |
| 2300 | Table_2300_PMBL_570_52281.txt | 182,653 | Aug. 28, 2004 |
| 2301 | Table_2301_PMBL_621_52282.txt | 182,458 | Aug. 28, 2004 |
| 2302 | Table_2302_PMBL_691_52283.txt | 182,463 | Aug. 28, 2004 |
| 2303 | Table_2303_PMBL_791_52284.txt | 182,606 | Aug. 28, 2004 |
| 2304 | Table_2304_PMBL_824_52285.txt | 182,716 | Aug. 28, 2004 |
| 2305 | Table_2305_PMBL_906_52286.txt | 182,549 | Aug. 28, 2004 |
| 2306 | Table_2306_PMBL_994_52287.txt | 182,707 | Aug. 28, 2004 |
| 2307 | Table_2307_PTCL_2311_52837.txt | 182,602 | Aug. 28, 2004 |
| 2308 | Table_2308_PTCL_2312_52838.txt | 182,690 | Aug. 28, 2004 |
| 2309 | Table_2309_PTCL_2315_52839.txt | 182,718 | Aug. 28, 2004 |
| 2310 | Table_2310_PTCL_2318_52841.txt | 182,568 | Aug. 28, 2004 |
| 2311 | Table_2311_PTCL_2319_52840.txt | 182,541 | Aug. 28, 2004 |
| 2312 | Table_2312_PTCL_2320_53292.txt | 182,652 | Aug. 28, 2004 |
| 2313 | Table_2313_PTLD_1817_52820.txt | 182,507 | Aug. 28, 2004 |
| 2314 | Table_2314_PTLD_1824_52819.txt | 182,673 | Aug. 28, 2004 |
| 2315 | Table_2315_PTLD_1981_52818.txt | 182,480 | Aug. 28, 2004 |
| 2316 | Table_2316_PTLD_1986_52817.txt | 182,509 | Aug. 28, 2004 |
| 2317 | Table_2317_SLL_1151_52374.txt | 182,653 | Aug. 28, 2004 |
| 2318 | Table_2318_SLL_1153_52375.txt | 182,426 | Aug. 28, 2004 |
| 2319 | Table_2319_SLL_1155_52376.txt | 182,449 | Aug. 28, 2004 |
| 2320 | Table_2320_SLL_1156_52377.txt | 182,557 | Aug. 28, 2004 |
| 2321 | Table_2321_SLL_1158_52378.txt | 182,490 | Aug. 28, 2004 |
| 2322 | Table_2322_SLL_1213_53026.txt | 182,692 | Aug. 27, 2004 |
| 2323 | Table_2323_SLL_1214_51723.txt | 182,570 | Aug. 27, 2004 |
| 2324 | Table_2324_SLL_1216_53027.txt | 182,454 | Aug. 27, 2004 |
| 2325 | Table_2325_SLL_1217_53028.txt | 182,541 | Aug. 27, 2004 |
| 2326 | Table_2326_SLL_1218_52379.txt | 182,555 | Aug. 27, 2004 |
| 2327 | Table_2327_SLL_1220_52380.txt | 182,512 | Aug. 27, 2004 |
| 2328 | Table_2328_SLL_1229_52381.txt | 182,500 | Aug. 27, 2004 |
| 2329 | Table_2329_SLL_1231_52382.txt | 182,436 | Aug. 27, 2004 |
| 2330 | Table_2330_SLL_1235_52383.txt | 182,465 | Aug. 27, 2004 |
| 2331 | Table_2331_SLL_1236_52384.txt | 182,698 | Aug. 27, 2004 |
| 2332 | Table_2332_SLL_1238_52385.txt | 182,402 | Aug. 27, 2004 |
| 2333 | Table_2333_SLL_1240_52386.txt | 182,578 | Aug. 27, 2004 |
| 2334 | Table_2334_SLL_1620_52387.txt | 182,607 | Aug. 27, 2004 |
| 2335 | Table_2335_SPL_2061_52804.txt | 182,693 | Aug. 27, 2004 |
| 2336 | Table_2336_SPL_2074_52805.txt | 182,658 | Aug. 27, 2004 |
| 2337 | Table_2337_SPL_2075_52806.txt | 182,548 | Aug. 27, 2004 |
| 2338 | Table_2338_SPL_2077_52807.txt | 182,653 | Aug. 27, 2004 |
| 2339 | Table_2339_SPL_2079_52808.txt | 182,652 | Aug. 27, 2004 |
| 2340 | Table_2340_SPL_2104_52809.txt | 182,643 | Aug. 27, 2004 |

-continued

| | | | |
|---|---|---|---|
| 2341 | Table_2341_SPL_2105_52810.txt | 182,682 | Aug. 27, 2004 |
| 2342 | Table_2342_SPL_2106_52811.txt | 182,585 | Aug. 27, 2004 |
| 2343 | Table_2343_SPL_2256_52812.txt | 182,721 | Aug. 27, 2004 |
| 2344 | Table_2344_SPL_2257_52813.txt | 182,754 | Aug. 27, 2004 |
| 2345 | Table_2345_SPL_2258_52814.txt | 182,578 | Aug. 27, 2004 |
| 2346 | Table_2346_SPL_2259_52815.txt | 182,644 | Aug. 27, 2004 |
| 2347 | Table_2347_SPL_2260_52816.txt | 182,662 | Aug. 27, 2004 |
| 2348 | Table_2348_trDLBCL_1332_52305.txt | 182,606 | Aug. 27, 2004 |
| 2349 | Table_2349_trDLBCL_1336_53020.txt | 182,204 | Aug. 27, 2004 |
| 2350 | Table_2350_trDLBCL_1338_52307.txt | 182,460 | Aug. 27, 2004 |
| 2351 | Table_2351_trDLBCL_1353_52308.txt | 182,637 | Aug. 27, 2004 |
| 2352 | Table_2352_trDLBCL_1357_52309.txt | 182,640 | Aug. 27, 2004 |
| 2353 | Table_2353_trDLBCL_1508_52310.txt | 182,613 | Aug. 27, 2004 |
| 2354 | Table_2354_trDLBCL_1520_52311.txt | 182,675 | Aug. 27, 2004 |
| 2355 | Table_2355_trDLBCL_1535_52312.txt | 182,651 | Aug. 27, 2004 |
| 2356 | Table_2356_trDLBCL_1782_52313.txt | 182,621 | Aug. 27, 2004 |
| 2357 | Table_2357_trDLBCL_1784_52314.txt | 182,752 | Aug. 27, 2004 |
| 2358 | Table_2358_trDLBCL_1786_52725.txt | 182,570 | Aug. 24, 2004 |
| — | Table of Contents.txt | 146,716 | Sep. 2, 2004 |

Disc 22 of 22

| File Name | File size (bytes) | Date Created |
|---|---|---|
| GeneData.txt | 9,800,834 | Aug. 31, 2004 |
| GeneID.txt | 319,333 | Aug. 31, 2004 |
| PredictionResults.txt | 50,889 | Sep. 2, 2004 |
| SampleID.txt | 10,117 | Sep. 2, 2004 |
| SubtypePredictor.txt | 16,614 | Aug. 31, 2004 |
| Table of contents.txt | 255 | Sep. 2, 2004 |

As stated above, the foregoing is merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

Abbreviations used herein: ABC, activated B-cell-like diffuse large B cell lymphoma; BL, Burkitt lymphoma; CHOP, cyclophosphamide, doxorubicine, vincristine, and prednisone; CI, confidence interval; CNS, central nervous system; DLBCL, diffuse large B-cell lymphoma; ECOG, Eastern Cooperative Oncology Group; EST, expressed sequence tag; FACS, fluorescence-activated cell sorting; FH, follicular hyperplasia; FL, follicular lymphoma; GCB, germinal center B-cell-like diffuse large B cell lymphoma; IPI, International Prognostic Index; LPC, lymphoplasmacytic lymphoma; LPS, linear predictor score; MALT, mucosa-associated lymphoid tissue lymphomas; MCL, mantle cell lymphoma; MHC, major histocompatibility complex; NA, not available; NK, natural killer; NMZ, nodal marginal zone lymphoma; PCR, polymerase chain reaction; PMBL, primary mediastinal B-cell lymphoma; PTLD, post-transplant lymphoproliferative disorder; REAL, Revised European-American Lymphoma; RPA, RNase protection assay; RR, relative risk of death; RT-PCR, reverse transcriptase polymerase chain reaction; SAGE, serial analysis of gene expression; SLL, small lymphocytic lymphoma; WHO, World Health Organization.

REFERENCES

1. Alizadeh, A. A., et al. 1998. Probing lymphocyte biology by genomic-scale gene expression analysis. J Clin Immunol 18:373-79.
2. Alizadeh, A. A., et al. 1999. The Lymphochip: a specialized cDNA microarray for the genomic-scale analysis of gene expression in normal and malignant lymphocytes. Cold Spring Harbor Symp Quant Biol 64:71-78.
3. Alizadeh, A. A., et al. 2000. Distinct types of diffuse large B-cell lymphoma identified by gene expression profiling. Nature 403:503-511.
4. Alon, U., et al. 1999. Broad patterns of gene expression revealed by clustering analysis of tumor and normal colon tissues probed by oligonucleotide arrays. Proc Natl Acad Sci USA 96:6745-6750.
5. Bayes, T. 1763. An essay towards solving a problem in the doctrine of chances. Phil Trans Roy Soc London 53:370.
6. Chee, M., et al. 1996. Accessing genetic information with high density DNA arrays. Science 274:610-14.
7. Cho, R. J., et al. 1998. A genome-wide transcriptional analysis of the mitotic cell cycle. Mol Cell 2:65-73.
8. Chu, S., et al. 1998. The transcriptional program of sporulation in budding yeast. Science 282:699-705.
9. Copie-Bergman, C., et al. 2002. MAL expression in lymphoid cells: further evidence for MAL as a distinct molecular marker of primary mediastinal large B-cell lymphomas. Mod Pathol 15:1172-1180.
10. Copie-Bergman, C., et al. 2003. Interleukin 4-induced gene 1 is activated in primary mediastinal large B-cell lymphoma. Blood 101:2756-2761.
11. DeRisi, J., et al. 1996. Use of a cDNA microarray to analyze gene expression patterns in human cancer. Nat Genet 14:457-60.
12. DeRisi, J. L., Iyer, V. R., Brown, P. O. 1997. Exploring the metabolic and genetic control of gene expression on a genomic scale. Science 278:680-86.
13. Drapner, H. 1966. Applied regression. Wiley, New York.
14. Dudoit, S., Fridlyand, J., Speed, T. P. 2002. Comparison of discrimination methods for the classification of tumors using gene expression data. J Am Stat Assoc 97:77-87.

15. Eisen, M. B., Spellman, P. T., Brown, P. O., Botstein, D. 1998. Cluster analysis and display of genome-wide expression patterns. Proc Natl Acad Sci USA 95:14863-14868.
16. Fisher, R. I., et al. 1993. Comparison of a standard regimen (CHOP) with three intensive chemotherapy regimens for advanced non-Hodgkin's lymphoma. N Engl J Med 328:1002-1006.
17. Furey, T. S., et al. 2000. Support vector machine classification and validation of cancer tissue samples using microarray expression data. Bioinformatics 16:906-914.
18. Golub, T. R., et al. 1999. Molecular classification of cancer: class discovery and class prediction by gene expression monitoring, Science 286:531-537.
19. Gress, T. M., et al. 1996. A pancreatic cancer-specific expression profile. Oncogene 13:1819-30.
20. Harris, N. L., et al. 1994. A revised European-American classification of lymphoid neoplasms: a proposal from the International Lymphoma Study Group. Blood 84:1361-1392.
21. Heller, R. A., et al. 1997. Discovery and analysis of inflammatory disease-related genes using cDNA microarrays. Proc Natl Acad Sci USA 94:2150-55.
22. Holstege, F. C., et al. 1998. Dissecting the regulatory circuitry of a eukaryotic genome. Cell 95:717-728.
23. Irizarry, R. A., et al. 2003. Exploration, normalization, and summaries of high density oligonucleotide array probe level data. Biostatistics 4:249-264.
24. Hills, M. 1966. Allocation rules and error rates. J Royal Statis Soc Series B 28:1-31.
25. Jaffe, E. S., Harris, N. L., Stein, H., Vardiman, J. W. 2001. Tumors of hematopoietic and lymphoid tissues. IARC Press, Lyon.
26. Khouri, I. F., et al. 1998. Hyper-CVAD and high-dose methotrexate/cytarabine followed by stem-cell transplantation: an active regimen for aggressive mantle-cell lymphoma. J Clin Oncol 12:3803-3809.
27. Kohonen, T. 1997. Self-organizing maps. Springer Press, Berlin.
28. Lashkari, D. A., et al. 1997. Yeast microarrays for genome wide parallel genetic and gene expression analysis. Proc Natl Acad Sci USA 94:13057-62.
29. Li, C., Wong, W. H. 2001. Model-based analysis of oligonucleotide arrays: expression index computation and outlier detection. Proc Natl Acad Sci USA 98:31-36.
30. Lipshutz, R. J., et al. 1995. Using oligonucleotide probe arrays to access genetic diversity. Biotechniques 19:442-47.
31. Lockhart, D. J., et al. 1996. Expression monitoring by hybridization to high-density oligonucleotide arrays. Nat Biotechnol 14:1675-80.
32. Pease, A. C., et al. 1994. Light generated oligonucleotide arrays for rapid DNA sequence analysis. Proc Natl Acad Sci USA 91:5022-26.
33. Pietu, G., et al. 1996. Novel gene transcripts preferentially expressed in human muscles revealed by quantitative hybridization of a high density cDNA array. Genome Res 6:492-503.
34. Radmacher, M. D., McShane, L. M., Simon, R. 2002. A paradigm for class prediction using gene expression profiles. J Comput Biol 9:505-511.
35. Ramaswamy, S., et al. 2001. Multiclass cancer diagnosis using tumor gene expression signatures. Proc Natl Acad Sci USA 98:15149-15154.
36. Ransohoff, D. F. 2004. Rules of evidence for cancer molecular-marker discovery and validation. Nat Rev Cancer 4:309-314.
37. Rosenwald, A., et al. 2002. The use of molecular profiling to predict survival after chemotherapy for diffuse large-B-cell lymphoma. New Engl J Med 346:1937-1947.
38. Rosenwald, A., et al. 2003. The proliferation gene expression signature is a quantitative integrator of oncogenic events that predicts survival in mantle cell lymphoma. Cancer Cell 3:185-197.
39. Schena, M., Shalon, D., Davis, R. W., Brown, P. O. 1995. Quantitative monitoring of gene expression patterns with a complementary DNA microarray. Science 270:467-70.
40. Schena, M., et al. 1996. Parallel human genome analysis: microarray based expression monitoring of 1000 genes. Proc Natl Acad Sci USA 93:10614-19.
41. Shaffer, A. L., et al. 2001. Signatures of the immune response. Immunity 15:375-385.
42. Shalon, D., Smith, S. J., Brown, P. O. 1996. A DNA microarray system for analyzing complex DNA samples using two-color fluorescent probe hybridization. Genome Res 6:639-45.
43. Shipp, M. A., et al. 2002. Diffuse large B-cell lymphoma outcome prediction by gene-expression profiling and supervised machine learning. Nat Med 8:68-74.
44. Southern, E. M., Maskos, U., Elder, J. K. 1992. Analyzing and comparing nucleic acid sequences by hybridization to arrays of oligonucleotides: evaluation using experimental models. Genomics 13:1008-17.
45. Southern, E. M., et al. 1994. Arrays of complementary oligonucleotides for analysing the hybridisation behaviour of nucleic acids. Nucl Acids Res 22:1368-73.
46. Spellman, P. T., et al. 1998. Comprehensive identification of cell cycle regulated genes of the yeast *Saccharomyces cerevisiae* by microarray hybridization. Mol Biol Cell 9:3273-3297.
47. Tamayo, P., et al. 1999. Interpreting patterns of gene expression with self-organizing maps: methods and application to hematopoietic differentiation. Proc Natl Acad Sci USA 96:2907-2912.
48. Tavazoie, S., et al. 1999. Systematic determination of genetic network architecture. Nat Genet 22:281-285.
49. Tibshirani, R., Hastie, T., Narasimhan, B., Chu, G. 2002. Diagnosis of multiple cancer types by shrunken centroids of gene expression. Proc Natl Acad Sci USA 99:6567-6572.
50. Velculescu, V. E., Zhang, L., Vogelstein, B., Kinzler, K. W. 1995. Serial analysis of gene expression. Science 270:484-87.
51. Wodicka, L., et al. 1997. Genome-wide expression monitoring in *Saccharomyces cerevisiae*. Nat Biotechnol 15:1359-6714.
52. Wright, G., et al. 2003. A gene expression-based method to diagnose clinically distinct subgroups of diffuse large B cell lymphoma. Proc Natl Acad Sci USA 100:9991-9996.

What is claimed is:

1. A method for determining the lymphoma type of a sample X comprising the steps of:
 a) isolating gene expression product from lymphoma sample X;
 b) creating one or more lymphoma type pairs, wherein each lymphoma type pair represents a combination of a first lymphoma type and a second lymphoma type;
 c) for each lymphoma type pair, obtaining gene expression data for a set of genes G in said first lymphoma type and said second lymphoma type;
 d) calculating a series of scale factors, wherein each scale factor represents a difference in gene expression between said first lymphoma type and said second lymphoma type for one of the genes belonging to said set of genes G;
e) identifying a subset of genes g that are differentially expressed between said first lymphoma type and said second lymphoma type;
f) generating a series of linear predictor scores for a set of known samples belonging to said first lymphoma type and a set of known samples belonging to said second lymphoma type based on the expression of said subset of genes g identified in step (e);
g) contacting the gene expression product from sample X to a plurality of probes to thereby obtain gene expression data for said subset of genes g for sample X;
h) generating a linear predictor score for sample X based on the expression of said subset of genes g;
i) calculating a probability q that sample X belongs to said first lymphoma type by:

$$q = \frac{\phi(LPS(X); \hat{\mu}_1, \hat{\sigma}_1)}{\phi(LPS(X); \hat{\mu}_1, \hat{\sigma}_1) + \phi(LPS(X); \hat{\mu}_2, \hat{\sigma}_2)}$$

wherein LPS(X) is the linear predictor score for sample X, $\phi(x; \mu, \sigma)$ is the normal density function with mean $\mu$ and standard deviation $\sigma$, $\hat{\mu}_1$ and $\hat{\sigma}_1$ are the mean and variance of the linear predictor scores for said set of known samples belonging to said first lymphoma type, and $\hat{\mu}_2$ and $\hat{\sigma}_2$ are the mean and variance of the linear predictor scores for said known samples belonging to said second lymphoma type;
j) determining whether probability q is a high probability, middle probability, or low probability value, wherein the high probability and the middle probability have an upper cut-off point between 0.5 and 0.99, and the middle probability and the low probability have a lower cut-off point between 0.01 and 0.5; and
k) providing probability q to a user, wherein a high probability q indicates that sample X belongs to said first lymphoma type, a low probability q indicates that sample X belongs to said second lymphoma type, and a middle probability q indicates that sample X belongs to neither lymphoma type.

2. The method of claim 1, wherein said subset of genes g contains z genes from said set of genes G with the largest scale factors, wherein z is from 5 to 100.

3. The method of claim 2, wherein z=100.

4. The method of claim 2, wherein said series of linear predictor scores in step (f) comprises one or more linear predictor scores generated using from 1 to z of the genes from said subset of genes g.

5. The method of claim 2, further comprising the additional step of selecting a number of genes from 1 to z that generates the largest difference in linear predictor score between said first lymphoma type and said second lymphoma type, wherein the gene expression data obtained for sample X in step (g) is obtained only for said selected number of genes.

6. The method of claim 1, wherein step (c) further comprises placing each gene in said set of genes G into one of n gene-list categories, wherein placement in a gene-list category indicates correlation between expression of said gene and expression of a gene expression signature.

7. The method of claim 6, wherein said subset of genes g excludes genes belonging to a proliferation gene expression signature and genes belonging to a lymph node gene expression signature.

8. The method of claim 6, wherein n=3.

9. The method of claim 8, wherein said gene-list categories are a lymph node gene expression signature, a proliferation gene expression signature, and a standard gene expression signature, wherein said standard gene expression signature includes those genes not included in said lymph node and proliferation gene expression signatures.

10. The method of claim 9, wherein said series of linear predictor scores in step (f) comprises four linear predictor scores for each gene in said subset of genes g, wherein:
a) the first linear predictor score is generated using genes from the lymph node, proliferation, and standard gene expression signatures;
b) the second linear predictor score is generated using genes from the standard gene expression signature only;
c) the third linear predictor score is generated using genes from the standard and proliferation gene expression signatures only; and
d) the fourth linear predictor score is generated using genes from the standard and lymph node gene expression signatures only.

11. The method of claim 1 wherein the upper cut-off point between said high probability q and said middle probability q and the lower cut-off point between said middle probability q and said low probability q are determined by the following steps:
i) ranking samples of known lymphoma type according to their probability q, wherein the samples of known lymphoma type include samples of the first lymphoma type and samples of the second lymphoma type;
ii) analyzing each potential upper and lower cut-off point between adjacent samples in the ranking by: 3.99*[(% of said first lymphoma type misidentified as said second lymphoma type)+(% of said second lymphoma type misidentified as said first lymphoma type)]+[(% of said first lymphoma type classified as belonging to neither lymphoma type)+(% of said second lymphoma type classified as belonging to neither lymphoma type)]; and
iii) selecting the upper cut-off point and the lower cutoff point, wherein the upper and the lower cut-off points are those that minimize the equation of ii).

12. The method of claim 1 wherein the linear predictor scores are calculated by:

$$LPS(S) = \sum_{j \in G} t_j S_j,$$

wherein $S_j$ is the expression of gene j in a sample S and $t_j$ is the scale factor representing the difference in expression of gene j between said first lymphoma type and said second lymphoma type.

13. The method of claim 1 wherein said scale factors are t-statistics.

14. The method of claim 1, wherein steps (c) and/or (g) further comprise the use of a microarray.

15. The method of claim 1, wherein said sample X is classified as said first lymphoma type if said probability q is greater than 90%.

16. The method of claim 1, wherein said first lymphoma type and said second lymphoma type are independently selected from the group consisting of: follicular lymphoma (FL), Burkitt lymphoma (BL), mantle cell lymphoma (MCL), follicular hyperplasia (FH), small cell lymphocytic lymphoma (SLL), mucosa-associated lymphoid tissue lymphoma (MALT), splenic lymphoma, multiple myeloma, lymphoplasmacytic lymphoma, post-transplant lymphoproliferative disorder (PTLD), lymphoblastic lymphoma, nodal marginal zone lymphoma (NMZ), germinal center B cell-like diffuse large B cell lymphoma (GCB DLBCL), activated B cell-like diffuse large B cell lymphoma (ABC DLBCL) and primary mediastinal B cell lymphoma (PMBL).

17. The method of claim 1, wherein said first lymphoma type is mantle cell lymphoma (MCL) and said second lymphoma type is activated B cell-like diffuse large B cell lymphoma (DLBCL), and wherein said subset of genes g includes one or more genes selected from the group consisting of genes corresponding to (listed by GENBANK accession number): AK021895.1, NM_001001567.1, NM_002673.3, NM_003108.3, BC025340.1, NM_021211.2, NM_022037.1 NM_025249.2, NM_018387.2, BF196503.1, AF251293.1, NM_003498.4, AL110204.1, NM_178335.1, NM_001003789.1, NM_052909.3, XM_001124203.1, NM_003890.2, NM_021992.2, and NM_170672.1.

18. The method of claim 1, wherein said first lymphoma type is mantle cell lymphoma (MCL) and said second lymphoma type is Burkitt lymphoma (BL), and wherein said subset of genes g includes one or more genes selected from the group of genes corresponding to (listed by GENBANK accession number): NM_004445.2, NM_019064.3, BC025340.1, NM_004944.2, NM_052909.3, AW977010.1, NM_003436.2, NM_178335.1, NM_003108.3, NM_014638.2, NM_012276.3, NM_014698.1, AW135407.1, NM_022552.3, NM_001099269.1, AJ296290.1, NM_024761.3, NM_012408.3, NM_004305.2, and NM_001024847.2.

19. The method of claim 1, wherein said first lymphoma type is mantle cell lymphoma (MCL) and said second lymphoma type is follicular hyperplasia (FH), and wherein said subset of genes g includes one or more genes selected from the group of genes corresponding to (listed by GENBANK accession number): NM_003108.3, NM_030753.3, AI694444.1, NM_017784.3, NM_052909.3, NM_016083.3, NM_000698.2, NM_020805.1, NM_001013746.1, NM_003621.1, NM_013230.2, NM_001098503.1, NM_138738.2, NM_172004.2, NM_153026.1, NM_013230.2, XM_001128367.1, NM_012417.2, NM_014792.2, and AF161538.1.

20. The method of claim 1, wherein said first lymphoma type is mantle cell lymphoma (MCL) and said second lymphoma type is follicular lymphoma (FL), and wherein said subset of genes g includes one or more genes selected from the group consisting of genes corresponding to (listed by GENBANK accession number): NM_003108.3, NM_022552.3, AK021895.1, NM_002673.3, BC025340.1, NM_178335.1, NM_004772.1, NM_015915.3, NM_001853.3, NM_014322.2, NM_032488.2, NM_153026.1, NM_003105.3, NM_005522.4, NM_001706.2, NM_015150.1, AI809213.1, NM_001706.2, NM_002927.3, and NM_170672.1.

21. The method of claim 1, wherein said first lymphoma type is mantle cell lymphoma (MCL) and said second lymphoma type is germinal center B cell-like diffuse large B cell lymphoma (GCB DLBCL), and wherein said subset of genes g includes one or more genes selected from the group consisting of genes corresponding to (listed by GENBANK accession number): NM_178335.1, NM_003108.3, NM_002673.3, NM_024761.3, AK021895.1, NM_022552.3, NM_014322.2, NM_003498.4, NM_005921.1, NM_017699.2, NM_001099269.1, NM_001025616.2, NM_052909.3, NM_004445.2, AI479031.1, NM_0220371.1, NM_001400.3, NM_153026.1, NM_001003819.1, and NM_001706.2.

22. The method of claim 1, wherein said first lymphoma type is mantle cell lymphoma (MCL) and said second lymphoma type is mucosa-associated lymphoid tissue lymphoma (MALT), and wherein said subset of genes g includes one or more genes selected from the group consisting of genes corresponding to (listed by GENBANK accession number): NM_003108.3, NM_052909.3, NM_030753.3, NM_006805.3, NR_003238.1, NM_153026.1, NM_004772.1, NM_001024401.2, AK021895.1, NM_021727.3, NM_001400.3, NM_153026.1, NM_003436.2, NM_022552.3, NM_018387.2, NM_006614.2, NM_001098503.1, AF251293.1, NM_006866.1, and NM_021727.3.

23. The method of claim 1, wherein said first lymphoma type is mantle cell lymphoma (MCL) and said second lymphoma type is primary mediastinal B cell lymphoma (PMBL), and wherein said subset of genes g includes one or more genes selected from the group consisting of genes corresponding to (listed by GENBANK accession number): NM_003108.3, NM_030753.3, AF251293.1, NM_178335.1, NM_006352.3, NM_002738.5, AK021895.1, NM_005449.3 NM_000024.4, NM_138738.2, BC047541.1, AW516128.1, NM_021211.2, NM_004516.2, NM_006850.2, NM_001002909.1, NM_153026.1, NM_012290.3, NM_015184.3, and NM_006860.2.

24. The method of claim 1, wherein said first lymphoma type is mantle cell lymphoma (MCL) and said second lymphoma type is post-transplant lymphoproliferative disorder (PTLD), and wherein said subset of genes g includes one or more genes selected from the group consisting of genes corresponding to (listed by GENBANK accession number): BG749488.1, NM_013230.2, NM_013230.2, NM_001098670.1, NM_017784.3, NM_005449.3, NM_003108.3, NM_003436.2, NM_005921.1, NM_001025108.1, NM_004834.3, NM_001400.3, NM_001007231.1, AL833385.1, NM_006614.2, NM_014767.1, NM_001104925.1, NM_032966.1, NM_000917.2, and NM_005504.4.

25. The method of claim 1, wherein said first lymphoma type is mantle cell lymphoma (MCL) and said second lymphoma type is small cell lymphocytic lymphoma (SLL), and wherein said subset of genes g includes one or more genes selected from the group consisting of genes corresponding to (listed by GENBANK accession number): NM_003108.3, NM_052909.3, AK021895.1, NM_022552.3, NM_004772.1, NM_021727.3, NM_021727.3, NM_015183.1, B1759100.1, NM_015183.1, NM_015180.4, NM_015183.1, NM_145693.1, NM_024507.2, NM_002356.5, NM_006614.2, NM_006317.3, NM_001498.2, NM_002372.2, and NM_001039538.1.

26. The method of claim 1, wherein said first lymphoma type is mantle cell lymphoma (MCL) and said second lymphoma type is splenic lymphoma, and wherein said subset of genes g includes one or more genes selected from the group consisting of genes corresponding to (listed by GENBANK accession number): NM_052909.3, NM_003436.2, BC047698.1, NM_133368.1, NM_006805.3, NM_003030.3, NM_001006684.1, NM_001105539.1, NM_002814.2, NM_003108.3, NM_002356.5, NM_014456.3, NM_177531.4, NM_001008495.2, NM_018387.2, NM_000516.4, NM_001001992.1, NM_001024401.2, NM_007014.3, and NM_001030005.

27. The method of claim 1, wherein said first lymphoma type is activated B cell-like diffuse large B cell lymphoma (ABC DLBCL) and said second lymphoma type is germinal center B cell-like diffuse large B cell lymphoma (GCB DLBCL), and wherein said subset of genes g includes one or more genes selected from the group consisting of genes corresponding to (listed by GENBANK accession number): AK097859.1, NM_001759.2, NM_002827.2, NM_005574.2, NM_004513.4, NM_001080416.1, XM_378655.2, NM_002827.2, NM_001018009.2, AK097859.1, NM_001012505.1, NM_001987.4, BC106050.1, NM_001042518.1, NM_001706.2, NM_001101676.1, NM_002460.1, NM_002648.2, NM_014957.2, NM_013314.2, NM_004480.3, NM_004480.3, NM_001098175.1, NM_006152.2, NM_0143973, NM_002221.2, NM_013314.2, NM_001003940.1, and NM_174908.2.

28. The method of claim 14, wherein said microarray is selected from the group consisting of an Affymetrix U133A microarray and an Affymetrix U133B microarray.

29. The method of claim 1, wherein the method further comprises providing a therapy or course of treatment based on whether sample X belongs to said first lymphoma type, said second lymphoma type, or neither said first lymphoma type nor said second lymphoma type.

* * * * *